(12) United States Patent
Kelly et al.

(10) Patent No.: US 7,338,950 B2
(45) Date of Patent: Mar. 4, 2008

(54) AMIDE COMPOUNDS AS ION CHANNEL LIGANDS AND USES THEREOF

(75) Inventors: Michael G. Kelly, Thousand Oaks, CA (US); Satyanarayana Janagani, Santa Clara, CA (US); Guoxian Wu, Foster City, CA (US); John Kincaid, Foster City, CA (US)

(73) Assignee: Renovis, Inc., South San Francisco, CA (US)

( * ) Notice: Subject to any disclaimer, the term of this patent is extended or adjusted under 35 U.S.C. 154(b) by 368 days.

(21) Appl. No.: 10/962,195

(22) Filed: Oct. 7, 2004

(65) Prior Publication Data

US 2005/0192293 A1 Sep. 1, 2005

Related U.S. Application Data

(60) Provisional application No. 60/508,865, filed on Oct. 7, 2003, provisional application No. 60/575,937, filed on Jun. 1, 2004.

(51) Int. Cl.
*C07D 401/10* (2006.01)
*A61K 31/444* (2006.01)

(52) U.S. Cl. .............................. 514/235.5; 514/253.01; 514/332; 514/347; 514/357; 544/124; 544/360; 546/265; 546/294; 546/337

(58) Field of Classification Search ................ 546/265, 546/294, 337; 544/124, 360; 514/235.5, 514/253.01, 332, 347, 357
See application file for complete search history.

(56) References Cited

U.S. PATENT DOCUMENTS

| 4,942,236 A | 7/1990 | Musser et al. |
| 5,859,033 A | 1/1999 | Takaki et al. |
| 2005/0085512 A1 | 4/2005 | Lee et al. |

FOREIGN PATENT DOCUMENTS

| EP | 1 099 701 A1 | 5/2001 |
| WO | WO 96/40640 | 12/1996 |
| WO | WO 98/41508 | 9/1998 |
| WO | WO 01/70673 A2 | 9/2001 |
| WO | WO 03/068749 A1 | 8/2003 |
| WO | WO 2004/056774 A2 | 7/2004 |
| WO | WO 2005/030766 | 4/2005 |

*Primary Examiner*—Deepak Rao
(74) *Attorney, Agent, or Firm*—Klauber & Jackson L.L.C.

(57) ABSTRACT

Compounds are disclosed that have a formula represented by the following:

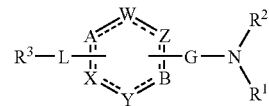

The compounds may be prepared as pharmaceutical compositions, and may be used for the prevention and treatment of a variety of conditions in mammals including humans, including by way of non-limiting example, pain, inflammation, traumatic injury, and others.

30 Claims, 6 Drawing Sheets

AMIDE COMPOUNDS AS ION CHANNEL LIGANDS AND USES THEREOF

CROSS REFERENCE TO RELATED APPLICATIONS

The present application claims the priority of co-pending provisional applications U.S. Ser. No. 60/508,865, filed on Oct. 7, 2003, and U.S. Ser. No. 60/575,937, filed Jun. 1, 2004. The disclosures of both applications are incorporated by reference herein in their entireties. Applicants claim the benefits of both applications under 35 U.S.C. §119(e).

FIELD OF THE INVENTION

This invention relates to novel compounds and to pharmaceutical compositions containing such compounds. This invention also relates to methods for preventing and/or treating pain and inflammation-related conditions in mammals, such as (but not limited to) arthritis, Parkinson's disease, Alzheimer's disease, stroke, uveitis, asthma, myocardial infarction, the treatment and prophylaxis of pain syndromes (acute and chronic or neuropathic), traumatic brain injury, acute spinal cord injury, neurodegenerative disorders, alopecia (hair loss), inflammatory bowel disease and autoimmune disorders, using the compounds and pharmaceutical compositions of the invention.

BACKGROUND OF THE INVENTION

Studies of signaling pathways in the body have revealed the existence of ion channels and sought to explain their role. Ion channels are integral membrane proteins with two distinctive characteristics: they are gated (open and closed) by specific signals such as membrane voltage or the direct binding of chemical ligands and, once open, they conduct ions across the cell membrane at very high rates.

There are many types of ion channels. Based on their selectivity to ions, they can be divided into calcium channel, potassium channel, sodium channel, etc. The calcium channel is more permeable to calcium ions than other types of ions, the potassium channel selects potassium ions over other ions, and so forth. Ion channels may also be classified according to their gating mechanisms. In a voltage-gated ion channel, the opening probability depends on the membrane voltage, whereas in a ligand-gated ion channel, the opening probability is regulated by the binding of small molecules (the ligands). Since ligand-gated ion channels receive signals from the ligand, they may also be considered as "receptors" for ligands.

Examples of ligand-gated ion channels include nAChR (nicotinic acetylcholine receptor) channel, GluR (glutamate receptor) channel, ATP-sensitive potassium channel, G-protein activated channel, cyclic-nucleotide-gated channel, etc.

Transient receptor potential (TRP) channel proteins constitute a large and diverse family of proteins that are expressed in many tissues and cell types. This family of channels mediates responses to nerve growth factors, pheromones, olfaction, tone of blood vessels and metabolic stress et al., and the channels are found in a variety of organisms, tissues and cell types including nonexcitable, smooth muscle and neuronal cells. Furthermore, TRP-related channel proteins are implicated in several diseases, such as several tumors and neurodegenerative disorders and the like. See, for example, Minke, et al., *APStracts* 9:0006P (2002).

Nociceptors are specialized primary afferent neurons and the first cells in a series of neurons that lead to the sensation of pain. The receptors in these cells can be activated by different noxious chemical or physical stimuli. The essential functions of nociceptors include the transduction of noxious stimuli into depolarizations that trigger action potentials, conduction of action potentials from primary sensory sites to synapses in the central nervous system, and conversion of action potentials into neurotransmitter release at presynaptic terminals, all of which depend on ion channels.

One TRP channel protein of particular interest is the vanilloid receptor. Also known as VR1, the vanilloid receptor is a non-selective cation channel which is activated or sensitized by a series of different stimuli including capsaicin, heat and acid stimulation and products of lipid bilayer metabolism (anandamide), and lipoxygenase metabolites. See, for example Smith, et al., *Nature*, 418:186-190 (2002). VR1 does not discriminate among monovalent cations, however, it exhibits a notable preference for divalent cations with a permeability sequence of $Ca^{2+}>Mg^{2+}>Na^+=K^+=Cs^+$. $Ca^{2+}$ is especially important to VR1 function, as extracellular $Ca^{2+}$ mediates desensitization, a process which enables a neuron to adapt to specific stimuli by diminishing its overall response to a particular chemical or physical signal. VR1 is highly expressed in primary sensory neurons in rats, mice and humans, and innervates many visceral organs including the dermis, bones, bladder, gastrointestinal tract and lungs. It is also expressed in other neuronal and non-neuronal tissues including the CNS, nuclei, kidney, stomach and T-cells. The VR1 channel is a member of the superfamily of ion channels with six membrane-spanning domains, with highest homology to the TRP family of ion channels.

VR1 gene knockout mice have been shown to have reduced sensory sensitivity to thermal and acid stimuli. See, for example, Caterina, et al. *Science*, 14:306-313 (2000). This supports the concept that VR1 contributes not only to generation of pain responses but also to the maintenance of basal activity of sensory nerves. VR1 agonists and antagonists have use as analgesics for the treatment of pain of various genesis or etiology, for example acute, inflammatory and neuropathic pain, dental pain and headache (such as migraine, cluster headache and tension headache). They are also useful as anti-inflammatory agents for the treatment of arthritis, Parkinson's Disease, Alzheimer's Disease, stroke, uveitis, asthma, myocardial infarction, the treatment and prophylaxis of pain syndromes (acute and chronic [neuropathic]), traumatic brain injury, spinal cord injury, neurodegenerative disorders, alopecia (hair loss), inflammatory bowel disease and autoimmune disorders, renal disorders, obesity, eating disorders, cancer, schizophrenia, epilepsy, sleeping disorders, cognition, depression, anxiety, blood pressure, lipid disorders, and atherosclerosis.

Compounds, such as those of the present invention, which interact with the vanilloid receptor can thus play a role in treating or preventing or ameliorating these conditions.

A wide variety of Vanilloid compounds of different structures are known in the art, for example those disclosed in European Patent Application Numbers, EP 0 347 000 and EP 0 401 903, UK Patent Application Number GB 2226313 and International Patent Application, Publication Number WO 92/09285. Particularly notable examples of vanilloid compounds or vanilloid receptor modulators are capsaicin or trans 8-methyl-N-vanillyl-6-nonenamide which is isolated from the pepper plant, capsazepine (Tetrahedron, 53, 1997, 4791) and olvanil or- N-(4-hydroxy-3-methoxybenzyl)oleamide (J. Med. Chem., 36, 1993, 2595).

International Patent Application, Publication Number WO 02/08221 discloses diaryl piperazine and related compounds which bind with high selectivity and high affinity to vanilloid receptors, especially Type I Vanilloid receptors, also known as capsaicin or VR1 receptors. The compounds are said to be useful in the treatment of chronic and acute pain conditions, itch and urinary incontinence.

International Patent Application, Publication Numbers WO 02/16317, WO 02/16318 and WO 02/16319 suggest that compounds having a high affinity for the vanilloid receptor are useful for treating stomach-duodenal ulcers.

WO04/56774 describe certain substituted biphenyl-4-carboxylic acid arylamide analogues having possible application as receptor modulators.

U.S. Pat. Nos. 3,424,760 and 3,424,761 both describe a series of 3-Ureidopyrrolidines that are said to exhibit analgesic, central nervous system, and pyschopharmacologic activities. These patents specifically disclose the compounds 1-(1-phenyl-3-pyrrolidinyl)-3-phenyl urea and 1-(1-phenyl-3-pyrrolidinyl)-3-(4-methoxyphenyl) urea respectively. International Patent Applications, Publication Numbers WO 01/62737 and WO 00/69849 disclose a series of pyrazole derivatives which are stated to be useful in the treatment of disorders and diseases associated with the NPY receptor subtype Y5, such as obesity. WO 01/62737 specifically discloses the compound 5-amino-N-isoquinolin-5-yl-1-[3-(trifluoromethyl)phenyl]-1H-pyrazole-3-carboxamide. WO 00/69849 specifically discloses the compounds 5-methyl-N-quinolin-8-yl-1-[3-(trifluoromethyl)phenyl]-1H-pyrazole-3-carboxamide, 5-methyl-N-quinolin-7-yl-1-[3-trifluoromethyl)phenyl]-1H-pyrazole-3-carboxamide, 5-methyl-N-quinolin-3-yl-1-[3-(trifluoromethyl)phenyl]-1H-pyrazole-3-carboxamide, N-isoquinolin-5-yl-5-methyl-1-[3-(trifluoromethyl)phenyl]-1H-pyrazole-3-carboxamide, 5-methyl-N-quinolin-5-yl-1-[3-(trifluoromethyl)phenyl]-1H-pyrazole-3-carboxamide, 1-(3-chlorophenyl)-N-isoquinolin-5-yl-5-methyl-1H-pyrazole-3-carboxamide, N-isoquinolin-5-yl-1-(3-methoxyphenyl)-5-methyl-1H-pyrazole-3-carboxamide, 1-(3-fuorophenyl)-N-isoquinolin-5-yl-5-methyl-1H-pyrazole-3-carboxamide, 1-(2-chloro-5-trifluoromethylphenyl)-N-isoquinolin-5-yl-5-methyl-1N-pyrazole-3-carboxamide, 5-methyl-N-(3-methylisoquinolin-5-yl)-1-[3-(trifluoromethyl)phenyl]-1N-pyrazole-3-carboxamide, 5-methyl-N-(1,2,3,4-tetrahydroisoquinolin-5-yl)-1-[3-(trifluoromethyl)phenyl]-1H-pyrazole-3-carboxamide.

German Patent Application Number 2502588 describes a series of piperazine derivatives. This application specifically discloses the compound N-[3-[2-(diethylamino) ethyl]-1,2-dihydro-4-methyl-2-oxo-7-quinolinyl]-4-phenyl-1-piperazinecarboxamide.

We have now discovered that certain compounds have surprising potency and selectivity as VR-1 antagonists. The compounds of the present invention are considered to be particularly beneficial as VR-1 antagonists as certain compounds exhibit improved aqueous solubility and metabolic stability.

SUMMARY OF THE INVENTION

It has now been found that compounds such as those set forth herein, are capable of modifying mammalian ion channels such as the VR1 cation channel. This finding leads to novel compounds having therapeutic value. It also leads to pharmaceutical compositions having the compounds of the present invention as active ingredients and to their use to treat, prevent or ameliorate a range of conditions in mammals such as but not limited to pain of various genesis or etiology, for example acute, chronic, inflammatory and neuropathic pain, dental pain and headache (such as migraine, cluster headache and tension headache).

Accordingly, in a first aspect of the invention, compounds are disclosed that are capable of modifying ion channels, in vivo, having a formula:

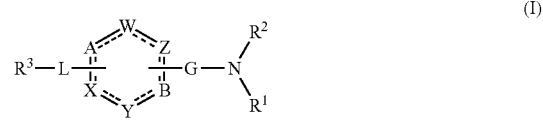

(I)

wherein:

A is N, $CR^4$, a carbon atom bound to L, or is not an atom;

one of W, Z, B, Y and X is a carbon atom bound to L if A is not an atom, another of W, Z, B, Y and X is a carbon atom bound to G, and each of the remaining W, Z, B, Y and X is independently N or $CR^4$;

L is a bond or $-(CH_2)_n-$, wherein n is an integer of 1-3;

G is C=O, C=S or $SO_2$;

$R^1$ is substituted or unsubstituted aliphatic, alkyl, heteroalkyl, aryl, heteroaryl, aralkyl, or heteroaralkyl;

$R^2$ is hydrogen or substituted or unsubstituted alkyl;

$R^3$ is substituted or unsubstituted aliphatic, alkyl, heteroalkyl, aryl, heteroaryl, aralkyl, or heteroaralkyl; and each $R^4$ is independently hydrogen, alkyl, substituted or unsubstituted alkyl, acyl, acylamino, alkylamino, alkylthio, alkoxy, alkoxycarbonyl, alkylarylamino, arylalkyloxy, amino, aryl, arylalkyl, sulfoxide, sulfone, sulfanyl, aminosulfonyl, arylsulfonyl, sulfuric acid, sulfuric acid ester, dihydroxyphosphoryl, aminohydroxyphosphoryl, azido, carboxy, carbamoyl, carboxyl, cyano, cycloheteroalkyl, dialkylamino, halo, heteroaryloxy, heteroaryl, heteroalkyl, hydroxyl, nitro or thio, or a pharmaceutically acceptable salt, solvate or prodrug thereof; and isomers and stereoisomers thereof.

In a further embodiment of the invention, compounds are capable of modifying ion channels, in vivo, having a formula IA

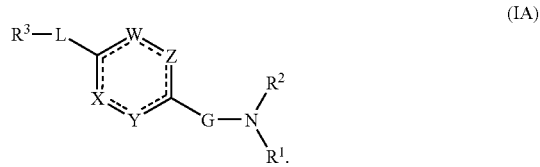

(IA)

In compounds of formula IA, L will be a bond and G will be carbonyl. $R^1$ is substituted or unsubstituted aliphatic, alkyl, heteroalkyl, heteroaryl, aralkyl, or heteroaralkyl; $R^2$ is hydrogen; and $R^3$ is substituted heteroaryl.

In a further embodiment of the compounds of formula IA, $R^3$ is of the formula

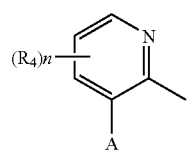

wherein $R^4$ is as described above; n is an integer of from 1-3; and A is independently selected from alkyl, substituted alkyl, acyl, substituted acyl, acylamino, substituted acylamino, alkylamino, substituted alkylamino, alkylthio, substituted alkylthio, alkoxy, substituted alkoxy, alkoxycarbonyl, substituted alkoxycarbonyl, alkylarylamino, substituted alkylarylamino, arylalkyloxy, substituted arylalkyloxy, amino, aryl, substituted aryl, arylalkyl, substituted arylalkyl, sulfoxide, substituted sulfoxide, sulfone, substituted sulfone, sulfanyl, substituted sulfanyl, aminosulfonyl, substituted aminosulfonyl, arylsulfonyl, substituted arylsulfonyl, sulfuric acid, sulfuric acid ester, dihydroxyphosphoryl, substituted dihydroxyphosphoryl, aminohydroxyphosphoryl, substituted aminohydroxyphosphoryl, azido, carboxy, carbamoyl, substituted carbamoyl, carboxyl, cyano, cycloalkyl, substituted cycloalkyl, cycloheteroalkyl, substituted cycloheteroalkyl, dialkylamino, substituted dialkylamino, halo, heteroaryloxy, substituted heteroaryloxy, heteroaryl, substituted heteroaryl, heteroalkyl, substituted heteroalkyl, hydroxyl, nitro or thio.

In a more particular embodiment of the invention, compounds capable of modifying ion channels, in vivo, have a formula II

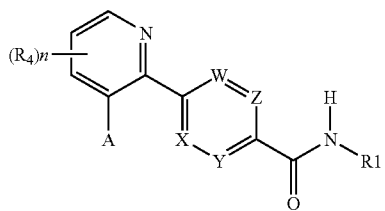

(II)

wherein: $R^1$ is substituted alkyl. In some compounds, $R^1$ is $-(CR^2_2)x$-$R^{4'}$; $R^2$ is hydrogen or alkyl; $R^{4'}$ is $R^4$; $R^4$ is as described for formula I; and x is an integer from 1-3.

In preferred embodiments of compounds of formula II, $R^{4'}$ is selected from t-butyl, aryl, cycloalkyl, cycloheteroalkyl and heteroaryl. In some of these preferred embodiments, $R^{4'}$ is substituted or unsubstituted phenyl, or naphthalene. In yet other of these preferred embodiments, $R^{4'}$ is substituted or unsubstituted cyclopropyl, cyclopentyl or cyclohexyl. In still others, $R^{4'}$ is substituted or unsubstituted pyrrolidinyl, piperidinyl, or morpholinyl. In yet others, $R^{4'}$ is substituted or unsubstituted pyridinyl, pyrimidinyl quinoline, benzodioxane, tetrahydroquinoline, indole, indazole or carbazole. Further preferred embodiments have $R^{4'}$ that is substituted or unsubstituted furanyl, imidazolyl, thiophenyl, pyrazolyl, or thiazolyl. In especially preferred embodiments, $R^{4'}$ is t-Bu.

In some specific compounds of Formula II, x is 1 or 2.

In some other specific compounds of Formula II, $R^1$ is substituted or unsubstituted cycloalkyl, cycloheteroalkyl or heteroaryl. In some preferred of these embodiments, $R^1$ is substituted or unsubstituted cyclopropyl, cyclopentyl, pyrrolidinyl, piperidinyl, morpholinyl, pyridinyl, pyrimidinyl quinoline, benzodioxane, tetrahydroquinoline, indole, indazole, carbazole, furanyl, imidazolyl, thiophenyl, pyrazolyl or thiazolyl.

In additional specific compounds of formula II, A is halo, $NR^2_2$, trihaloalkyl, alkoxy, $SO_2R^2$, or $SO_2NR^2_2$. In some preferred embodiments, A is selected from the group consisting of Cl, $CF_3$, OMe, $NMe_2$, $SO_2CF_3$, and $SO_2NMe_2$.

In certain specific compounds where A is selected from the group consisting of Cl, $CF_3$, OMe, $NMe_2$, $SO_2CF_3$, and $SO_2NMe_2$, each of W, X, Y and Z is $CR^4$. In other specific compounds, W is N and each of X, Y and Z is $CR^4$. In still other specific compounds, Y is N and each of W, X and Z is $CR^4$. In still further specific compounds, two of W, X, Y and Z are Ns.

In yet another particular embodiment, compounds capable of modifying ion channels, in vivo. have a formula II

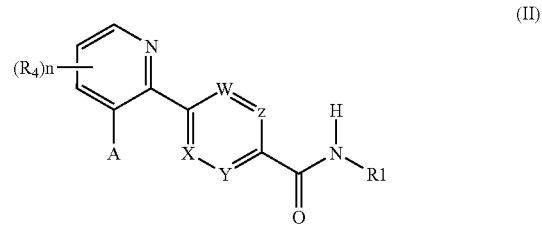

(II)

wherein: $R^1$ is substituted aryl. In some compounds, the substitution on aryl is $SO_2R^{14}$; and in a particular embodiment, $R^{14}$ is alkyl.

In yet another particular embodiment, compounds capable of modifying ion channels, in vivo, have a formula II

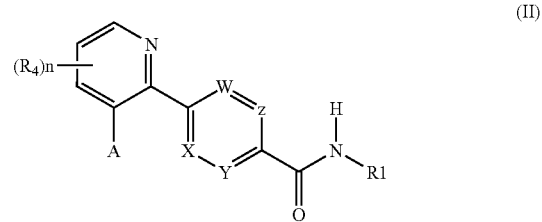

(II)

wherein: $R^1$ is substituted aryl. In some compounds, the substitution on aryl is $SO_2R^{14}$; and in a particular embodiment, $R^{14}$ is aryl, heteroaryl, aralkyl, and heteroaralkyl.

In yet another particular embodiment, compounds capable of modifying ion channels, in vivo, have a formula II

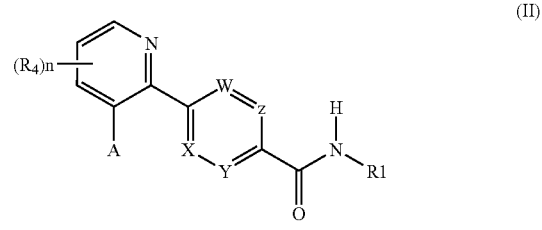

(II)

wherein: $R^1$ is substituted aryl. In some compounds, the substitution on aryl is $SO_2R^{14}$; and in a particular embodiment, $R^{14}$ is amino or substituted amino. In one particular embodiment, $R^{14}$ is $NR^{18}R^{19}$, and $R^{18}$ and $R^{19}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

In yet another particular embodiment of the invention, the compounds have the formula I':

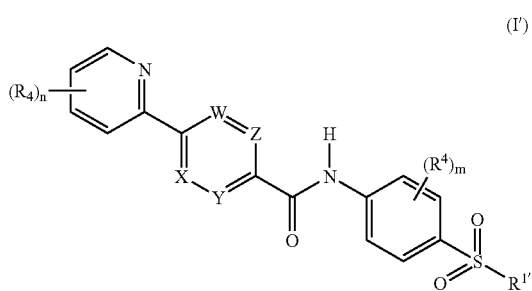

(I')

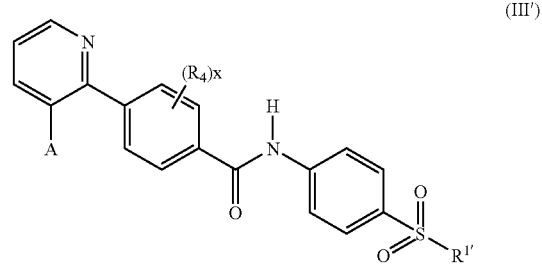

(III')

or a pharmaceutically acceptable salt, or solvate, or stereoisomers, or tautomers thereof, wherein:

each of W, X, Y and Z is independently $CR^4$;

$R^{1'}$ is alkyl, aryl, heteroaryl, aralkyl, heteroaralkyl, amino or substituted amino;

each $R^4$ is independently hydrogen, substituted or unsubstituted alkyl, hydroxyalkyl, haloalkyl, amino, alkylamino, dialkylamino, arylamino, alkylarylamino, alkoxy, aryloxy, heteroaryloxy, aminoalkoxy, alkoxy, cycloalkylalkoxy, alkoxycarbonyl, arylalkyloxy, aryl, heteroaryl, arylalkyl, sulfo, sulfonyl, sulfanyl, aminosulfonyl, arylsulfonyl, carboxy, carbamoyl, cyano, cycloheteroalkyl, halo, heteroalkyl, hydroxyl, or thiol; and the subscript n and the subscript m are independently 0, 1, 2, 3, or 4.

In one embodiment, with respect to compounds of formula I', the compound is of the formula II':

wherein A is as described for formula II'; $R^1$ and $R^4$ are as described for formula I'; and the subscript x is 0, 1, 2, 3, or 4.

In one embodiment, with respect to compounds of formula III', A is Cl, $CF_3$, OMe, $NMe_2$ or $SO_2Me$.

In one embodiment, with respect to compounds of formulae I-III', $R^{1'}$ is alkyl, substituted alkyl, aryl, substituted aryl, heteroaryl, or substituted heteroaryl.

In another embodiment, with respect to compounds of formulae I-III', $R^{1'}$ is alkyl.

In another embodiment, with respect to compounds of formulae I-III', $R^{1'}$ is amino or substituted amino.

In another embodiment, with respect to compounds of formulae I-III', $R^{1'}$ is $NR^{2'}R^{2'}$ wherein each $R^{2'}$ is independently hydrogen, alkyl, substituted alkyl, cycloalkyl, aryl, substituted aryl, heteroaryl, or substituted heteroaryl.

In one embodiment, with respect to compounds of formulae I-III', $R^{1'}$ is $NR^{2'}R^{2'}$; and the two $R^{2'}$s are independently alkyl.

In one embodiment, with respect to compounds of formulae I-III', $R^{1'}$ is $NR^{2'}$ and the two $R^{2'}$s are joined together to form a cycloheteroalkyl ring of 5-7 atoms.

In another embodiment, with respect to compounds of formula I', the compound is of the formula IV':

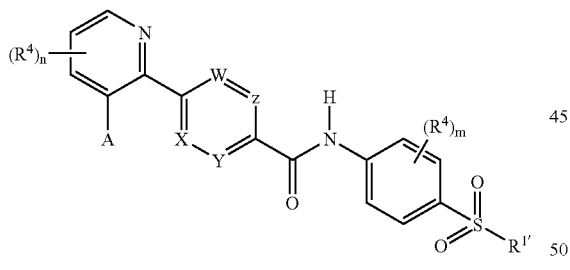

(II')

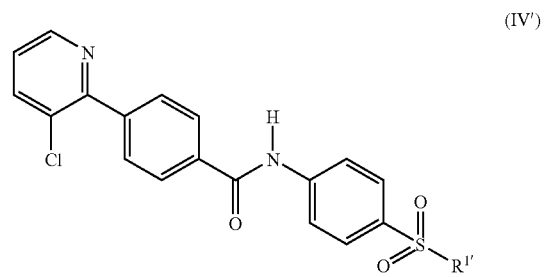

(IV')

wherein W, X, Y, Z, $R^1$ and $R^4$ are as described for formula I'; A is halo, alkyl, substituted alkyl, alkoxy, amino, substituted amino or $SO_2R^{1''}$; $R^{1'''}$ is alkyl, aryl, heteroaryl, aralkyl, heteroaralkyl, amino or substituted amino; and the subscript n is 0, 1, 2, or 3.

In one embodiment, with respect to compounds of formula II', each W, X, Y, and Z is CH.

In one embodiment, with respect to compounds of formula II', each $R^4$ is H.

In another embodiment, with respect to compounds of formula I', the compound is of the formula III':

and wherein $R^{1'}$ is alkyl, substituted alkyl, aryl, substituted aryl, heteroaryl, or substituted heteroaryl.

In one embodiment, with respect to compounds of formula IV', $R^{1'}$ is alkyl or substituted alkyl.

In another embodiment, with respect to compounds of formula IV', $R^{1'}$ is methyl, ethyl, n-Pr, i-Pr, t-Bu or CHB.

In another embodiment, with respect to compounds of formula IV', $R^{1'}$ is $CF_3$.

In another embodiment, with respect to compounds of formula I', the compound is of the formula V':

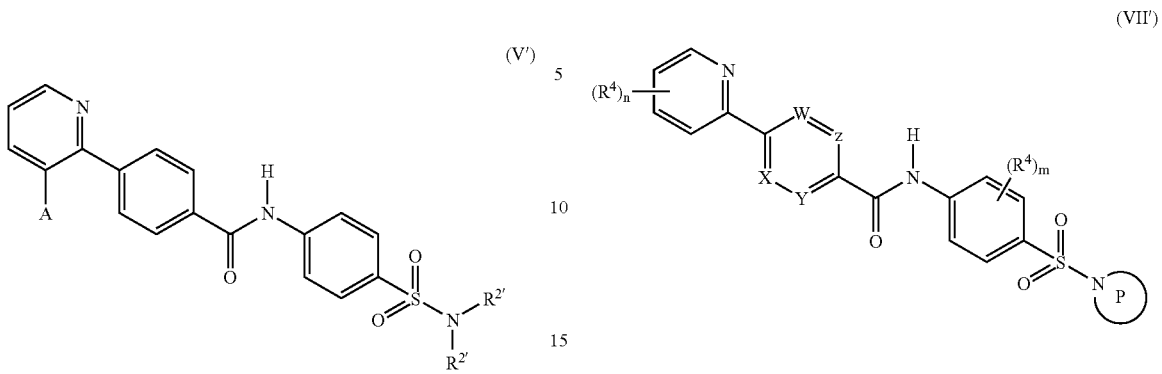

(V')

wherein each $R^{2'}$ is independently hydrogen, alkyl, substituted alkyl, cycloalkyl, aryl, substituted aryl, heteroaryl, or substituted heteroaryl.

In another embodiment, with respect to compounds of formula I', the compound is of the formula VI':

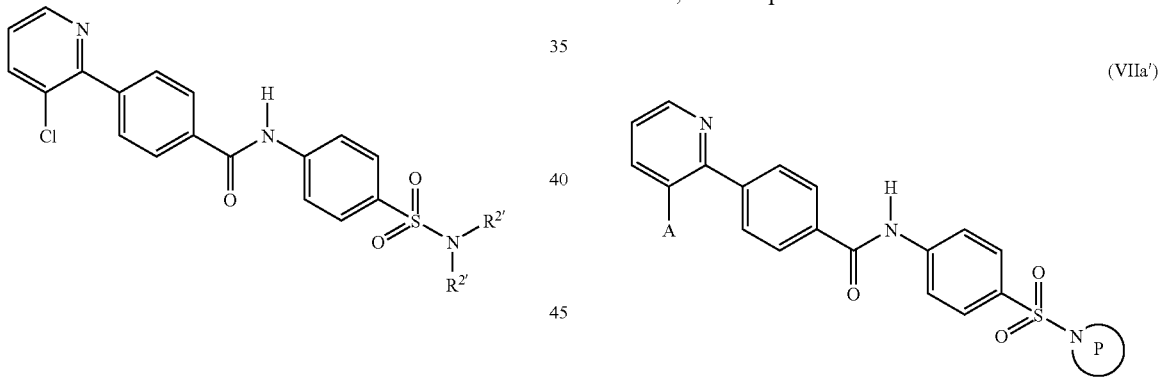

(VI')

wherein each $R^{2'}$ is independently hydrogen, alkyl, substituted alkyl, cycloalkyl, aryl, substituted aryl, heteroaryl, or substituted heteroaryl.

In one embodiment, with respect to compounds of formulae V'-VI', each $R^{2'}$ is H.

In another embodiment, with respect to compounds of formulae V'-VI', $R^{2'}$ is independently alkyl.

In another embodiment, with respect to compounds of formulae V'-VI', $R^{2'}$ is independently H, Me, or Et.

In another embodiment, with respect to compounds of formulae V'-VI', the two $R^{2'}$ are joined together to form a cycloheteroalkyl ring of 5-7 atoms.

In yet another particular embodiment of the invention, the compounds have the formula VII':

(VII')

or a pharmaceutically acceptable salt, or solvate, or stereoisomers, or tautomers thereof, wherein:

each of W, X, Y and Z is independently $CR^4$;

ring P is cycloheteroalkyl, substituted cycloheteroalkyl, heteroaryl, or substituted heteroaryl each Ri is independently hydrogen, substituted or unsubstituted alkyl, hydroxyalkyl, haloalkyl, amino, alkylamino, dialkylamino, arylamino, alkylarylamino, alkoxy, aryloxy, heteroaryloxy, aminoalkoxy, alkoxy, cycloalkylalkoxy, alkoxycarbonyl, arylalkyloxy, aryl, heteroaryl, arylalkyl, sulfo, sulfonyl, sulfanyl, aminosulfonyl, arylsulfonyl, carboxy, carbamoyl, cyano, cycloheteroalkyl, halo, heteroalkyl, hydroxyl, or thiol; and the subscript n and the subscript m is independently 0, 1, 2, 3, or 4.

In one embodiment, with respect to compounds of formula VII', the compound is of the formula VIIa':

(VIIa')

wherein A is Cl, $CF_3$ or $SO_2Me$.

In one embodiment, with respect to compounds of formulae VII'-VIIa', the ring P is selected from substituted or unsubstituted

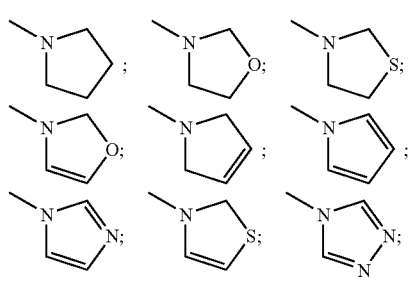

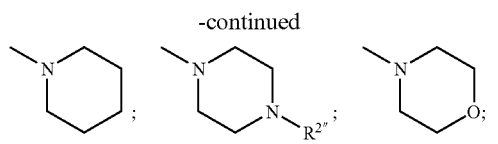
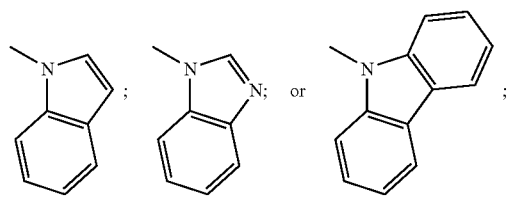
and wherein R[2″] is selected from H and alkyl.
In one particular embodiment the compound selected from the group consisting of:
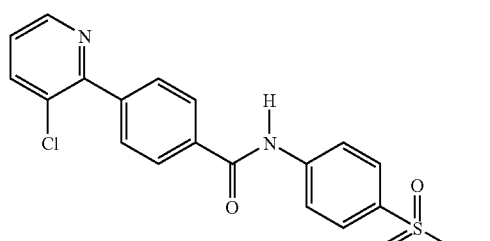
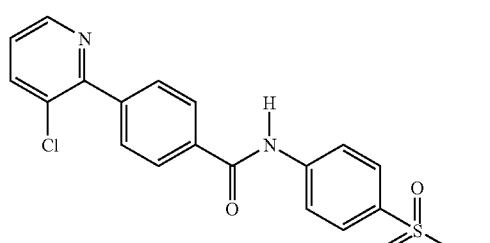
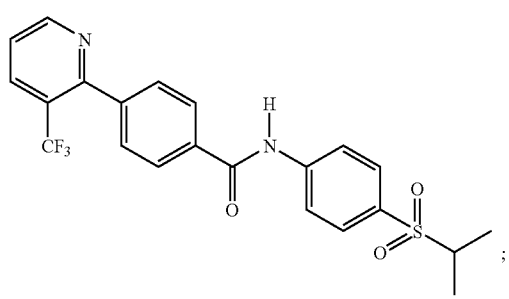
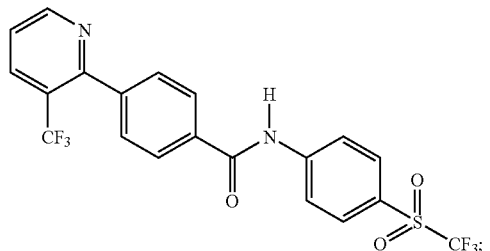
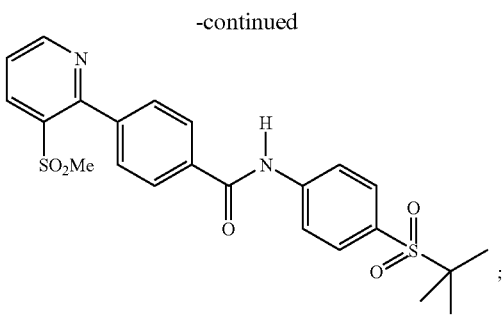
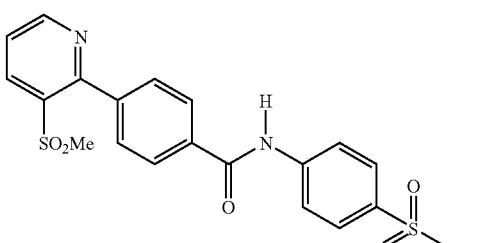
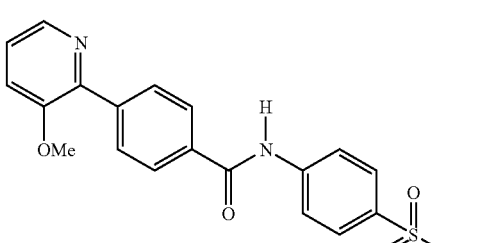
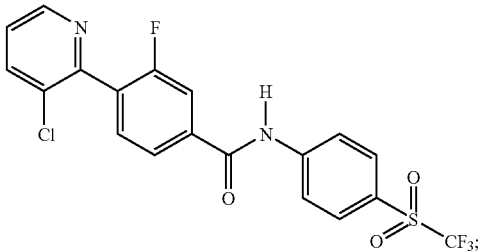
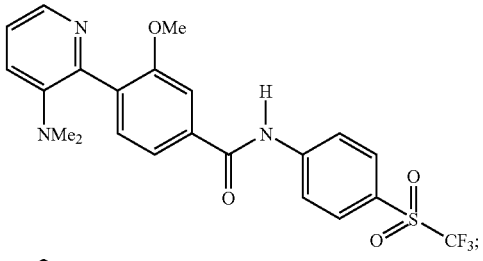
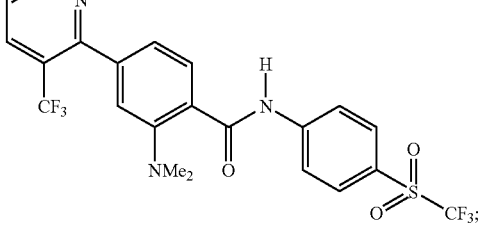

-continued
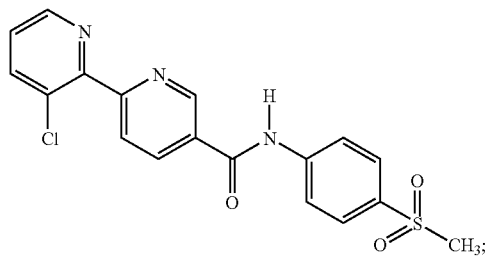
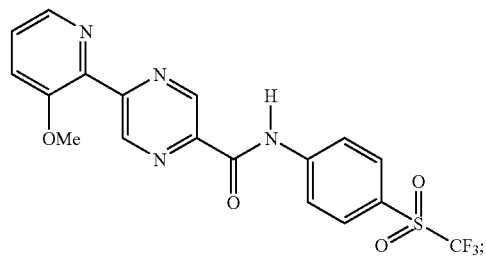
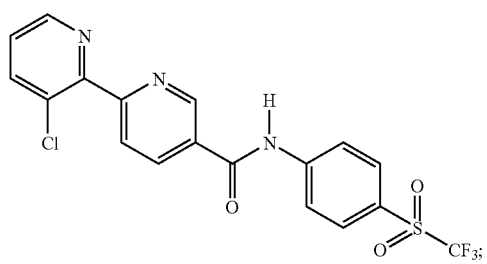
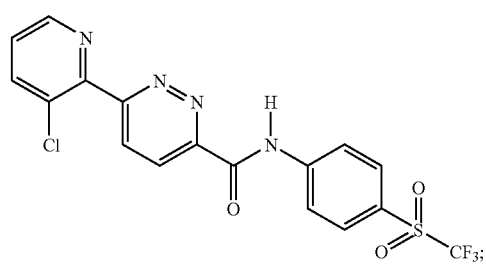
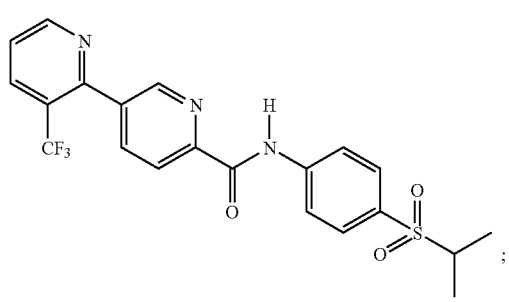
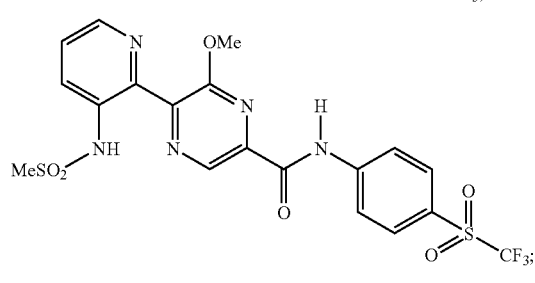
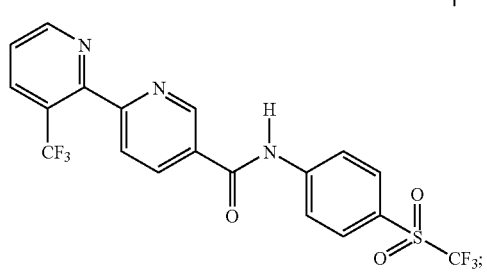
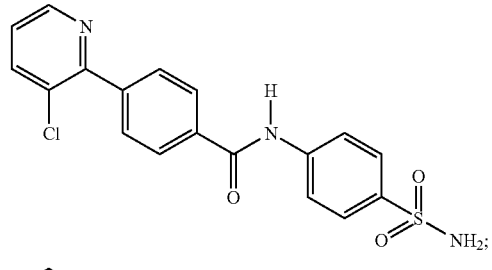
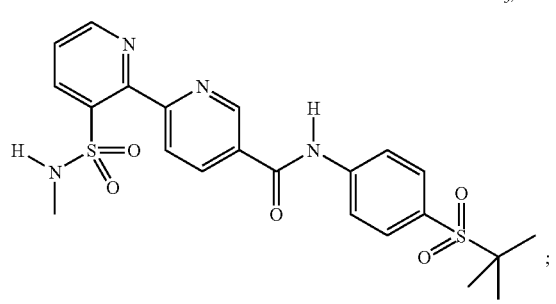
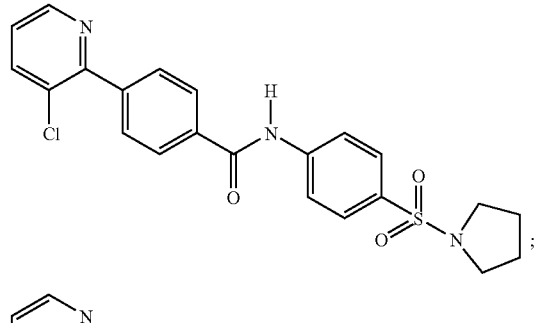
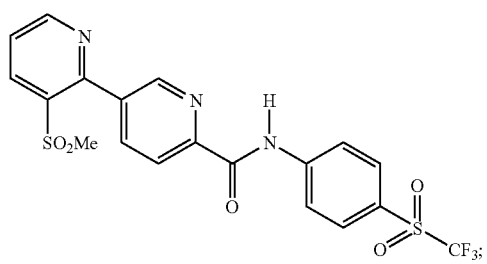
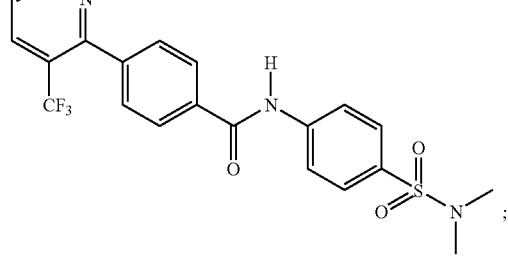

-continued
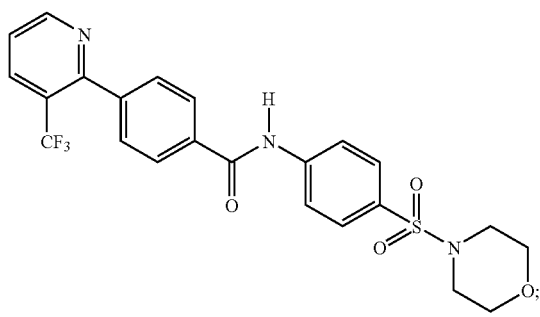
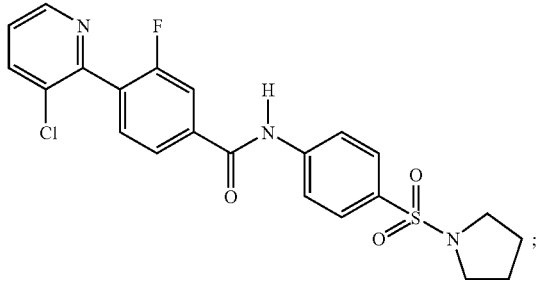
and
or a pharmaceutically acceptable salt, or solvate, or stereoisomers, or tautomers thereof.
In one particular embodiment the compound selected from the group consisting of:
| STRUCTURE | NAME |
|---|---|
| 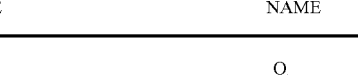 | 4-(3-Chloro-pyridin-2-yl)-N-(4-methanesulfonyl-phenyl)-benzamide; |

-continued

| STRUCTURE | NAME |
|---|---|
| 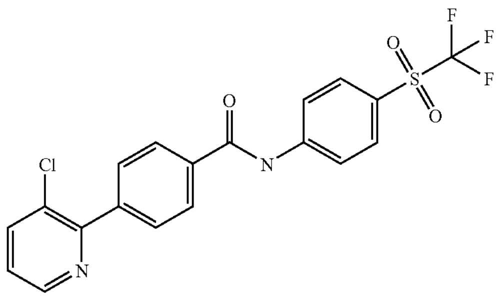 | 4-(3-Chloro-pyridin-2-yl)-N-(4-trifluoromethanesulfonyl-phenyl)-benzamide; |
| 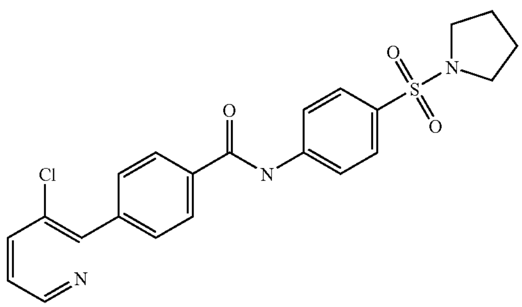 | 4-(3-Chloro-pyridin-2-yl)-N-[4-(pyrrolidine-1-sulfonyl)-phenyl]-benzamide; |
| 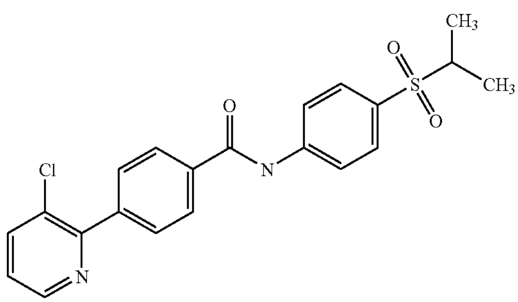 | 4-(3-Chloro-pyridin-2-yl)-N-[4-(propane-2-sulfonyl)-phenyl]-benzamide; |
| 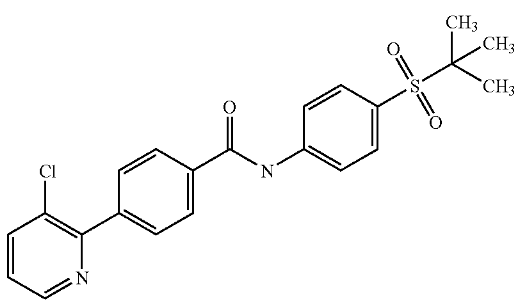 | 4-(3-Chloro-pyridin-2-yl)-N-[4-(2-methyl-propane-2-sulfonyl)-phenyl]-benzamide; |
| 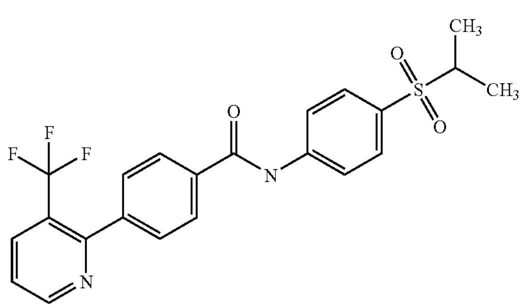 | N-[4-(Propane-2-sulfonyl)-phenyl]-4-(3-trifluoromethyl-pyridin-2-yl)-benzamide; |

-continued

| STRUCTURE | NAME |
|---|---|
| 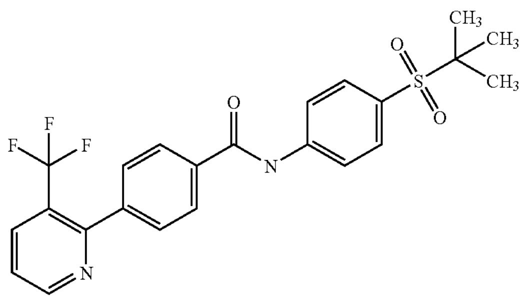 | N-[4-(2-Methyl-propane-2-sulfonyl)-phenyl]-4-(3-trifluoromethyl-pyridin-2-yl)-benzamide; |
| 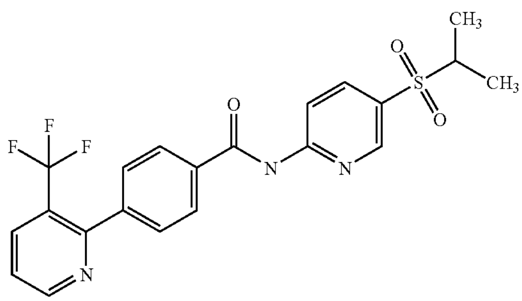 | N-[5-(Propane-2-sulfonyl)-pyridin-2-yl]-4-(3-trifluoromethyl-pyridin-2-yl)-benzamide; |
| 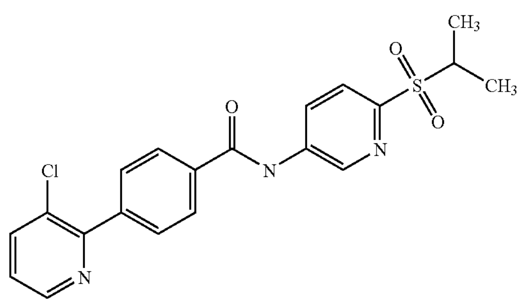 | 4-(3-Chloro-pyridin-2-yl)-N-[6-(propane-2-sulfonyl)-pyridin-3-yl]-benzamide; |
| 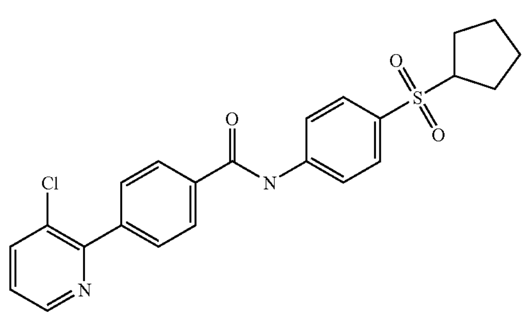 | 4-(3-Chloro-pyridin-2-yl)-N-(4-cyclopentanesulfonyl-phenyl)-benzamide; |
| 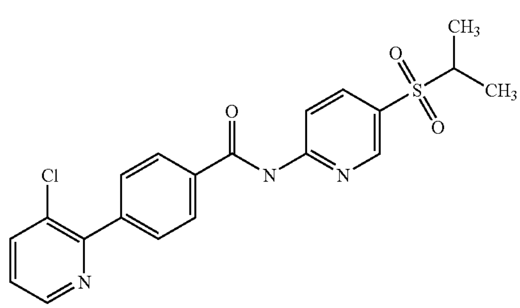 | 4-(3-Chloro-pyridin-2-yl)-N-[5-(propane-2-sulfonyl)-pyridin-2-yl]-benzamide; |

-continued

| STRUCTURE | NAME |
|---|---|
| 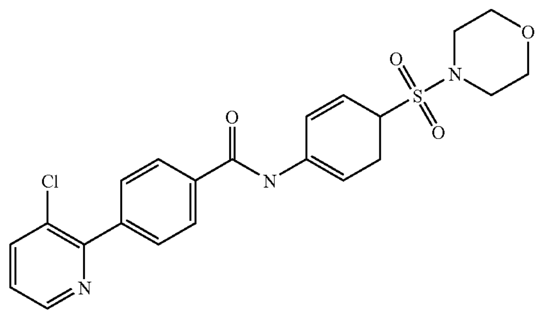 | 4-(3-Chloro-pyridin-2-yl)-N-[4-(morpholine-4-sulfonyl)-phenyl]-benzamide; |
| 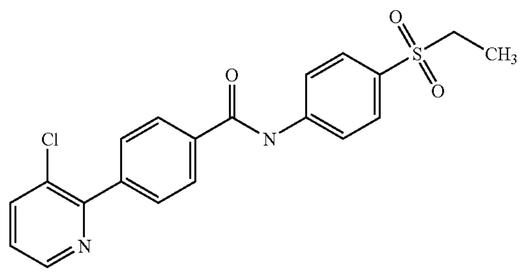 | 4-(3-Chloro-pyridin-2-yl)-N-(4-ethanesulfonyl-phenyl)-benzamide; |
| 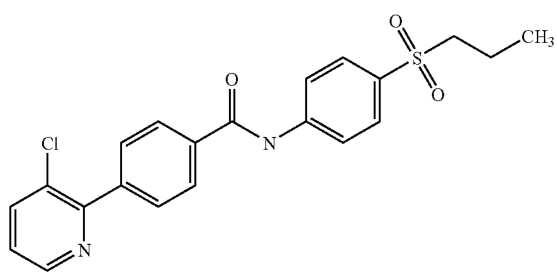 | 4-(3-Chloro-pyridin-2-yl)-N-[4-(propane-1-sulfonyl)-phenyl]-benzamide; |
| 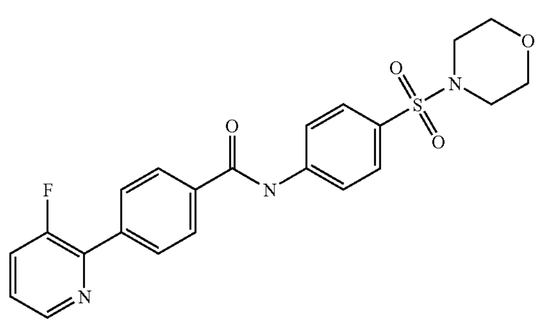 | 4-(3-Fluoro-pyridin-2-yl)-N-[4-(morpholine-4-sulfonyl)-phenyl]-benzamide; |
| 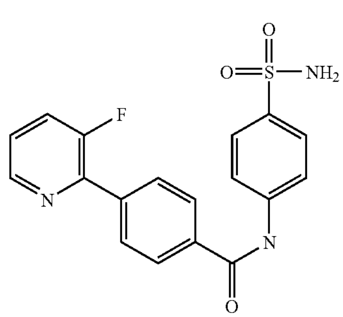 | 4-(3-Fluoro-pyridin-2-yl)-N-(4-sulfamoyl-phenyl)-benzamide; |

| STRUCTURE | NAME |
|---|---|
| 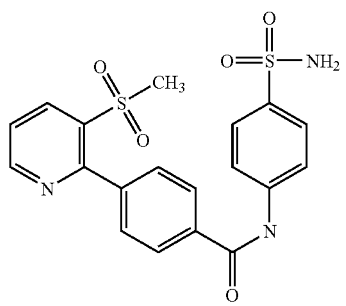 | 4-(3-Methanesulfonyl-pyridin-2-yl)-N-(4-sulfamoyl-phenyl)-benzamide; |
| 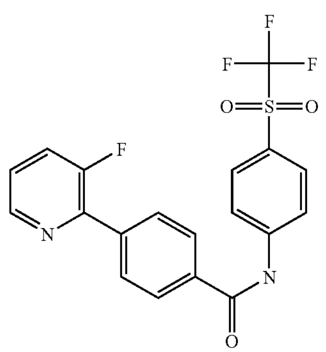 | 4-(3-Fluoro-pyridin-2-yl)-N-(4-trifluoromethanesulfonyl-phenyl)-benzamide; |
| 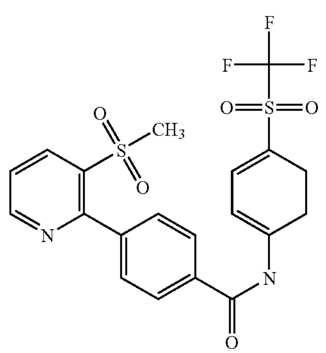 | 4-(3-Methanesulfonyl-pyridin-2-yl)-N-(4-trifluoromethanesulfonyl-phenyl)-benzamide; |
| 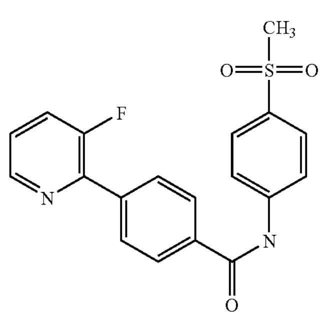 | 4-(3-Fluoro-pyridin-2-yl)-N-(4-methanesulfonyl-phenyl)-benzamide; |

| STRUCTURE | NAME |
|---|---|
| 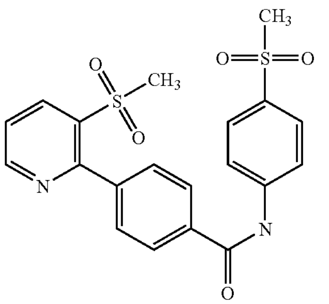 | N-(4-Methanesulfonyl-phenyl)-4-(3-methanesulfonyl-pyridin-2-yl)-benzamide; |
| 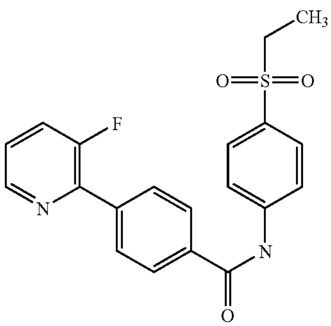 | N-(4-Ethanesulfonyl-phenyl)-4-(3-fluoro-pyridin-2-yl)-benzamide; |
| 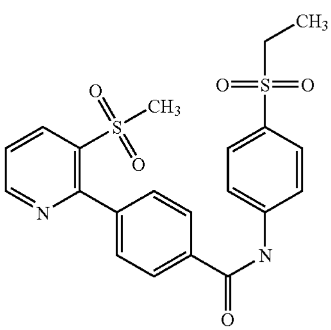 | N-(4-Ethanesulfonyl-phenyl)-4-(3-methanesulfonyl-pyridin-2-yl)-benzamide; |
| 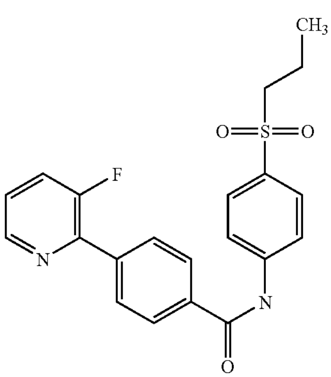 | 4-(3-Fluoro-pyridin-2-yl)-N-[4-(propane-1-sulfonyl)-phenyl]-benzamide; |

-continued

| STRUCTURE | NAME |
|---|---|
| 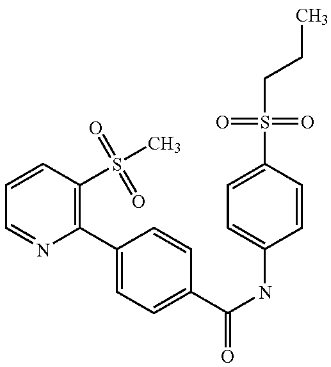 | 4-(3-Methanesulfonyl-pyridin-2-yl)-N-[4-(propane-1-sulfonyl)-phenyl]-benzamide; |
| 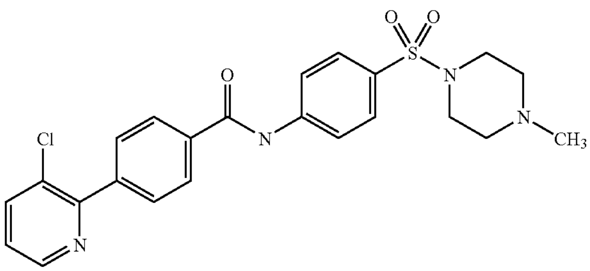 | 4-(3-Chloro-pyridin-2-yl)-N-[4-(4-methyl-piperazine-1-sulfonyl)-phenyl]-benzamide; |
| 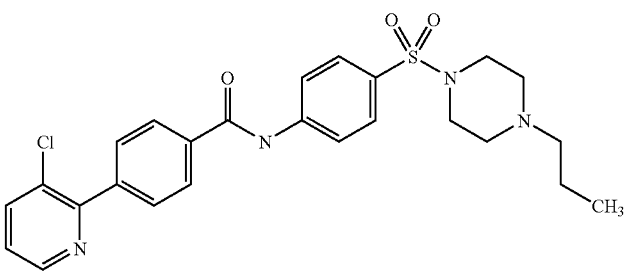 | 4-(3-Chloro-pyridin-2-yl)-N-[4-(4-propyl-piperazine-1-sulfonyl)-phenyl]-benzamide; |
| 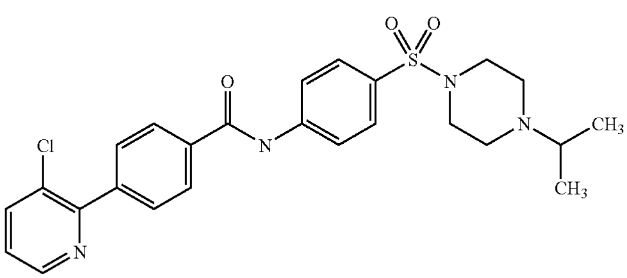 | 4-(3-Chloro-pyridin-2-yl)-N-[4-(4-isopropyl-piperazine-1-sulfonyl)-phenyl]-benzamide; and |
| 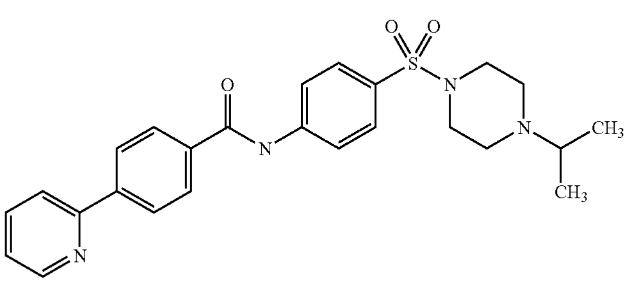 | N-[4-(4-Isopropyl-piperazine-1-sulfonyl)-phenyl]-4-pyridin-2-yl-benzamide; |

In yet further particular embodiments, the compounds of the invention are set forth and may be selected from a comprehensive listing of such compounds, set forth later on herein in Table 1. The Table contains in excess of 1420 compounds that have been synthesized and have as a group, demonstrated activity in their capacity of modifying ion channels, in vivo, and thereby functioning in the therapeutic applications set forth herein in relation to capsaicin and the vanilloid receptor.

The compounds of the present invention are useful for the treatment of inflammatory pain and associated hyperalgesia and allodynia. They are also useful for the treatment of neuropathic pain and associated hyperalgesis and allodynia (e.g. trigeminal or herpetic neuralgia, diabetic neuropathy, causalgia, sympathetically maintained pain and deafferentation syndromes such as brachial plexus avulsion). The compounds of the present invention are also useful as anti-inflammatory agents for the treatment of arthritis, and as agents to treat Parkinson's Disease, Alzheimer's Disease, stroke, uveitis, asthma, myocardial infarction, traumatic brain injury, spinal cord injury, neurodegenerative disorders, alopecia (hair loss), inflammatory bowel disease and autoimmune disorders, renal disorders, obesity, eating disorders, cancer, schizophrenia, epilepsy, sleeping disorders, cognition, depression, anxiety, blood pressure, lipid disorders, and atherosclerosis.

In one aspect, this invention provides compounds which are capable of modifying ion channels, in vivo. Representative ion channels so modified include voltage-gated channels and ligand-gated channels, including cation channels such as vanilloid channels.

In a further aspect, the present invention provides pharmaceutical compositions comprising a compound of the invention, and a pharmaceutical carrier, excipient or diluent. In this aspect of the invention, the pharmaceutical composition can comprise one or more of the compounds described herein.

In a further aspect of the invention, a method is disclosed for treating mammals, including humans, as well as lower mammalian species, susceptible to or afflicted with a condition from among those listed herein, and particularly, such condition as may be associated with e.g. arthritis, uveitis, asthma, myocardial infarction, traumatic brain injury, acute spinal cord injury, alopecia (hair loss), inflammatory bowel disease and autoimmune disorders, which method comprises administering an effective amount of one or more of the pharmaceutical compositions just described. Correspondingly, the invention extends and includes the use of the compounds of the invention for the treatment of the mentioned maladies, as well as for the preparation of pharmaceutical compositions and like medicaments, which include among their applications and uses, the treatment of the stated maladies. Likewise the invention extends to compounds of the invention for use as pharmaceuticals and medicaments.

In yet another method of treatment aspect, this invention provides a method of treating a mammal susceptible to or afflicted with a condition that gives rise to pain responses or that relates to imbalances in the maintenance of basal activity of sensory nerves. Compounds have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with neurodegenerative diseases and disorders such as, for example Parkinson's disease, Alzheimer's disease and multiple sclerosis; diseases and disorders which are mediated by or result in neuroinflammation such as, for example traumatic brain injury, stroke, and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; alopecia (hair loss); obesity; lipid disorders; cancer; blood pressure; spinal cord injury; and renal disorders method comprises administering an effective condition-treating or condition-preventing amount of one or more of the pharmaceutical compositions just described.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description, in conjunction with the following illustrative drawings.

DETAILED DESCRIPTION OF THE INVENTION

Definitions

Figure 1:
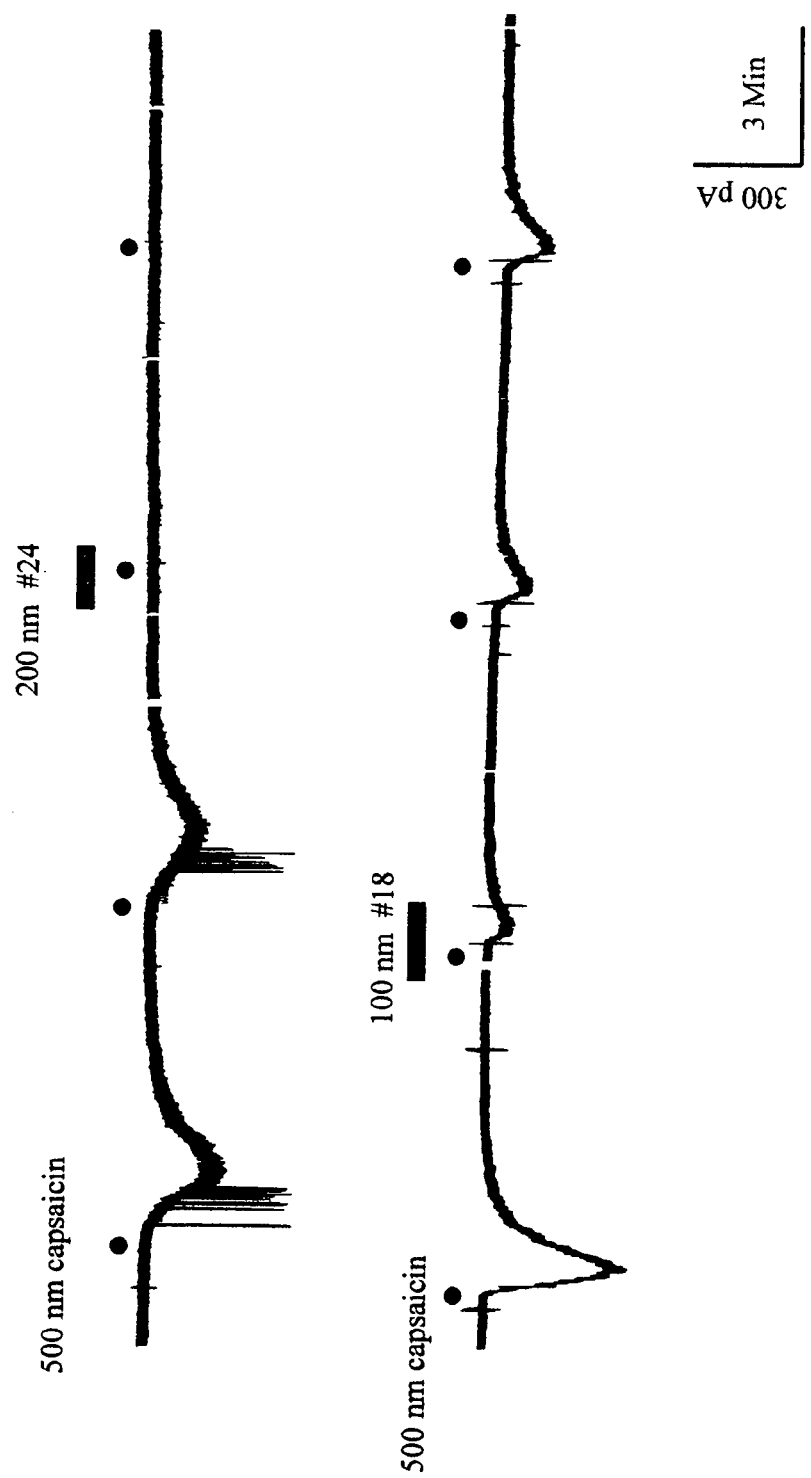
FIG. 1: A graph demonstrating the activity of Compounds 18 and 24 in inhibiting a capsaicin induced intracellular current. The functional activity of compounds at a VR1 receptor may be determined by measuring changes in intracellular calcium levels in neurons such as those in the dorsal root ganglion (DRG neurons).

When describing the compounds, pharmaceutical compositions containing such compounds and methods of using such compounds and compositions, the following terms have the following meanings unless otherwise indicated. It should also be understood that any of the moieties defined below may be substituted with a variety of substituents, and that the respective definitions are intended to include such substituted moieties within their scope. By way of non-limiting example, such substituents may include e.g. halo (such as fluoro, chloro, bromo), —CN, —CF$_3$, —OH, —OCF$_3$, C$_{2-6}$ alkenyl, C$_{3-6}$ alkynyl, C$_{1-6}$ alkoxy, aryl and di-C$_{1-6}$ alkylamino.

"Acyl" refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

"Acylamino" refers to a radical —NR'C(O)R, where R' is hydrogen, alkyl, cycloalkyl, cycloheteroalkyl, aryl, arylalkyl, heteroalkyl, heteroaryl, heteroarylalkyl and R is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)R where R is hydrogen, alkyl, aryl or cycloalkyl.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —OR where R is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —NRC(O)OR' where R is hydrogen, alkyl, aryl or cycloalkyl, and R' is alkyl or cycloalkyl.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkenylene, alkynyl and alkynylene. Aliphatic groups typically have from 1 or 2 to about 12 carbon atoms.

"Alkyl" refers to monovalent saturated aliphatic hydrocarbyl groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyls" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated aliphatic hydrocarbyl groups particularly having up to about 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having up to about 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH$_3$)═CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH═CH—), the propenylene isomers (e.g., —CH═CHCH$_2$— and —C(CH$_3$)═CH— and —CH═C (CH$_3$)—) and the like.

"Alkynyl" refers to acetylenically unsaturated hydrocarbyl groups particularly having up to about 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S (O)—, aryl-S(O)—, alkyl-S(O)$_2$— and aryl-S(O)$_2$—.

"Alkanoyl" or "acyl" as used herein refers to the group R—C(O)—, where R is hydrogen or alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-NR'R", wherein each of R' and R" are independently selected from hydrogen and alkyl.

"Arylamino" refers to the group aryl-NR'R", wherein each of R' and R" are independently selected from hydrogen, aryl and heteroaryl.

"Alkoxyamino" refers to a radical —N(H)OR where R represents an alkyl or cycloalkyl group as defined herein.

"Alkoxycarbonyl" refers to a radical —C(O)-alkoxy where alkoxy is as defined herein.

"Alkylarylamino" refers to a radical —NRR' where R represents an alkyl or cycloalkyl group and R' is an aryl as defined herein.

"Alkylsulfonyl" refers to a radical —S(O)$_2$R where R is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)R where R is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —SR where R is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Substituted amino" includes those groups recited in the definition of "substituted" herein, and particularly refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R)$_2$ is an amino group.

"Aminocarbonyl" refers to the group —C(O)NRR where each R is independently hydrogen, alkyl, aryl and cycloalkyl, or where the R groups are joined to form an alkylene group.

"Aminocarbonylamino" refers to the group —NRC(O) NRR where each R is independently hydrogen, alkyl, aryl or cycloalkyl, or where two R groups are joined to form an alkylene group.

"Aminocarbonyloxy" refers to the group —OC(O)NRR where each R is independently hydrogen, alkyl, aryl or cycloalky, or where the R groups are joined to form an alkylene group.

"Arylalkyloxy" refers to an —O-arylalkyl radical where arylalkyl is as defined herein.

"Arylamino" means a radical —NHR where R represents an aryl group as defined herein.

"Aryloxycarbonyl" refers to a radical —C(O)—O-aryl where aryl is as defined herein.

"Arylsulfonyl" refers to a radical —S(O)$_2$R where R is an aryl or heieroaryl group as defined herein.

"Azido" refers to the radical —N$_3$.

"Carbamoyl" refers to the radical —C(O)N(R)$_2$ where each R group is independently hydrogen, alkyl, cycloalkyl or aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methyl-cyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —OR where R is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C═C)—.

"Ethylene" refers to substituted or unsubstituted —(C—C)—.

"Ethynyl" refers to C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —NO$_2$.

"Substituted" refers to a group in which one or more hydrogen atoms are each independently replaced with the same or different substituent(s). Typical substituents include, but are not limited to, —X, —R$^{14}$, —O$^-$, ═O, —OR$^{14}$, —SR$^{14}$, —S, ═S, —NR$^{14}$R$^{15}$, ═NR$^{14}$, CX$_3$, —CF$_3$, —CN, —OCN, —SCN, —NO, —NO$_2$, ═N$_2$, —N$_3$, —S(O)$_2$O$^-$, —S(O)$_2$OH, —S(O)$_2$R$^{14}$, —OS(O$_2$)O$^-$, —OS(O)$_2$R$^{14}$, —P(O)(O$^-$)$_2$, —P(O)(OR$^{14}$)(O$^-$), —OP(O)(OR$^{14}$)(OR$^{15}$), —P(O)(OR$^{14}$, —C(S)R$^{14}$, —C(O)OR$^{14}$, —C(O) NR$^{14}$R$^{15}$, —C(O)O$^-$, —C(S)OR$^{14}$, —NR$^{16}$C(O)NR$^{14}$R$^{15}$, —NR$^{16}$C(S)NR$^{14}$R$^{15}$, —NR$^{17}$C(NR$^{16}$)NR$^{14}$R$^{15}$ and —C(NR$^{16}$)NR$^{14}$R$^{15}$, where each X is independently a halogen; each R$^{14}$, R$^{15}$, R$^{16}$ and R$^{17}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{18}$R$^{19}$, —C(O)R$^{18}$ or —S(O)$_2$R$^{18}$ or optionally R$^{18}$ and R$^{19}$ together with the atom to which they are both attached form a cycloheteroalkyl or substituted cycloheteroalkyl ring; and R$^{18}$ and R$^{19}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

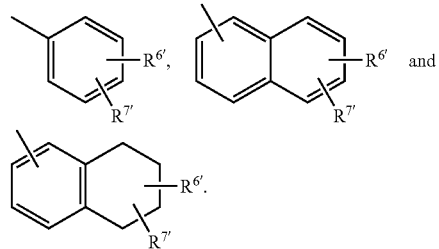

In these formulae one of R$^{6'}$ and R$^{7'}$ may be hydrogen and at least one of R$^{6'}$ and R$^{7'}$ is each independently selected from alkyl, alkenyl, alkynyl, cycloheteroalkyl, alkanoyl, alkoxy, aryloxy, heteroaryloxy, alkylamino, arylamino, heteroarylamino, NR$^{10}$COR$^{11}$, NR$^{10}$SOR$^{11}$, NR$^{10}$SO$_2$R$^{14}$, COOalkyl, COOaryl, CONR$^{10}$R$^{11}$, CONR$^{10}$OR$^{11}$, NR$^{10}$R$^{11}$, SO$_2$NR$^{10}$R$^{11}$, S-alkyl, S-alkyl, SOalkyl, SO$_2$alkyl, Saryl, SOaryl, SO2aryl; or R$^{6'}$ and R$^{7'}$ may be joined to form a cyclic ring (saturated or unsaturated) from 5 to 8 atoms, optionally containing one or more heteroatoms selected from the group N, O or S. R$^{10}$, R$^{11}$, and R$^{12}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-20 membered heteroaryl, with 5-10 membered heteroaryl being particularly preferred. Particlar heteroaryl groups are those derived from thiophene, pyrrole, benzothiophene, benzofuran, indole, pyridine, quinoline, imidazole, oxazole and pyrazine.

Examples of representative heteroaryls include the following:

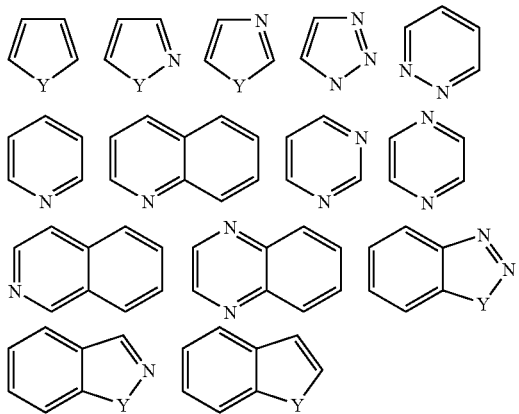

wherein each Y is selected from carbonyl, N, $NR^4$, O, and S.

Examples of representative cycloheteroalkyls include the following

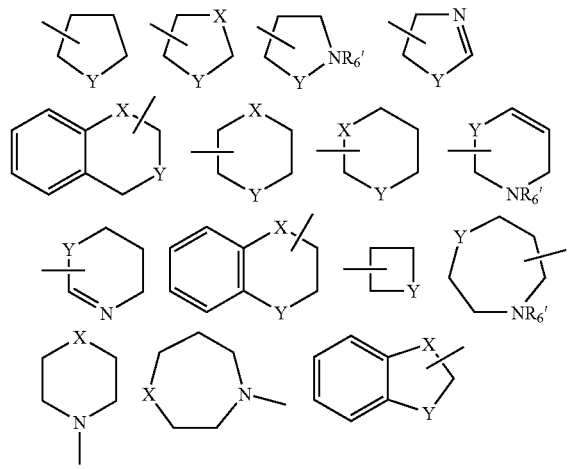

wherein each X is selected from $CR^4$, $NR^4$, O and S; and each Y is selected from N. $NR^4$, O and S, and where $R^{6'}$ is $R^2$.

Examples of representative cycloheteroalkenyls include the following:

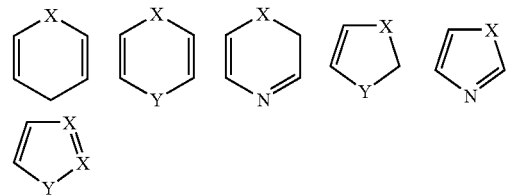

wherein each X is selected from $CR^4$, $NR^4$, O and S; and each Y is selected from carbonyl, NH, $NR^4$, O and S.

Examples of representative aryl having hetero atoms containing substitution include the following:

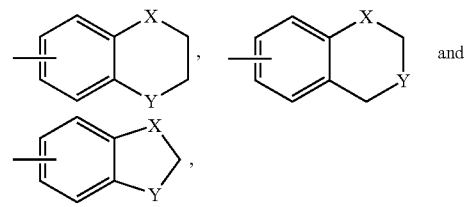

wherein each X is selected from $C(R^4)_2$, $NR^4$, O and S; and each Y is selected from carbonyl, $NR^4$, O and S.

"Hetero substituent" refers to a halo, O, S or N atom-containing functionality that may be present as an $R^4$ in a $R^4$ C group present as substituents directly on A, B, W, X, Y or Z of the compounds of this invention or may be present as a substituent in the "substituted" aryl and aliphatic groups present in the compounds.

Examples of hetero substituents include:
-halo,
—$NO_2$, —$NH_2$, —NHR, —$N(R)_2$,
—NRCOR, —NRSOR, —$NRSO_2R$, OH, CN, $CO_2R$,
—$CO_2H$,
—R—OH, —O—R, —COOR,
—$CON(R)_2$, —CONROR,
—$SO_2H$, —R—S, —$SO_2N(R)_2$,
—S(O)R, —$S(O)_2R$, wherein each R is independently an aryl or aliphatic, optionally with substitution. Among hetero substituents containing R groups, preference is given to those materials having aryl and alkyl R groups as defined herein. Preferred hetero substituents are those listed above.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

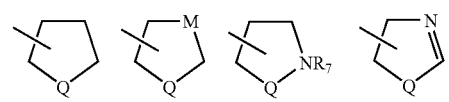

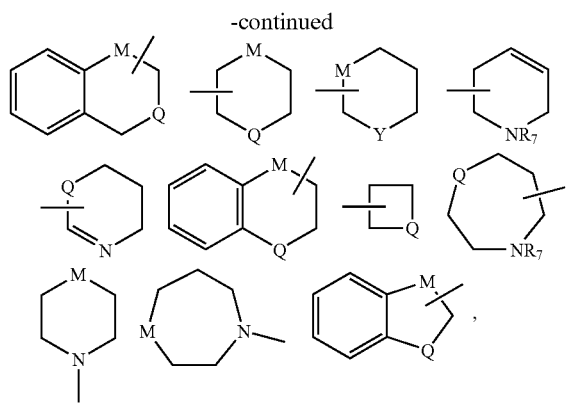

optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives. In the examples, M is $CR^7$, $NR_2$, O, or S; Q is O, $NR_2$ or S. $R^7$ and $R^8$ are independently selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Dihydroxyphosphoryl" refers to the radical —PO(OH)$_2$.

"Substituted dihydroxyphosphoryl" includes those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —PO(OH)NH$_2$.

"Substituted aminohydroxyphosphoryl" includes those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the group —SR where R is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Sulfanyl" refers to the radical HS—. "Substituted sulfanyl" refers to a radical such as RS— wherein R is any substituent described herein.

"Sulfonyl" refers to the divalent radical —S(O$_2$)—. "Substituted sulfonyl" refers to a radical such as R—(O$_2$)S— wherein R is any substituent described herein. "Aminosulfonyl" or "Sulfonamide" refers to the radical H$_2$N(O$_2$)S—, and "substituted aminosulfonyl" "substituted sulfonamide" refers to a radical such as R$_2$N(O$_2$)S— wherein each R is independently any substituent described herein.

"Sulfone" refers to the group —SO$_2$R. In particular embodiments, R is selected from H, lower alkyl, alkyl, aryl and heteroaryl.

"Thioaryloxy" refers to the group —SR where R is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

The term "solvate" refers to forms of the compound that are associated with a solvent, usually by a solvolysis reaction. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Compounds

As set forth earlier herein, the compounds of the present invention are useful for preventing and/or treating a broad range of conditions, among them, arthritis, Parkinson's disease, Alzheimer's disease, stroke, uveitis, asthma, myocardial infarction, the treatment and prophylaxis of pain syndromes (acute and chronic or neuropathic), traumatic brain injury, acute spinal cord injury, neurodegenerative disorders, alopecia (hair loss), inflammatory bowel disease and autoimmune disorders or conditions in mammals.

In order that the invention described herein may be more fully understood, the following structures representing compounds typical of the invention are set forth. It should be understood that these examples are for illustrative purposes only and are not to be construed as limiting this invention in any manner.

Accordingly, additional groups of particular compounds are provided. Thus, and as discussed earlier herein, suitable compounds capable of modifying ion channels in vivo, may be selected from those listed in Table 1, below, and may be prepared either as shown or in the form of a pharmaceutically acceptable salt, solvate or prodrug thereof; and isomers and stereoisomers thereof. All such variants are contemplated herein and are within the scope of the present invention.

In certain aspects, the present invention provides prodrugs and derivatives of the compounds according to the formulae above. Prodrugs are derivatives of the compounds of the invention, which have cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Pharmaceutical Compositions

When employed as pharmaceuticals, the amide compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including by way of non limiting example, oral, rectal, transdermal, subcutaneous, intravenous, intramuscular and intranasal. Depending upon the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences*, 17th edition, 1985, Mack Publishing Company, Easton, Pennsylvania, which is incorporated herein by reference.

The compounds of this invention can also be administered in sustained release forms or from sustained release drug delivery systems. A description of representative sustained release materials can be found in *Remington's Pharmaceutical Sciences*.

The following formulation examples illustrate representative pharmaceutical compositions of this invention. The present invention, however, is not limited to the following pharmaceutical compositions.

Formulation 1—Tablets

A compound of formula I is admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2—Capsules

A compound of formula I is admixed as a dry powder with a starch diluent in an approximate 1:1 weight ratio. The mixture is filled into 250 mg capsules (125 mg of active compound per capsule).

Formulation 3—Liquid

A compound of formula I (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

The compound of formula I is admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5—Injection

The compound of formula I is dissolved or suspended in a buffered sterile saline injectable aqueous medium to a concentration of approximately 5 mg/ml.

Formulation 6—Topical

Stearyl alcohol (250 g) and a white petrolatum (250 g) are melted at about 75° C. and then a mixture of a compound of formula I (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds are used as therapeutic agents for the treatment of conditions in mammals. Accordingly, the compounds and pharmaceutical compositions of this invention find use as therapeutics for preventing and/or treating neurodegenerative, autoimmune and inflammatory conditions in mammals including humans.

In a method of treatment aspect, this invention provides a method of treating a mammal susceptible to or afflicted with a condition associated with arthritis, uveitis, asthma, myocardial infarction, traumatic brain injury, acute spinal cord injury, alopecia (hair loss), inflammatory bowel disease and autoimmune disorders, which method comprises administering an effective amount of one or more of the pharmaceutical compositions just described.

In yet another method of treatment aspect, this invention provides a method of treating a mammal susceptible to or afflicted with a condition that gives rise to pain responses or that relates to imbalances in the maintenance of basal activity of sensory nerves. Compounds have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with neurodegenerative diseases and disorders such as, for example Parkinson's disease, Alzheimer's disease and multiple sclerosis; diseases and disorders which are mediated by or result in neuroinflammation such as, for example traumatic brain injury, stroke, and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; alopecia (hair loss); obesity; lipid disorders; cancer; blood pressure; spinal cord injury; and renal disorders method comprises administering an effective condition-treating or condition-preventing amount of one or more of the pharmaceutical compositions just described.

In further aspect of the invention there is provided the present compounds for use in the treatment of the above mentioned conditions; there is also provided use of the present compounds in the treatment of the above mentioned conditions; there is also provided use of the present compounds in the manufacure of a medicament for the treatment of the above mentioned conditions.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound or its derivative, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of a neurodegenerative, autoimmune or inflammatory condition, the compounds or their derivatives of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other active derivatives.

General Synthetic Procedures

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The target compounds are synthesized by known reactions outlined in the following schemes. The products are isolated and purified by known standard procedures. Such procedures include (but are not limited to) recrystallization, column chromatography or HPLC. The target compounds, for example, may be prepared by the reaction of an appropriately substituted halopyridine with an appropriately functionalized carboxy boronic acid to obtain the desired biaryl carboxylic acid. The carboxylic acid intermediate thus obtained can be conveniently converted to its corresponding amide by activation followed by reacting with an appropriately substituted amine. The products are isolated and purified by known standard procedures. Such procedures include (but are not limited to) recrystallization, column chromatography or HPLC.

Synthesis of intermediate pyridin-2-yl-benzoic acids

Intermediate 1

Synthesis of 3-chloro-12,3'bipyridinyl-6'-carboxylic acid

1a) Synthesis of 5-bis(hydroxyl)boron-2-methylpicoline:

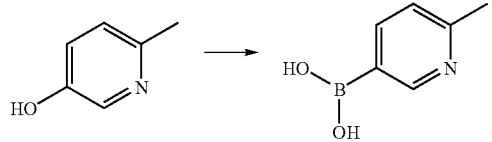

5-Hydroxy-2-methylpyridine (1.0 g, 9.2 mmol) was dissolved in 20 ml of dichloromethane and stirred at 0° C. To the reaction mixture was added 1.10 ml of anhydrous pyridine (13.8 mmol), followed by 2.32 ml of triflic anhydride (13.8 mmol). The reaction mixture was warmed to room temperature and allowed to stir until completion (monitored by LC-MS/TLC). The mixture was poured into a separatory funnel and washed with water three times. The organic layer was washed with brine, dried over $MgSO_4$, filtered and evaporated under vacuum. The material was used as crude material for the next step.

The triflate (4.6 mmol) was dissolved in acetonitrile (30 ml) and placed into a 5 ml microwave vessel. To the solution was added 1.5 eq of bis(pinacolato)diboron (6.9 mmol; 1.71 g). The mixture was stirred on a magnetic stir plate until dissolution. To the mixture was added KOAc (13.8 mmol; 1.35 g) and 98 mg of [1,1'-bis(diphenylphosphino)-ferrocene] dichloropalladium(II) (0.03 mol %). The reaction mixture was heated at 160° C. for 2×600s. After completion (monitored by LC-MS), the acetonitrile was evaporated to give a black solid. The solid was dissolved in DMSO, ms and purified by HPLC to give the boronic acid (580 mg, 92%; 4.2 mmol).

MS: MH+=138

1b) Synthesis of 3-chloro-6'-methyl-[2,3']bipyridinyl:

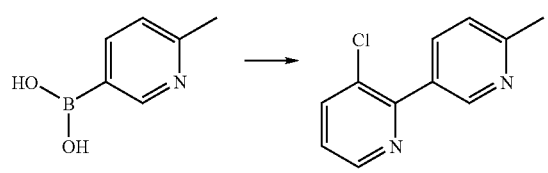

The above boronic acid (4.2 mmol) was dissolved in acetonitrile (2 ml) and added to a 5 ml microwave vessel. To the solution was 6.9 mmol of 2,3-dichloropyridine (1.01 g), 53 mg of tetrakis(triphenylphosphine)palladium(0). After stirring until dissolution, 13.8 mmol of potassium carbonate (1.90 g) was added, followed by 1 ml of water. The mixture was then heated at 160° C. for 300 seconds. After reaction completion, the solvents were evaporated under vacuum. The target compound was purified by HPLC to give a yellow solid (800 mg; 85%).

MS: MH+=205

1c) Synthesis of 3-chloro-[2,3']bipyridinyl-6'-carboxylic acid:

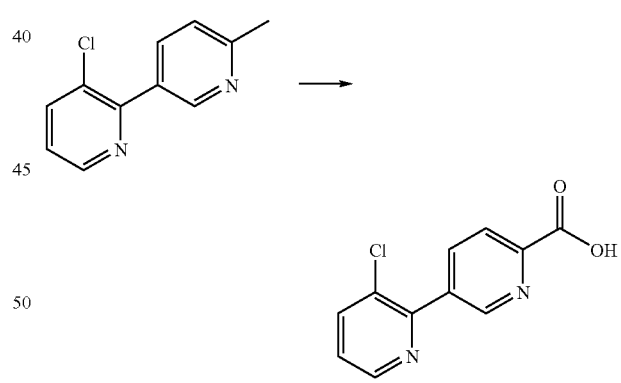

The above 3-chloro-6'-methyl-[2,3']bipyridinyl (2.5 mmol) was added to a 5 ml microwave vessel, followed by 3 ml of water. 3.75 mmol of potassium permanganate was added and the mixture was heated at 120° C. for 600 seconds. An additional 3.75 mmol of potassium permanganate was added and the mixture was resubmitted to microwave heating (same temperature) for 600s. After completion (monitored by LC-MS), the mixture was filtered through celite and the manganese salts were washed with water. The water was evaporated to ~10 ml and the product was purified by HPLC to give 293 mg as a white solid (51%).

MS: MH+=235

Intermediate 2

Synthesis of 4-(3-chloro-pyridin-2-yl)-3-methoxybenzoic acid

2a) Synthesis of 3-methoxy-4-boronicacid-benzoic acid methyl ester:

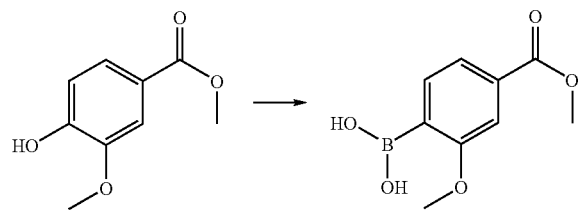

1.0 g of 4-hydroxy-3-methoxybenzoic acid methyl ester (5.5 mmol) was dissolved in 20 ml of dichloromethane and stirred at 0° C. To the reaction mixture was added 0.66 ml of anhydrous pyridine (8.25 mmol), followed by 1.39 ml of triflic anhydride (8.25 mmol). The reaction mixture was warmed to room temperature and allowed to stir until completion (monitored by LC-MS/TLC). The mixture was poured into a separatory funnel and washed with water three times. The organic layer was washed with brine, dried over MgSO$_4$, filtered and evaporated under vacuum to give the triflate (used as crude for boronoic acid formation).

The triflate (5.5 mmol) was dissolved in acetonitrile (30 ml) and placed into an 80 ml microwave vessel. To the solution was added 1.5 eq of Bis(pinacolato)diboron (8.25 mmol; 2.08 g). The mixture was stirred on a magnetic stir plate until dissolution. To the mixture was added KOAc (16.5 mmol; 1.62 g) and 134 mg of [1,1'-Bis(diphenylphosphino)ferrocene] dichloropalladium(II) (0.03mol%). The reaction mixture was heated at 160° C. for 2×600s. After completion (monitored by LC-MS), the acetonitrile was evaporated to give a black solid. The solid was dissolved in EtOAc and washed with water, brine and dried over MgSO$_4$. After filtration, the solvent was evaporated under vacuum. The solid material was then dissolved in chloroform and filtered through silica. The chloroform was evaporated to give a dark green solid (used as crude for the next reaction).

2b) Synthesis of 4-(3-chloro-pyridin-2-yl)-3-methoxybenzoic acid:

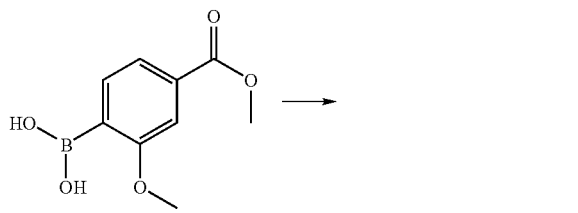

Boronic acid 3 (5.5 mmol) was dissolved in acetonitrile (10 ml) and added to an 80 ml microwave vessel. To the solution was 8.25 mmol of 2,3-dichloropyridine (1.2 g), 63 mg of tetrakis(triphenylphosphine)palladium(0). After stirring until dissolution, 5 ml of a 1 M potassium carbonate solution (aqueous) was added and the mixture was heated at 160° C. for 300s. After reaction compleation, the acetonitrile was evaporated under vacuum and 2 N KOH was added (20 ml), followed by 10 ml of THF. The reaction was heated until hydrolysis was complete (15 minutes). The solution was acidified (cHCl) and extracted 3× with EtOAc. After drying over MgSO$_4$, the organic layer was filtered and evaporated under vacuum. The compound was purified by HPLC to give a yellow solid (263 mg, 18%).

MS: MH+=264

Intermediate 3

Synthesis of 4-(3-Trifluoromethylpyridin-2-yl)benzoic acid:

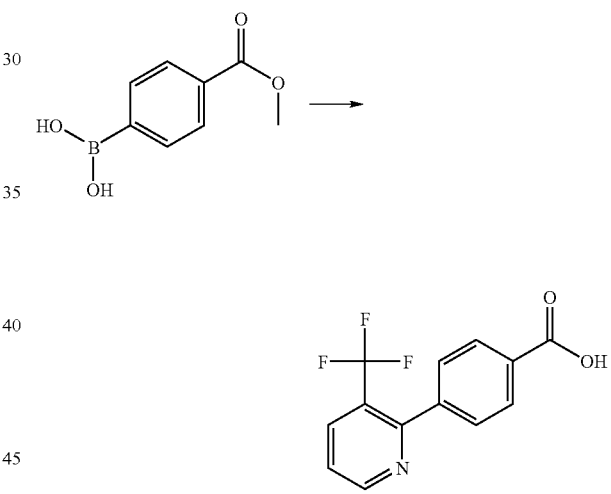

4-Bis(hydroxyl)boron-1-methylbenzoate (2.8 mmol) was dissolved in acetonitrile (2 ml) and added to a 5 ml microwave vessel. To the solution was 3.5 mmol of 2-chloro-3-trifluoromethylpyridine (633 mg), 34 mg of tetrakis(triphenylphosphine)-palladium(0). After stirring until dissolution, 8.4 mmol of potassium carbonate (1.16 g) was added, followed by 1 ml of water. The mixture was then heated at 160° C. for 300 seconds. After reaction completion, the solvents were evaporated under vacuum. The residue was dissolved in 2N KOH and THF and heated for 10 min. After hydrolysis, the THF was evaporated and the basic layer was washed with EtOAC. The aqueous layer was then acidified and extracted 3 times with EtOAc. The organic layers were combined and washed with water and brine. After drying, filtration and evaporation, the residue was prufied by HPLC to give of the target compound as a white solid (602 mg; 81%).

MS: MH+=268

Intermediate 4

3-Fluoro-4-(3-trifluoromethylpyridin-2-yl)benzoic acid:

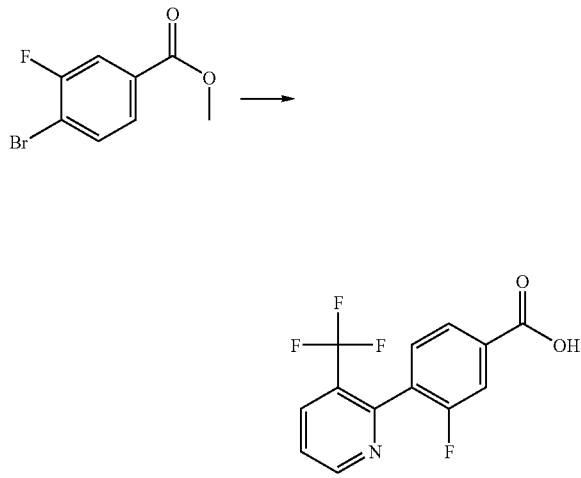

The 4-Bromo-3-fluorobenzoic acid methyl ester (700 mg; 2.45 mmol) was dissolved in acetonitrile (3.0 ml) and placed into a 2 ml microwave vessel. To the solution was added 1.5 eq of Bis(pinacolato)diboron (3.67 mmol; 1.08 g). The mixture was stirred on a magnetic stir plate until dissolution. To the mixture was added KOAc (7.33 mmol; 7.16 mg) and 60 mg of [1,1'-Bis(diphenylphosphino)ferrocene] dichloropalladium(II) (0.03 mol %). The reaction mixture was heated at 160° C. for 2×600s. After completion (monitored by LC-MS), the acetonitrile was evaporated to give a black solid. The solid was dissolved in EtOAc and washed with water, brine and dried over MgSO₄. After filtration, the solvent was evaporated under vacuum. The solid material was then dissolved in chloroform and filtered through silica. The chloroform was evaporated to give a dark green solid (used as crude for the next reaction).

The boronic acid (2.45 mmol) was dissolved in acetonitrile (2.4 ml) and 3-(trifluoromethyl)-2-chloropyridine was added. After mixing, tetrakis palladium was added (25 mg; 0.01 mol %), follwed by 0.8 ml of water and K₂CO₃ (912 mg; 3.0 mmol). The reaction mixture was heated at 160° C. in a Personal Chemistry Emrys Microwave for 300s. After reaction completion, the solvents were evaporated and the residue was dissolved in EtOAc and washed with water and brine. The organic layer was dried over MgSO₄, filtered and evaporated. The residue was then dissolved in a 1:1 mixture of THF/2NKOH and heated until saponification was complete. The basic layer was then extracted with EtOAc and acidified with conc.HCl. The aqueos layer was then extracted three times with EtOAc. The combined organic layers were dried over MgSO₄, filtered and evaporated to give the desired material as a white solid (530 mg; 76%).

MS: MH+=286

Intermediate 5

4-(3-Trifluoromethylpyridin-2-yl)-3-methoxybenzoic acid

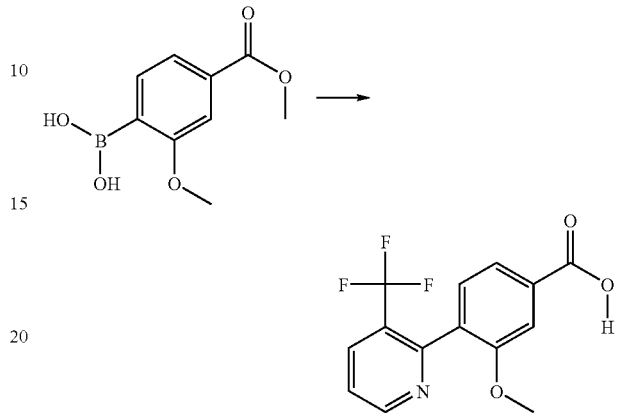

The boronic acid was prepared as described in Intermediate 2 to give 410 mg (78%). The boronic acid (2.55 mmol) was dissolved in acetonitrile (2.4 ml) and 3-(trifluoromethyl)-2-chloropyridine was added. After mixing, tetrakis palladium was added (29 mg; 0.01 mol %), followed by 0.8 ml of water and K₂CO₃ (912 mg; 6.6 mmol). The reaction mixture was heated at 160° C. in a Personal Chemistry Emrys Microwave for 300s. After reaction completion, the solvents were evaporated and the residue was dissolved in EtOAc and washed with water and brine. The organic layer was dried over MgSO₄, filtered and evaporated. The residue was then dissolved in a 1:1 mixture of THF/2NKOH and heated until saponification was complete. The basic layer was then extracted with EtOAc and acidified with conc.HCl. The aqueos layer was then extracted three times with EtOAc. The combined organic layers were dried over MgSO₄, filtered and evaporated to give the desired material as a white solid (495 mg; 68%).

MS: MH+=298

Intermediate 6

4-(3-Methoxypyridin-2-yl)-3-fluorobenzoic acid:

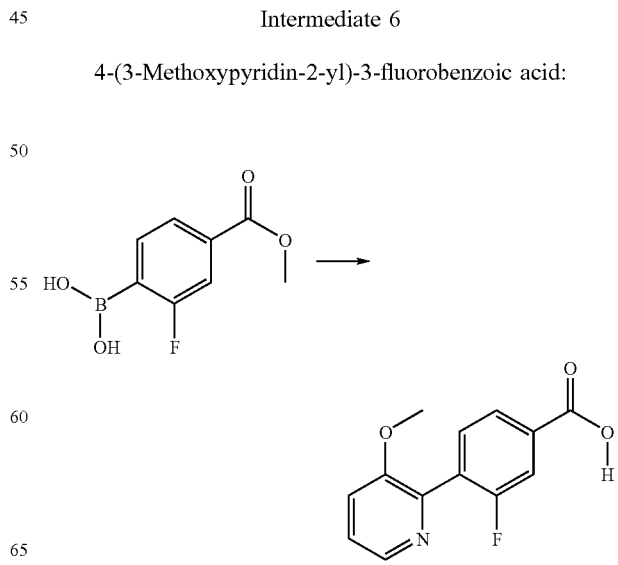

The boronic acid was prepared as described in Intermediate 4 to give 2.2 mmole. (quant.crude). The boronic acid (2.2 mmol) was dissolved in acetonitrile (2.4 ml) and 3-methoxy-2-chloropyridine (380 mg; 2.88 mmol) was added. After mixing, tetrakis palladium was added (25 mg; 0.01 mol %), follwed by 0.8 ml of water and $K_2CO_3$ (912 mg; 6.6 mmol). The reaction mixture was heated at 160° C. in a Personal Chemistry Emrys Microwave for 300s. After reaction completion, the solvents were evaporated and the residue was dissolved in EtOAc and washed with water and brine. The organic layer was dried over $MgSO_4$, filtered and evaporated. The residue was then dissolved in a 1:1 mixture of THF/2NKOH and heated until saponification was complete. The basic layer was then extracted with EtOAc and acidified with conc.HCl. The aqueos layer was then extracted three times with EtOAc. The combined organic layers were dried over $MgSO_4$, filtered and evaporated to give the desired material as a beige solid (312 mg; 57%).

MS: MH+=248

Intermediate 7

4-(3-Methoxypyridin-2-yl)benzoic acid

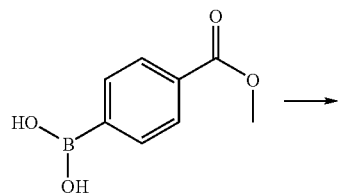

4-bis(hydroxyl)boron-1-methylbenzoate (2.8 mmol; 582 mg) was dissolved in acetonitrile (2 ml) and added to a 5 ml microwave vessel. To the solution was 3.5 mmol of 2-chloro-3-methoxypyridine (482 mg), 34 mg of tetrakis (triphenylphosphine)palladium(0). After stirring until dissolution, 8.4 mmol of potassium carbonate (1.16 g) was added, followed by 1 ml of water. The mixture was then heated at 160° C. for 300 seconds. After reaction completion, the solvents were evaporated under vacuum. The residue was dissolved in 2N KOH and THF and heated for 10 min. After hydrolysis, the THF was evaporated and the basic layer was washed with EtOAC. The aqueous layer was then acidified and extracted 3 times with EtOAc. The organic layers were combined and washed with water and brine. After drying, filtration and evaporation, the residue was triterated with ether to give the desired product as a yellow solid (423 mg; 77%).

MS: MH+=230

Intermediate 8

4-(3-Trifluoromethylpyridin-2-yl)-3-chlorobenzoic acid 8a) 4-bromo-3-chloromethylbenzoate:

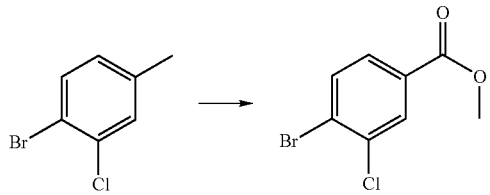

The 4-bromo-3chlorotoluene (4.0 g; 19.5 mmol) was added to a 250 ml round bottom flask, followed by 50 ml of water. To the mixture was added 3.22 g of potassium permanganate (23.4 mmol) and the reaction was refluxed until completion. After cooling, the mixture was filtered through celite. The aqueous layer was acidified and extracted three times with ethylacetate. The organic layers were washed with brine, dried over $MgSO_4$. After filtration and evaporation, the resulting white solid was dissolved in 1.0 M HCl in ether and stirred overnight. The methanol was removed under vacuum and the residue was dissolved in ethylacetate and washed with saturated sodium bicarbonate. The organic layer was dried over $MgSO_4$, filtered and evaporated to give the desired material as a clear oil (713 mg; 15%).

8b) 4-(3-Trifluoromethylpyridin-2-yl)-3-chlorobenzoic acid:

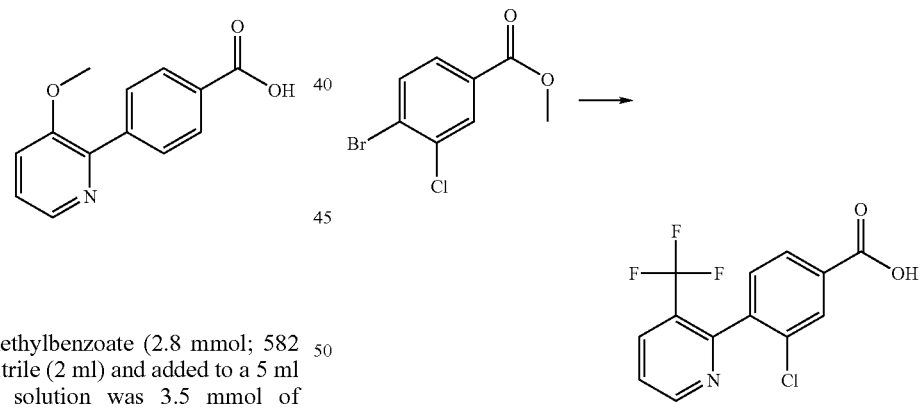

The boronic acid was prepared as described in Intermediate 4 to give 2.8 mmole. (quant.crude). The boronic acid (2.8 mmol) was dissolved in acetonitrile (2.4 ml) and 2-chloro 3-trifluoromethylpyridine (620 mg; 3.3 mmol) was added. After mixing, tetrakis palladium was added (33 mg; 0.01 mol %), follwed by 0.8 ml of water and $K_2CO_3$ (1182 mg; 6.6 mmol). The reaction mixture was heated at 160° C. in a Personal Chemistry Emrys Microwave for 300s. After reaction completion, the solvents were evaporated and the residue was dissolved in EtOAc and washed with water and brine. The organic layer was dried over $MgSO_4$, filtered and evaporated. The residue was then dissolved in a 1:1 mixture of THF/2NKOH and heated until saponification was complete. The basic layer was then extracted with EtOAc and acidified with conc. HCl. The aqueos layer was then extracted three times with EtOAc. The combined organic layers were dried over MgSO$_4$, filtered and evaporated to give the desired material as a white solid (460 mg; 55%).

MS: MH+=303

Intermediate 9

4-(3-methoxypyridin-2-yl)-3-methoxybenzoic acid

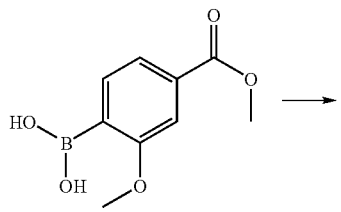

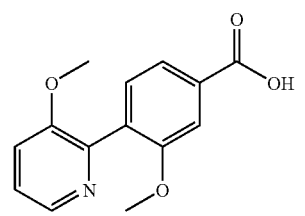

The boronic acid was prepared as described in Intermediate 5 (2.5 mmol; crude) and was dissolved in acetonitrile (2 ml) and added to a 5 ml microwave vessel. To the solution was 3.0 mmol of 2-chloro-3-methoxypyridine (432 mg), 29 mg of tetrakis(triphenylphosphine)palladium(0). After stirring until dissolution, 7.5 mmol of potassium carbonate (1.06 g) was added, followed by 1 ml of water. The mixture was then heated at 160° C. for 300 seconds. After reaction completion, the solvents were evaporated under vacuum. The residue was dissolved in 2N KOH and THF and heated for 10 min. After hydrolysis, the THF was evaporated and the basic layer was washed with EtOAC. The aqueous layer was then acidified and extracted 3 times with EtOAc. The organic layers were combined and washed with water and brine. After drying, filtration and evaporation, the residue was triterated with ether to give the desired product as a yellow solid (310 mg; 47%).

MS: MH+=260

Intermediate 10

4-(3-Methoxypyridin-2-yl)-3-chlorobenzoic acid:

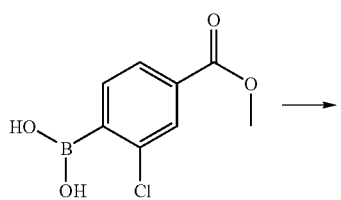

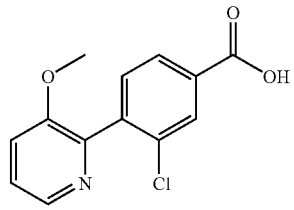

The boronic acid was prepared as described in Intermediate 4 to give 2.8 mmole. (quant.crude). The boronic acid (2.14 mmol) was dissolved in acetonitrile (2.4 ml) and 3-methoxy-2-chloropyridine (368 mg; 2.6 mmol) was added. After mixing, tetrakis palladium was added (25 mg; 0.01 mol %), follwed by 0.8 ml of water and K$_2$CO$_3$ (887 mg; 6.5 mmol). The reaction mixture was heated at 160° C. in a Personal Chemistry Emrys Microwave for 300s. After reaction completion, the solvents were evaporated and the residue was dissolved in EtOAc and washed with water and brine. The organic layer was dried over MgSO$_4$, filtered and evaporated. The residue was then dissolved in a 1:1 mixture of THF/2NKOH and heated until saponification was complete. The basic layer was then extracted with EtOAc and acidified with conc. HCl. The aqueous layer was then extracted three times with EtOAc. The combined organic layers were dried over MgSO$_4$, filtered and evaporated to give the desired material as a yellow solid (425 mg; 76%).

MS: MH+=264

Intermediate 11

4-(3-Chloropyridin-2-yl)-3-fluorobenzoic acid:

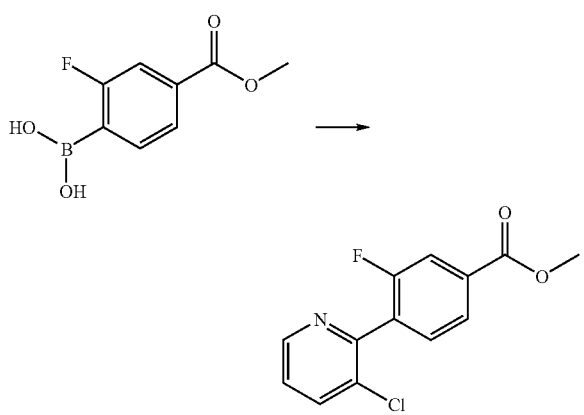

The boronic acid was prepared as described in Intermediate 4 (2.45 mmol) was dissolved in acetonitrile (2.4 m) and 2,3-dichloropyridine was added. After mixing, tetrakis palladium was added (25 mg; 0.01 mol %), follwed by 0.8 ml of water and K$_2$CO$_3$ (912 mg; 3.0 mmol). The reaction mixture was heated at 160° C. in a Personal Chemistry Emrys Microwave for 300s. After reaction completion, the solvents were evaporated and the residue was dissolved in EtOAc and washed with water and brine. The organic layer was dried over MgSO$_4$, filtered and evaporated. The residue was then dissolved in a 1:1 mixture of THF/2NKOH and heated until saponification was complete. The basic layer was then extracted with EtOAc and acidified with conc.

HCl. The aqueos layer was then extracted three times with EtOAc. The combined organic layers were dried over MgSO$_4$, filtered and evaporated to give the desired material as a white solid (403 mg; 56%).

MS: MH+=252

Intermediate 12

4-(3-Chloropyridin-2-yl)-2-aminobenzoic acid 12a) 4-Bromo-2-aminomethylbenzoate:

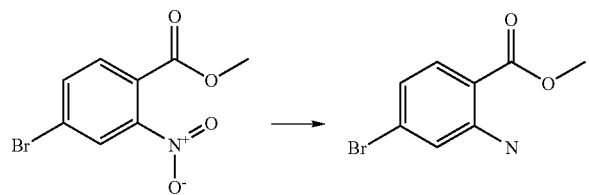

4-Bromo-2-nitromethylbenzoate (300 mg; 1.15 mmol) was dissolved in 25 ml of methanol and shaken with 5% Pd(c) under hydrogen atmosphere (50 PSI) for 1 hour. The reaction was filtered through celite and evaporated to give the product as a white solid (255 mg; 96%).

MS: MH+=230

12b) 4-(3-Chloropyridin-2-yl)-2-aminobenzoic acid:

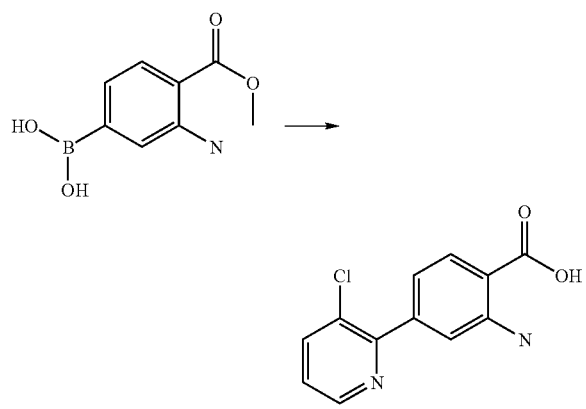

The boronic acid was prepared as described in Intermediate 4 to give 3.4 mmole. (quant.crude). The boronic acid 656 mg (3.4 mmol) was dissolved in acetonitrile (2.4 ml) and 2,3-dichloropyridine (600 mg; 4.08 mmol) was added. After mixing, tetrakis palladium was added (40 mg; 0.01 mol %), follwed by 0.8 ml of water and K$_2$CO$_3$ (1.40 g; 10.8 mmol). The reaction mixture was heated at 160° C. in a Personal Chemistry Emrys Microwave for 300s. After reaction completion, the solvents were evaporated and the residue was dissolved in EtOAc and washed with water and brine. The organic layer was dried over MgSO$_4$, filtered and evaporated. The residue was then dissolved in a 1:1 mixture of THF/2NKOH and heated until saponification was complete. The basic layer was then extracted with EtOAc and acidified with conc.HCl. The aqueos layer was then extracted three times with EtOAc. The combined organic layers were dried over MgSO$_4$, filtered and evaporated to give the desired material as a yellow solid (466 mg; 55%).

MS: MH+=249

Intermediate 13

4-(3-Chloropyridin-2-yl)-2-N-methylaminobenzoic acid 13a) 4-(3-Chloropyridin-2-yl)-2-(trifluoromethylacetamide) methylbenzoate:

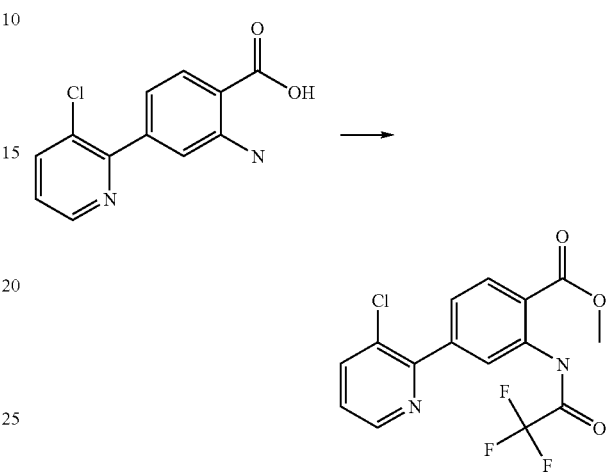

The 4-(3-Chloropyridin-2-yl)-2aminomethylbenzoate (1.43 mg; 0.55 mmol) was dissolved in 1,2-dichloroethane (5 ml). To the mixture was added trifluoroacetic anhydride (7.2 mmol; 1.0 ml) and pyridine (7.7 mmol; 0.63 ml) and the reaction was stirred for 2 hrs. The solution was diluted with dichloromethane and washed with water. The organic layer was dried over MgSO$_4$, filtered and evaporated to give the desired product as a white solid (1.5 g; 79%).

MS: MH+=359

13b) 4-(3-Chloropyridin-2-yl)-2-N-methylaminobenzoic acid:

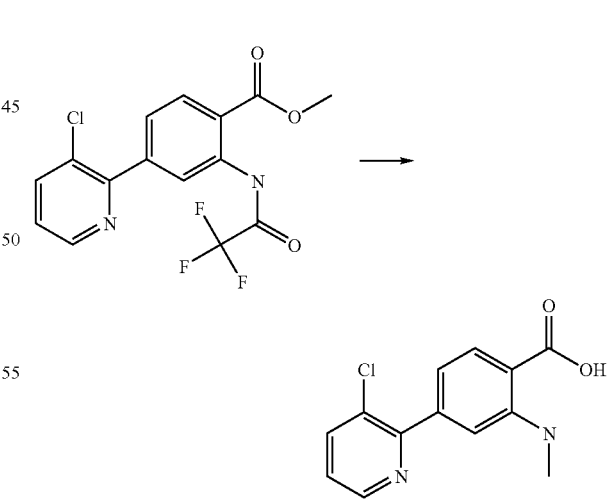

4-(3-Chloropyridin-2-yl)-2-(trifluoromethylacetamide) methylbenzoate (540 mg; 1.5 mmol) was dissolved in dry tetrahydrofuran. Triphenylphosphine (446 mg; 1.7 mmol) and DIAD (0.36 ml; 1.7 mmol), followed by anhydrous methanol (0.07 ml; 1.7 mmol). The THF was evaporated and the residue was dissolved in EtOAc. The organic layer was washed with water, brine, dried over MgSO₄, filtered and dried. The crude material was purified by flash chromatography using 2:1 hexanes:ethylacetate to give 465 mg of the desired product (83%).

The methylated product (464 mg; 1.24 mmol) was dissolved in methanol (8 ml) and 4 ml of aqueous lithium hydroxide (4 ml; 10%). The methanol was evaporated snd the mixture was acidified and extracted with EtOAc. The organic layer was washed with water, dried over MgSO₄, filtered and evaporated to give the desired product as a yellow solid (338 mg; 91%).

MS: MH+=263

Intermediate 14

4-(3-Chloropyridin-2-yl)-2-N-methoxyethylaminobenzoic acid:

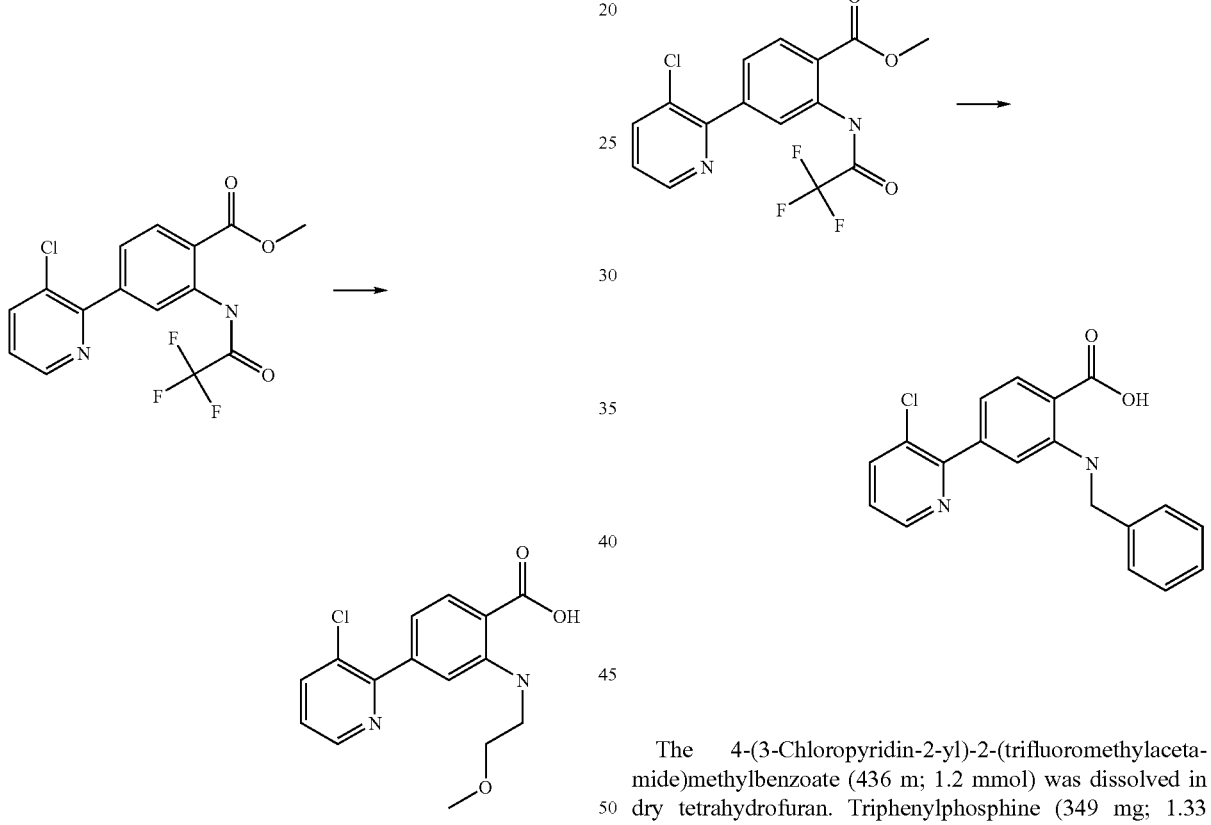

The 4-(3-Chloropyridin-2-yl)-2-(trifluoromethylacetamide)methylbenzoate (1.2 g; 3.3 mmol) was dissolved in dry tetrahydrofuran. Triphenylphosphine (2.2 g; 8.3 mmol) and DIAD (1.7 ml; 8.3 mmol), followed by anhydrous methoxyethanol (0.66 ml; 8.3 mmol). The THF was evaporated and the residue was dissolved in EtOAc. The organic layer was washed with water, brine, dried over MgSO₄, filtered and dried. The crude material was purified by flash chromatography using 2:1 hexanes:ethylacetate to give 676 mg of the desired product (66%).

The alkylated product (525 mg; 1.24 mmol) was dissolved in methanol (8 ml) and 4 ml of aqueous lithium hydroxide (4 ml; 10%). The methanol was evaporated snd the mixture was acidified and extracted with EtOAc. The organic layer was washed with water, dried over MgSO₄, filtered and evaporated to give the desired product as a yellow solid (260 mg; 66%).

MS: M+=307

Intermediate 15

4-(3-Chloropyridin-2-yl)-2-N-benzylaminobenzoic acid:

The 4-(3-Chloropyridin-2-yl)-2-(trifluoromethylacetamide)methylbenzoate (436 m; 1.2 mmol) was dissolved in dry tetrahydrofuran. Triphenylphosphine (349 mg; 1.33 mmol) and DIAD (0.28 ml; 1.33 mmol), followed by anhydrous benzylalcohol (0.14 ml; 1.33 mmol). The THF was evaporated and the residue was dissolved in EtOAc. The organic layer was washed with water, brine, dried over MgSO₄, filtered and dried. The crude material was purified by flash chromatography using 2:1 hexanes:ethylacetate to give 435 mg of the desired product (80%).

The alkylated product (68 mg; 0.1 5 mmol) was dissolved in methanol (6 ml) and 4 ml of aqueous lithium hydroxide (2 ml; 10%). The methanol was evaporated snd the mixture was acidified and extracted with EtOAc. The organic layer was washed with water, dried over MgSO₄, filtered and evaporated to give the desired product as a yellow solid (51 mg; 75%).

MS: M+=339

Intermediate 16

4-(3-Chloropyridin-2-yl)benzoic acid

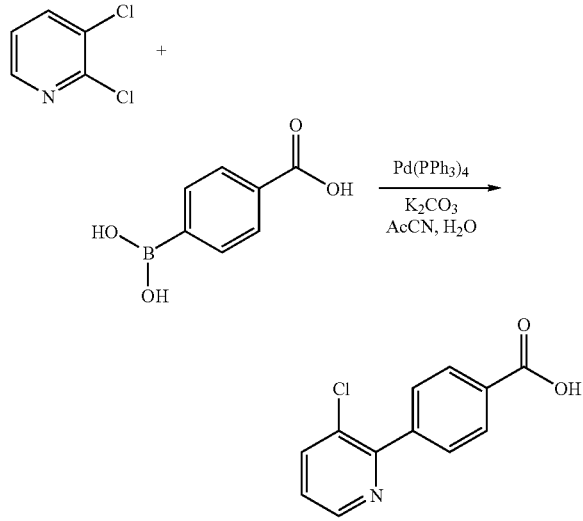

Tetrakis palladium (0.1 2 g, 0.1 mMol) was added to a suspension of carboxybenzene boronic acid (0.33 g, 2.0 mMol) and 2,3-dichloropyridine (0.296 g, 2.0 mMol) in a mixture of 0.4M $K_2CO_3$ (10 mL) and acetonitrile (10 mL) and the mixture was heated at 90° C. for 12 hrs under a blanket of nitrogen. The hot suspension was filtered, the filtrate concentrated to about half the original volume before being washed with methylene chloride. The aq. layer was carefully acidified with conc. HCl and the precipitate was collected, washed with water and vacuum dried to obtain the product as a white solid.

MS: m/z =232 (M−1)

Following the procedure described above for Intermediate 1-16 and the appropriate reagents, starting materials and purification methods known to those skilled in the art, the other benzoic acids, employed in synthesizing amide compounds of this invention, were prepared.

Amidation of Carboxylic Acid

EXAMPLE 1

A representative Synthesis of Benzamide 4-(3-Chloropyridin-2-yl)-N-(4-trifluoromethyl-phenyl)benzamide (Compound 18)

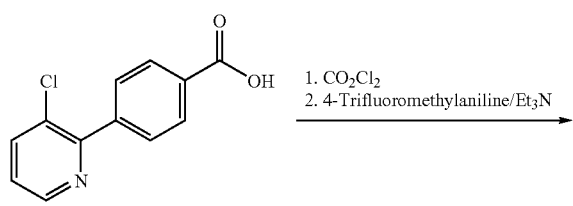

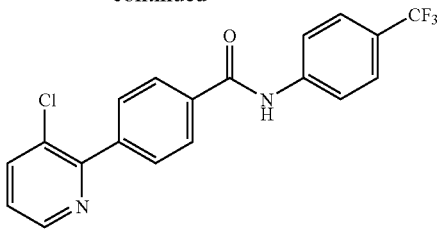

To a suspension of 4-(3-chloro-pyridin-2-yl)-benzoic acid (5.0 g, 21.4 mmol) in methylene chloride (100 mL) at ambient temperature was added oxalyl chloride (5.43 g, 42.79 mmol) followed by two drops of DMF and the mixture was heated to reflux for 30 minutes. The clear solution was then concentrated to dryness, dissolved in methylene chloride (100 mL) and was treated with 4-trifluoromethyl aniline (4.14 g, 25.68 mmol) followed by triethylamine (2.6 g, 25.68 mmol) and the mixture was gently heated to reflux for 30 minutes and agitated overnight at ambient temperature. After treating the mixture with sat. $Na_2CO_3$, the organic layer was separated, washed with water, dried and concentrated to give the crude product which was chromatographed on silicagel to obtain 4.0 g (49.6%) of the title compound as a white solid.

MS: m/z=367(M+1)

$^1$H NMR (DMSO-d6): δ 7.45-7.53 (m, 1H); 7.75 (d, 8.8 Hz, 2H); 7.86 (d, 5.2 Hz, 2H); 8.04-8.13 (m, 5H); 8.67 (dd, 4.8 Hz, 1.6 Hz, 1H); 10.72 (s, 1H).

EXAMPLE 2

A Representative Synthesis of Benzamides Using an Automated Parallel Synthesis Method The appropriate benzoic acid (2 mmol) was dissolved or suspended in 15 ml of chloroform and treated with 20 mmol of thionyl chloride. The reaction mixture was refluxed for fifteen minutes and the solvents were removed under vacuum. The residue was dissolved in 4 ml of anhydrous chloroform and 60 µl (30 µmole) of this solution was added to each well of the 96 well glass plates. Appropriate amine was then added to the corresponding well (60 µmole), followed by N,N-diisopropylethylamine (120 µmole). The plate was then heated at 65° C. for 15 minutes. The solvents were removed using an HT-12 Genevac centrifugal evacuator and 100 µl of DMSO was added to each well and the compounds were transferred to a 96-well polypropylene reaction plate. The plates were then sealed using an ABgene plate sealer and submitted to LC-MS purification.

General Method for Automated parallel LC-MS Purification of Libraries

The libraries were purified using a Perkin Elmer API100 mass spectrometer coupled to Shimadzu LC pumps. The chromatographic method employed was 10-100% gradient of acetonitrile to water over 8 minutes at a flow rate of 6 ml per minute. The column used was a 1×50 mm YMC C18 and the compounds were collected using a Gilson 204 fraction collector.

Following the procedure described above for Example 1 or 2 and the appropriate reagents, starting materials and purification methods known to those skilled in the art, the amide compounds of this invention were prepared.

The following synthetic and biological examples are offered to illustrate this invention and are not to be construed in any way as limiting the scope of this invention. In the examples below, all temperatures are in degrees Celsius (unless otherwise indicated). The compounds that have been prepared in accordance with the invention, are presented in tabular form below. The syntheses of these representative compounds were carried out in accordance with the methods set forth above.

Exemplary Compounds of the Invention

The following compounds have been prepared according to the methods of the invention.

TABLE 1

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1 | 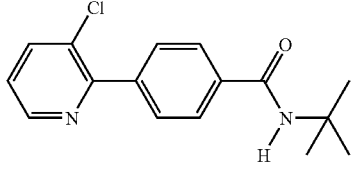 | 288.78 | 289.07 | 2.92 | 2.85 | 3.35 | |
| 2 | 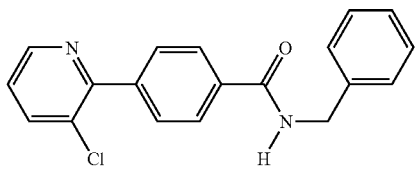 | 322.80 | 323.12 | 2.99 | 2.92 | 3.36 | |
| 3 | 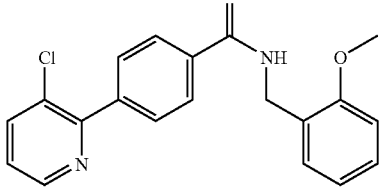 | 352.82 | 353.23 | 3.08 | 2.95 | 3.39 | + |
| 4 | 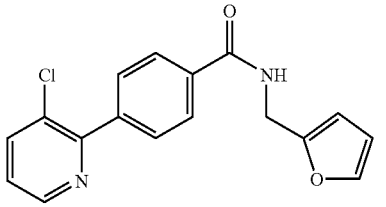 | 312.76 | 313.08 | 2.75 | 2.68 | 3.11 | + |
| 5 | 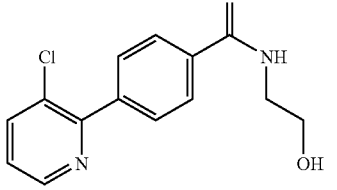 | 276.72 | 277.08 | 1.99 | 1.86 | 2.39 | |
| 6 | 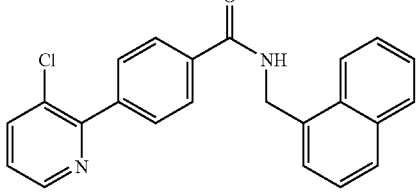 | 372.86 | 373.10 | 3.39 | 3.29 | 4.07 | + |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 7 | 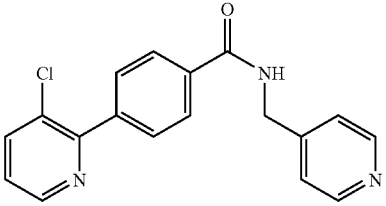 | 323.78 | 324.28 | 1.99 | 1.89 | 2.22 | |
| 8 | 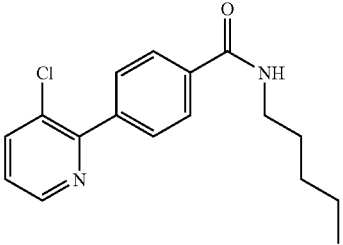 | 302.81 | 303.08 | 3.13 | 3.03 | 3.66 | + |
| 9 | 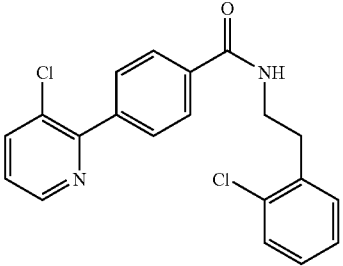 | 371.27 | 371.04 | 3.31 | 3.22 | 3.75 | +++ |
| 10 | 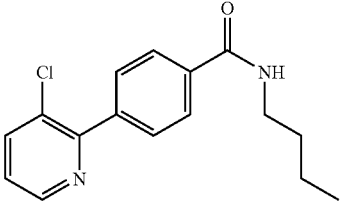 | 288.78 | 289.07 | 2.86 | 2.79 | 3.13 | |
| 11 | 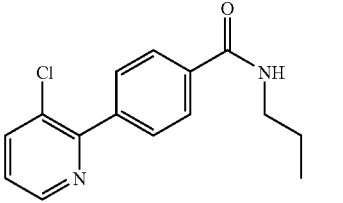 | 274.75 | 275.11 | 2.58 | 2.43 | 3.02 | |
| 12 | 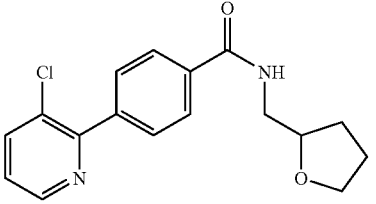 | 316.79 | 317.09 | 2.50 | 2.43 | 2.88 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 13 | 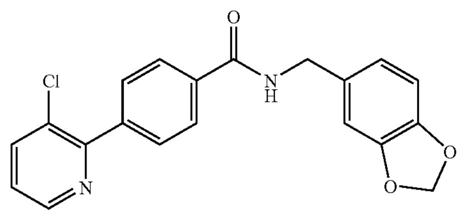 | 366.81 | 367.09 | 2.96 | 2.88 | 3.45 | |
| 14 | 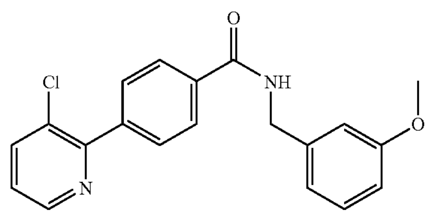 | 352.82 | 353.22 | 3.00 | 2.88 | 3.31 | + |
| 15 | 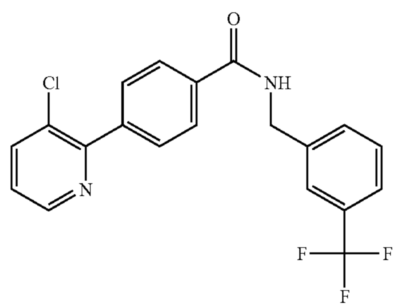 | 390.80 | 391.26 | 3.39 | 3.32 | 3.76 | ++ |
| 16 | 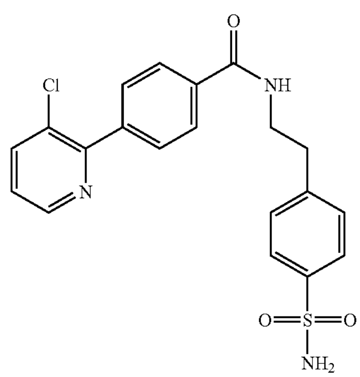 | 415.90 | 416.29 | 2.48 | 2.42 | 2.81 | + |
| 17 | 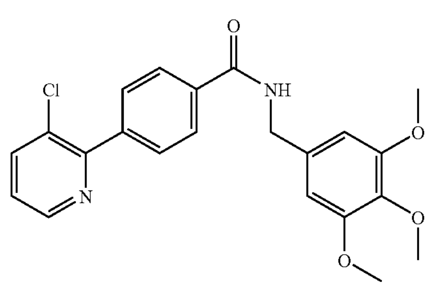 | 412.88 | 413.22 | 2.82 | 2.75 | 3.22 | + |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 18 | 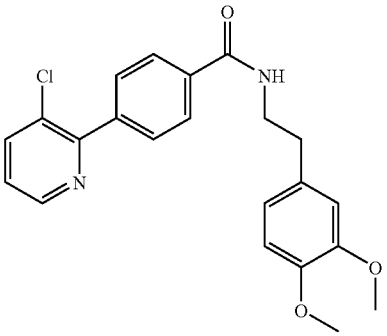 | 396.88 | 397.14 | 2.85 | 2.71 | 3.31 | ++ |
| 19 | 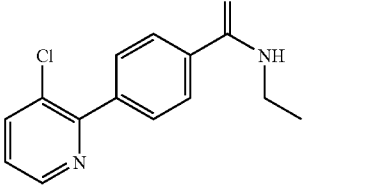 | 260.73 | 261.06 | 2.35 | 2.28 | 2.65 | + |
| 20 | 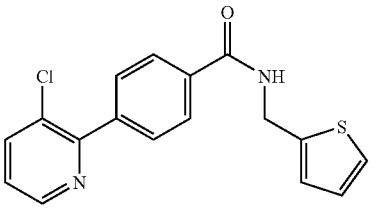 | 328.82 | 329.14 | 2.92 | 2.85 | 3.22 | + |
| 21 | 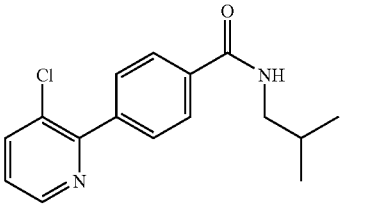 | 288.78 | 289.07 | 2.82 | 2.73 | 3.22 | + |
| 22 | 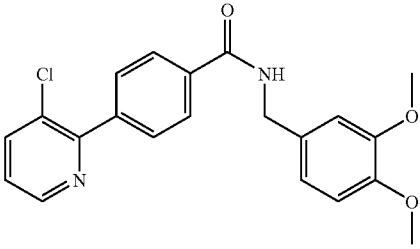 | 382.85 | 383.14 | 2.78 | 2.68 | 3.19 | + |
| 23 | 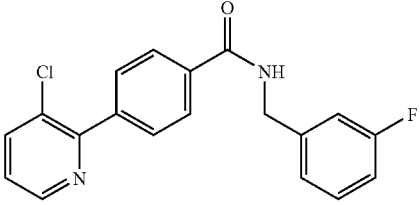 | 340.79 | 341.06 | 3.09 | 3.00 | 3.52 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 24 | 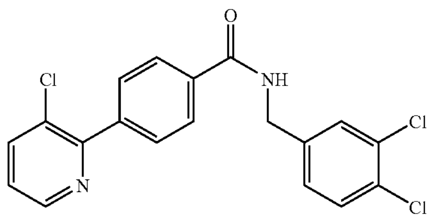 | 391.69 | 393.02 | 3.51 | 3.36 | 3.88 | + |
| 25 | 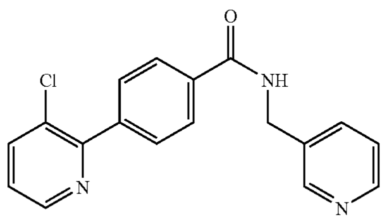 | 323.78 | 324.28 | 1.97 | 1.89 | 2.20 | |
| 26 | 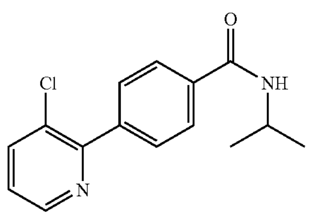 | 274.75 | 275.11 | 2.58 | 2.49 | 2.91 | + |
| 27 | 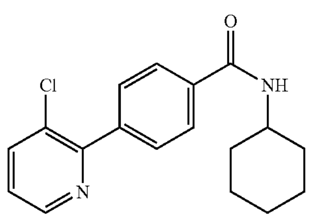 | 314.82 | 315.03 | 3.11 | 3.00 | 3.42 | |
| 28 | 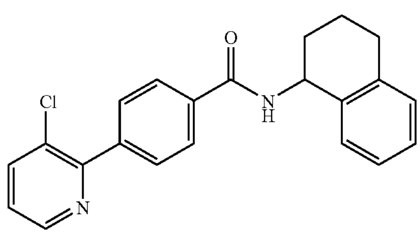 | 362.86 | 363.34 | 3.41 | 3.29 | 3.71 | |
| 29 | 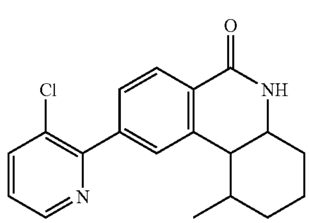 | 342.87 | 343.19 | 3.45 | 3.32 | 3.99 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 30 | 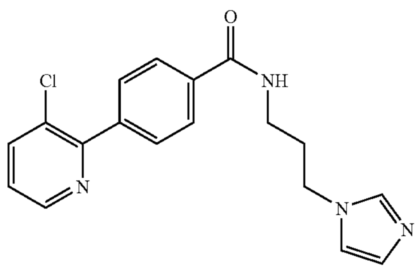 | 340.82 | 341.09 | 1.97 | 1.87 | 2.29 | |
| 31 | 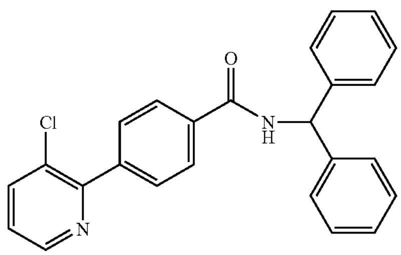 | 398.90 | 399.10 | 3.58 | 3.51 | 4.09 | |
| 32 | 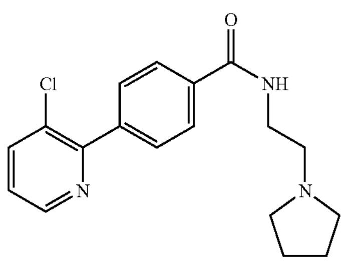 | 329.83 | 330.18 | 2.02 | 1.83 | 2.50 | + |
| 33 | 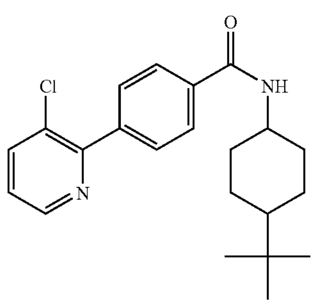 | 370.93 | 371.16 | 3.99 | 3.78 | 4.45 | ++++ |
| 34 | 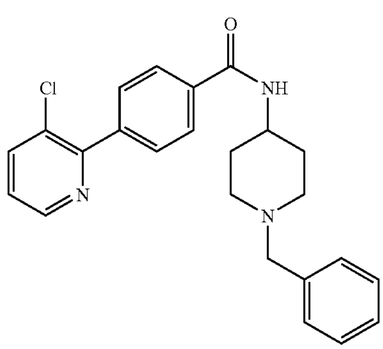 | 405.93 | 406.30 | 2.32 | 2.23 | 2.66 | +++ |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 35 | 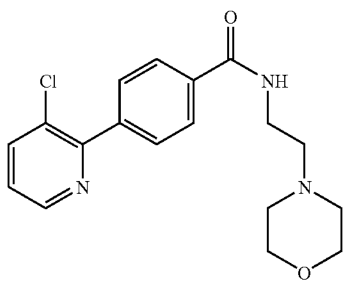 | 345.83 | 346.12 | 1.95 | 1.85 | 2.39 | |
| 36 | 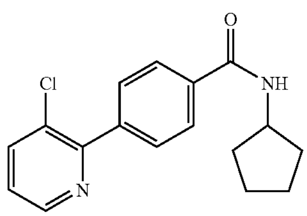 | 300.79 | 301.21 | 2.89 | 2.79 | 3.13 | |
| 37 | 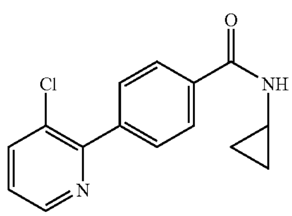 | 272.74 | 273.07 | 2.38 | 2.30 | 2.75 | + |
| 38 | 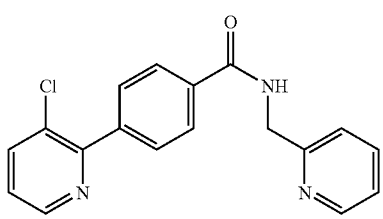 | 323.78 | 324.28 | 1.97 | 1.89 | 2.39 | |
| 39 | 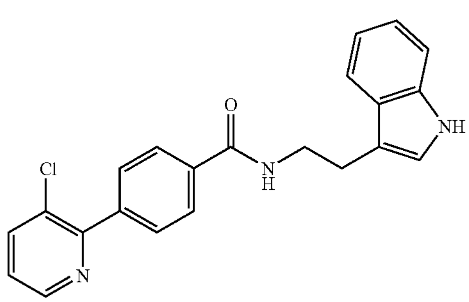 | 375.86 | 376.16 | 3.08 | 2.90 | 3.49 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 40 | 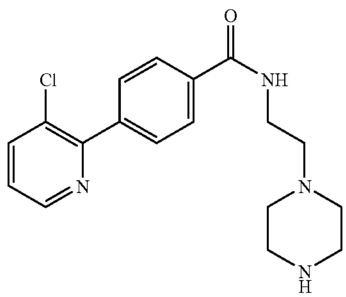 | 344.85 | 345.09 | 1.83 | 1.72 | 1.98 | |
| 41 | 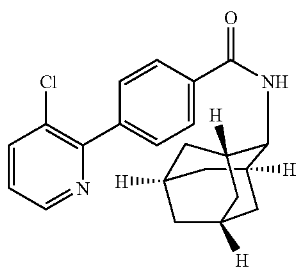 | 366.89 | 367.17 | 3.72 | 3.63 | 4.22 | + |
| 42 | 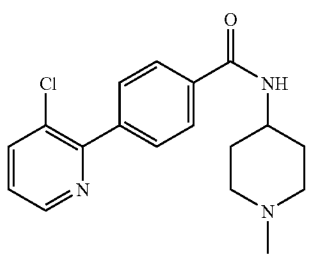 | 329.83 | 330.19 | 1.96 | 1.85 | 2.20 | |
| 43 | 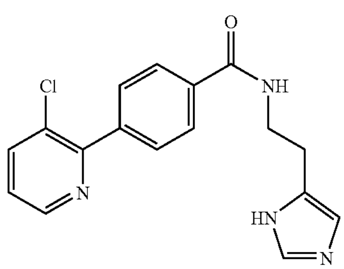 | 326.79 | 327.19 | 1.95 | 1.83 | 2.23 | + |
| 44 | 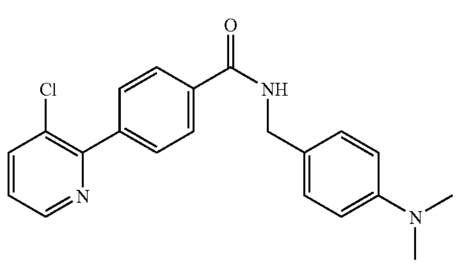 | 365.87 | 366.21 | 2.13 | 2.05 | 2.39 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 45 | 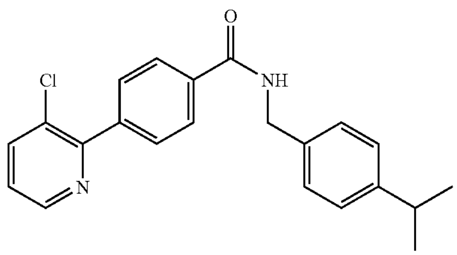 | 364.88 | 365.09 | 3.58 | 3.48 | 4.37 | ++ |
| 46 | 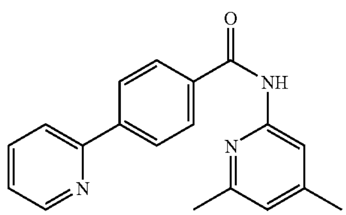 | 303.37 | 304.16 | 1.77 | 1.73 | 1.97 | |
| 47 | 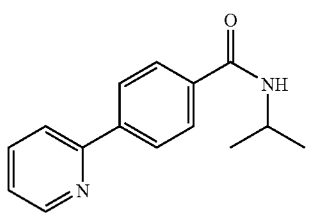 | 240.31 | 241.08 | 1.72 | 1.66 | 1.92 | + |
| 48 | 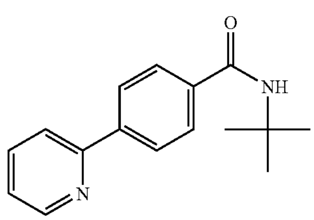 | 254.33 | 255.36 | 1.99 | 1.92 | 2.28 | |
| 49 | 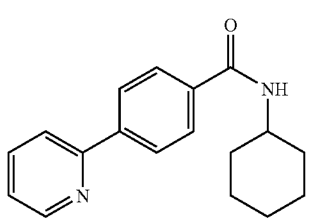 | 280.37 | 281.33 | 2.20 | 2.09 | 2.46 | |
| 50 | 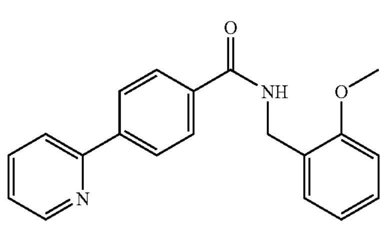 | 318.38 | 319.05 | 2.22 | 2.16 | 2.49 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 51 | 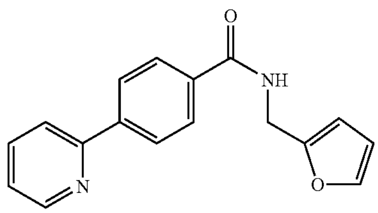 | 278.31 | 279.19 | 1.89 | 1.83 | 2.16 | |
| 52 | 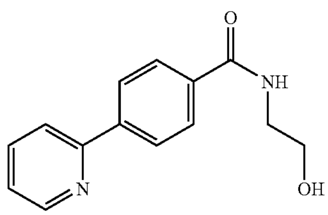 | 242.28 | 243.25 | 1.35 | 1.27 | 1.46 | + |
| 53 | 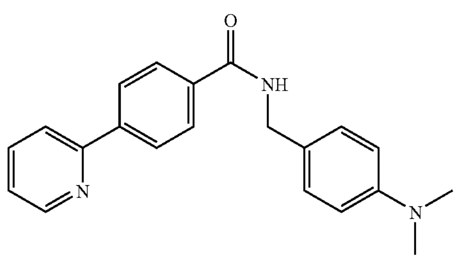 | 331.42 | 332.28 | 1.55 | 1.43 | 1.73 | |
| 54 | 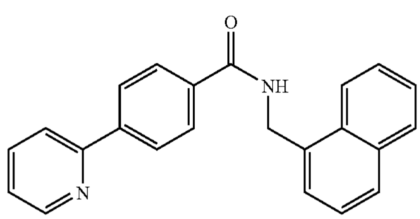 | 338.41 | 339.21 | 2.56 | 2.46 | 2.88 | +++ |
| 55 | 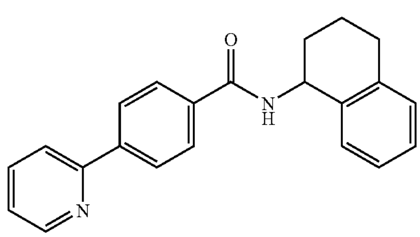 | 328.42 | 329.24 | 2.53 | 2.48 | 2.66 | |
| 56 | 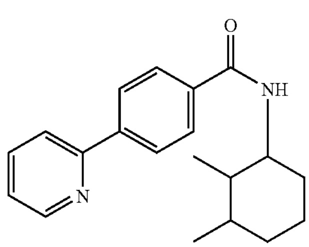 | 308.43 | 309.39 | 2.60 | 2.46 | 2.95 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 57 | 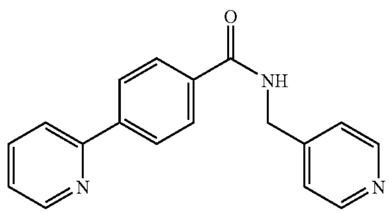 | 289.34 | 290.22 | 1.37 | 1.26 | 1.49 | + |
| 58 | 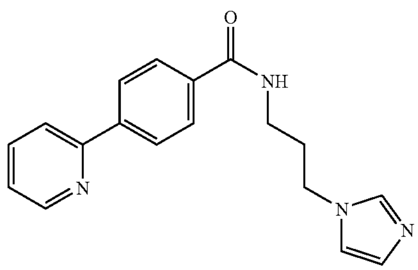 | 306.37 | 307.29 | 1.42 | 1.28 | 1.50 | ++ |
| 59 | 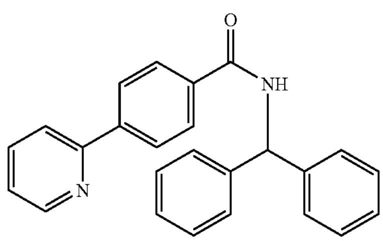 | 364.45 | 365.09 | 2.75 | 2.68 | 3.00 | + |
| 60 | 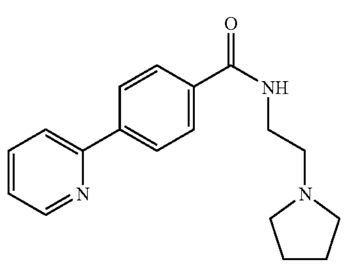 | 295.39 | 296.28 | 1.43 | 1.29 | 1.50 | + |
| 61 | 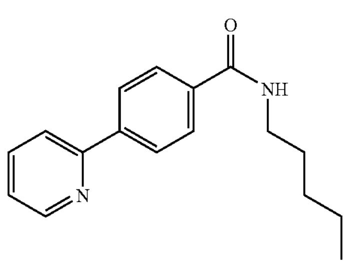 | 268.36 | 269.31 | 2.25 | 2.16 | 2.45 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 62 | (structure) | 336.82 | 337.33 | 2.46 | 2.29 | 2.76 | |
| 63 | (structure) | 336.48 | 337.48 | 2.99 | 2.89 | 3.33 | ++++ |
| 64 | (structure) | 288.35 | 289.11 | 2.13 | 2.06 | 2.48 | + |
| 65 | (structure) | 254.33 | 255.36 | 1.99 | 1.87 | 2.33 | |
| 66 | (structure) | 240.31 | 241.08 | 1.76 | 1.69 | 1.99 | |
| 67 | (structure) | 274.33 | 275.17 | 2.19 | 2.09 | 2.39 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 68 | 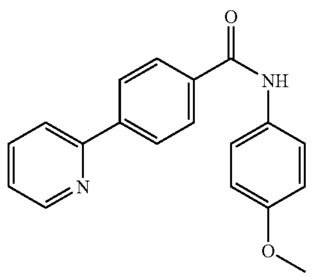 | 304.35 | 305.27 | 2.19 | 2.10 | 2.58 | ++ |
| 69 | 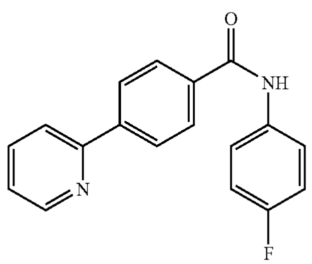 | 292.32 | 293.07 | 2.29 | 2.23 | 2.59 | |
| 70 | 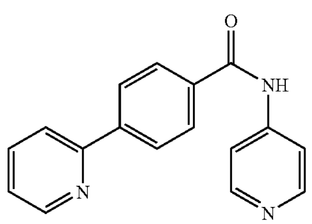 | 275.31 | 276.27 | 1.55 | 1.42 | 1.79 | |
| 71 | 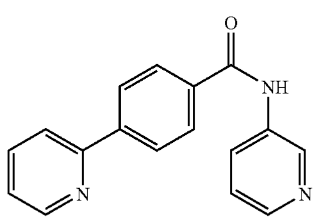 | 275.31 | 276.26 | 1.55 | 1.40 | 1.77 | |
| 72 | 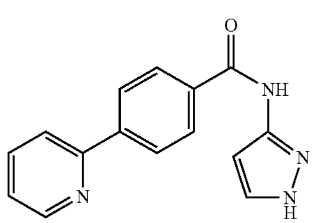 | 264.29 | 265.06 | 1.55 | 1.48 | 1.85 | ++ |
| 73 | 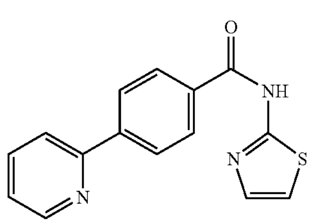 | 281.34 | 282.27 | 1.98 | 1.92 | 2.12 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 74 | 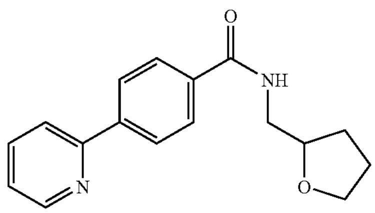 | 282.35 | 283.34 | 1.67 | 1.60 | 1.98 | |
| 75 | 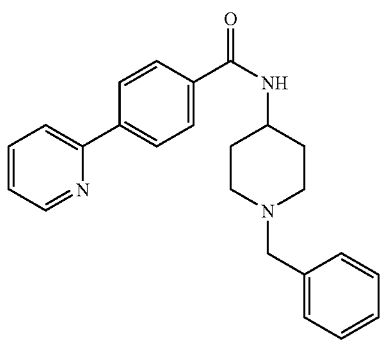 | 371.49 | 372.19 | 1.79 | 1.65 | 2.08 | |
| 76 | 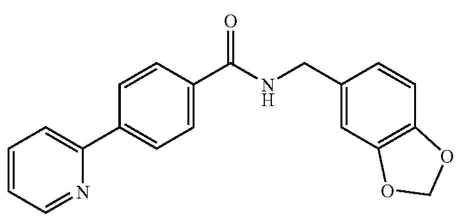 | 332.36 | 333.22 | 2.16 | 2.03 | 2.36 | |
| 77 | 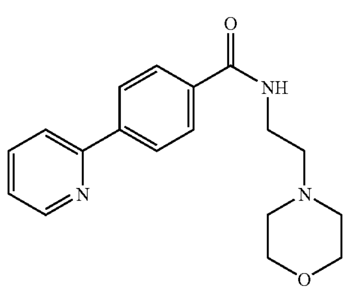 | 311.39 | 312.23 | 1.39 | 1.29 | 1.52 | + |
| 78 | 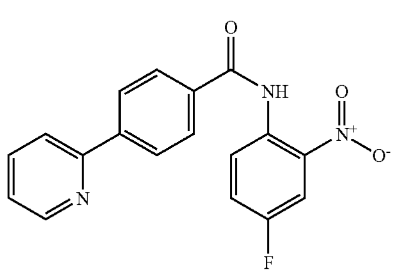 | 337.31 | 338.29 | 2.59 | 2.52 | 2.75 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 79 | 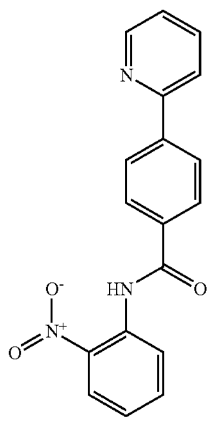 | 319.32 | | | | | |
| 80 | 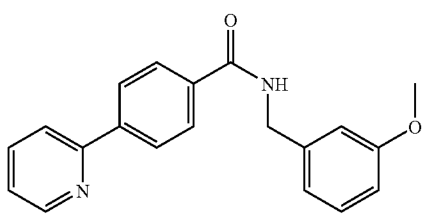 | 318.38 | 319.05 | 2.20 | 2.09 | 2.52 | |
| 81 | 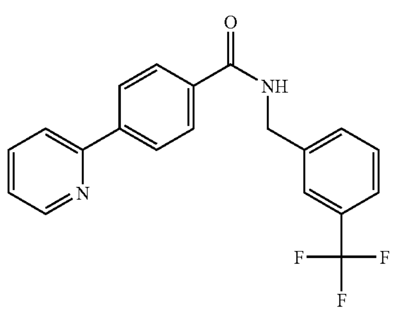 | 356.35 | 357.09 | 2.59 | 2.52 | 2.89 | ++ |
| 82 | 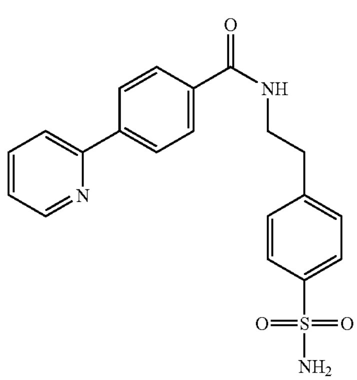 | 381.46 | 382.17 | 1.79 | 1.72 | 2.07 | + |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 83 | 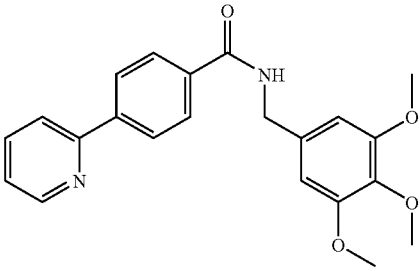 | 378.43 | 379.32 | 2.05 | 1.99 | 2.36 | + |
| 84 | 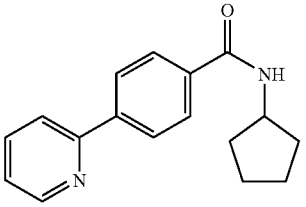 | 266.35 | 267.07 | 2.02 | 1.92 | 2.26 | |
| 85 | 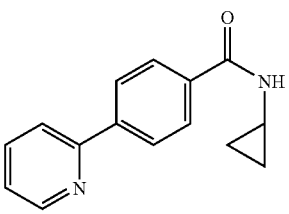 | 238.29 | 239.06 | 1.60 | 1.50 | 1.96 | |
| 86 | 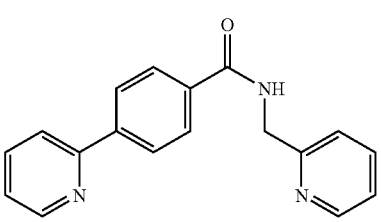 | 289.34 | 290.22 | 1.40 | 1.17 | 1.50 | + |
| 87 | 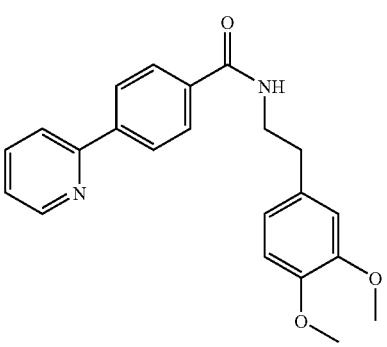 | 362.43 | 363.38 | 2.10 | 2.05 | 2.43 | + |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 88 | 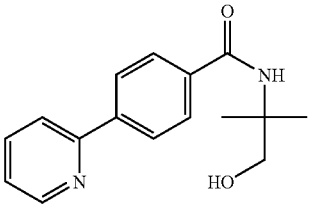 | 270.33 | 271.29 | 1.62 | 1.59 | 1.81 | |
| 89 | 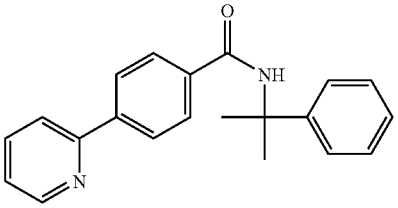 | 316.41 | | | | | |
| 90 | 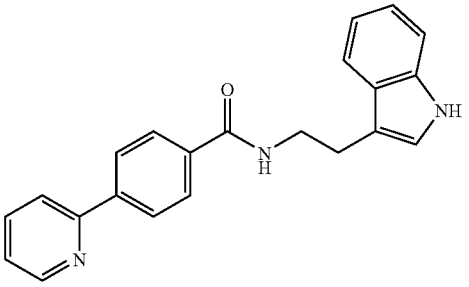 | 341.42 | 342.22 | 2.32 | 2.16 | 2.58 | |
| 91 | 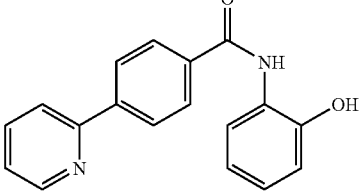 | 290.32 | 291.07 | 2.04 | 1.95 | 2.21 | |
| 92 | 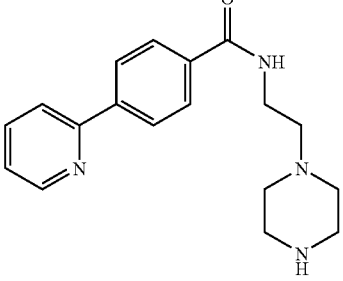 | 310.40 | | | | | |
| 93 | 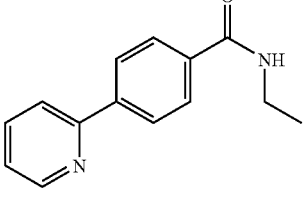 | 226.28 | 227.25 | 1.56 | 1.36 | 1.77 | |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 94 | 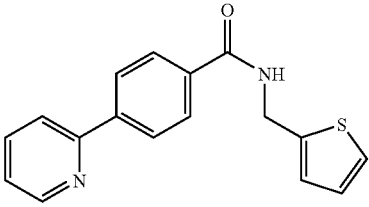 | 294.38 | 295.18 | 2.05 | 1.99 | 2.29 | ++ |
| 95 | 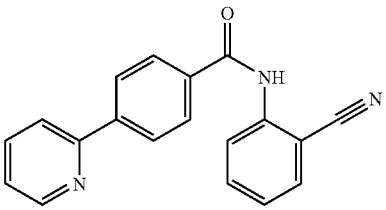 | 299.33 | 300.21 | 2.05 | 1.97 | 2.26 | ++++ |
| 96 | 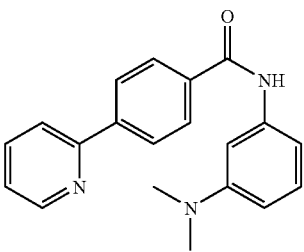 | 317.39 | 318.13 | 1.68 | 1.63 | 1.88 | |
| 97 | 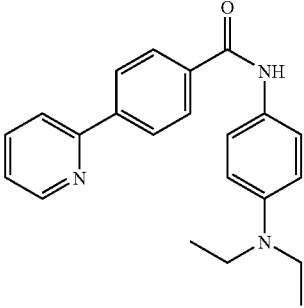 | 345.45 | 346.24 | 1.76 | 1.69 | 1.92 | + |
| 98 | 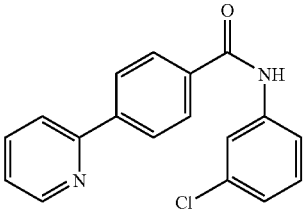 | 308.77 | 309.28 | 2.58 | 2.50 | 2.79 | ++ |
| 99 | 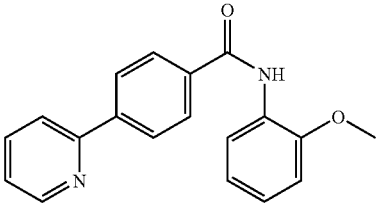 | 304.35 | 305.28 | 2.31 | 2.22 | 2.57 | ++++ |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 100 | 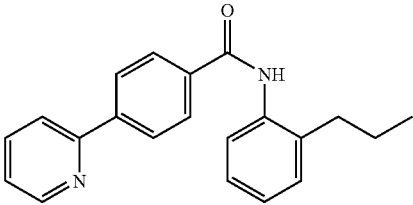 | 316.41 | 317.19 | 2.53 | 2.48 | 2.76 | |
| 101 | 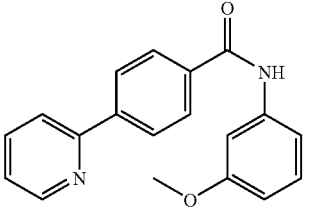 | 304.35 | 305.30 | 2.26 | 2.20 | 2.72 | + |
| 102 | 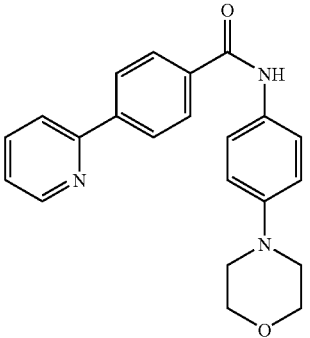 | 359.43 | 360.29 | 1.79 | 1.72 | 1.97 | |
| 103 | 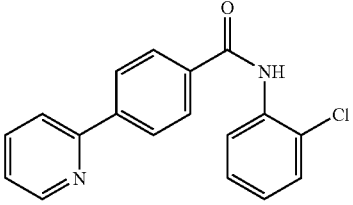 | 308.77 | 309.28 | 2.35 | 2.16 | 2.65 | |
| 104 | 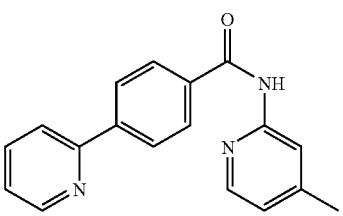 | 289.34 | 290.18 | 1.66 | 1.62 | 1.83 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 105 | 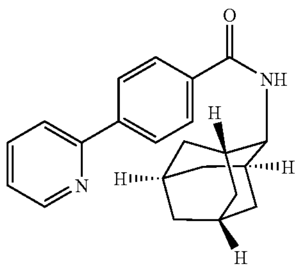 | 332.45 | 333.27 | 2.73 | 2.65 | 2.89 | |
| 106 | 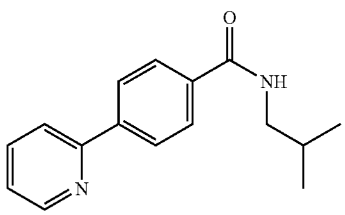 | 254.33 | 255.36 | 1.96 | 1.86 | 2.23 | ++ |
| 107 | 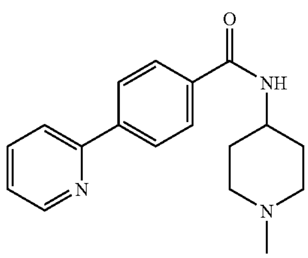 | 295.39 | 296.34 | 1.40 | 1.24 | 1.57 | + |
| 108 | 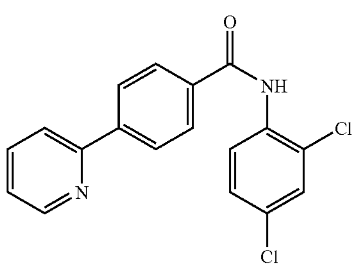 | 343.22 | 343.09 | 2.72 | 2.62 | 2.98 | |
| 109 | 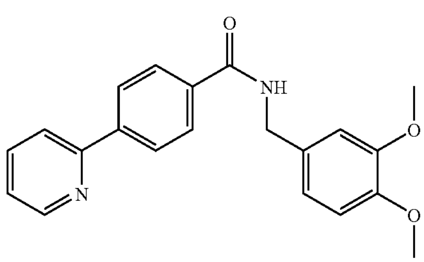 | 348.41 | 349.27 | 2.00 | 1.93 | 2.28 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 110 | 4-(pyridin-2-yl)-N-(3-fluorobenzyl)benzamide | 306.34 | 307.25 | 2.25 | 2.13 | 2.39 | |
| 111 | 4-(pyridin-2-yl)-N-(3,4-dichlorobenzyl)benzamide | 357.24 | 357.09 | 2.66 | 2.54 | 2.96 | +++ |
| 112 | 4-(pyridin-2-yl)-N-(3-chloro-4-methoxyphenyl)benzamide | 338.80 | 339.09 | 2.45 | 2.38 | 2.69 | |
| 113 | 4-(pyridin-2-yl)-N-(4-trifluoromethylphenyl)benzamide | 342.32 | 343.10 | 2.82 | 2.72 | 3.23 | ++ |
| 114 | 4-(pyridin-2-yl)-N-(2,3-dichlorophenyl)benzamide | 343.22 | 343.09 | 2.69 | 2.55 | 3.00 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 115 | 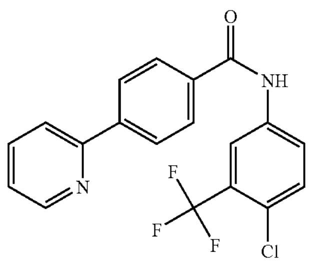 | 376.77 | 377.26 | 3.01 | 2.92 | 3.28 | |
| 116 | 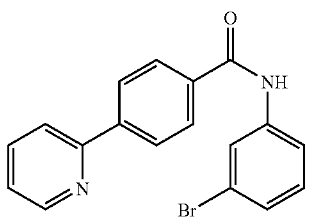 | 353.22 | 353.09 | 2.63 | 2.55 | 2.85 | + |
| 117 | 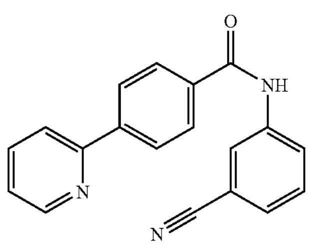 | 299.33 | 300.24 | 2.26 | 2.19 | 2.53 | ++++ |
| 118 | 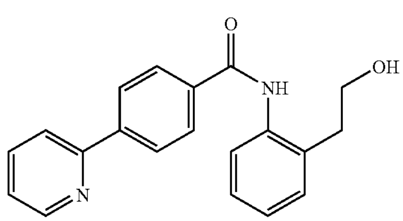 | 318.38 | 319.08 | 1.97 | 1.90 | 2.15 | ++++ |
| 119 | 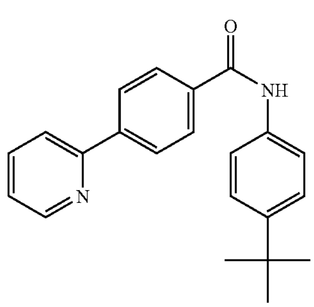 | 330.43 | 331.26 | 2.93 | 2.86 | 3.26 | |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 120 | 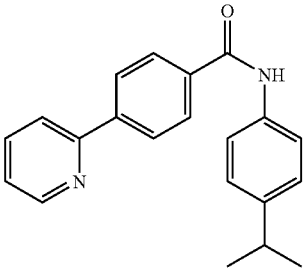 | 316.41 | 317.19 | 2.80 | 2.69 | 3.05 | + |
| 121 | 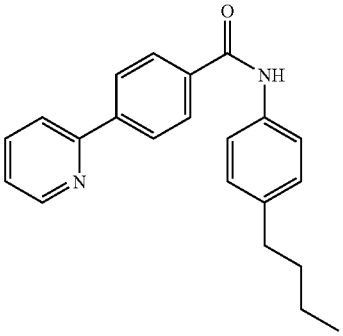 | 330.43 | 331.27 | 3.06 | 2.93 | 3.41 | ++++ |
| 122 | 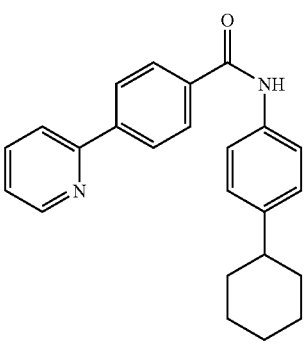 | 356.47 | 357.21 | 3.28 | 3.18 | 3.49 | |
| 123 | 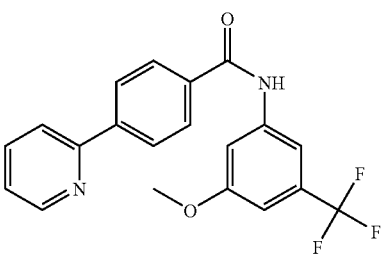 | 372.35 | 373.10 | 2.86 | 2.79 | 3.52 | |
| 124 | 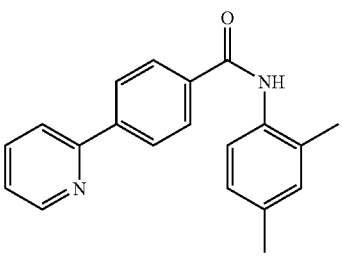 | 302.38 | 303.08 | 2.38 | 2.29 | 2.68 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 125 | 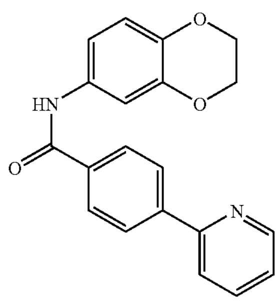 | 332.36 | 333.22 | 2.19 | 2.10 | 2.35 | |
| 126 | 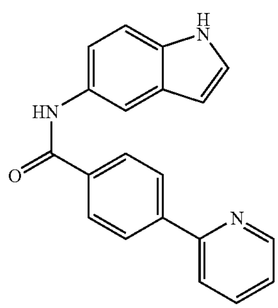 | 313.36 | 314.14 | 2.09 | 2.02 | 2.28 | |
| 127 | 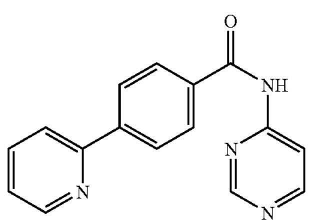 | 276.30 | | | | | |
| 128 | 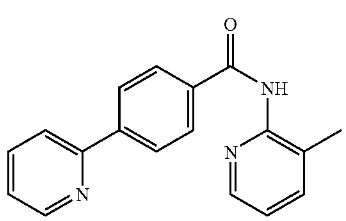 | 289.34 | 290.19 | 1.55 | 1.50 | 1.79 | |
| 129 | 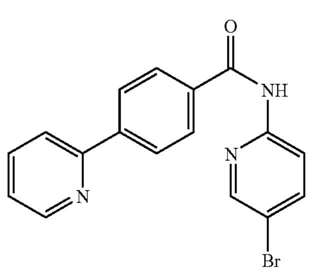 | 354.21 | 356.09 | 2.43 | 2.28 | 2.59 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 130 | 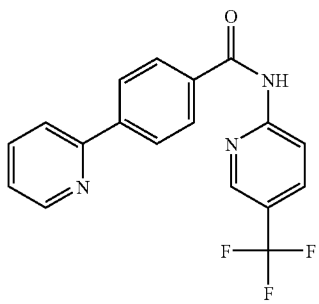 | 343.31 | 344.13 | 2.65 | 2.58 | 2.75 | |
| 131 | 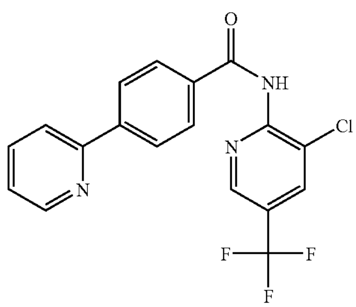 | 377.76 | 378.18 | 2.42 | 2.32 | 2.52 | |
| 132 | 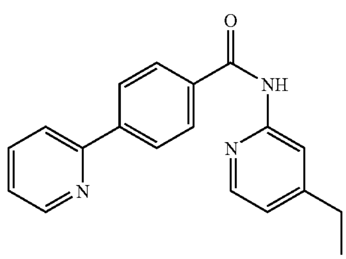 | 303.37 | 304.17 | 1.80 | 1.70 | 2.06 | |
| 133 | 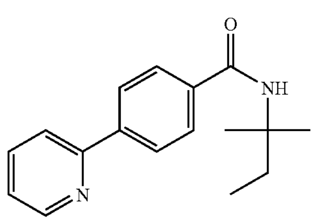 | 268.36 | 269.31 | 2.19 | 1.79 | 2.65 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 134 | *N-(2-chlorophenyl)-[1,1'-biphenyl]-4-carboxamide structure* | 309.76 | 310.28 | 1.92 | 1.85 | 2.16 | |
| 135 | *4-(pyridin-2-yl)-N-(6-chloropyridin-3-yl)benzamide structure* | 309.76 | 310.28 | 2.15 | 2.09 | 2.42 | ++++ |
| 136 | *4-(pyridin-2-yl)-N-(6-methoxypyridin-3-yl)benzamide structure* | 305.34 | 306.28 | 1.89 | 1.85 | 2.20 | + |
| 137 | *4-(pyridin-2-yl)-N-(2-chloropyridin-4-yl)benzamide structure* | 309.76 | 310.68 | 0.82 | 0.67 | 0.83 | |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 138 | 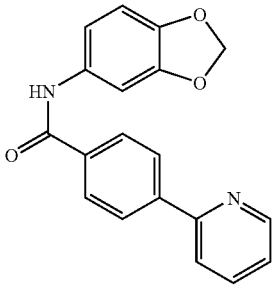 | 318.34 | 319.05 | 2.16 | 2.12 | 2.49 | + |
| 139 | 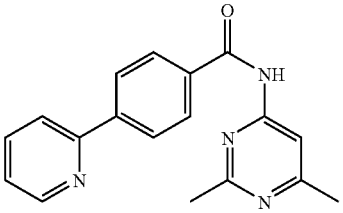 | 304.35 | 305.35 | 1.55 | 1.42 | 1.83 | |
| 140 | 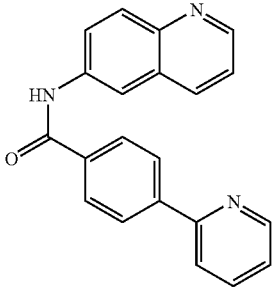 | 325.37 | 326.28 | 1.73 | 1.69 | 1.93 | |
| 141 | 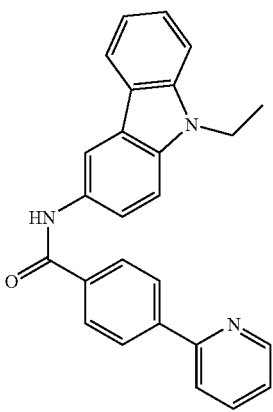 | 391.48 | 392.27 | 2.93 | 2.88 | 3.25 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 142 | 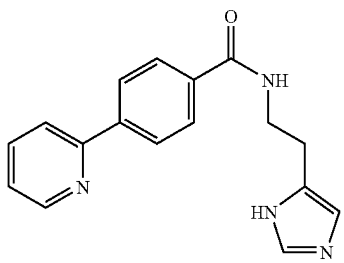 | 292.34 | 293.07 | 1.42 | 1.29 | 1.47 | ++ |
| 143 | 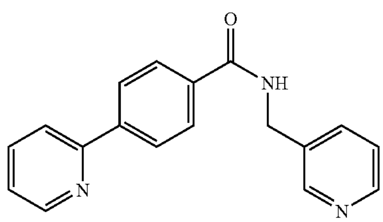 | 289.34 | 290.18 | 1.39 | 1.30 | 1.50 | ++++ |
| 144 | 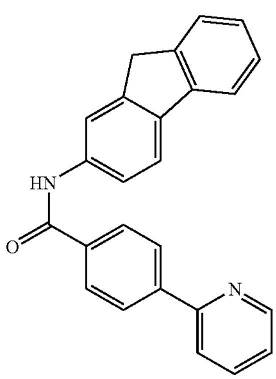 | 362.44 | 363.36 | 2.93 | 2.88 | 3.13 | +++ |
| 145 | 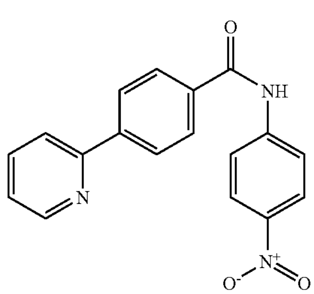 | 319.32 | 320.12 | 2.48 | 2.32 | 2.65 | ++ |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|----|-----------|-----------|----------|---------------|----------------------|--------------------|--------------------|
| 146 | 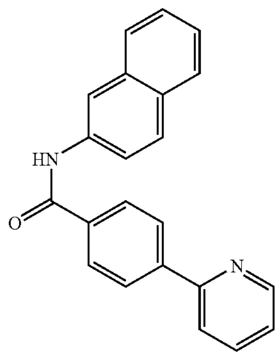 | 324.39 | 325.29 | 2.70 | 2.48 | 3.06 | + |
| 147 | 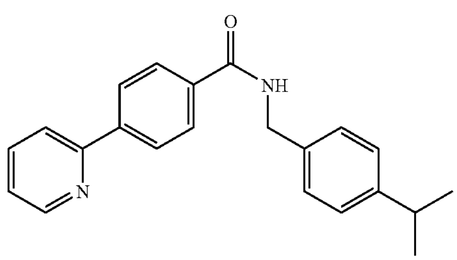 | 330.43 | 331.26 | 2.75 | 2.63 | 3.13 | + |
| 148 | 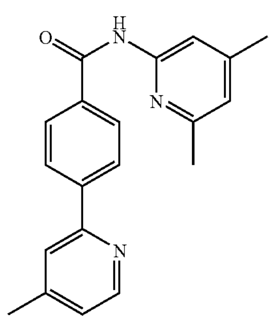 | 317.39 | 318.12 | 1.79 | 1.72 | 2.12 | |
| 149 | 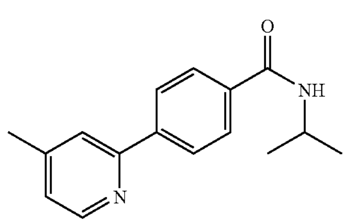 | 254.33 | 255.35 | 1.80 | 1.65 | 2.16 | ++ |
| 150 | 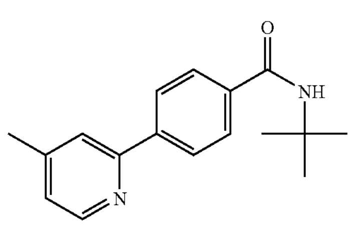 | 268.36 | 269.31 | 2.06 | 1.99 | 2.46 | ++ |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 151 | 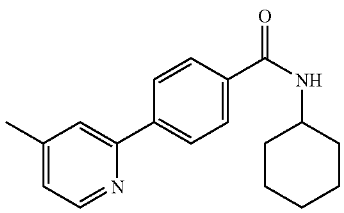 | 294.40 | 295.28 | 2.25 | 2.17 | 2.65 | |
| 152 | 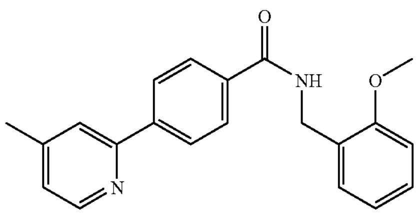 | 332.41 | 333.25 | 2.26 | 2.17 | 2.66 | ++ |
| 153 | 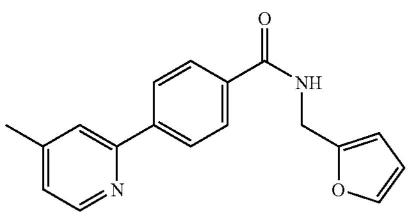 | 292.34 | 293.07 | 1.95 | 1.86 | 2.36 | |
| 154 | 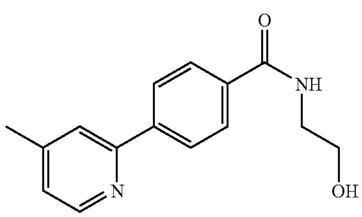 | 256.31 | 257.30 | 1.46 | 1.37 | 1.79 | + |
| 155 | 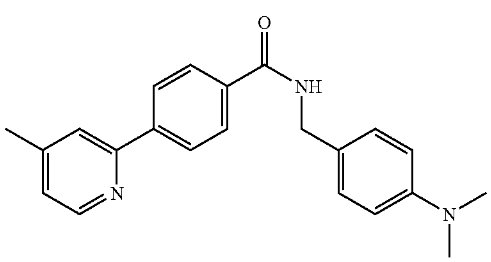 | 345.45 | 346.20 | 1.60 | 1.45 | 1.93 | ++ |
| 156 | 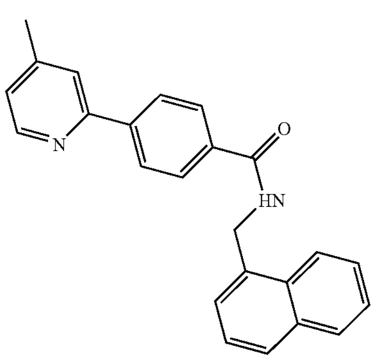 | 352.44 | 353.28 | 2.56 | 2.45 | 2.91 | + |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 157 | 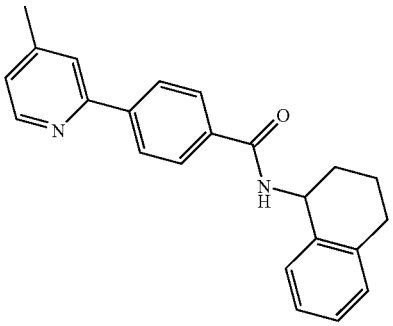 | 342.44 | 343.22 | 2.53 | 2.45 | 2.83 | + |
| 158 | 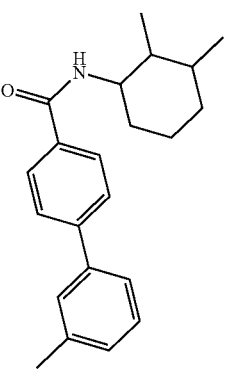 | 322.45 | 323.25 | 2.60 | 2.46 | 2.96 | ++ |
| 159 | 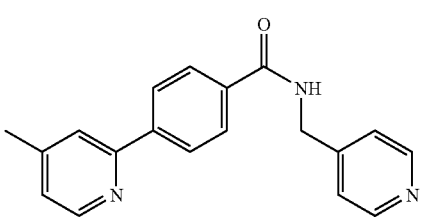 | 303.37 | 304.14 | 1.46 | 1.40 | 1.60 | ++ |
| 160 | 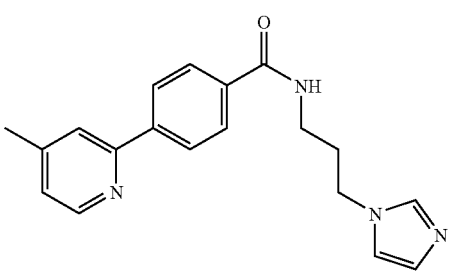 | 320.40 | 321.25 | 1.48 | 1.41 | 1.71 | +++ |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 161 | 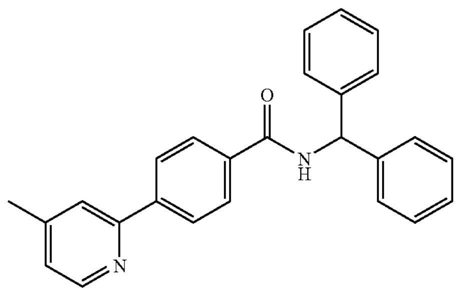 | 378.48 | 379.33 | 2.73 | 2.58 | 3.06 | ++ |
| 162 | 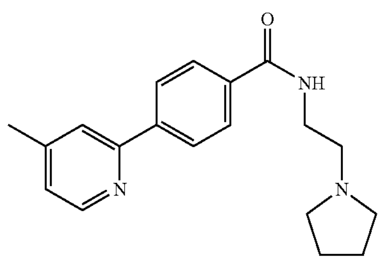 | 309.41 | 310.42 | 1.49 | 1.36 | 1.65 | |
| 163 | 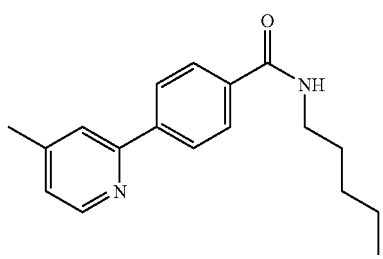 | 282.39 | 283.38 | 2.28 | 2.16 | 2.75 | + |
| 164 | 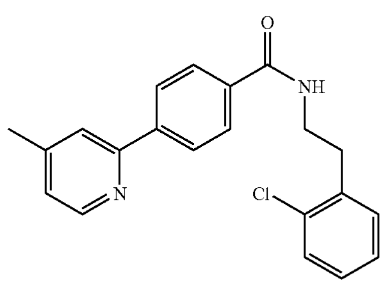 | 350.85 | 351.30 | 2.49 | 2.25 | 2.85 | + |
| 165 | 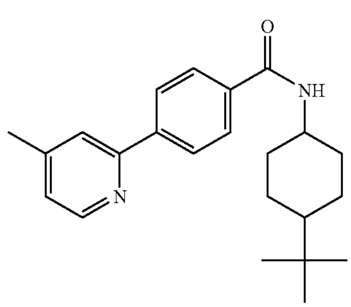 | 350.51 | 351.43 | 2.99 | 2.86 | 3.31 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 166 | 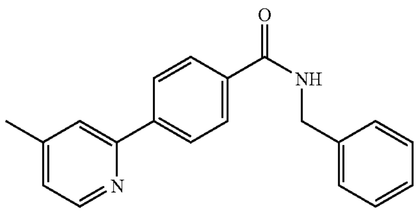 | 302.38 | 303.08 | 2.18 | 2.08 | 2.48 | |
| 167 | 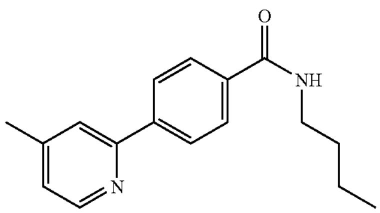 | 268.36 | 269.31 | 2.05 | 1.99 | 2.35 | |
| 168 | 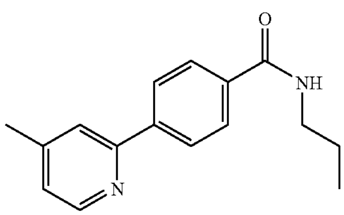 | 254.33 | 255.35 | 1.86 | 1.78 | 1.98 | |
| 169 | 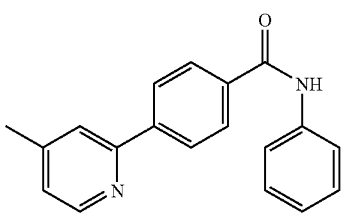 | 288.35 | 289.11 | 2.23 | 2.12 | 2.53 | |
| 170 | 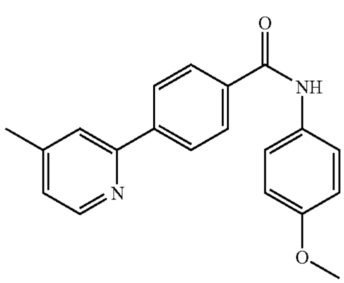 | 318.38 | 319.08 | 2.22 | 2.12 | 2.38 | |
| 171 | 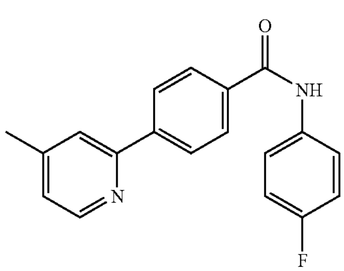 | 306.34 | 307.25 | 2.33 | 2.17 | 2.69 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 172 | 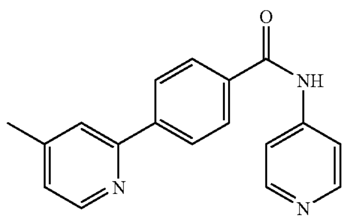 | 289.34 | 290.20 | 1.65 | 1.49 | 1.87 | |
| 173 | 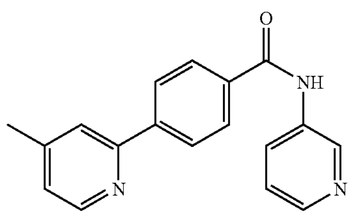 | 289.34 | 290.21 | 1.56 | 1.50 | 1.86 | ++ |
| 174 | 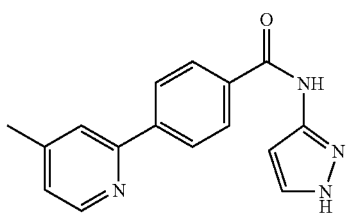 | 278.32 | 279.20 | 1.69 | 1.55 | 1.95 | ++ |
| 175 | 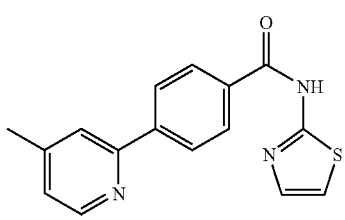 | 295.37 | 296.26 | 2.02 | 1.95 | 2.26 | +++ |
| 176 | 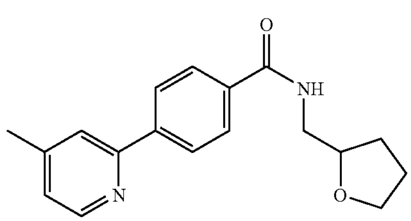 | 296.37 | 297.35 | 1.76 | 1.65 | 2.06 | ++ |
| 177 | 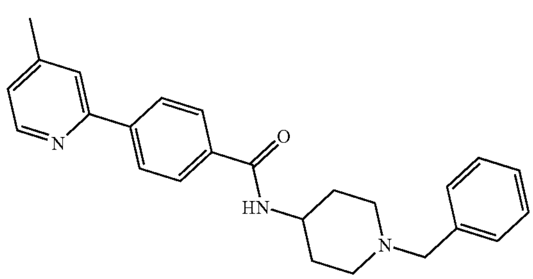 | 385.51 | 386.26 | 1.82 | 1.72 | 2.09 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 178 | 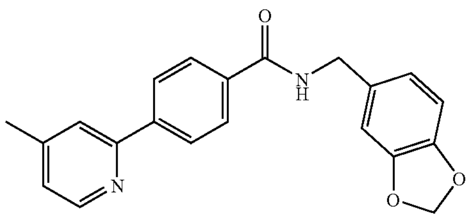 | 346.39 | 347.14 | 2.18 | 2.09 | 2.46 | |
| 179 | 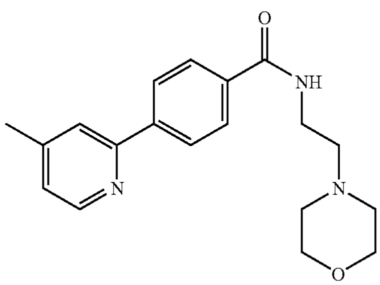 | 325.41 | 326.28 | 1.46 | 1.16 | 1.85 | ++ |
| 180 | 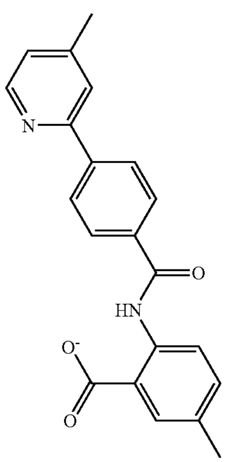 | 351.34 | 352.29 | 2.52 | 2.40 | 2.79 | |
| 181 | 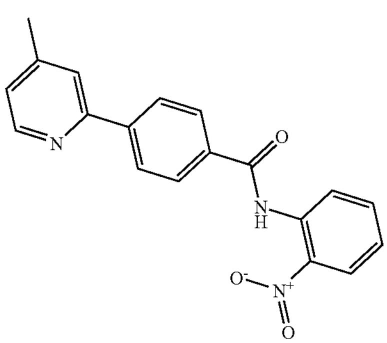 | 333.35 | 334.18 | 2.46 | 2.40 | 2.69 | + |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 182 | 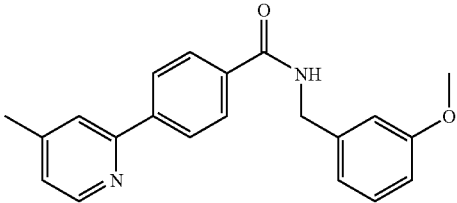 | 332.41 | 333.25 | 2.22 | 2.15 | 2.69 | + |
| 183 | 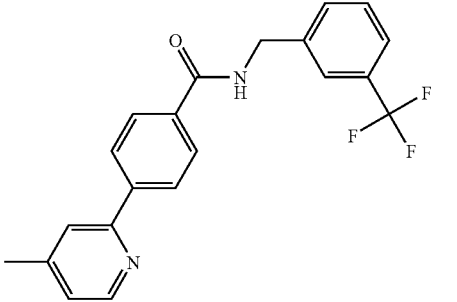 | 370.38 | 371.10 | 2.63 | 2.59 | 2.78 | |
| 184 | 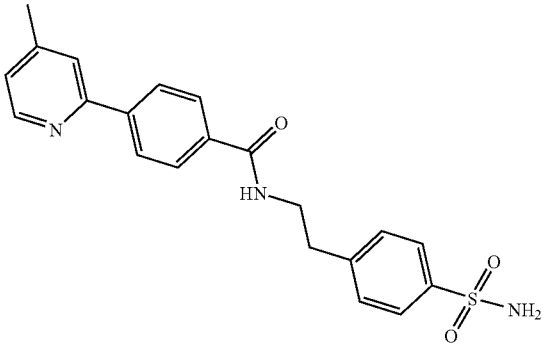 | 395.48 | 396.11 | 1.86 | 1.80 | 2.05 | |
| 185 | 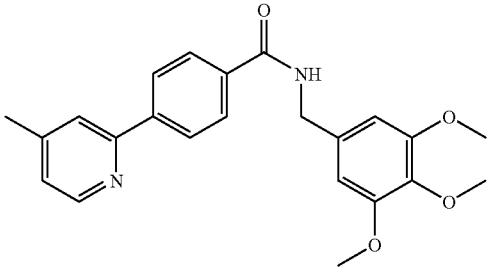 | 392.46 | 393.25 | 2.09 | 2.00 | 2.46 | |
| 186 | 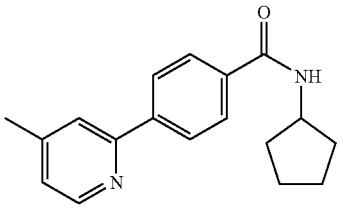 | 280.37 | 281.31 | 2.06 | 1.98 | 2.39 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 187 | 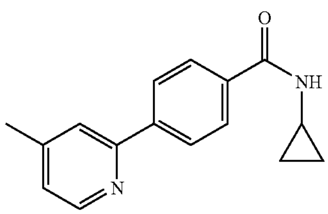 | 252.32 | 253.16 | 1.70 | 1.59 | 2.00 | + |
| 188 | 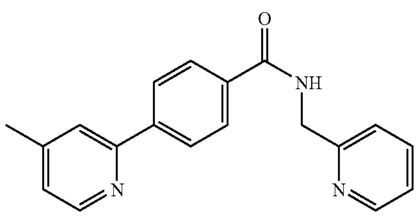 | 303.37 | 304.16 | 1.47 | 1.40 | 1.92 | ++ |
| 189 | 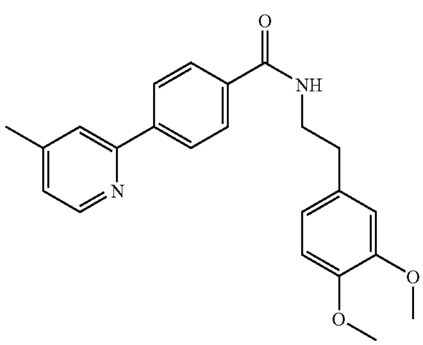 | 376.46 | 377.34 | 2.13 | 2.06 | 2.43 | + |
| 190 | 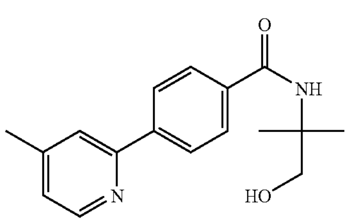 | 284.36 | 285.24 | 1.72 | 1.59 | 1.97 | |
| 191 | 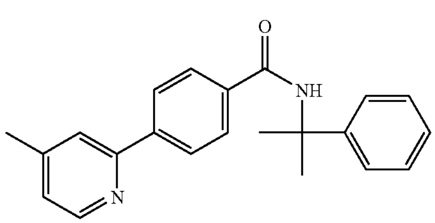 | 330.43 | 331.26 | 2.43 | 2.35 | 2.71 | ++ |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 192 | 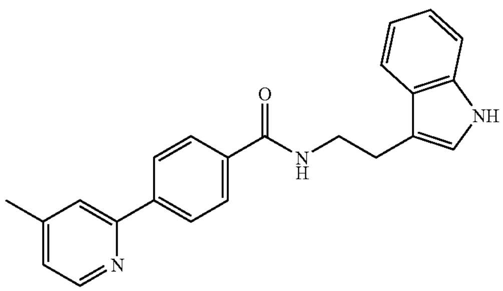 | 355.44 | 356.21 | 2.33 | 2.25 | 2.65 | ++ |
| 193 | 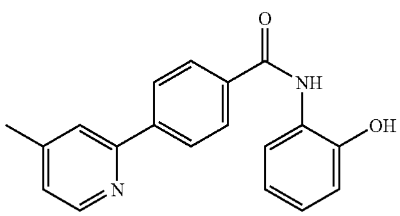 | 304.35 | 305.29 | 2.09 | 2.03 | 2.40 | ++ |
| 194 | 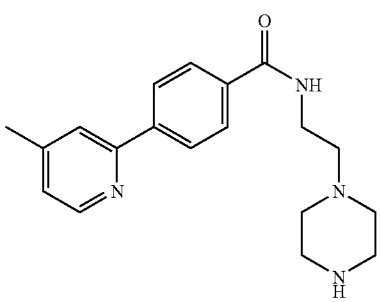 | 324.43 | | | | | |
| 195 | 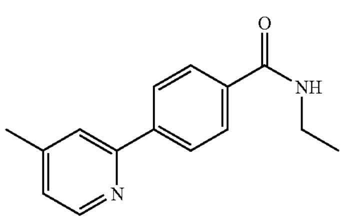 | 240.31 | 241.06 | 1.66 | 1.46 | 2.03 | +++ |
| 196 | 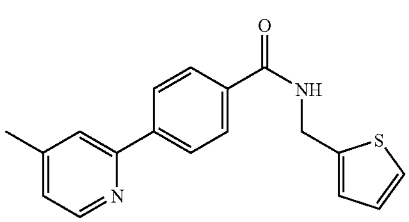 | 308.41 | 309.30 | 2.12 | 2.03 | 2.45 | ++++ |
| 197 | 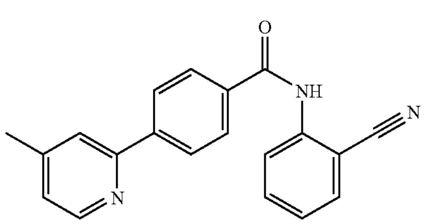 | 313.36 | 314.12 | 2.06 | 1.93 | 2.25 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 198 | 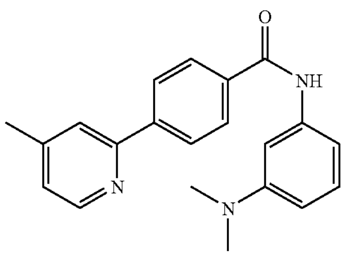 | 331.42 | 332.28 | 1.72 | 1.59 | 1.97 | +++ |
| 199 | 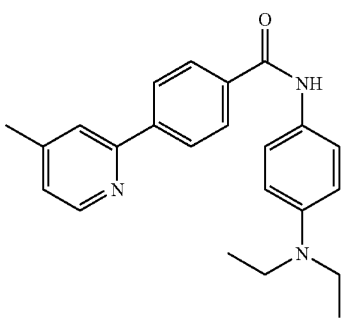 | 359.48 | 360.29 | 1.79 | 1.70 | 2.15 | |
| 200 | 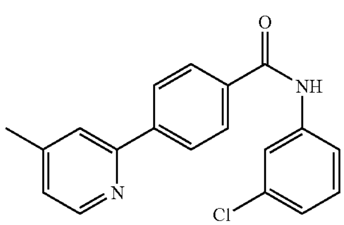 | 322.80 | 323.14 | 2.56 | 2.42 | 2.85 | ++++ |
| 201 | 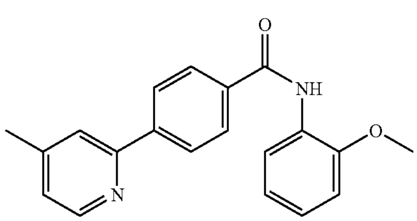 | 318.38 | 319.06 | 2.32 | 2.19 | 2.72 | |
| 202 | 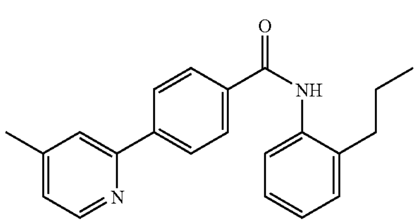 | 330.43 | 331.26 | 2.55 | 2.32 | 2.90 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 203 | 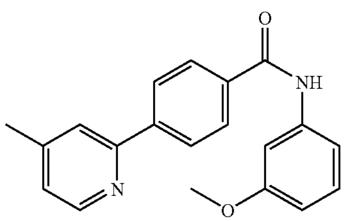 | 318.38 | 319.06 | 2.29 | 2.13 | 2.79 | |
| 204 | 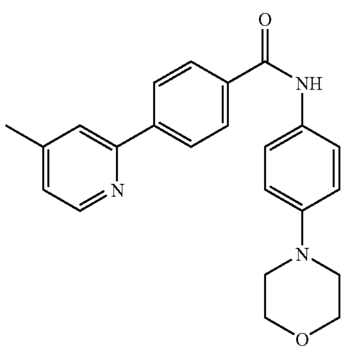 | 373.46 | 374.22 | 1.85 | 1.69 | 1.93 | |
| 205 | 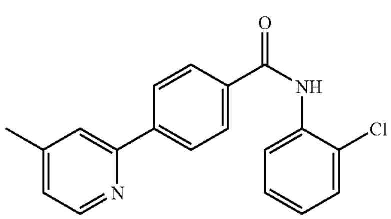 | 322.80 | 323.14 | 2.33 | 2.19 | 2.65 | + |
| 206 | 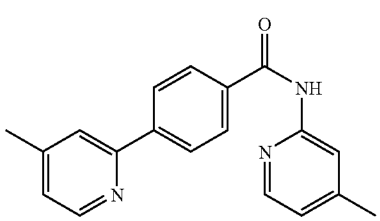 | 303.37 | 304.15 | 1.67 | 1.56 | 2.00 | |
| 207 | 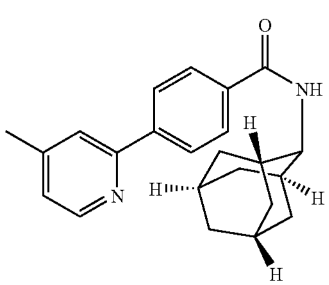 | 346.48 | 347.25 | 2.72 | 2.62 | 3.11 | |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 208 | 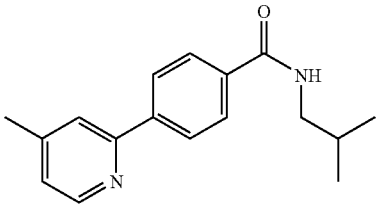 | 268.36 | 269.30 | 2.02 | 1.92 | 2.32 | + |
| 209 | 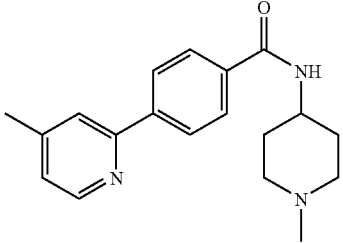 | 309.41 | 310.43 | 1.46 | 1.24 | 1.59 | +++ |
| 210 | 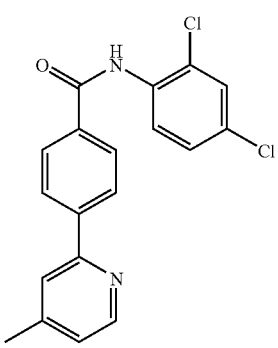 | 357.24 | 357.09 | 2.65 | 2.55 | 2.95 | + |
| 211 | 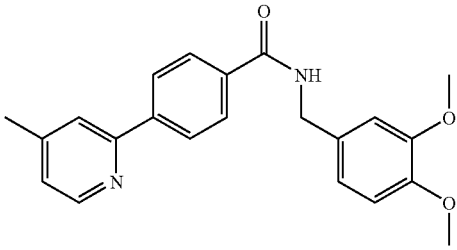 | 362.43 | 363.37 | 2.05 | 1.90 | 2.38 | |
| 212 | 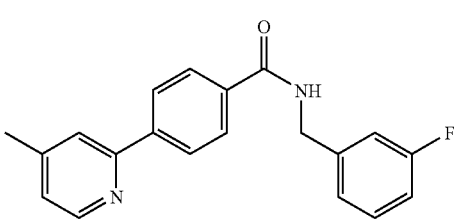 | 320.37 | 321.22 | 2.26 | 2.18 | 2.63 | ++ |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 213 | 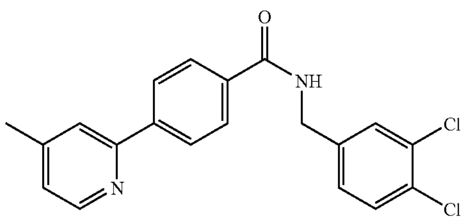 | 371.27 | 371.05 | 2.66 | 2.58 | 2.92 | + |
| 214 | 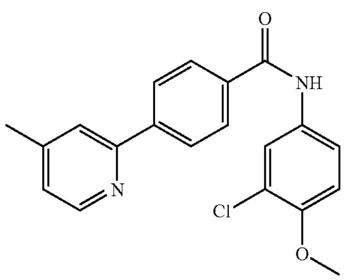 | 352.82 | 353.22 | 2.46 | 2.39 | 2.86 | ++ |
| 215 | 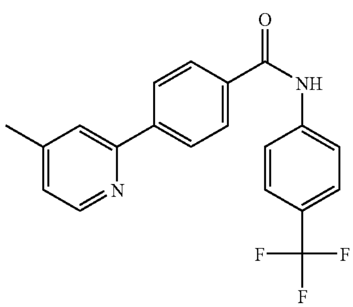 | 356.35 | 357.09 | 2.78 | 2.70 | 3.05 | + |
| 216 | 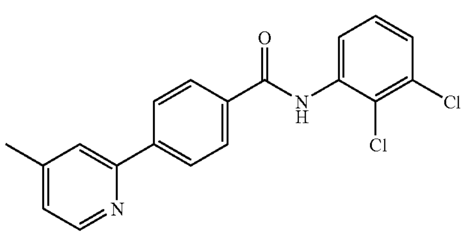 | 357.24 | 357.09 | 2.59 | 2.49 | 2.99 | + |
| 217 | 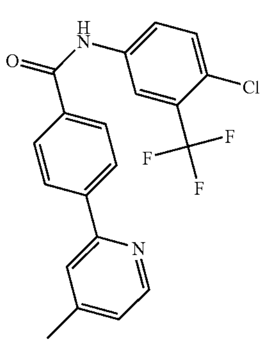 | 390.80 | 391.26 | 2.93 | 2.72 | 3.21 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 218 | 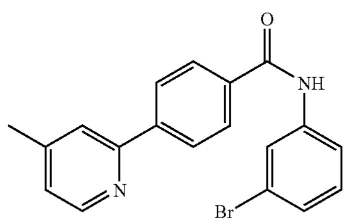 | 367.25 | 369.04 | 2.61 | 2.51 | 2.98 | ++++ |
| 219 | 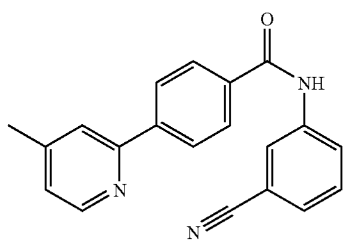 | 313.36 | 314.12 | 2.28 | 2.19 | 2.60 | ++++ |
| 220 | 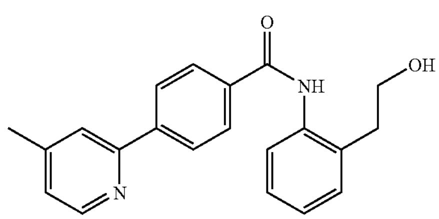 | 332.41 | 333.25 | 2.04 | 1.86 | 2.41 | + |
| 221 | 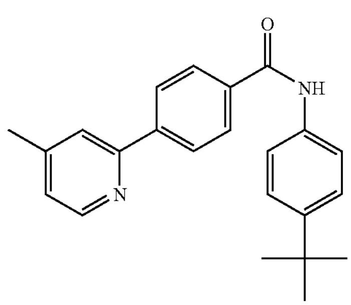 | 344.46 | 345.09 | 2.92 | 2.82 | 3.28 | ++ |
| 222 | 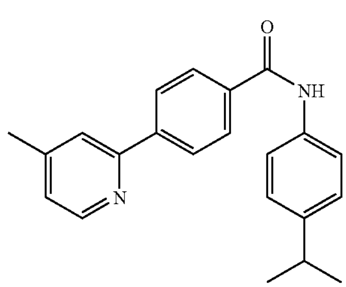 | 330.43 | 331.26 | 2.79 | 2.73 | 3.13 | ++ |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 223 | 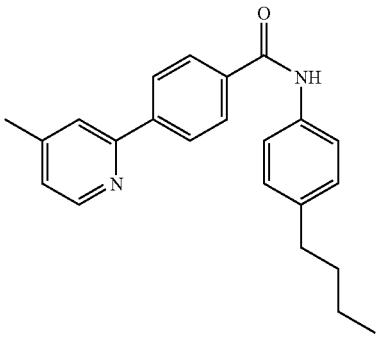 | 344.46 | 345.09 | 3.04 | 2.82 | 3.36 | ++++ |
| 224 | 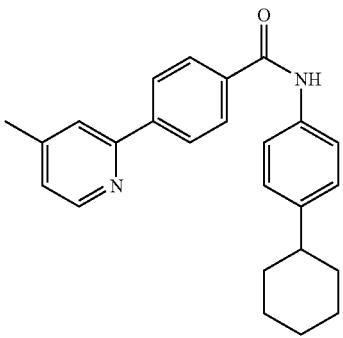 | 370.50 | 371.18 | 3.25 | 3.13 | 3.55 | |
| 225 | 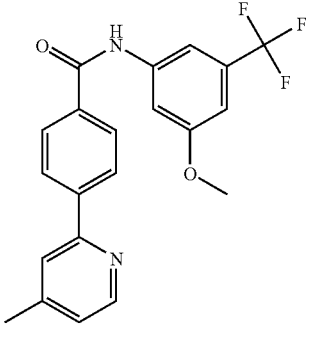 | 386.38 | 387.20 | 2.82 | 2.72 | 3.12 | |
| 226 | 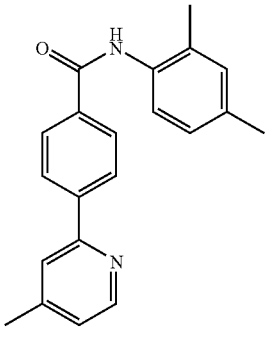 | 316.41 | 317.20 | 2.41 | 2.31 | 2.74 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 227 | 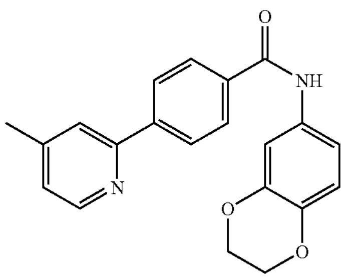 | 346.39 | 347.14 | 2.20 | 1.96 | 2.55 | +++ |
| 228 | 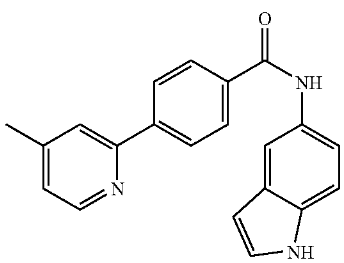 | 327.39 | 328.28 | 2.13 | 2.00 | 2.46 | +++ |
| 229 | 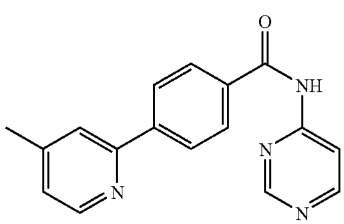 | 290.33 | | | | | |
| 230 | 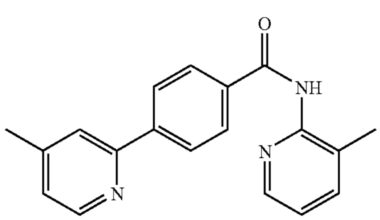 | 303.37 | 304.16 | 1.65 | 1.55 | 2.08 | + |
| 231 | 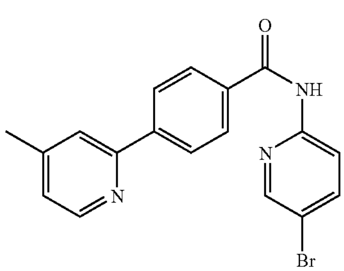 | 368.24 | 370.07 | 2.43 | 2.23 | 2.65 | + |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 232 | 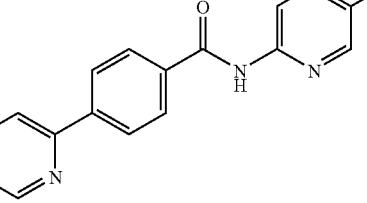 | 357.34 | 358.17 | 2.62 | 2.48 | 2.82 | + |
| 233 | 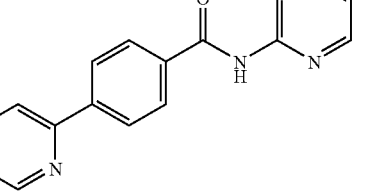 | 391.78 | 392.10 | 2.44 | 2.36 | 2.65 | + |
| 234 | 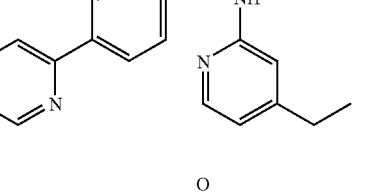 | 317.39 | 318.12 | 1.82 | 1.76 | 2.05 | |
| 235 | 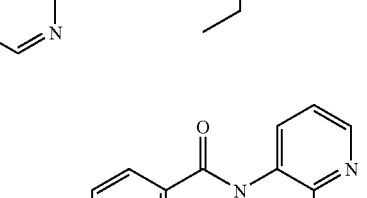 | 282.39 | 283.38 | 2.23 | 2.16 | 2.52 | |
| 236 | 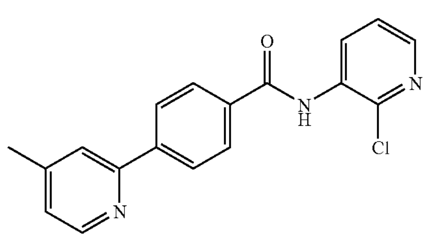 | 323.78 | 324.28 | 1.96 | 1.86 | 2.06 | |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 237 | 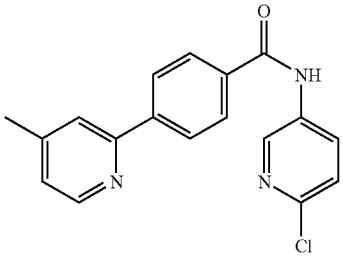 | 323.78 | 324.28 | 2.16 | 2.05 | 2.46 | + |
| 238 | 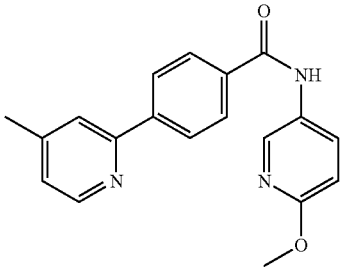 | 319.37 | 320.14 | 1.95 | 1.88 | 2.20 | |
| 239 | 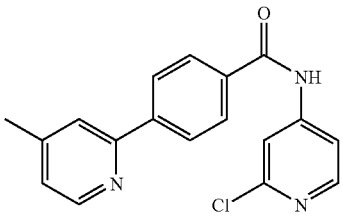 | 323.78 | 324.28 | 2.16 | 2.07 | 2.49 | + |
| 240 | 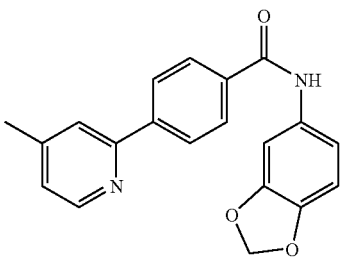 | 332.36 | 333.22 | 2.20 | 2.09 | 2.63 | + |
| 241 | 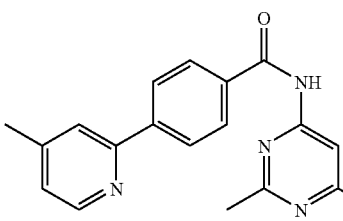 | 318.38 | 319.08 | 1.65 | 1.57 | 1.92 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|----|-----------|-----------|----------|---------------|----------------------|---------------------|---------------------|
| 242 | 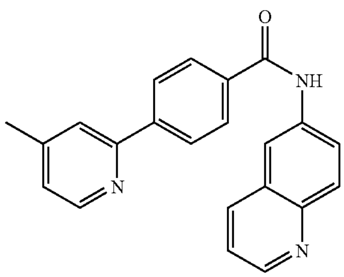 | 339.40 | 340.18 | 1.78 | 1.72 | 2.02 | + |
| 243 | 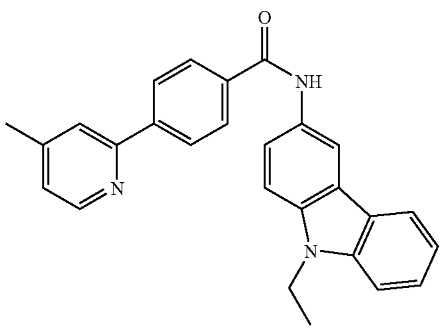 | 405.50 | 406.35 | 2.93 | 2.79 | 3.19 | ++ |
| 244 | 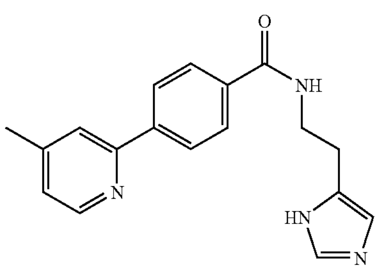 | 306.37 | 307.28 | 1.47 | 1.39 | 1.59 | + |
| 245 | 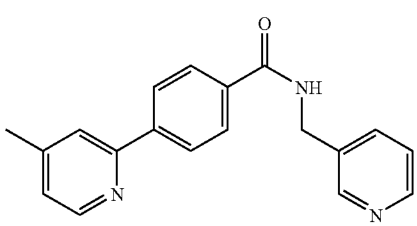 | 303.37 | 304.15 | 1.47 | 1.37 | 1.82 | + |
| 246 | 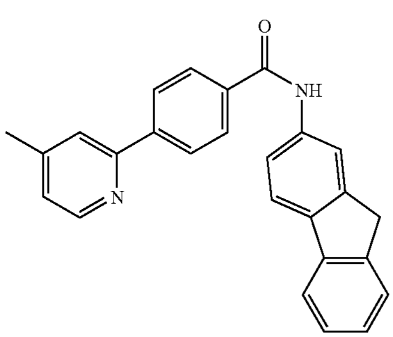 | 376.46 | 377.34 | 2.93 | 2.88 | 3.12 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 247 | 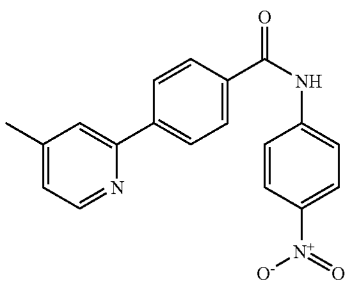 | 333.35 | 334.18 | 2.48 | 2.33 | 2.72 | |
| 248 | 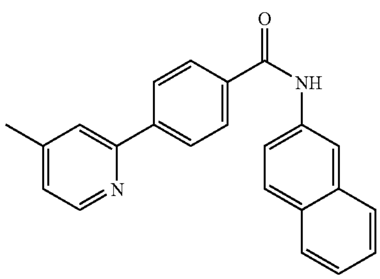 | 338.41 | 339.20 | 2.68 | 2.60 | 2.88 | + |
| 249 | 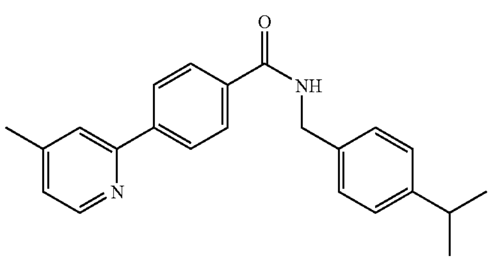 | 344.46 | 345.09 | 2.75 | 2.66 | 3.12 | |
| 250 | 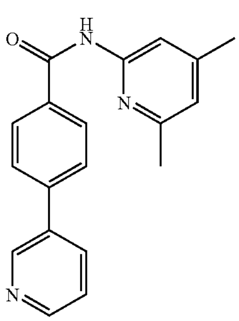 | 303.37 | 304.16 | 1.70 | 1.65 | 1.92 | |
| 251 | 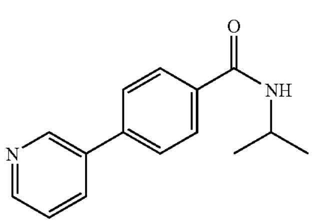 | 240.31 | 241.07 | 1.72 | 1.67 | 1.82 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 252 | 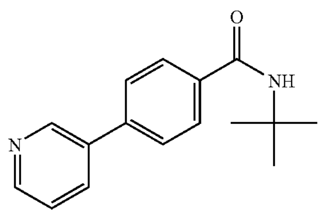 | 254.33 | 255.40 | 1.99 | 1.89 | 2.25 | |
| 253 | 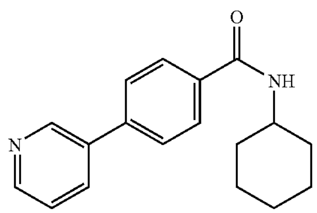 | 280.37 | 281.35 | 2.19 | 2.10 | 2.53 | |
| 254 | 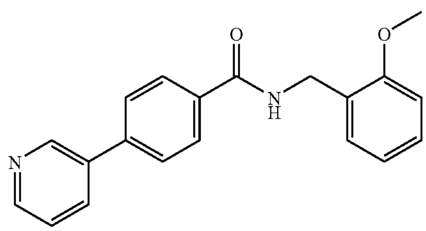 | 318.38 | 319.08 | 2.19 | 2.10 | 2.56 | |
| 255 | 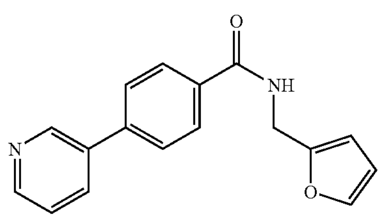 | 278.31 | 279.21 | 1.83 | 1.76 | 2.11 | + |
| 256 | 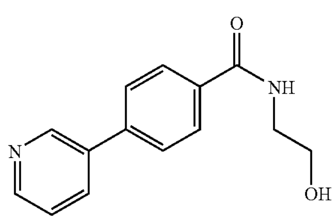 | 242.28 | 243.27 | 1.32 | 1.19 | 1.42 | ++ |
| 257 | 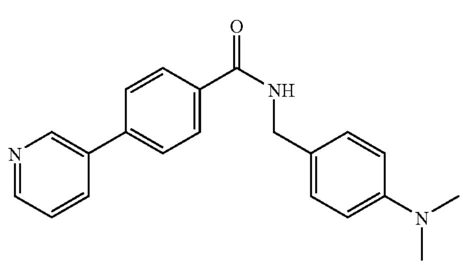 | 331.42 | 332.28 | 1.50 | 1.42 | 1.75 | ++ |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 258 | 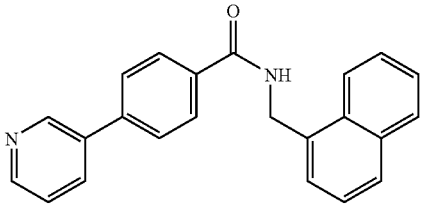 | 338.41 | 339.22 | 2.49 | 2.40 | 2.88 | |
| 259 | 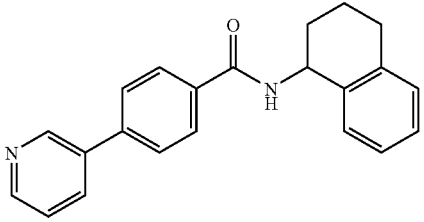 | 328.42 | 329.29 | 2.45 | 2.35 | 2.79 | |
| 260 | 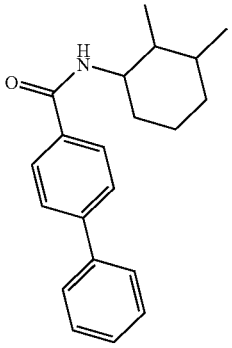 | 308.43 | 309.43 | 2.50 | 2.38 | 2.90 | + |
| 261 | 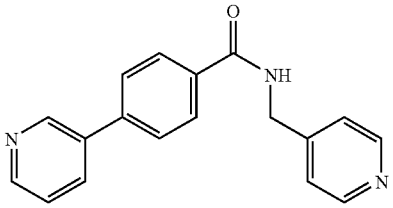 | 289.34 | 290.27 | 1.30 | 1.09 | 1.42 | + |
| 262 | 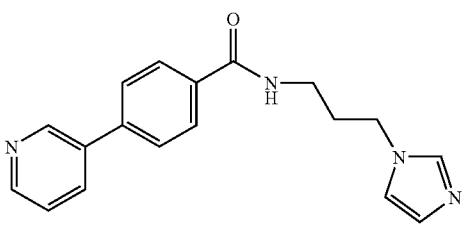 | 306.37 | | | | | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 263 | 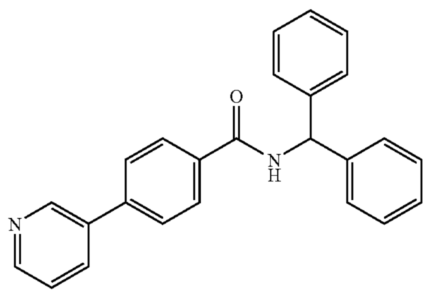 | 364.45 | 365.15 | 2.69 | 2.56 | 2.92 | + |
| 264 | 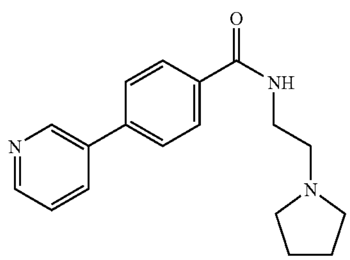 | 295.39 | 296.31 | 1.35 | 1.23 | 1.67 | + |
| 265 | 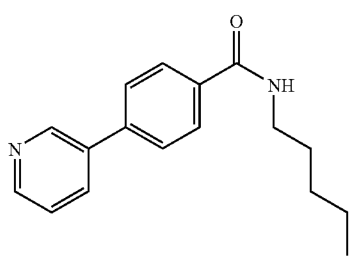 | 268.36 | 269.33 | 2.22 | 2.05 | 2.60 | |
| 266 | 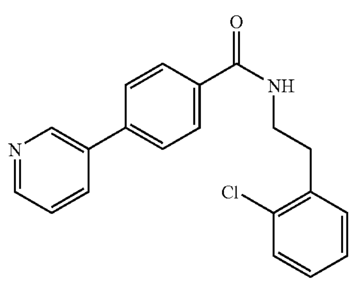 | 336.82 | 337.37 | 2.42 | 2.33 | 2.69 | +++ |
| 267 | 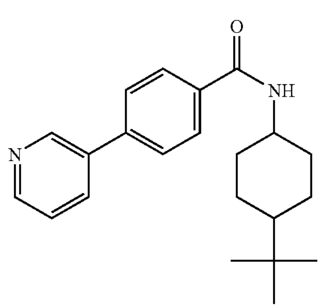 | 336.48 | 337.49 | 2.96 | 2.80 | 3.32 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 268 | 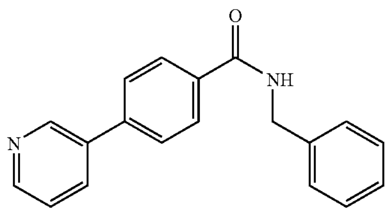 | 288.35 | 289.14 | 2.11 | 1.98 | 2.41 | |
| 269 | 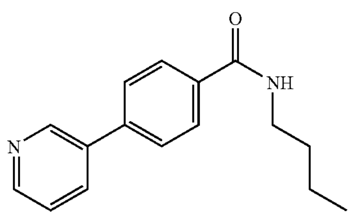 | 254.33 | 255.40 | 1.98 | 1.89 | 2.26 | |
| 270 | 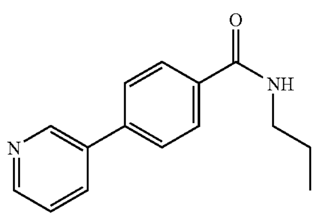 | 240.31 | 241.10 | 1.73 | 1.63 | 1.95 | |
| 271 | 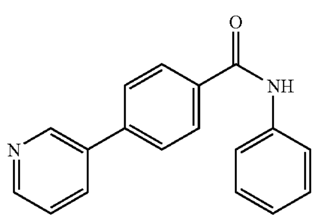 | 274.33 | 275.18 | 2.18 | 2.09 | 2.39 | |
| 272 | 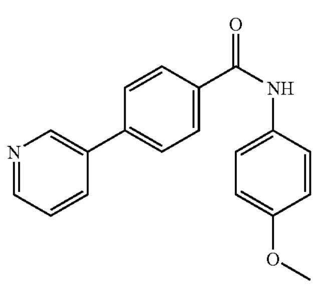 | 304.35 | 305.31 | 2.17 | 2.10 | 2.33 | |
| 273 | 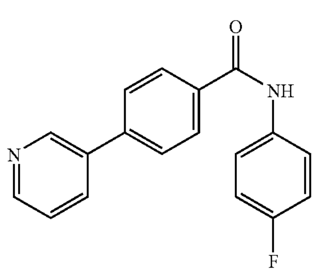 | 292.32 | 293.07 | 2.28 | 2.10 | 2.50 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 274 | 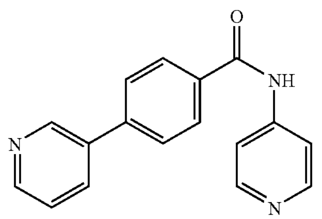 | 275.31 | 276.27 | 1.50 | 1.40 | 1.73 | |
| 275 | 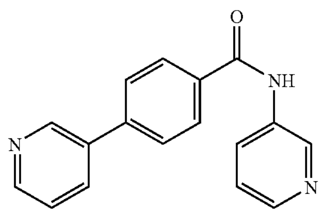 | 275.31 | 276.25 | 1.47 | 1.40 | 1.66 | + |
| 276 | 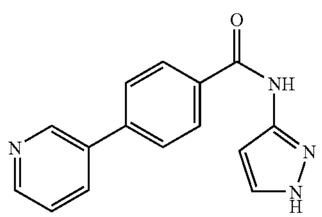 | 264.29 | 265.06 | 1.57 | 1.45 | 1.85 | + |
| 277 | 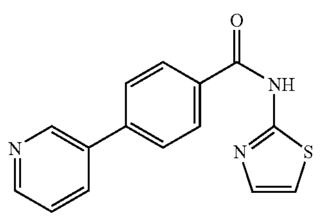 | 281.34 | 282.27 | 1.95 | 1.87 | 2.12 | +++ |
| 278 | 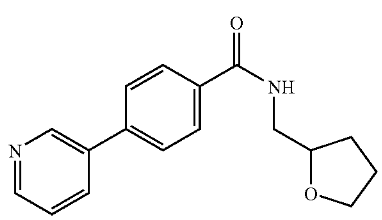 | 282.35 | 283.38 | 1.65 | 1.56 | 1.96 | + |
| 279 | 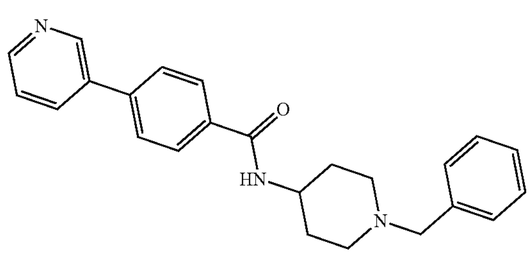 | 371.49 | 372.23 | 1.73 | 1.63 | 2.00 | |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 280 | 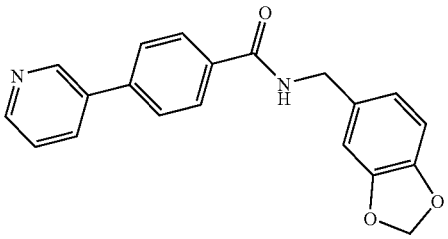 | 332.36 | 333.25 | 2.09 | 2.02 | 2.52 | |
| 281 | 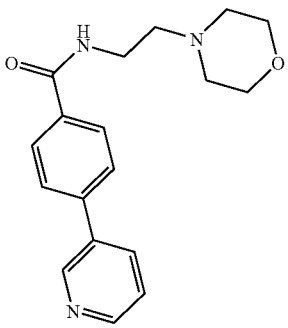 | 311.39 | 312.28 | 1.32 | 1.09 | 1.43 | + |
| 282 | 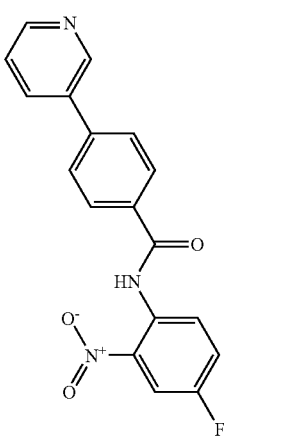 | 337.31 | 338.29 | 2.46 | 2.40 | 2.65 | + |
| 283 | 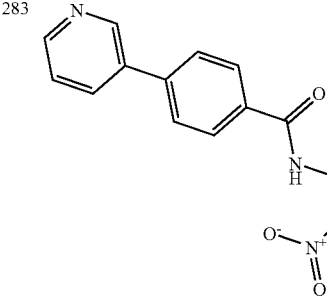 | 319.32 | 320.12 | 2.40 | 2.35 | 2.58 | |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 284 | 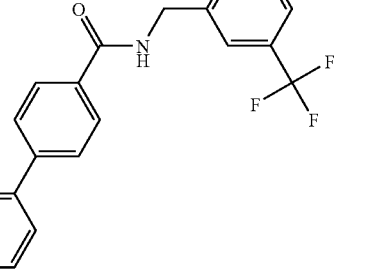 | 318.38 | 319.08 | 2.12 | 2.08 | 2.51 | + |
| 285 | 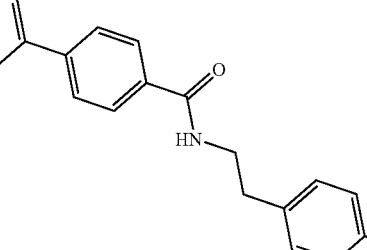 | 356.35 | 357.09 | 2.52 | 2.42 | 2.88 | + |
| 286 | 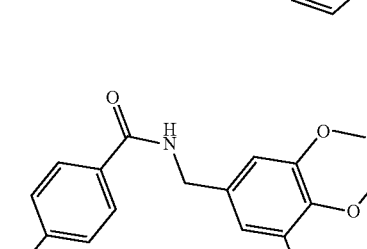 | 381.46 | 382.24 | 1.75 | 1.60 | 1.92 | + |
| 287 | 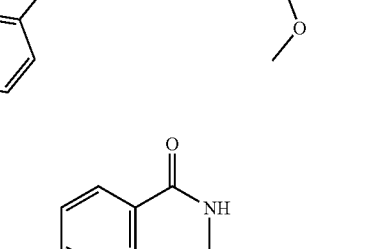 | 378.43 | 379.34 | 2.00 | 1.93 | 2.30 | |
| 288 | 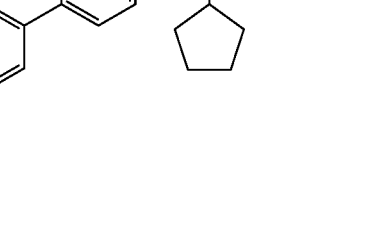 | 266.35 | 267.10 | 1.98 | 1.92 | 2.31 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 289 | 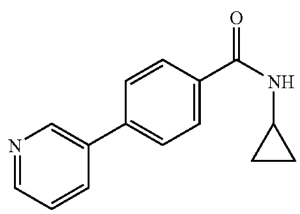 | 238.29 | 239.06 | 1.56 | 1.50 | 1.79 | |
| 290 | 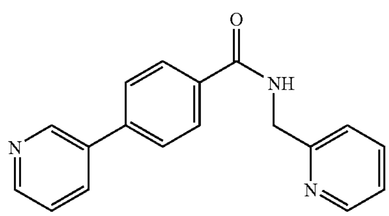 | 289.34 | 290.27 | 1.32 | 1.23 | 1.62 | + |
| 291 | 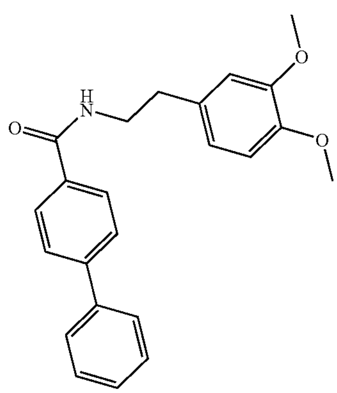 | 362.43 | 363.42 | 2.06 | 1.99 | 2.39 | + |
| 292 | 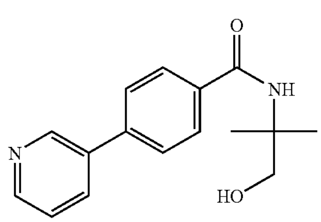 | 270.33 | 271.33 | 1.59 | 1.53 | 1.81 | + |
| 293 | 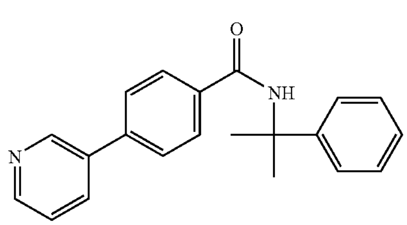 | 316.41 | 317.22 | 2.36 | 2.26 | 2.65 | + |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|----|-----------|-----------|----------|---------------|------------------------|----------------------|---------------------|
| 294 | 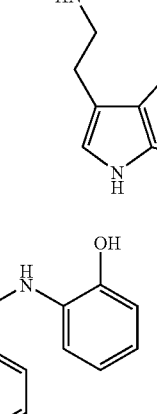 | 341.42 | 342.25 | 2.25 | 2.07 | 2.59 | |
| 295 | 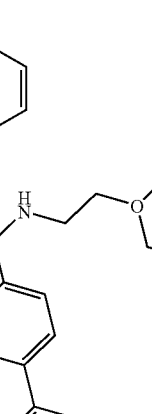 | 290.32 | 291.07 | 2.01 | 1.91 | 2.33 | |
| 296 | 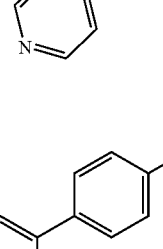 | 310.40 | | | | | |
| 297 | 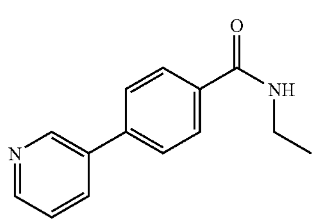 | 226.28 | 227.26 | 1.53 | 1.42 | 1.77 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 298 | 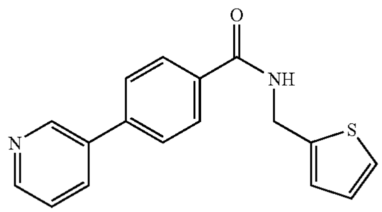 | 294.38 | 295.20 | 2.00 | 1.93 | 2.31 | +++ |
| 299 | 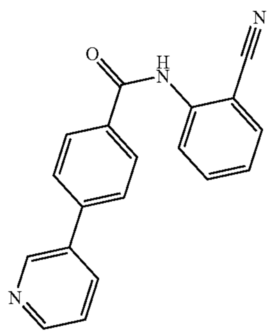 | 299.33 | 300.26 | 2.02 | 1.95 | 2.35 | + |
| 300 | 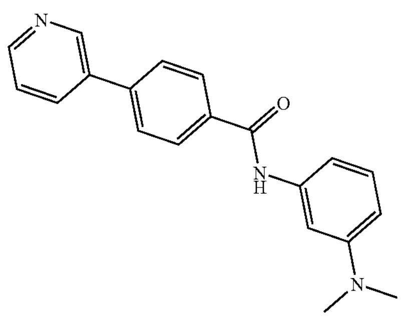 | 317.39 | 318.13 | 1.62 | 1.56 | 1.95 | + |
| 301 | 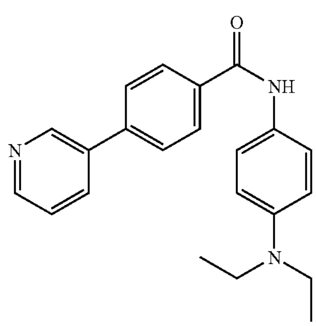 | 345.45 | 346.22 | 1.69 | 1.60 | 2.15 | ++ |
| 302 | 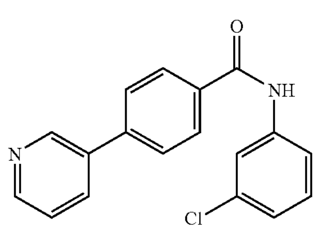 | 308.77 | 309.30 | 2.52 | 2.40 | 2.72 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 303 | 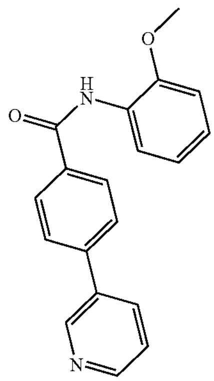 | 304.35 | 305.31 | 2.25 | 2.13 | 2.59 | + |
| 304 | 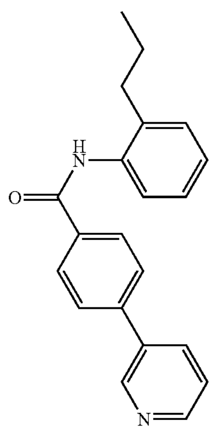 | 316.41 | 317.22 | 2.48 | 2.36 | 2.86 | |
| 305 | 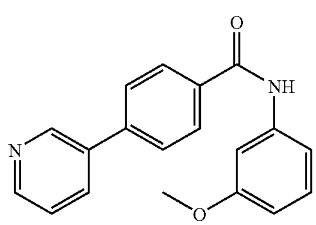 | 304.35 | 305.30 | 2.24 | 2.14 | 2.55 | + |
| 306 | 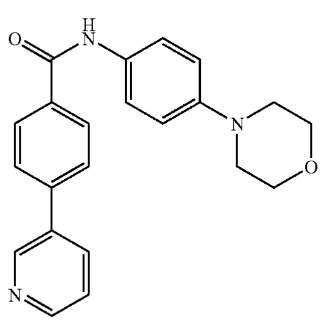 | 359.43 | 360.29 | 0.72 | 0.63 | 0.86 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 307 | 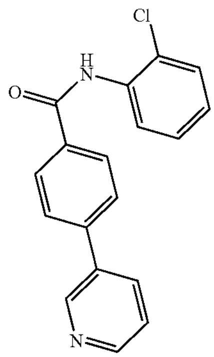 | 308.77 | 309.29 | 2.26 | 2.10 | 2.58 | |
| 308 | 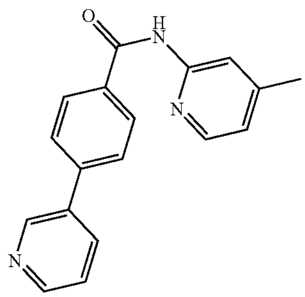 | 289.34 | 290.21 | 1.59 | 1.55 | 1.81 | |
| 309 | 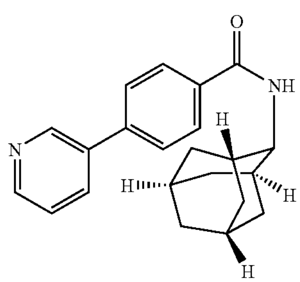 | 332.45 | 333.30 | 2.65 | 2.59 | 2.92 | |
| 310 | 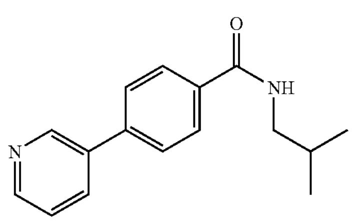 | 254.33 | 255.40 | 1.93 | 1.85 | 2.16 | + |
| 311 | 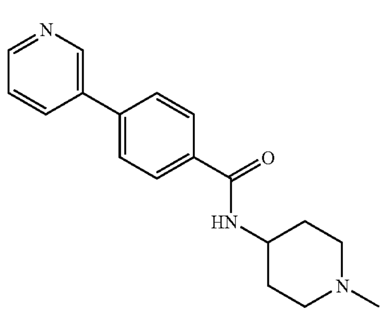 | 295.39 | 296.33 | 1.30 | 1.00 | 1.57 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 312 | N-(2,4-dichlorophenyl)-4-(pyridin-3-yl)benzamide | 343.22 | 343.09 | 2.62 | 2.52 | 2.80 | + |
| 313 | N-(3,4-dimethoxybenzyl)-4-(pyridin-3-yl)benzamide | 348.41 | 349.30 | 1.99 | 1.93 | 2.25 | + |
| 314 | N-(3-fluorobenzyl)-4-(pyridin-3-yl)benzamide | 306.34 | 307.27 | 2.19 | 2.12 | 2.45 | + |
| 315 | N-(3,4-dichlorobenzyl)-4-(pyridin-3-yl)benzamide | 357.24 | 357.09 | 2.58 | 2.49 | 2.91 | + |
| 316 | N-(3-chloro-4-methoxyphenyl)-4-(pyridin-3-yl)benzamide | 338.80 | 339.13 | 2.39 | 2.29 | 2.72 | ++++ |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 317 | 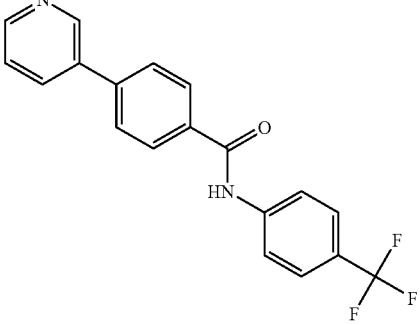 | 342.32 | 343.09 | 2.73 | 2.62 | 3.09 | |
| 318 | 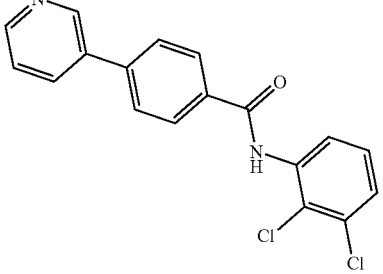 | 343.22 | 343.09 | 2.56 | 2.45 | 2.95 | + |
| 319 | 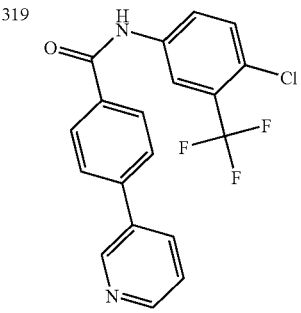 | 376.77 | 377.27 | 2.88 | 2.82 | 3.18 | + |
| 320 | 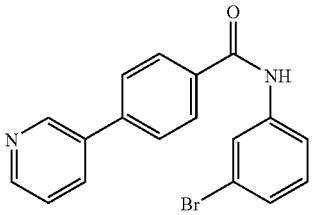 | 353.22 | 355.12 | 2.58 | 2.49 | 2.85 | |
| 321 | 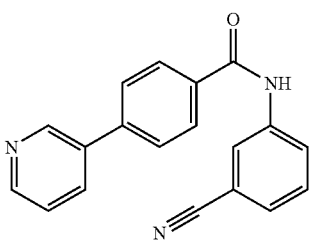 | 299.33 | 300.24 | 2.22 | 2.12 | 2.39 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 322 | 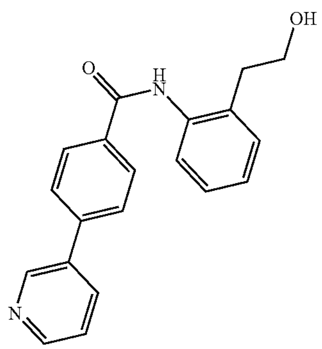 | 318.38 | 319.08 | 1.96 | 1.88 | 2.29 | + |
| 323 | 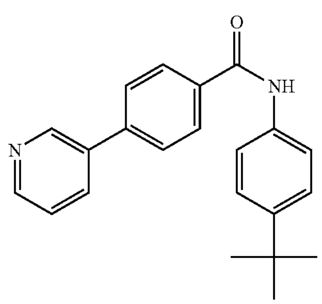 | 330.43 | 331.27 | 2.88 | 2.80 | 3.16 | |
| 324 | 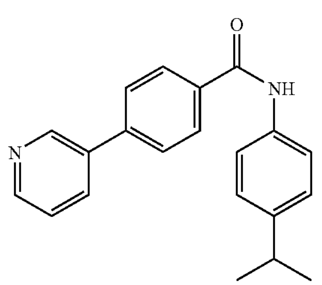 | 316.41 | 317.22 | 2.75 | 2.66 | 3.09 | + |
| 325 | 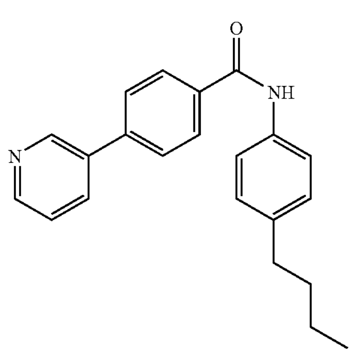 | 330.43 | 331.28 | 3.00 | 2.75 | 3.26 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 326 | 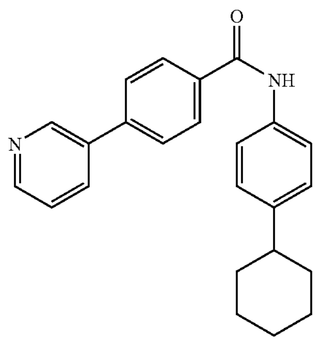 | 356.47 | 357.22 | 3.21 | 2.95 | 3.38 | + |
| 327 | 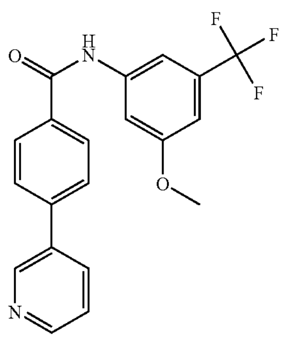 | 372.35 | 373.10 | 2.78 | 2.68 | 3.05 | |
| 328 | 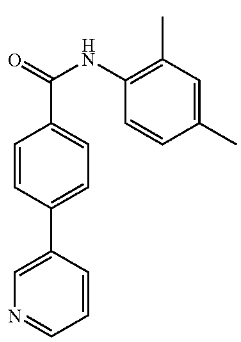 | 302.38 | 303.08 | 2.36 | 2.26 | 2.69 | + |
| 329 | 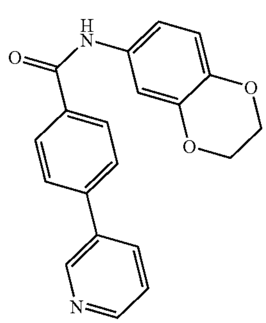 | 332.36 | 333.24 | 2.13 | 2.08 | 2.46 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 330 | 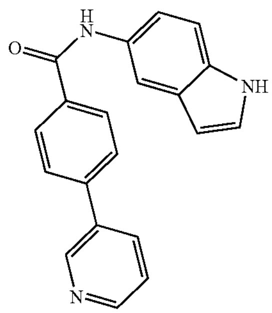 | 313.36 | 314.14 | 2.05 | 1.95 | 2.28 | + |
| 331 | 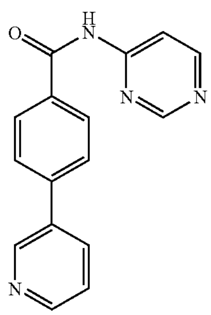 | 276.30 | 277.12 | 1.50 | 1.40 | 1.72 | |
| 332 | 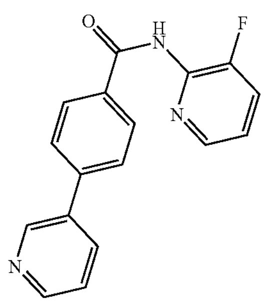 | 289.34 | 290.22 | 1.50 | 1.45 | 1.73 | |
| 333 | 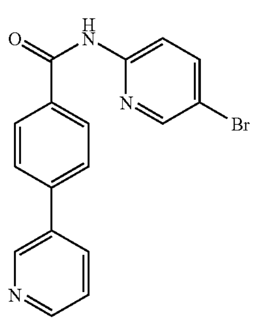 | 354.21 | 354.11 | 2.39 | 2.32 | 2.53 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 334 | 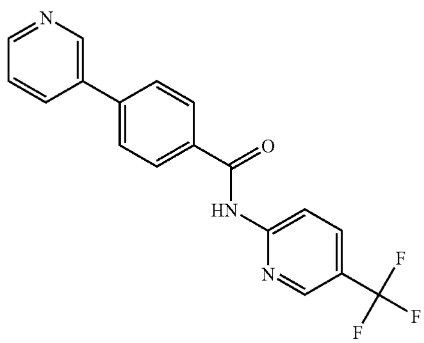 | 343.31 | 344.13 | 2.65 | 2.45 | 2.85 | |
| 335 | 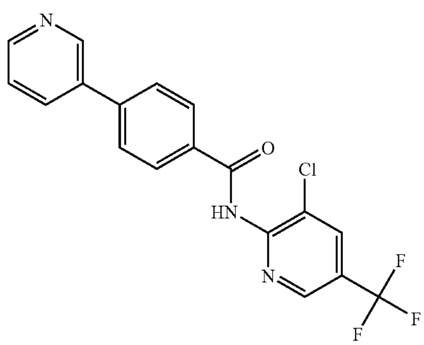 | 377.76 | | | | | |
| 336 | 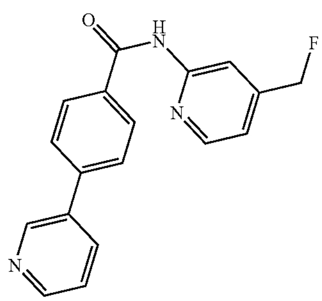 | 303.37 | 304.15 | 1.72 | 1.67 | 2.03 | |
| 337 | 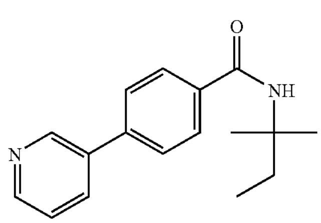 | 268.36 | 269.34 | 2.16 | 2.09 | 2.40 | ++ |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 338 | 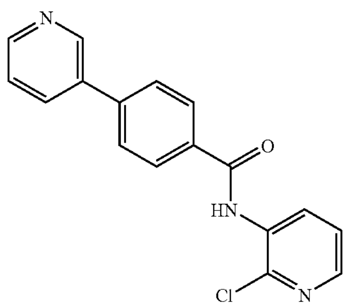 | 309.76 | 310.28 | 1.86 | 1.70 | 1.99 | |
| 339 | 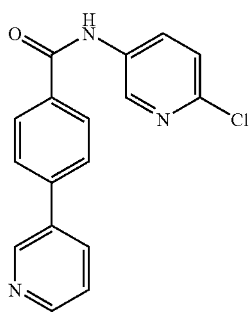 | 309.76 | 310.28 | 2.11 | 1.98 | 2.31 | + |
| 340 | 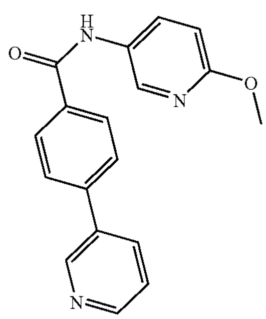 | 305.34 | 306.28 | 1.86 | 1.81 | 2.12 | |
| 341 | 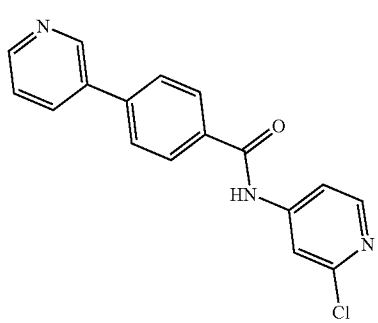 | 309.76 | 310.28 | 2.08 | 1.99 | 2.22 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 342 | 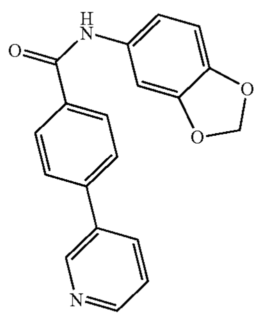 | 318.34 | 319.04 | 2.13 | 2.03 | 2.46 | + |
| 343 | 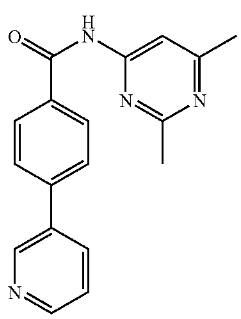 | 304.35 | 305.31 | 1.50 | 1.43 | 1.73 | |
| 344 | 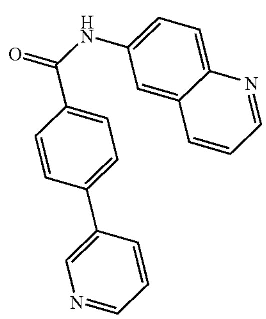 | 325.37 | 326.28 | 1.67 | 1.62 | 1.87 | + |
| 345 | 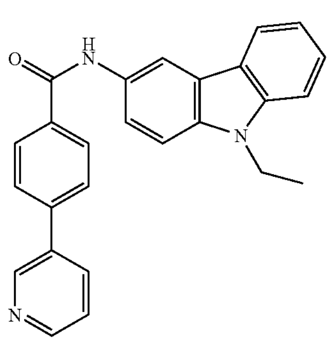 | 391.48 | 392.29 | 2.87 | 2.77 | 3.19 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 346 | 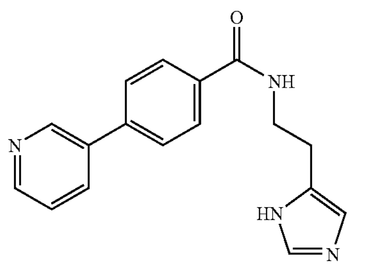 | 292.34 | 293.07 | 1.35 | 1.04 | 1.62 | + |
| 347 | 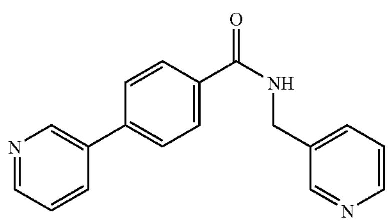 | 289.34 | 290.24 | 1.35 | 1.26 | 1.45 | + |
| 348 | 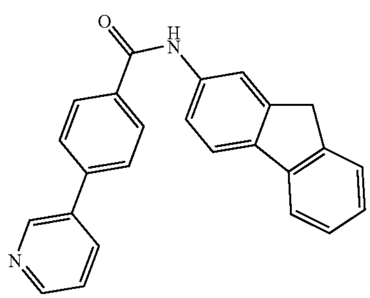 | 362.44 | 363.38 | 2.90 | 2.85 | 3.06 | |
| 349 | 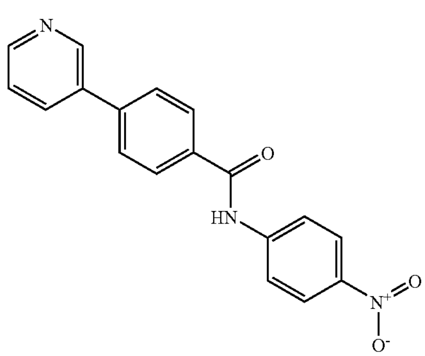 | 319.32 | 320.12 | 2.42 | 2.35 | 2.60 | |
| 350 | 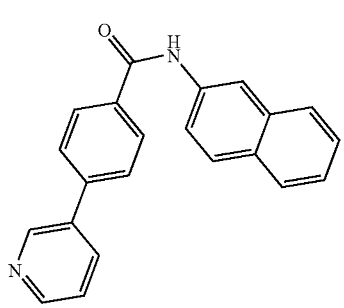 | 324.39 | 325.32 | 2.62 | 2.49 | 2.90 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 351 | 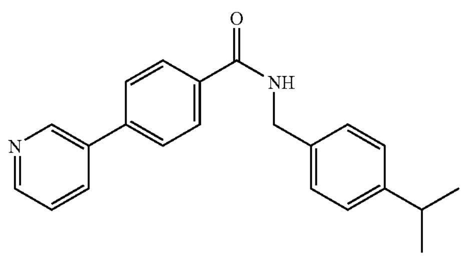 | 330.43 | 331.26 | 2.66 | 2.56 | 3.14 | |
| 352 | 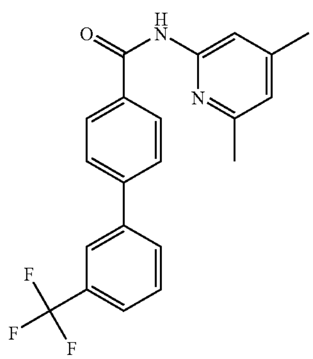 | 371.37 | 372.09 | 2.82 | 2.65 | 3.08 | + |
| 353 | 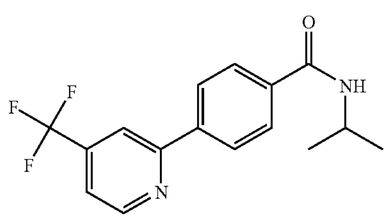 | 308.31 | 309.31 | 3.13 | 3.02 | 3.38 | |
| 354 | 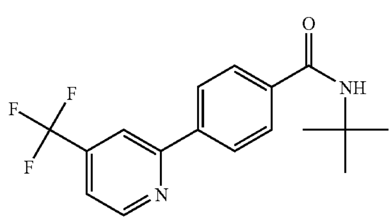 | 322.33 | 323.19 | 3.49 | 3.36 | 3.73 | ++ |
| 355 | 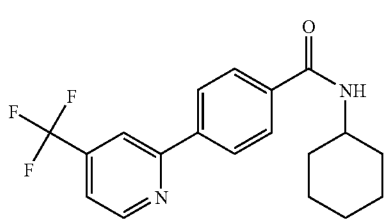 | 348.37 | 349.28 | 3.61 | 3.48 | 3.92 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 356 | 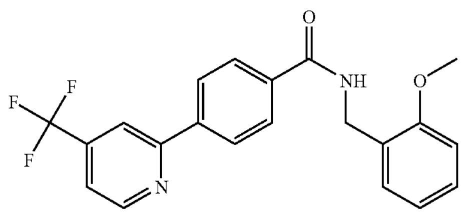 | 386.38 | 387.19 | 3.55 | 3.46 | 3.92 | |
| 357 | 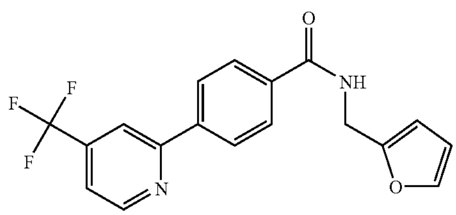 | 346.31 | 347.09 | 3.29 | 3.16 | 3.52 | |
| 358 | 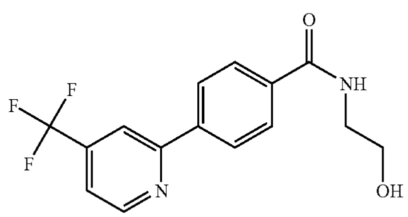 | 310.28 | 311.29 | 2.50 | 2.40 | 2.76 | + |
| 359 | 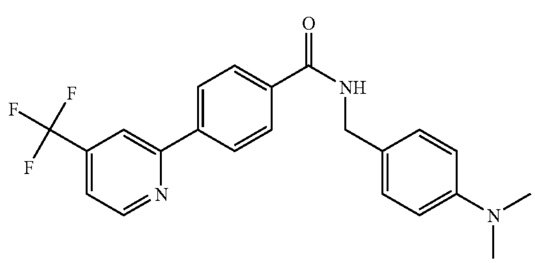 | 399.42 | 400.17 | 2.58 | 2.45 | 2.79 | |
| 360 | 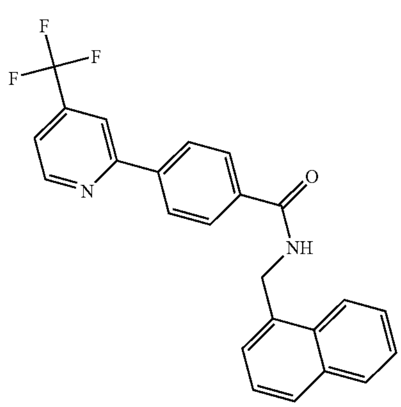 | 406.41 | 407.23 | 3.81 | 3.69 | 4.19 | |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 361 | 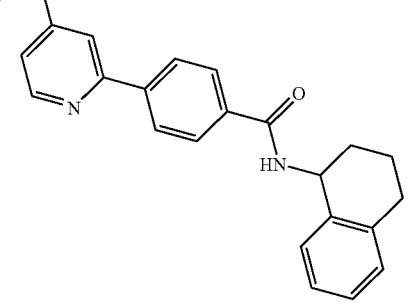 | 396.42 | 397.16 | 3.88 | 3.75 | 4.18 | + |
| 362 | 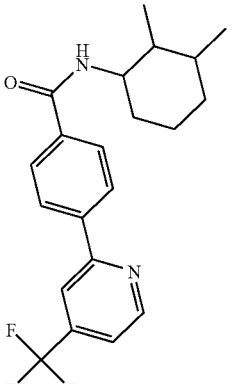 | 376.43 | 377.35 | 3.96 | 3.63 | 4.41 | + |
| 363 | 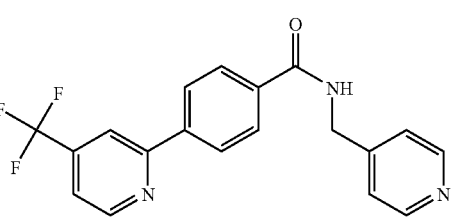 | 357.34 | 358.15 | 2.42 | 2.36 | 2.58 | + |
| 364 | 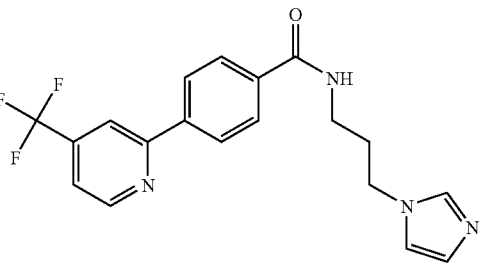 | 374.37 | 375.19 | 2.41 | 2.32 | 2.68 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 365 | 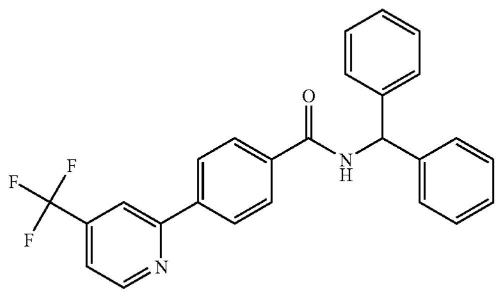 | 432.45 | 433.25 | 3.95 | 3.86 | 4.39 | + |
| 366 | 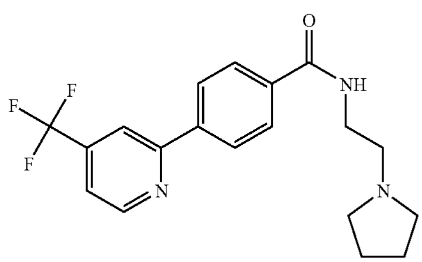 | 363.39 | 364.29 | 2.44 | 2.36 | 2.68 | |
| 367 | 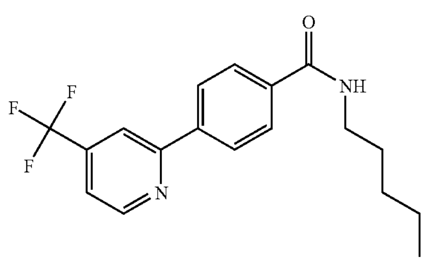 | 336.36 | 337.40 | 3.65 | 3.55 | 3.93 | |
| 368 | 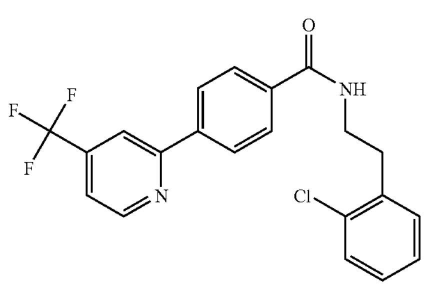 | 404.82 | 405.29 | 3.78 | 3.68 | 4.02 | + |
| 369 | 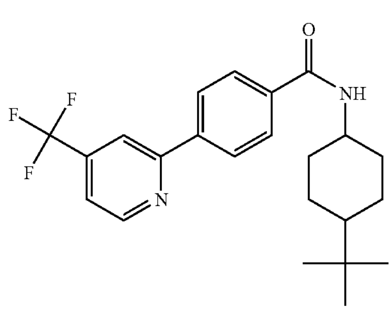 | 404.48 | 405.40 | 4.38 | 4.21 | 4.64 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 370 | 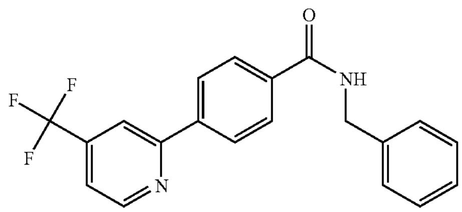 | 356.35 | 357.09 | 3.48 | 3.37 | 3.68 | |
| 371 | 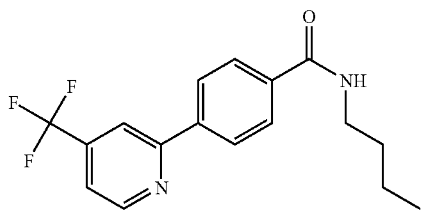 | 322.33 | 323.18 | 3.42 | 3.26 | 3.73 | |
| 372 | 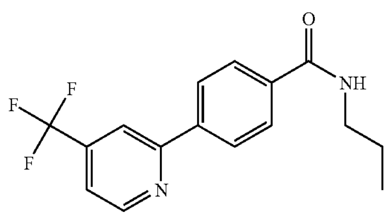 | 308.31 | 309.31 | 3.16 | 3.01 | 3.38 | |
| 373 | 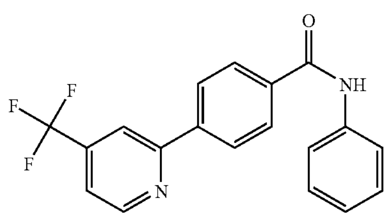 | 342.32 | 343.10 | 3.62 | 3.53 | 3.82 | |
| 374 | 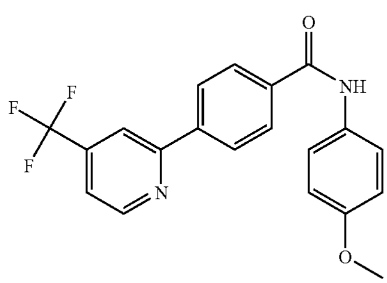 | 372.35 | 373.10 | 3.55 | 3.45 | 3.73 | |
| 375 | 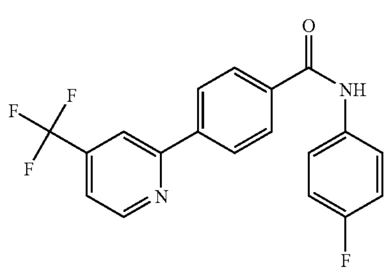 | 360.31 | 361.24 | 3.65 | 3.59 | 3.88 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 376 | 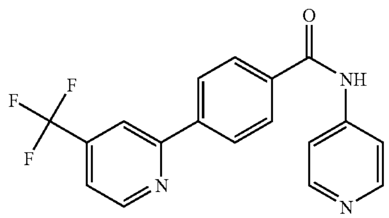 | 343.31 | 344.10 | 2.63 | 2.56 | 2.76 | |
| 377 | 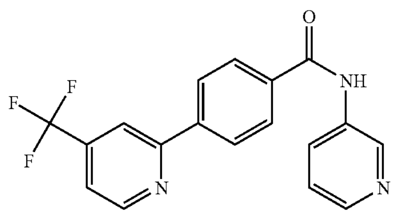 | 343.31 | 344.12 | 2.55 | 2.48 | 2.73 | |
| 378 | 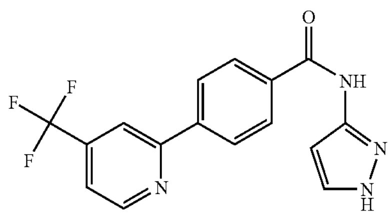 | 332.29 | 333.21 | 2.78 | 2.71 | 3.14 | + |
| 379 | 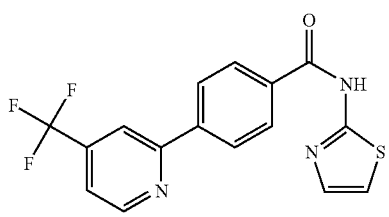 | 349.34 | 350.24 | 3.32 | 3.23 | 3.56 | |
| 380 | 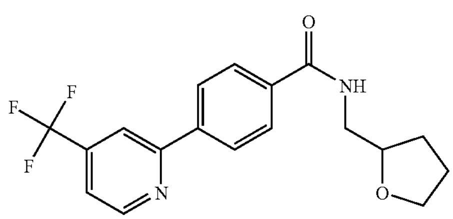 | 350.34 | 351.30 | 2.98 | 2.82 | 3.21 | |
| 381 | 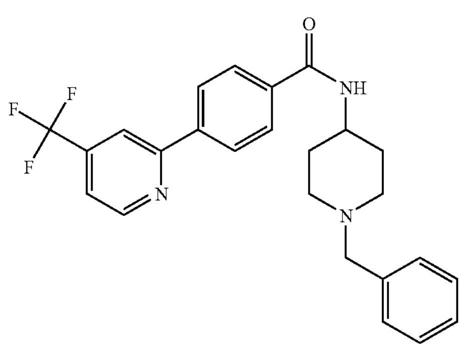 | 439.48 | 440.32 | 2.73 | 2.66 | 2.98 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|----|-----------|-----------|----------|---------------|------------------------|----------------------|----------------------|
| 382 | 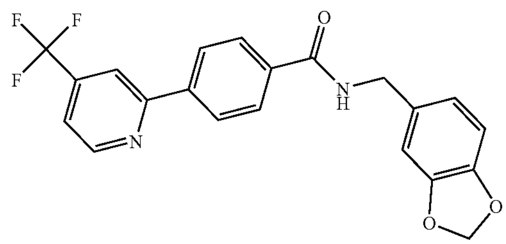 | 400.36 | 401.15 | 3.42 | 3.31 | 3.64 | |
| 383 | 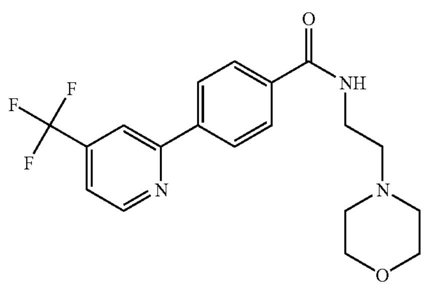 | 379.39 | 380.28 | 2.39 | 2.30 | 2.60 | + |
| 384 | 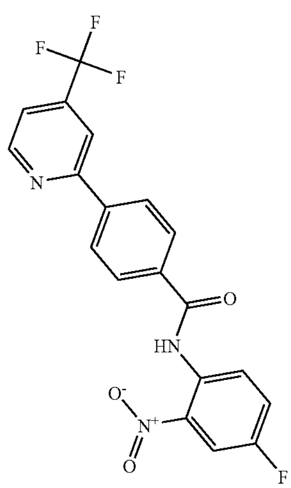 | 405.31 | 406.21 | 4.01 | 3.88 | 4.09 | + |
| 385 | 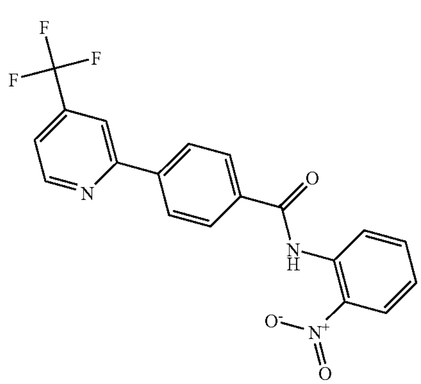 | 387.32 | 388.23 | 4.02 | 3.88 | 4.29 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 386 | 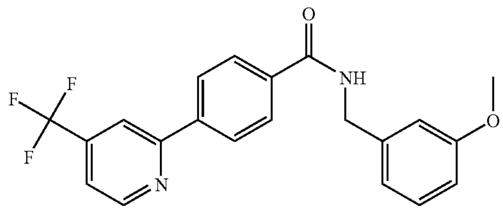 | 386.38 | 387.19 | 3.46 | 3.38 | 3.72 | |
| 387 | 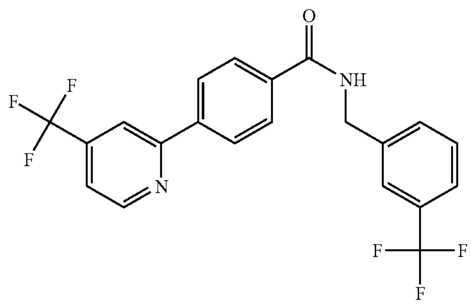 | 424.35 | 425.11 | 3.82 | 3.71 | 4.06 | |
| 388 | 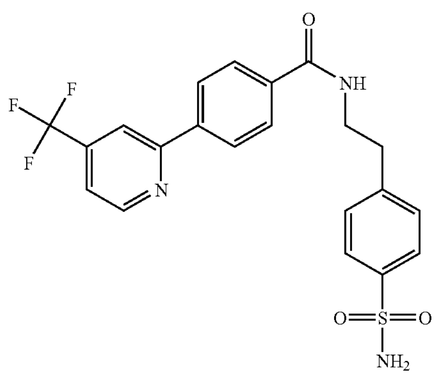 | 449.46 | 450.12 | 2.96 | 2.83 | 3.16 | + |
| 389 | 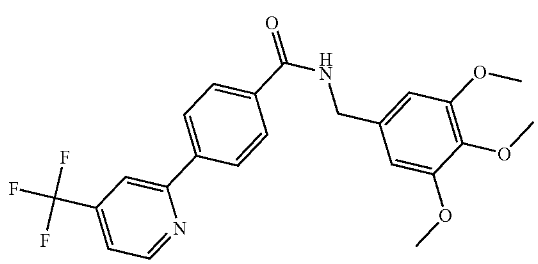 | 446.43 | 447.13 | 3.28 | 3.18 | 3.56 | |
| 390 | 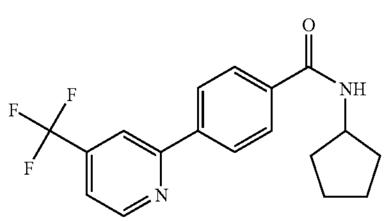 | 334.34 | 335.32 | 3.42 | 3.33 | 3.71 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 391 | 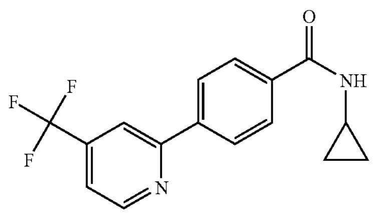 | 306.29 | 307.23 | 2.98 | 2.85 | 3.22 | |
| 392 | 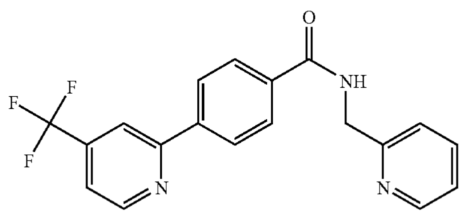 | 357.34 | 358.16 | 2.42 | 2.30 | 2.71 | |
| 393 | 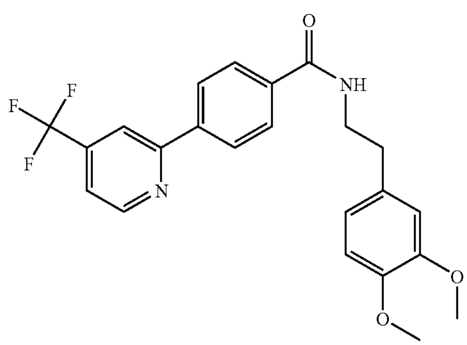 | 430.43 | 431.33 | 3.32 | 3.22 | 3.66 | + |
| 394 | 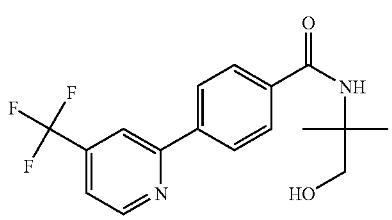 | 338.33 | 339.19 | 2.68 | 2.59 | 2.83 | + |
| 395 | 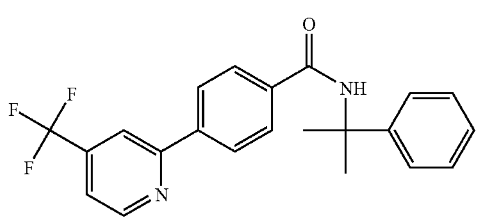 | 384.40 | 385.24 | 3.75 | 3.66 | 4.02 | |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 396 | 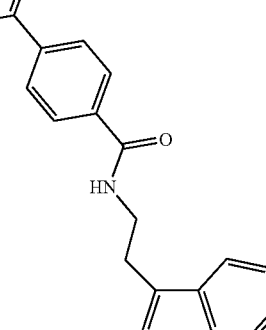 | 409.41 | 410.25 | 3.49 | 3.41 | 3.76 | ++ |
| 397 | 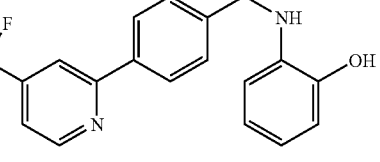 | 358.32 | 359.11 | 3.43 | 3.36 | 3.61 | + |
| 398 | 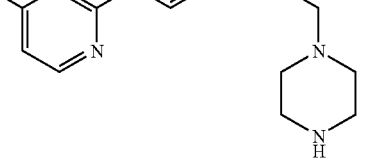 | 378.40 | | | | | |
| 399 | 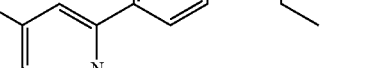 | 294.28 | 295.21 | 2.95 | 2.85 | 3.28 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 400 | 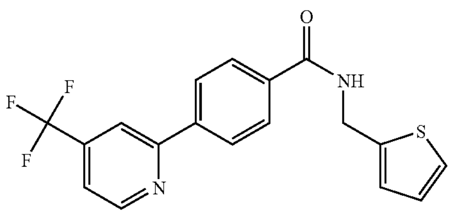 | 362.38 | 363.31 | 3.41 | 3.32 | 3.68 | |
| 401 | 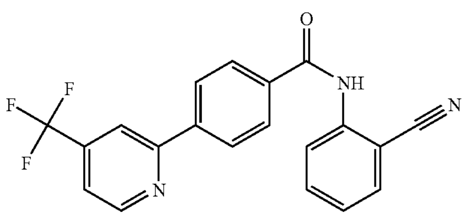 | 367.33 | 368.09 | 3.41 | 3.31 | 3.77 | + |
| 402 | 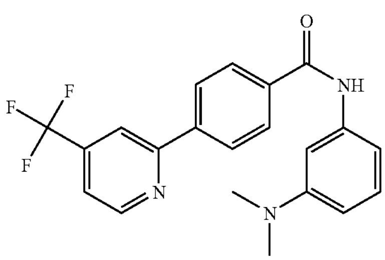 | 385.39 | 386.19 | 2.71 | 2.64 | 3.04 | + |
| 403 | 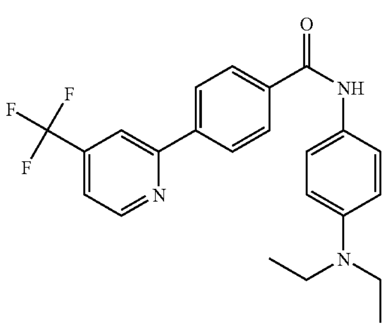 | 413.45 | 414.20 | 2.82 | 2.68 | 3.05 | + |
| 404 | 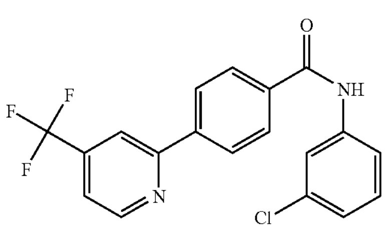 | 376.77 | 377.28 | 3.93 | 3.86 | 4.22 | ++ |
| 405 | 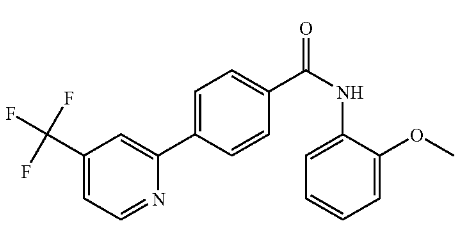 | 372.35 | 373.10 | 3.85 | 3.74 | 4.12 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 406 | 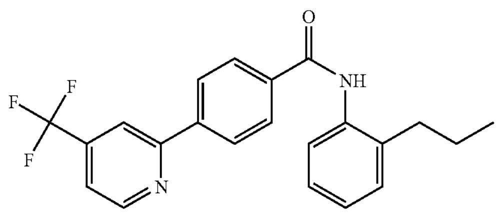 | 384.40 | 385.25 | 3.91 | 3.81 | 4.11 | + |
| 407 | 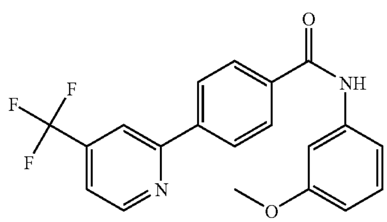 | 372.35 | 373.10 | 3.65 | 3.55 | 3.88 | |
| 408 | 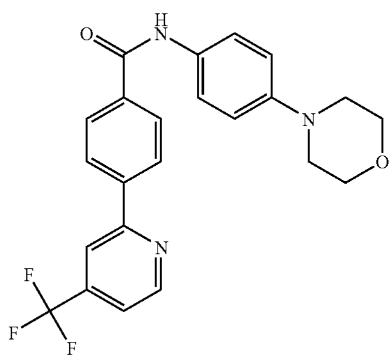 | 427.43 | 428.17 | 2.89 | 2.78 | 3.15 | |
| 409 | 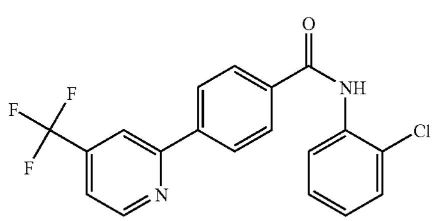 | 376.77 | 377.24 | 3.89 | 3.82 | 4.15 | |
| 410 | 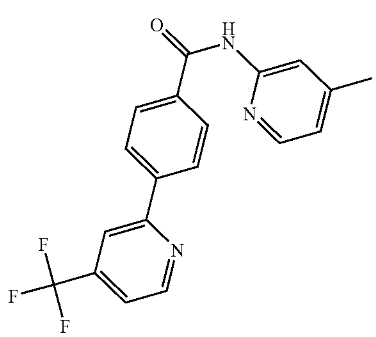 | 357.34 | 358.17 | 2.69 | 2.59 | 3.05 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 411 | 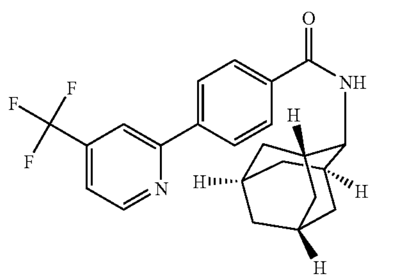 | 400.45 | 401.24 | 4.21 | 4.08 | 4.49 | + |
| 412 | 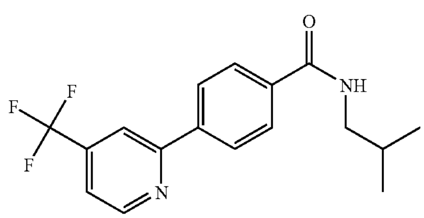 | 322.33 | 323.18 | 3.35 | 3.18 | 3.58 | |
| 413 | 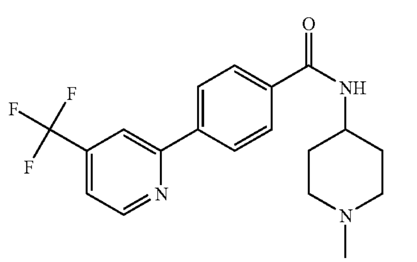 | 363.39 | 364.29 | 2.39 | 2.30 | 2.62 | |
| 414 | 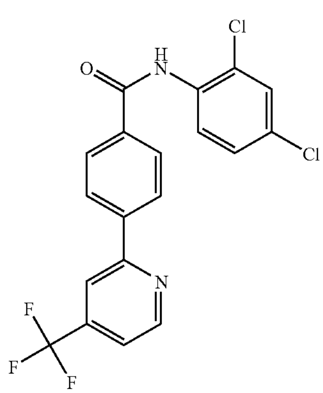 | 411.21 | 411.02 | 4.24 | 4.08 | 4.41 | |
| 415 | 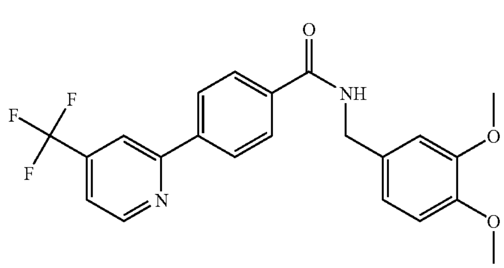 | 416.40 | 417.33 | 3.28 | 3.18 | 3.55 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 416 | 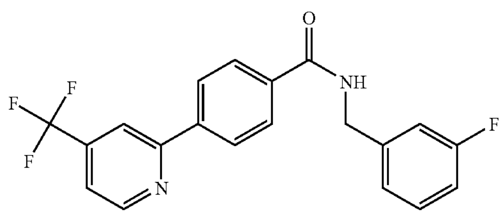 | 374.34 | 375.13 | 3.55 | 3.42 | 3.79 | |
| 417 | 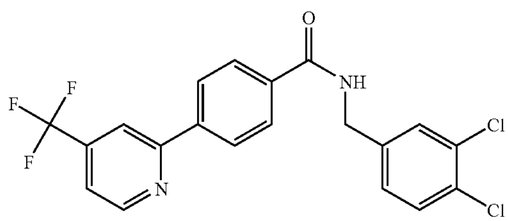 | 425.24 | 425.02 | 3.95 | 3.78 | 4.18 | |
| 418 | 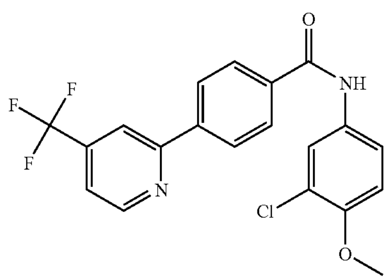 | 406.79 | 407.15 | 3.77 | 3.71 | 3.92 | + |
| 419 | 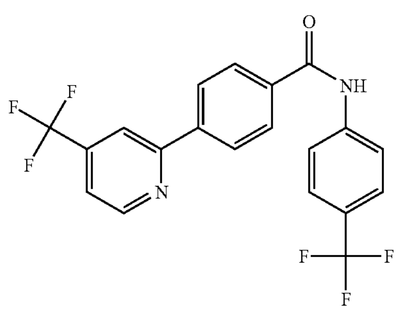 | 410.32 | 411.18 | 4.08 | 3.97 | 4.22 | + |
| 420 | 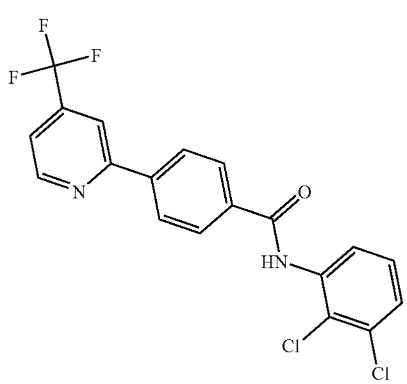 | 411.21 | 410.98 | 4.19 | 4.06 | 4.32 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 421 | 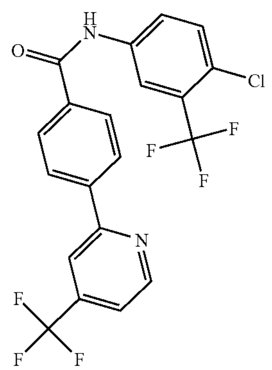 | 444.77 | 445.18 | 4.29 | 4.15 | 4.49 | + |
| 422 | 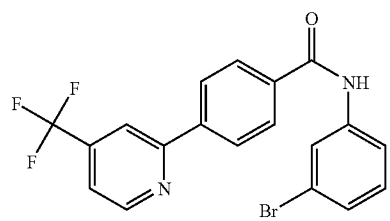 | 421.22 | 422.95 | 4.02 | 3.92 | 4.39 | ++ |
| 423 | 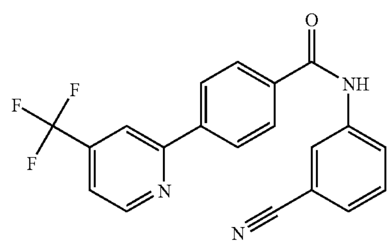 | 367.33 | 368.13 | 3.63 | 3.48 | 3.81 | + |
| 424 | 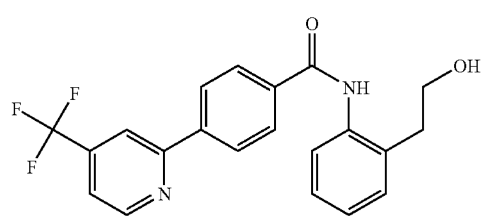 | 386.38 | 387.17 | 3.28 | 3.19 | 3.58 | |
| 425 | 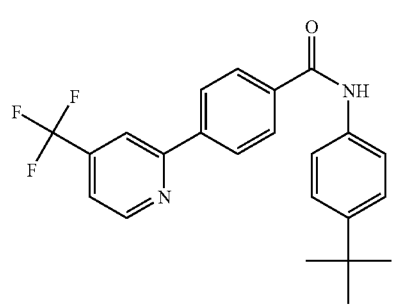 | 398.43 | 399.17 | 4.25 | 4.11 | 4.54 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 426 | 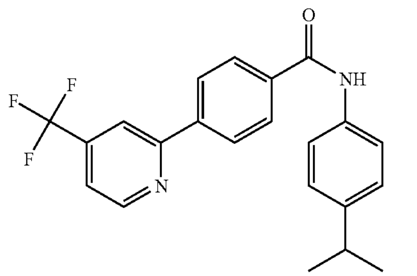 | 384.40 | 385.25 | 4.11 | 3.99 | 4.49 | + |
| 427 | 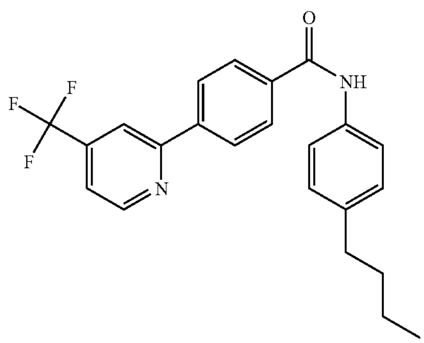 | 398.43 | 399.15 | 4.35 | 4.21 | 4.49 | +++ |
| 428 | 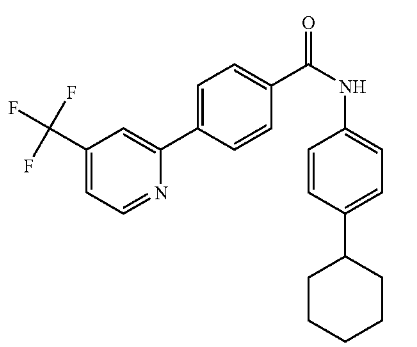 | 424.47 | 425.18 | 4.54 | 4.45 | 4.94 | +++ |
| 429 | 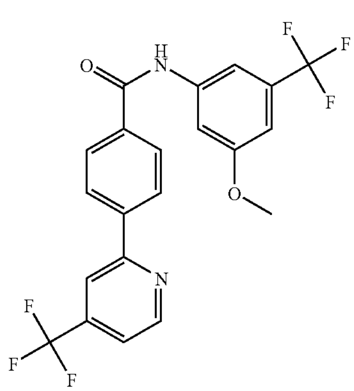 | 440.35 | 441.20 | 4.12 | 4.04 | 4.28 | |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 430 | 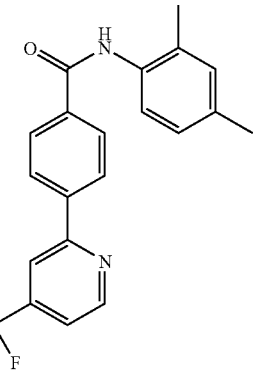 | 370.38 | 371.10 | 3.72 | 3.63 | 4.09 | |
| 431 | 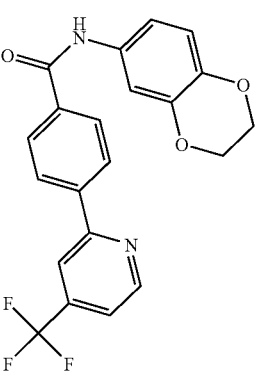 | 400.36 | 401.14 | 3.52 | 3.43 | 3.76 | |
| 432 | 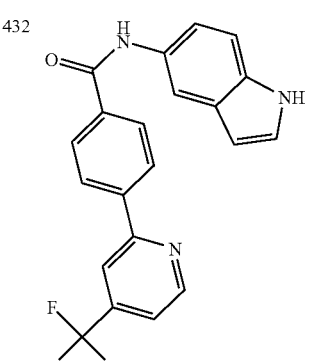 | 381.36 | 382.18 | 3.36 | 3.25 | 3.63 | |
| 433 | 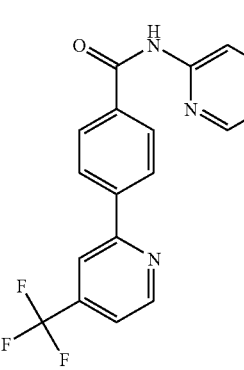 | 344.30 | 345.06 | 2.88 | 2.78 | 3.02 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 434 | 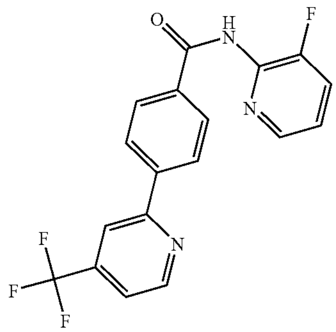 | 357.34 | 358.12 | 2.62 | 2.56 | 2.82 | |
| 435 | 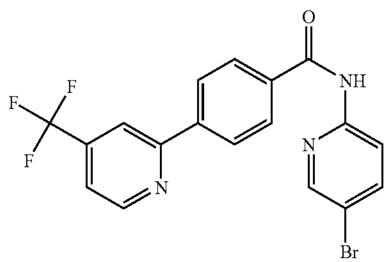 | 422.21 | 424.00 | 3.88 | 3.82 | 4.25 | |
| 436 | 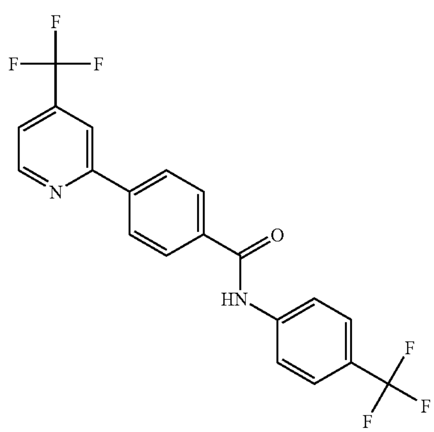 | 411.31 | 412.10 | 3.98 | 3.91 | 4.19 | |
| 437 | 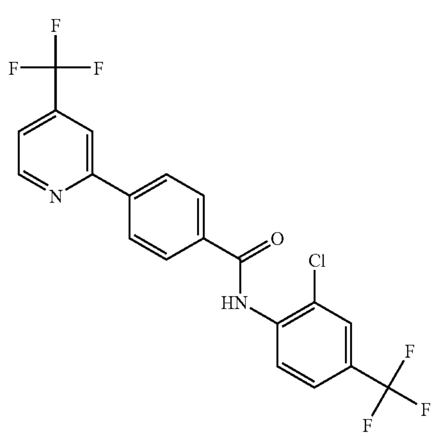 | 445.75 | 446.12 | 3.74 | 3.68 | 3.86 | |

TABLE 1-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 438 | 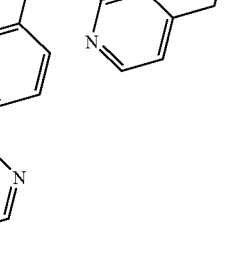 | 371.37 | 372.12 | 2.85 | 2.65 | 3.22 | |
| 439 | 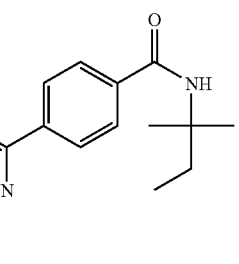 | 336.36 | 337.40 | 3.67 | 3.57 | 3.82 | + |
| 440 | 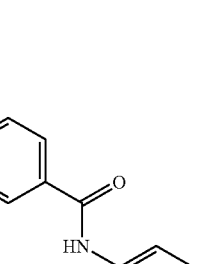 | 377.76 | 378.18 | 3.49 | 3.36 | 3.68 | |
| 441 | 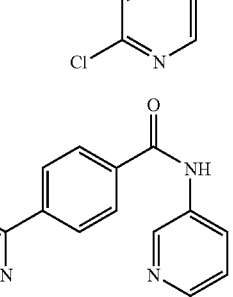 | 377.76 | 378.21 | 3.51 | 3.42 | 3.69 | |
| 442 | 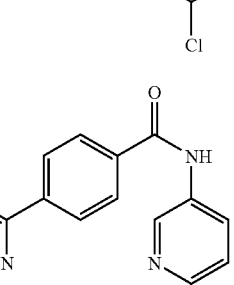 | 373.34 | 374.14 | 3.19 | 3.01 | 3.44 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 443 | 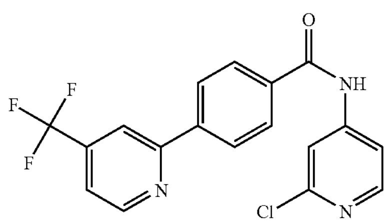 | 377.76 | | | | | |
| 444 | 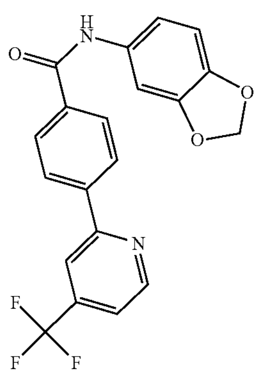 | 386.33 | 387.13 | 3.52 | 3.38 | 3.74 | + |
| 445 | 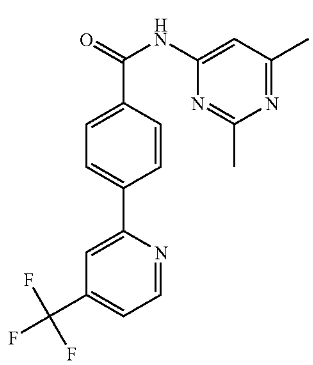 | 372.35 | 373.10 | 2.71 | 2.65 | 2.89 | + |
| 446 | 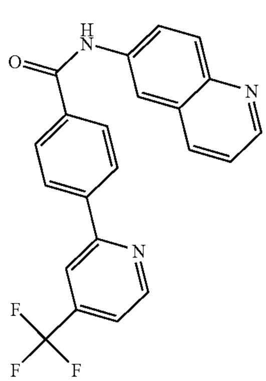 | 393.37 | 394.15 | 2.76 | 2.69 | 3.04 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 447 | 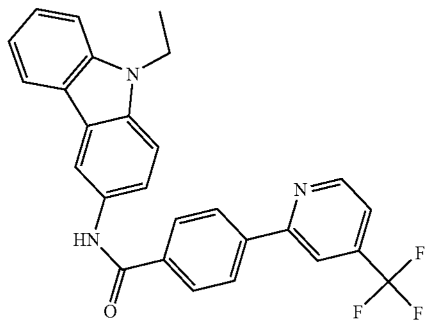 | 459.48 | 460.32 | 4.15 | 4.07 | 4.47 | |
| 448 | 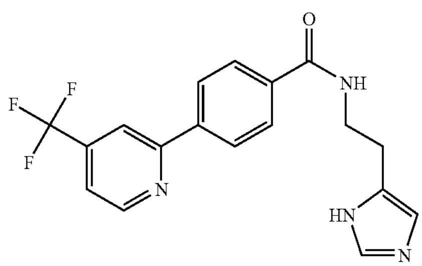 | 360.34 | 361.27 | 2.36 | 2.32 | 2.59 | + |
| 449 | 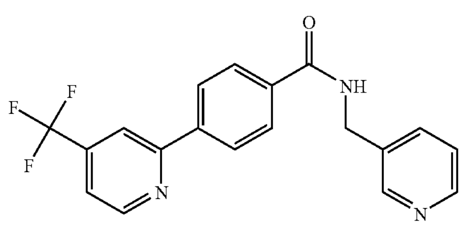 | 357.34 | 358.14 | 2.40 | 2.33 | 2.70 | |
| 450 | 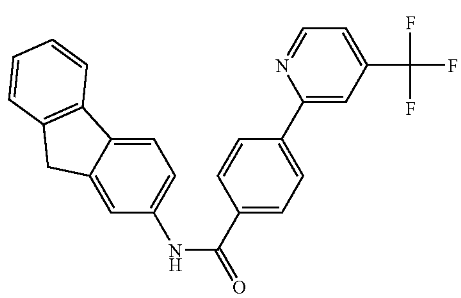 | 430.43 | | | | | |
| 451 | 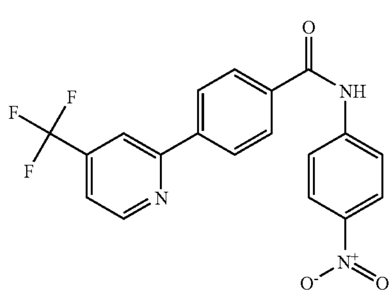 | 387.32 | | | | | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 452 | 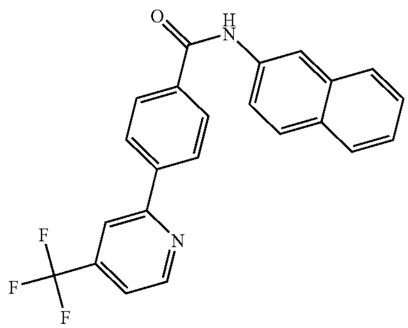 | 392.38 | 393.17 | 3.98 | 3.85 | 4.16 | |
| 453 | 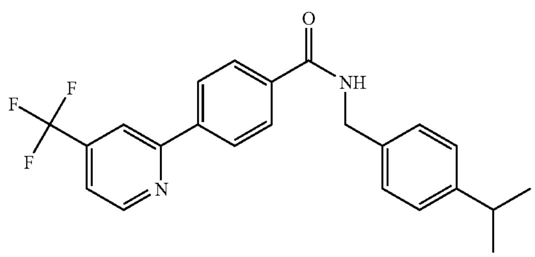 | 398.43 | 399.16 | 3.99 | 3.79 | 4.22 | + |
| 454 | 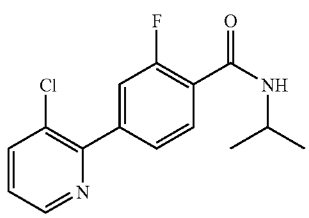 | 292.74 | 292.94 | 2.85 | 2.78 | 3.16 | + |
| 455 | 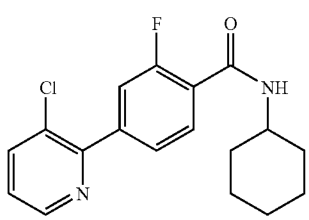 | 332.81 | 333.20 | 3.42 | 3.29 | 3.71 | ++ |
| 456 | 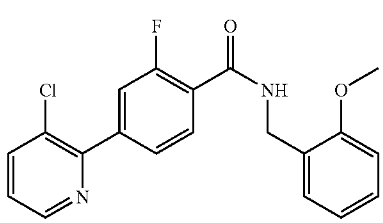 | 370.81 | 371.00 | 3.35 | 3.28 | 3.77 | |
| 457 | 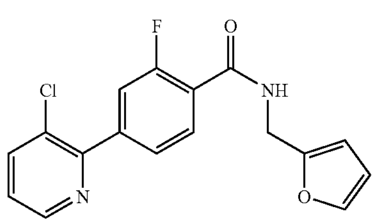 | 330.75 | 331.01 | 2.99 | 2.89 | 3.36 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 458 | 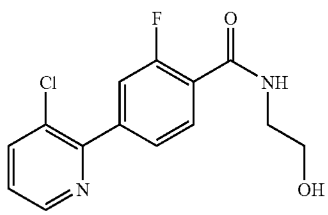 | 294.72 | 295.05 | 2.14 | 2.05 | 2.51 | |
| 459 | 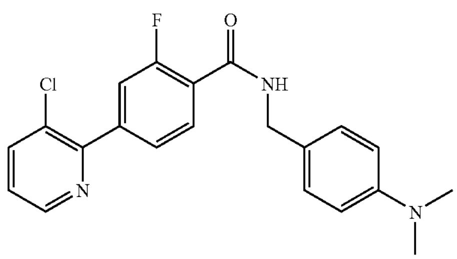 | 383.86 | 384.11 | 2.26 | 2.10 | 2.60 | + |
| 460 | 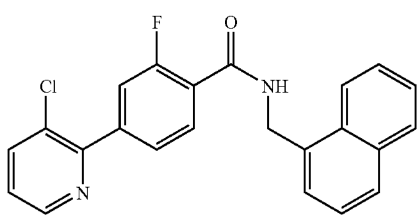 | 390.85 | 391.26 | 3.59 | 3.42 | 4.01 | + |
| 461 | 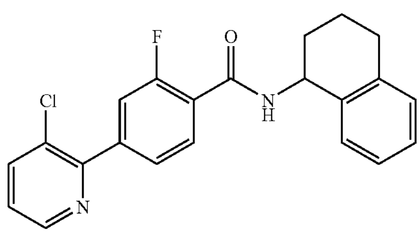 | 380.85 | 381.20 | 3.66 | 3.56 | 3.93 | |
| 462 | 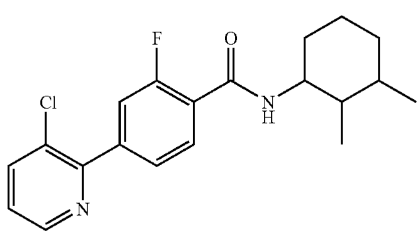 | 360.86 | 361.26 | 3.76 | 3.59 | 4.48 | + |
| 463 | 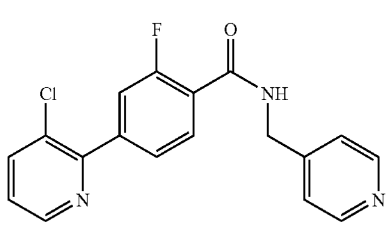 | 341.78 | 342.07 | 2.06 | 1.96 | 2.35 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 464 | 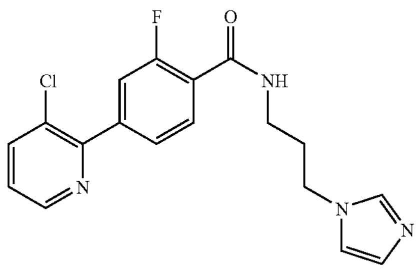 | 358.81 | 359.18 | 2.07 | 1.92 | 2.40 | |
| 465 | 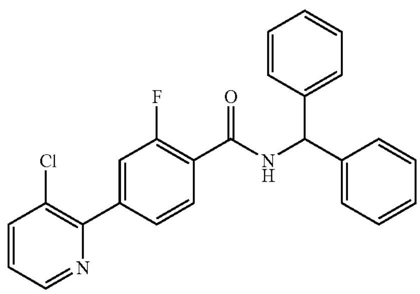 | 416.89 | 417.29 | 3.78 | 3.69 | 4.14 | + |
| 466 | 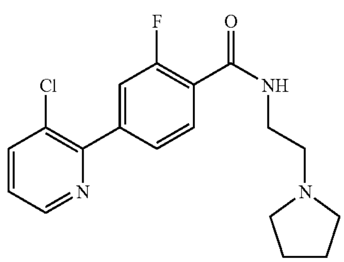 | 347.82 | 348.15 | 2.08 | 1.81 | 2.51 | ++ |
| 467 | 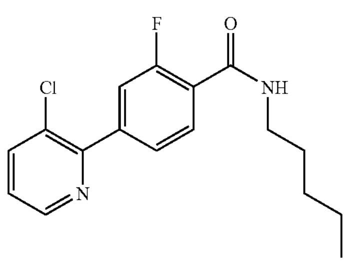 | 320.80 | 321.14 | 3.41 | 3.35 | 3.81 | |
| 468 | 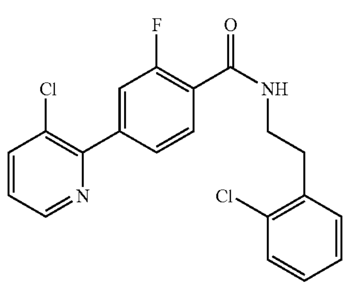 | 389.26 | 389.25 | 3.56 | 3.45 | 3.95 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 469 | 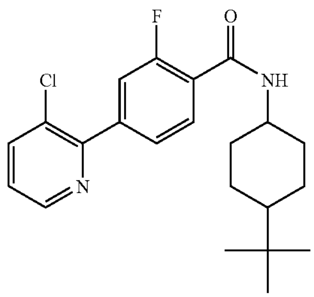 | 388.92 | 389.35 | 4.28 | 4.15 | 4.61 | + |
| 470 | 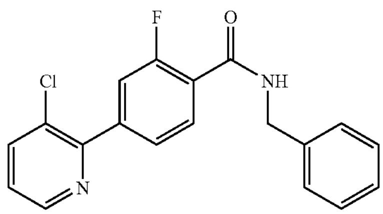 | 340.79 | 340.98 | 3.23 | 3.09 | 3.58 | |
| 471 | 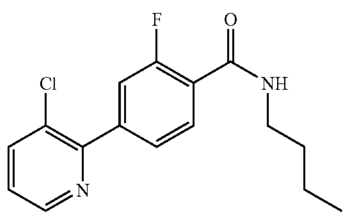 | 306.77 | 307.20 | 3.15 | 3.05 | 3.49 | |
| 472 | 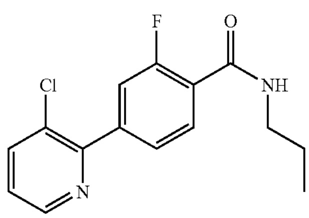 | 292.74 | 292.93 | 2.89 | 2.79 | 3.36 | + |
| 473 | 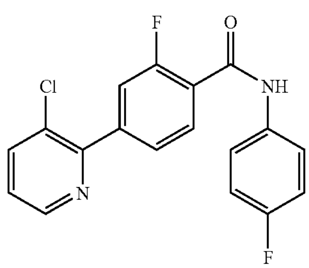 | 344.75 | | | | | |
| 474 | 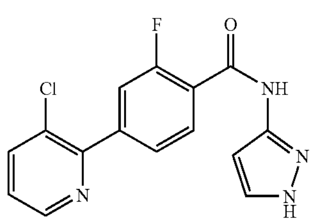 | 316.72 | | | | | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 475 | 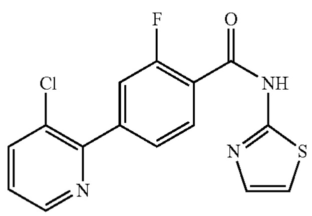 | 333.77 | | | | | |
| 476 | 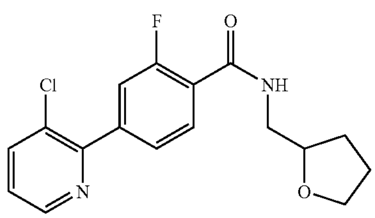 | 334.78 | 335.28 | 2.70 | 2.62 | 3.08 | + |
| 477 | 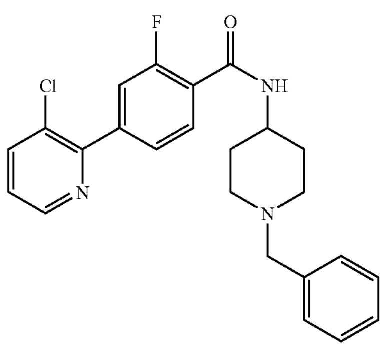 | 423.92 | 424.11 | 2.40 | 2.18 | 2.75 | + |
| 478 | 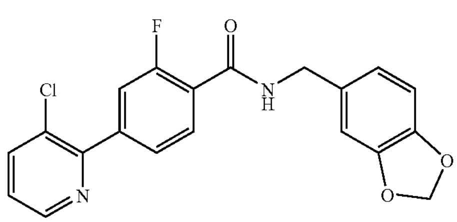 | 384.80 | 385.13 | 3.16 | 3.09 | 3.46 | |
| 479 | 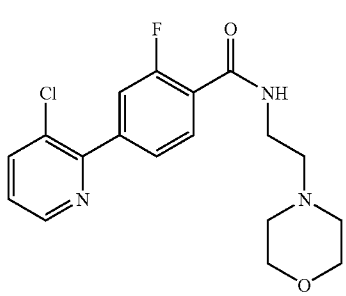 | 363.82 | 364.29 | 2.03 | 1.86 | 2.33 | + |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 480 | 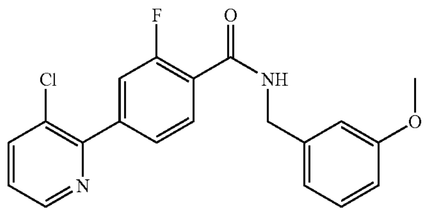 | 370.81 | 370.99 | 3.22 | 3.14 | 3.48 | + |
| 481 | 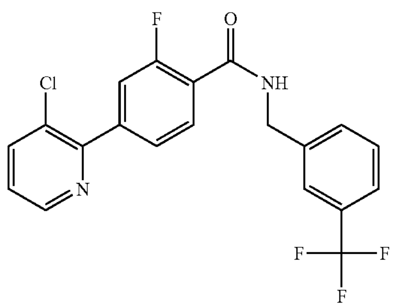 | 408.79 | 409.02 | 3.56 | 3.41 | 3.89 | + |
| 482 | 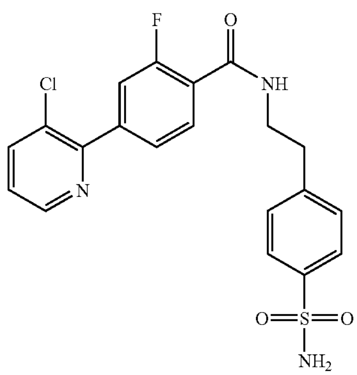 | 433.89 | 434.10 | 2.65 | 2.50 | 3.03 | + |
| 483 | 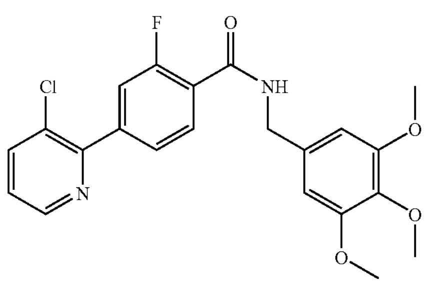 | 430.87 | 431.29 | 3.01 | 2.91 | 3.33 | |
| 484 | 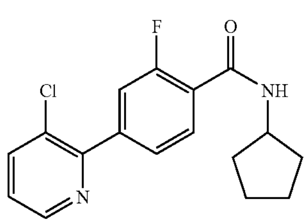 | 318.78 | 318.94 | 3.18 | 3.11 | 3.42 | |

TABLE 1-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 485 | 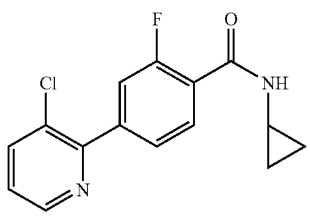 | 290.73 | 291.01 | 2.64 | 2.52 | 2.91 | + |

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 486 | 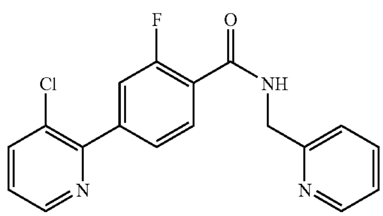 | 341.78 | 342.06 | 2.08 | 1.99 | 2.48 | |
| 487 | 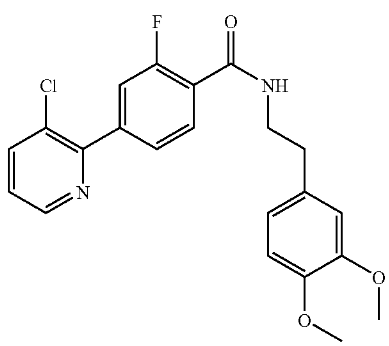 | 414.87 | 415.26 | 3.09 | 3.00 | 3.42 | + |
| 488 | 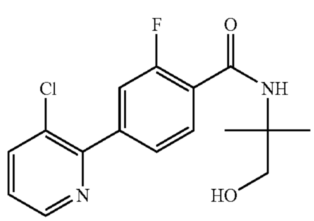 | 322.77 | | | | | |
| 489 | 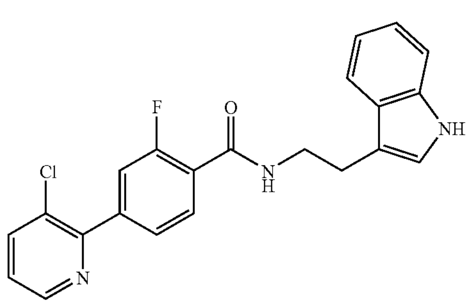 | 393.85 | 394.10 | 3.26 | 3.13 | 3.65 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 490 | 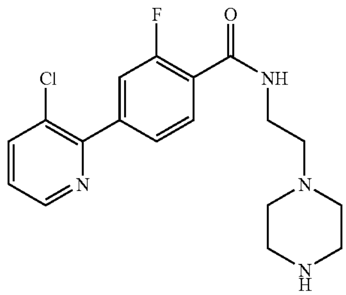 | 362.84 | 367.09 | 3.79 | 3.42 | 3.81 | |
| 491 | 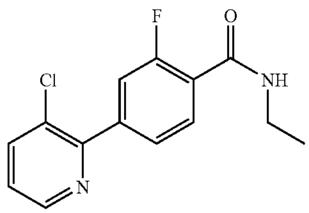 | 278.72 | 279.01 | 2.61 | 2.51 | 2.97 | |
| 492 | 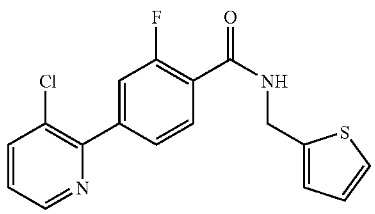 | 346.81 | 346.99 | 3.15 | 3.05 | 3.42 | + |
| 493 | 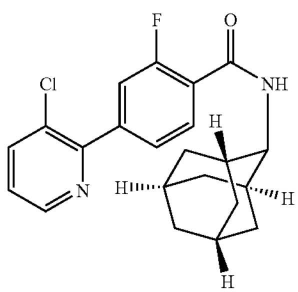 | 384.88 | 385.25 | 4.11 | 4.04 | 4.66 | + |
| 494 | 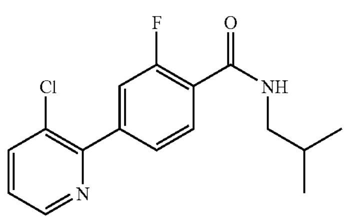 | 306.77 | 307.22 | 3.12 | 3.03 | 3.51 | ++ |
| 495 | 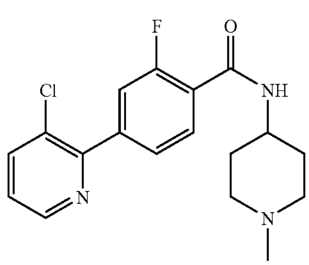 | 347.82 | 348.14 | 2.02 | 1.83 | 2.38 | + |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 496 | 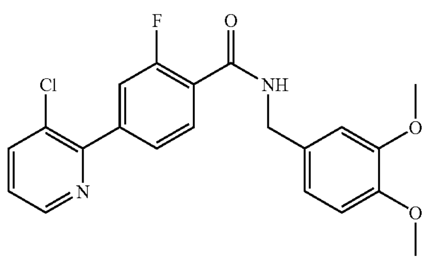 | 400.84 | 401.06 | 2.98 | 2.89 | 3.38 | + |
| 497 | 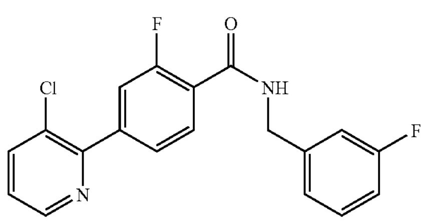 | 358.78 | 359.13 | 3.29 | 3.15 | 3.65 | + |
| 498 | 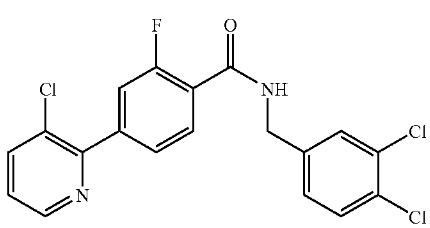 | 409.68 | 408.97 | 3.71 | 3.61 | 4.38 | |
| 499 | 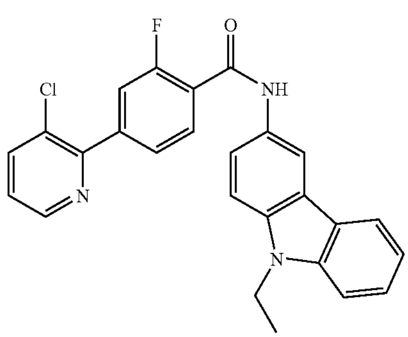 | 443.91 | | | | | |
| 500 | 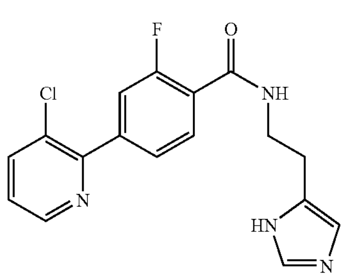 | 344.78 | | | | | |

-continued
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 501 | 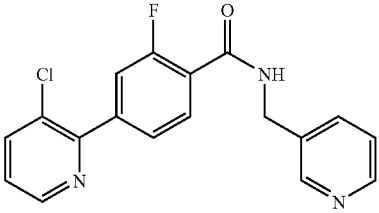 | 341.78 | 342.06 | 2.06 | 1.93 | 2.30 | |
| 502 | 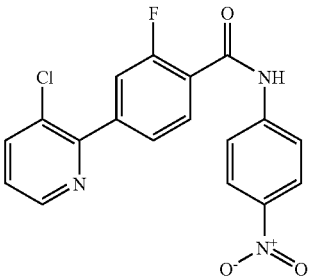 | 371.76 | | | | | |
| 503 | 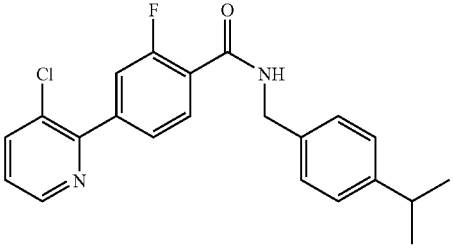 | 382.87 | 383.18 | 3.78 | 3.68 | 4.05 | ++++ |
| 504 | 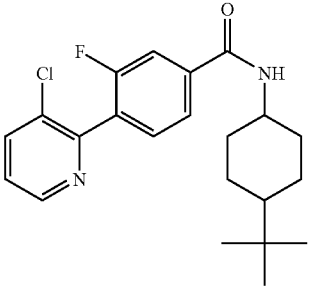 | 388.92 | 389.37 | 3.98 | 3.81 | 4.52 | + |
| 505 | 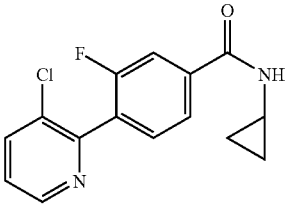 | 290.73 | 291.07 | 2.53 | 2.43 | 2.85 | + |
| 506 | 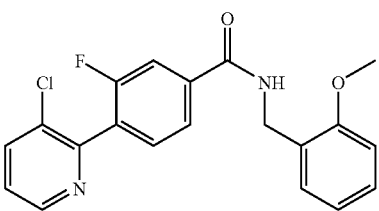 | 370.81 | 371.07 | 3.17 | 2.99 | 3.94 | + |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 507 | 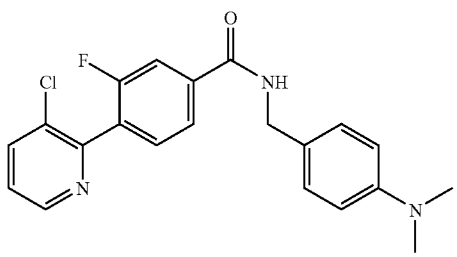 | 383.86 | 384.13 | 2.25 | 2.16 | 2.49 | |
| 508 | 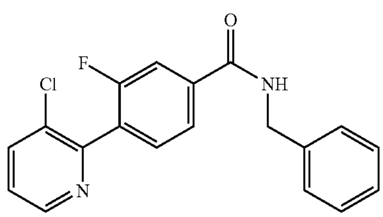 | 340.79 | 341.04 | 3.11 | 2.99 | 3.56 | ++ |
| 509 | 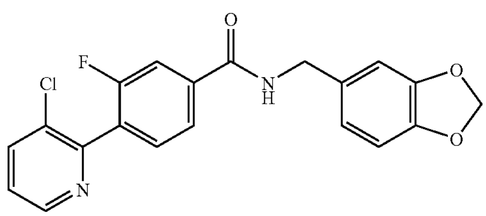 | 384.80 | 385.19 | 3.05 | 2.96 | 3.51 | + |
| 510 | 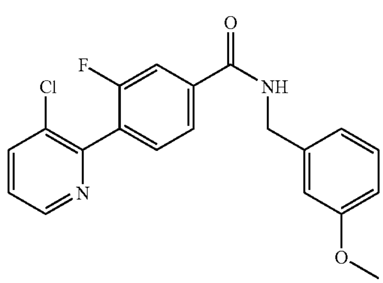 | 370.81 | 371.05 | 3.11 | 3.02 | 3.61 | + |
| 511 | 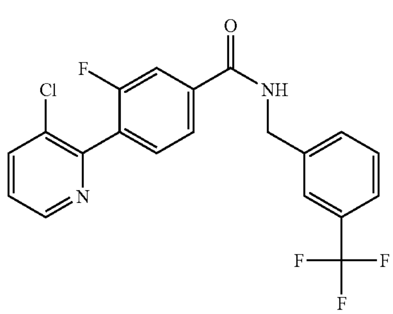 | 408.79 | 409.12 | 3.44 | 3.28 | 3.84 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 512 | 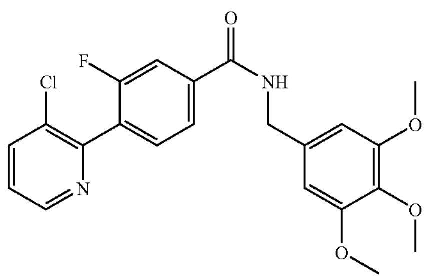 | 430.87 | 431.31 | 2.93 | 2.80 | 3.38 | + |
| 513 | 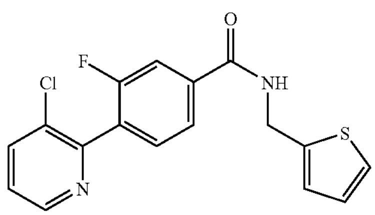 | 346.81 | | | | | |
| 514 | 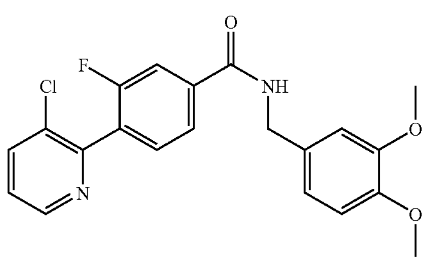 | 400.84 | 401.14 | 2.93 | 2.78 | 3.36 | |
| 515 | 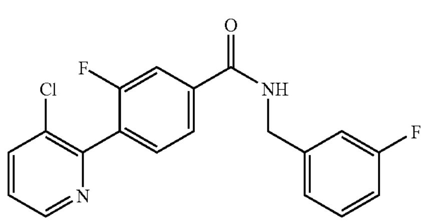 | 358.78 | 359.14 | 3.16 | 2.99 | 3.48 | +++ |
| 516 | 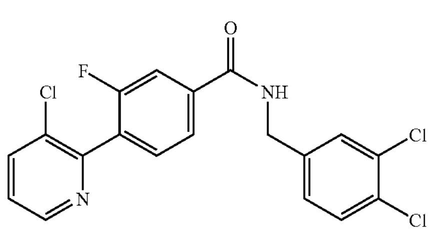 | 409.68 | 409.00 | 3.53 | 3.42 | 4.04 | + |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 517 | 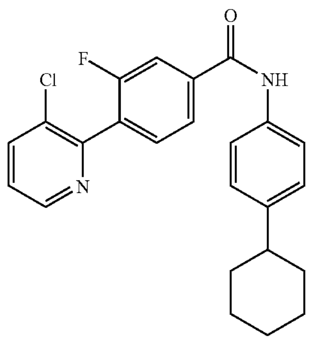 | 408.91 | | | | | |
| 518 | 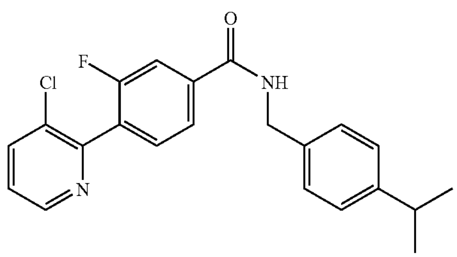 | 382.87 | 383.21 | 3.62 | 3.45 | 4.19 | |
| 519 | 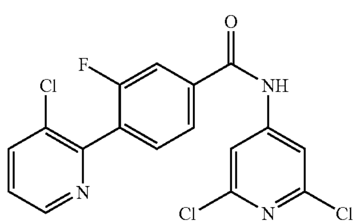 | 396.64 | | | | | |
| 520 | 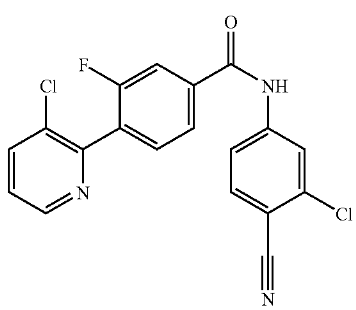 | 386.22 | | | | | |
| 521 | 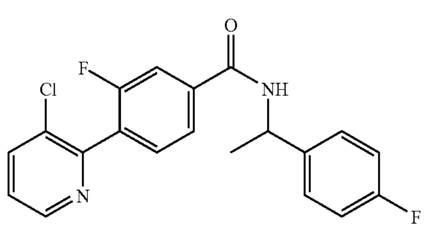 | 372.81 | 373.08 | 3.27 | 3.18 | 3.58 | + |

-continued
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 522 | 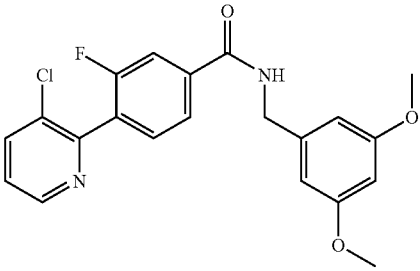 | 400.84 | 401.12 | 3.12 | 3.02 | 3.45 | ++++ |
| 523 | 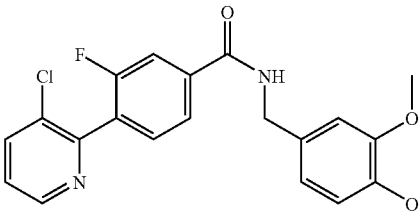 | 386.81 | 387.15 | 2.69 | 2.62 | 3.01 | |
| 524 | 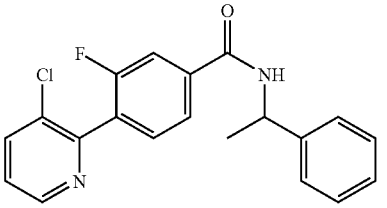 | 354.81 | 355.22 | 3.21 | 3.12 | 3.71 | |
| 525 | 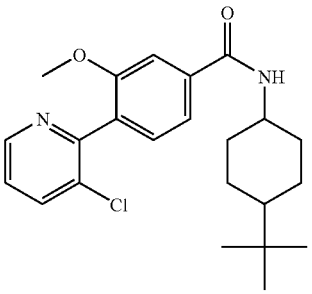 | 400.95 | 401.27 | 3.71 | 3.55 | 4.11 | |
| 526 | 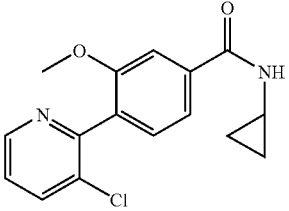 | 302.76 | 303.08 | 2.29 | 2.22 | 2.71 | + |
| 527 | 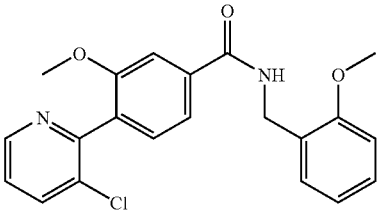 | 382.85 | 383.15 | 2.92 | 2.78 | 3.22 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 528 | 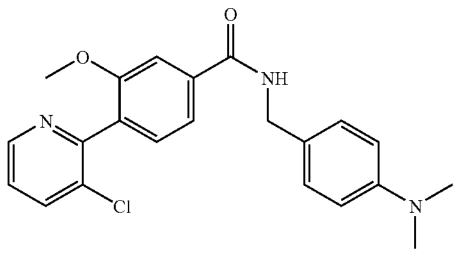 | 395.89 | 396.11 | 2.08 | 2.03 | 2.39 | |
| 529 | 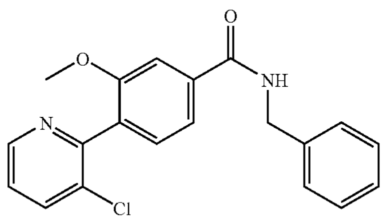 | 352.82 | 353.22 | 2.85 | 2.75 | 3.38 | +++ |
| 530 | 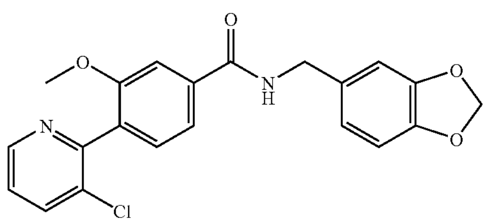 | 396.83 | 397.05 | 2.90 | 2.76 | 3.38 | |
| 531 | 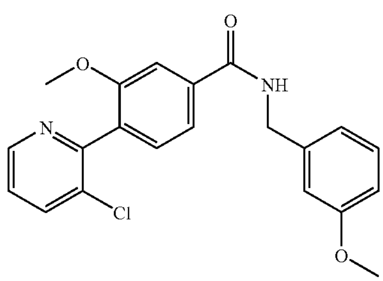 | 382.85 | 383.14 | 2.85 | 2.69 | 3.29 | |
| 532 | 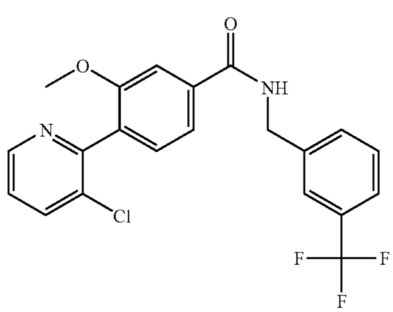 | 420.82 | 421.07 | 3.22 | 3.06 | 3.66 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 533 | 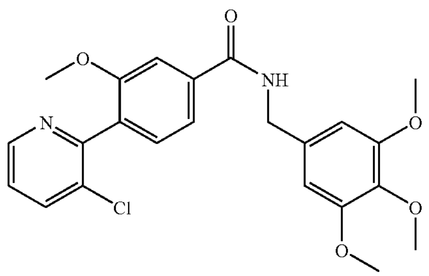 | 442.90 | 443.32 | 2.68 | 2.50 | 3.00 | |
| 534 | 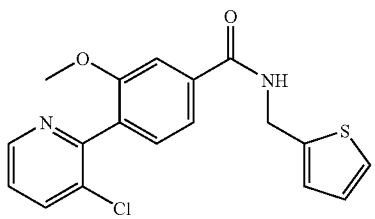 | 358.85 | 359.10 | 2.76 | 2.65 | 3.13 | + |
| 535 | 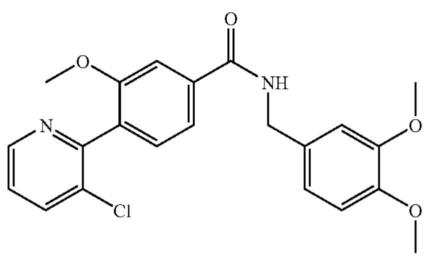 | 412.88 | 413.18 | 2.66 | 2.53 | 3.15 | + |
| 536 | 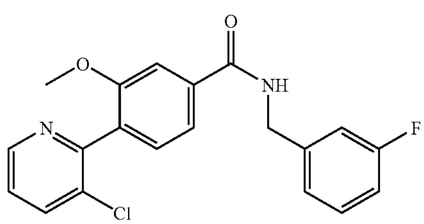 | 370.81 | 371.05 | 2.92 | 2.81 | 3.37 | + |
| 537 | 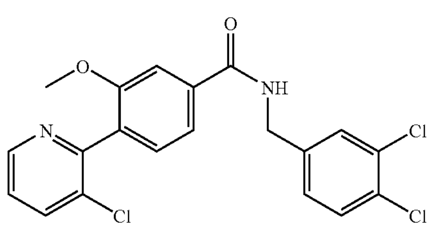 | 421.71 | 421.00 | 3.32 | 3.16 | 3.74 | + |
| 538 | 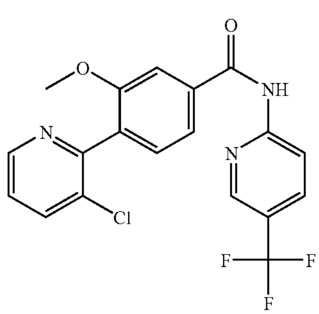 | 407.78 | | | | | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 539 | 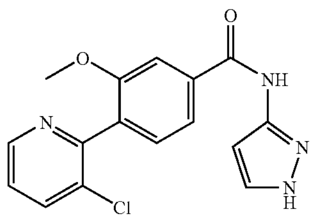 | 328.76 | | | | | |
| 540 | 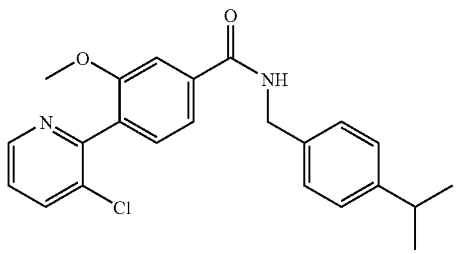 | 394.90 | 395.14 | 3.39 | 3.31 | 3.72 | |
| 541 | 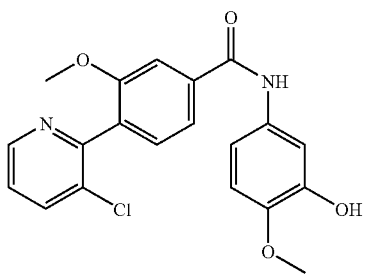 | 384.82 | | | | | |
| 542 | 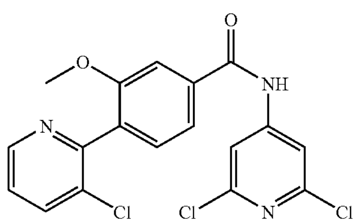 | 408.67 | | | | | |
| 543 | 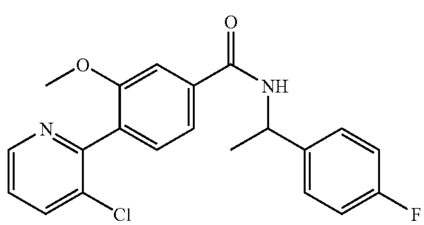 | 384.84 | 385.22 | 3.05 | 2.89 | 3.38 | + |
| 544 | 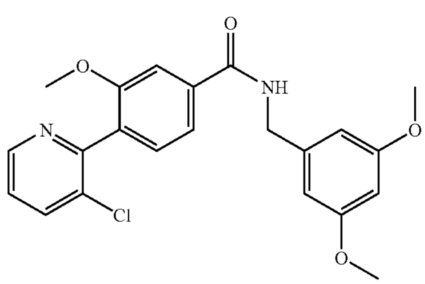 | 412.88 | 413.22 | 2.89 | 2.78 | 3.45 | +++ |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 545 | 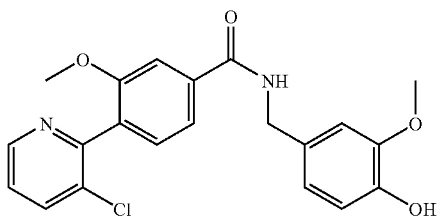 | 398.85 | 399.10 | 2.43 | 2.28 | 2.82 | |
| 546 | 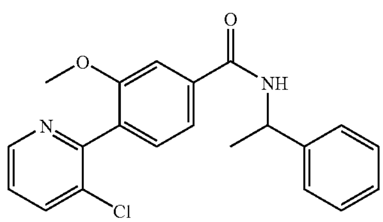 | 366.85 | 367.09 | 2.96 | 2.82 | 3.45 | |
| 547 | 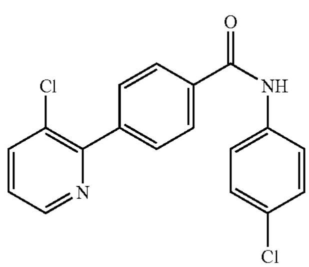 | 343.22 | | | | | |
| 548 | 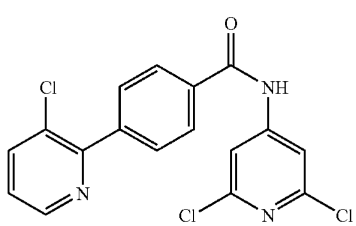 | 378.65 | | | | | |
| 549 | 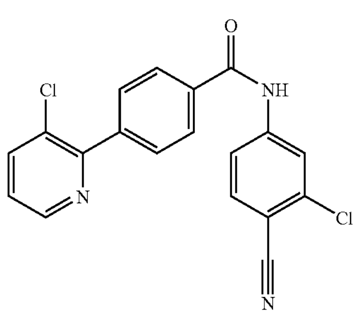 | 368.23 | | | | | |
| 550 | 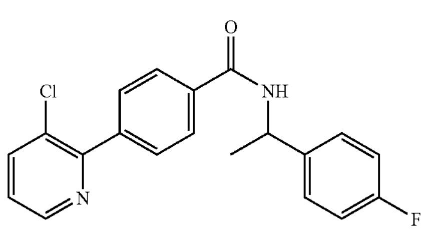 | 354.81 | 355.21 | 3.12 | 2.96 | 3.35 | |

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 551 | 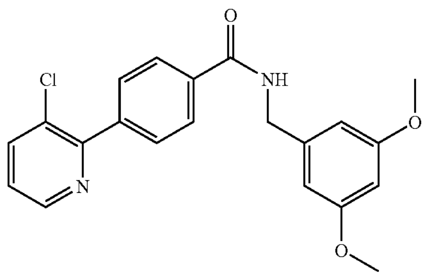 | 382.85 | 383.16 | 2.98 | 2.83 | 3.45 | ++++ |
| 552 | 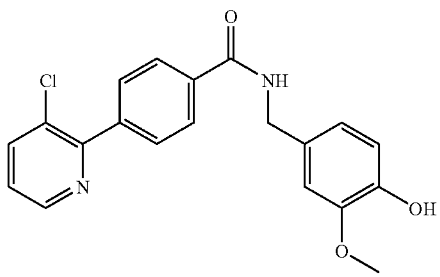 | 368.82 | 369.10 | 2.49 | 2.33 | 2.86 | + |
| 553 | 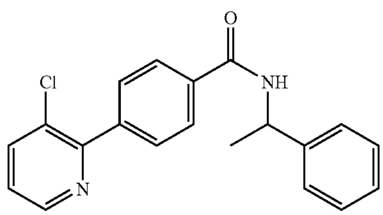 | 336.82 | 337.34 | 3.05 | 2.92 | 3.62 | + |
| 554 | 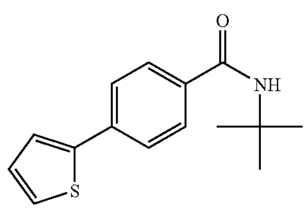 | 259.37 | 260.12 | 3.39 | 3.29 | 3.82 | |
| 555 | 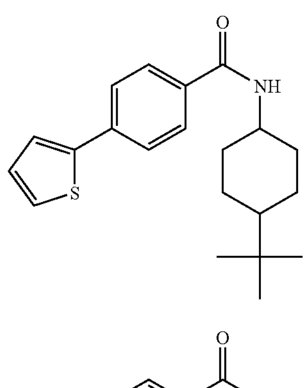 | 341.52 | 342.16 | 4.21 | 4.12 | 4.37 | |
| 556 | 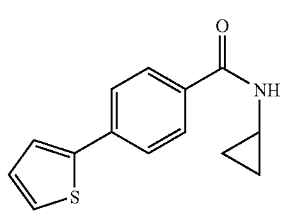 | 243.33 | | | | | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 557 | 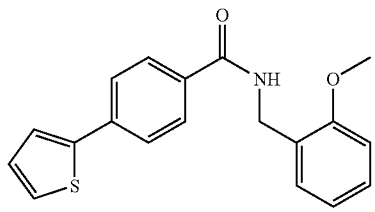 | 323.42 | | | | | |
| 558 | 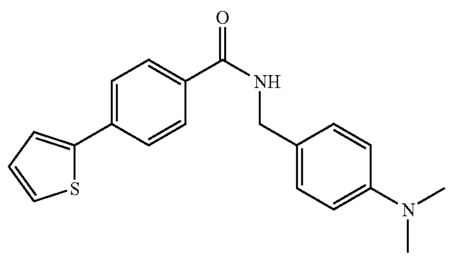 | 336.46 | 337.40 | 2.50 | 2.43 | 2.72 | |
| 559 | 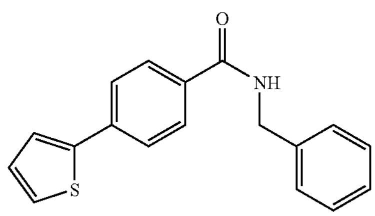 | 293.39 | | | | | |
| 560 | 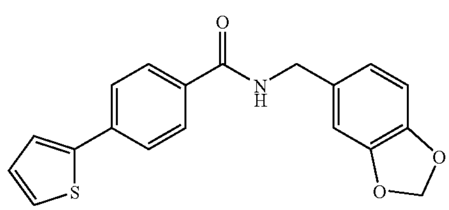 | 337.40 | | | | | |
| 561 | 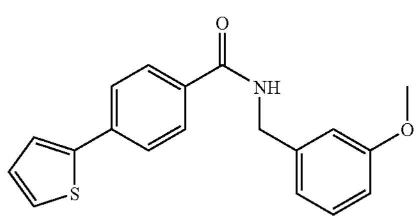 | 323.42 | | | | | |
| 562 | 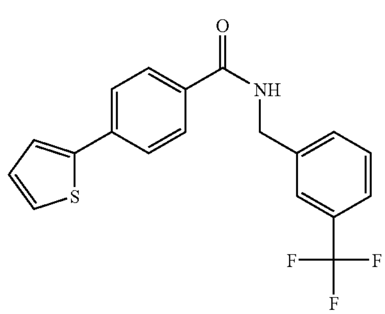 | 361.39 | | | | | |

|  |  |  |  | HPLC | HPLC |  |
|  |  |  | HPLC | START | END | % |
|  | MW | MS | RT | TIME | TIME | Inhibition |
| ID STRUCTURE | (Calc) | (Obs) | (Min) | (Min) | (Min) | @ 1 uM |
| --- | --- | --- | --- | --- | --- | --- |
| 563 | 383.47 | | | | | |
| 564 | 321.44 | 322.20 | 3.64 | 3.34 | 3.98 | + |
| 565 | 299.42 | | | | | |
| 566 | 353.44 | | | | | |
| 567 | 311.38 | | | | | |
| 568 | 362.28 | | | | | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 569 | 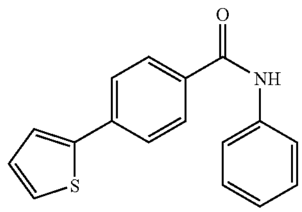 | 279.36 | | | | | |
| 570 | 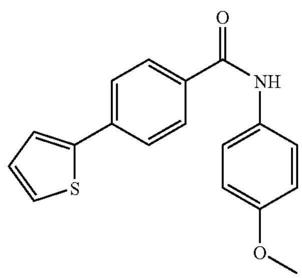 | 309.39 | | | | | |
| 571 | 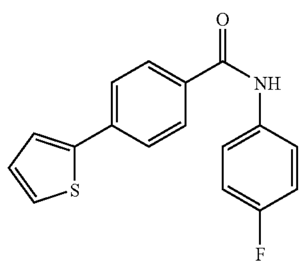 | 297.35 | | | | | |
| 572 | 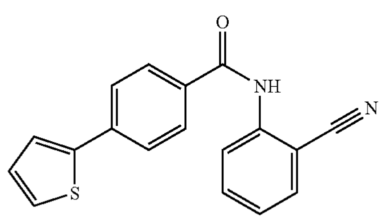 | 304.37 | 305.19 | 3.31 | 3.24 | 3.75 | ++ |
| 573 | 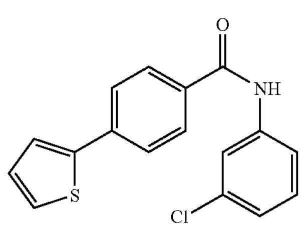 | 313.81 | | | | | |
| 574 | 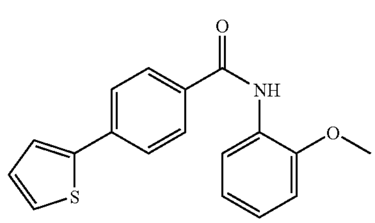 | 309.39 | 310.28 | 3.72 | 3.62 | 4.07 | |

-continued
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 575 | 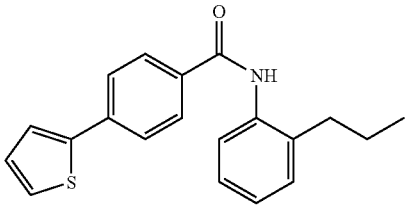 | 321.44 | 322.20 | 3.78 | 3.56 | 4.28 | |
| 576 | 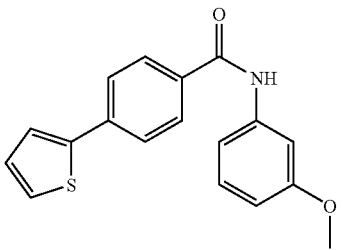 | 309.39 | 310.28 | 3.52 | 3.35 | 4.04 | |
| 577 | 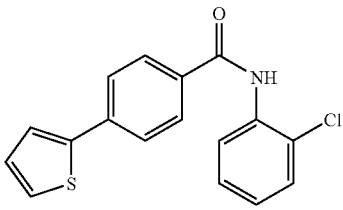 | 313.81 | 314.05 | 3.85 | 3.76 | 3.98 | |
| 578 | 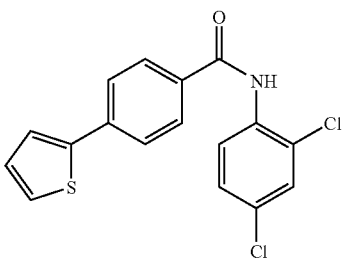 | 348.25 | 348.23 | 4.15 | 3.92 | 4.25 | |
| 579 | 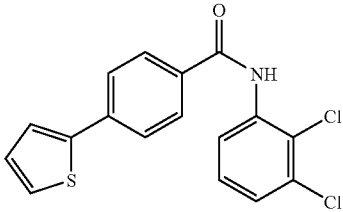 | 348.25 | 347.69 | 4.39 | 4.22 | 4.48 | |
| 580 | 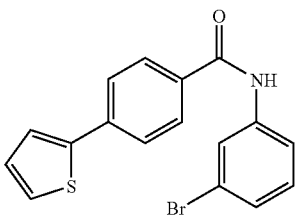 | 358.26 | | | | | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 581 | 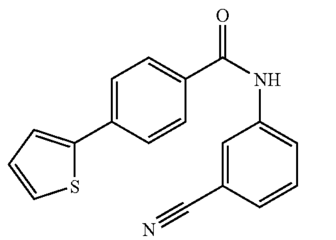 | 304.37 | 305.16 | 3.68 | 3.59 | 3.93 | + |
| 582 | 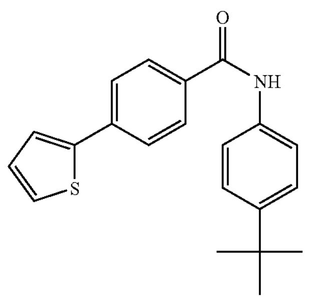 | 335.47 | 336.43 | 4.16 | 3.95 | 4.79 | |
| 583 | 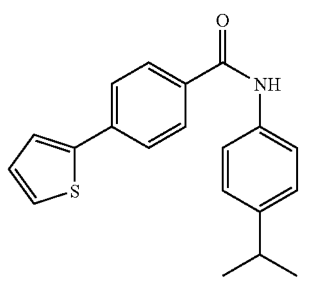 | 321.44 | 322.20 | 3.95 | 3.88 | 4.41 | + |
| 584 | 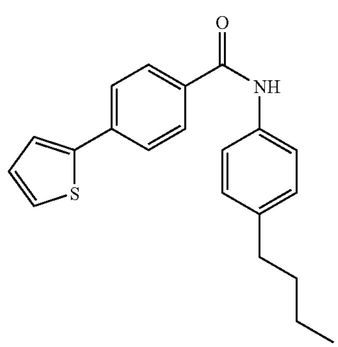 | 335.47 | 336.35 | 4.01 | 3.85 | 4.22 | +++ |
| 585 | 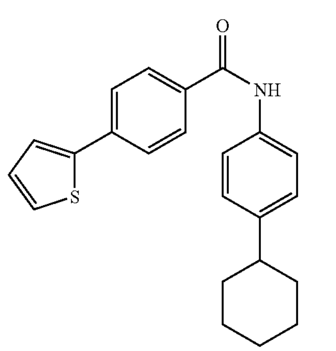 | 361.51 | 362.30 | 4.39 | 4.27 | 4.59 | + |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 586 | 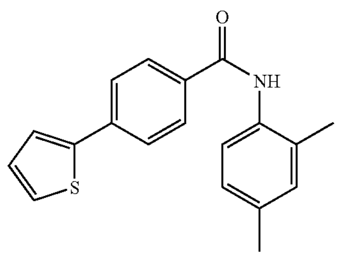 | 307.42 | 308.28 | 3.65 | 3.49 | 4.22 | + |
| 587 | 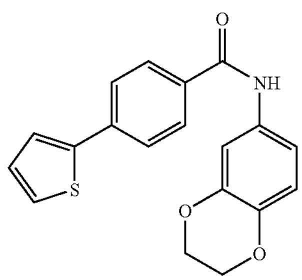 | 337.40 | 338.24 | 3.43 | 3.32 | 3.71 | + |
| 588 | 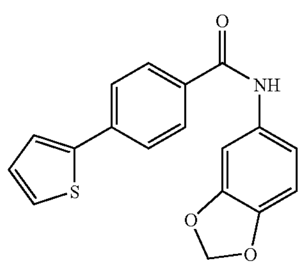 | 323.37 | 324.27 | 3.43 | 3.36 | 3.93 | + |
| 589 | 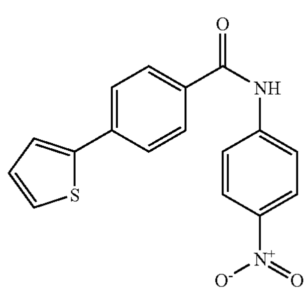 | 324.36 | | | | | |
| 590 | 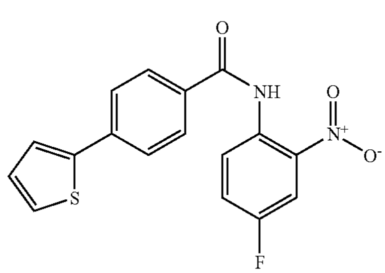 | 342.35 | | | | | |

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 591 | 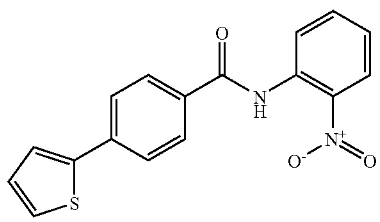 | 324.36 | | | | | |
| 592 | 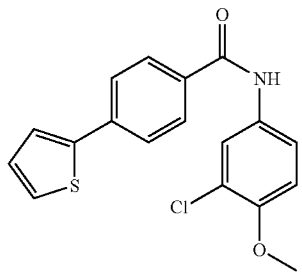 | 343.83 | 344.09 | 3.72 | 3.61 | 4.08 | + |
| 593 | 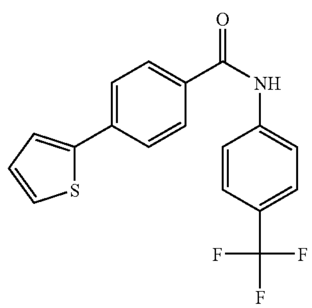 | 347.36 | | | | | + |
| 594 | 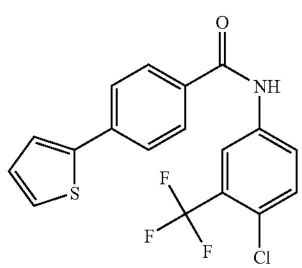 | 381.81 | | | | | |
| 595 | 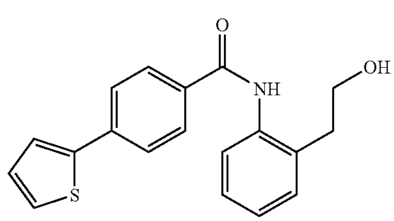 | 323.42 | | | | | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 596 | 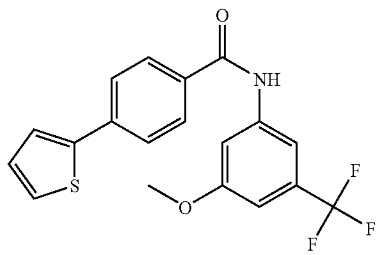 | 377.39 | 378.23 | 4.04 | 3.93 | 4.39 | + |
| 597 | 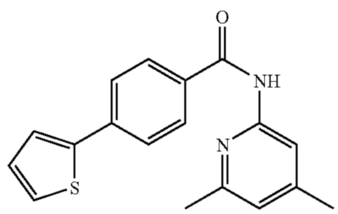 | 308.41 | 309.30 | 2.72 | 2.63 | 3.00 | ++ |
| 598 | 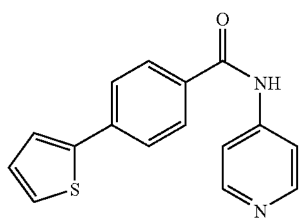 | 280.35 | | | | | |
| 599 | 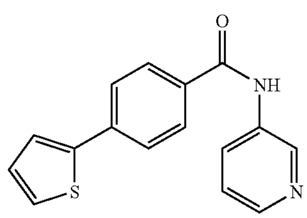 | 280.35 | 281.22 | 2.45 | 2.40 | 2.66 | |
| 600 | 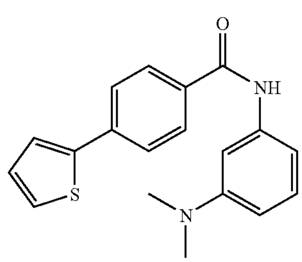 | 322.43 | 323.16 | 2.59 | 2.45 | 3.19 | + |
| 601 | 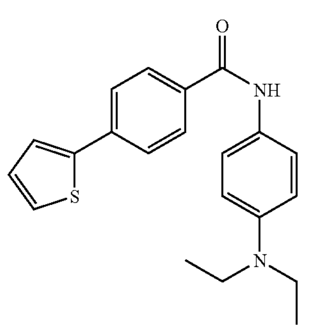 | 350.49 | 351.31 | 2.78 | 2.66 | 2.96 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 602 | 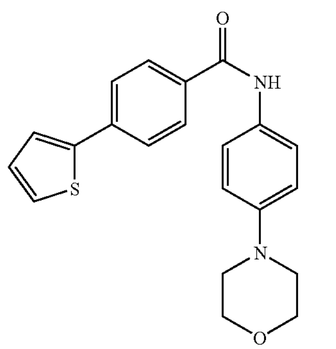 | 364.47 | 365.09 | 2.82 | 2.73 | 3.05 | |
| 603 | 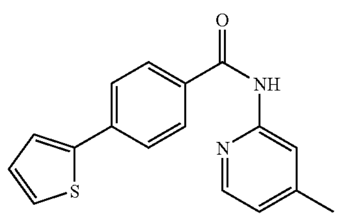 | 294.38 | | | | | |
| 604 | 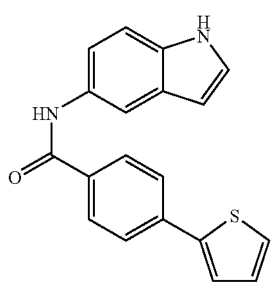 | 318.40 | 318.95 | 3.29 | 3.19 | 3.53 | + |
| 605 | 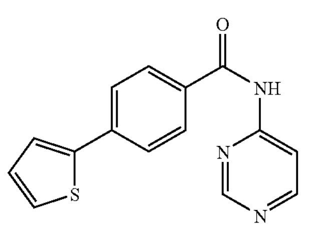 | 281.34 | | | | | |
| 606 | 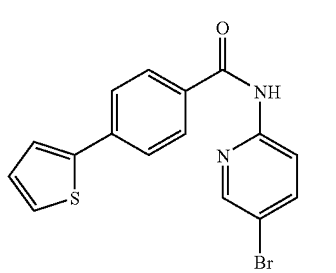 | 359.25 | 359.09 | 3.85 | 3.72 | 4.22 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 607 | 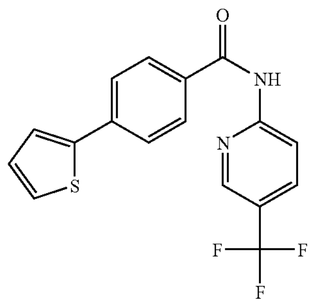 | 348.35 | 349.20 | 3.91 | 3.84 | 4.54 | + |
| 608 | 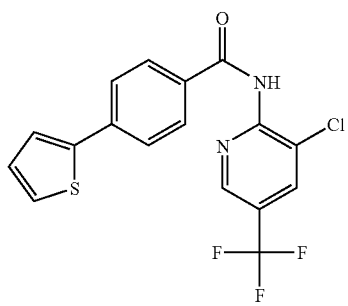 | 382.79 | 383.07 | 3.68 | 3.53 | 4.11 | + |
| 609 | 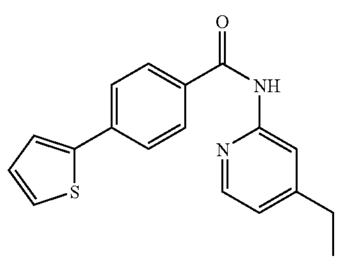 | 308.41 | | | | | |
| 610 | 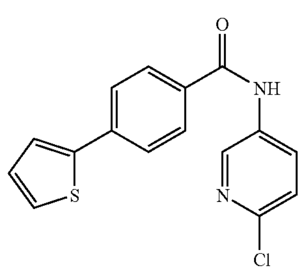 | 314.80 | 314.87 | 3.42 | 3.36 | 3.61 | + |
| 611 | 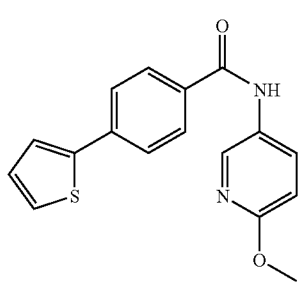 | 310.38 | 311.24 | 3.08 | 3.00 | 3.38 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 612 | 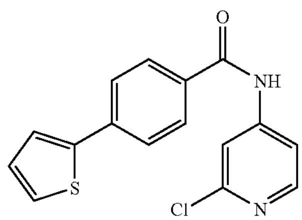 | 314.80 | | | | | |
| 613 | 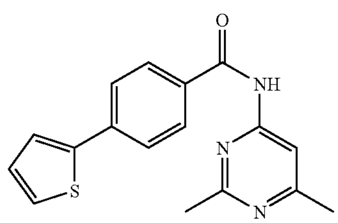 | 309.39 | | | | | |
| 614 | 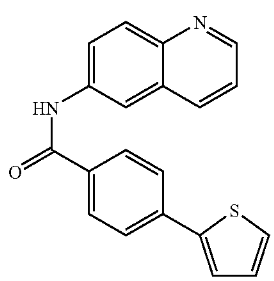 | 330.41 | 331.12 | 2.68 | 2.56 | 2.91 | |
| 615 | 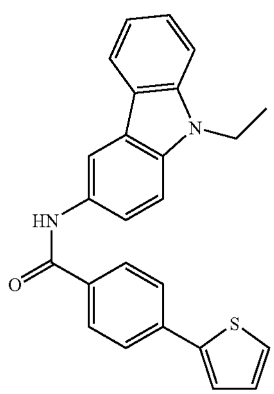 | 396.51 | | | | | |
| 616 | 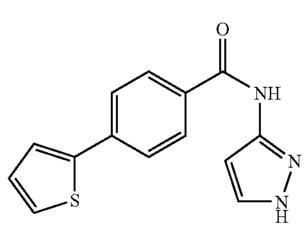 | 269.33 | | | | | |

-continued
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 617 | 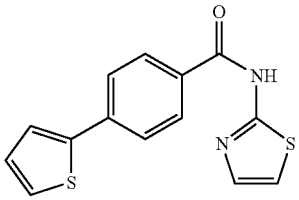 | 286.38 | 287.07 | 3.22 | 3.16 | 3.55 | |
| 618 | 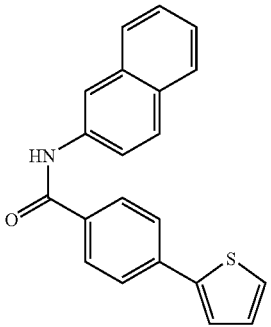 | 329.42 | 330.10 | 3.86 | 3.83 | 3.98 | |
| 619 | 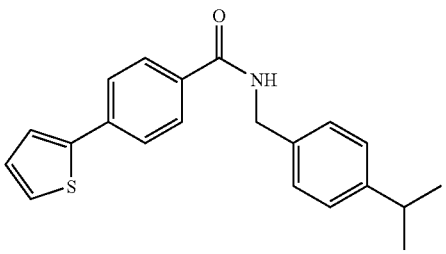 | 335.47 | 336.38 | 3.88 | 3.71 | 4.15 | + |
| 620 | 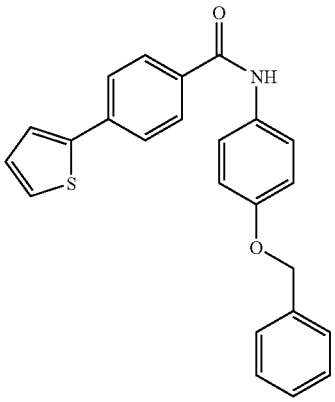 | 385.49 | | | | | |
| 621 | 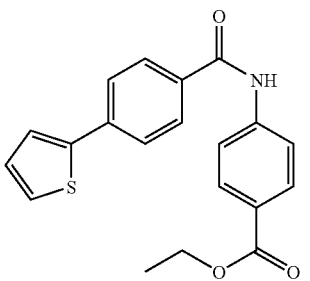 | 351.43 | 352.29 | 3.69 | 3.58 | 3.85 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 622 | 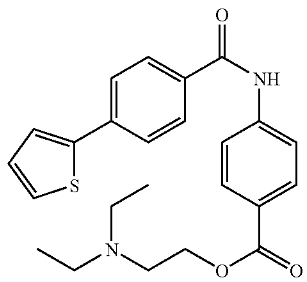 | 422.55 | 423.07 | 2.86 | 2.65 | 3.49 | + |
| 623 | 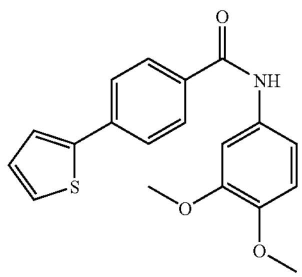 | 339.42 | 340.11 | 3.31 | 3.19 | 3.53 | |
| 624 | 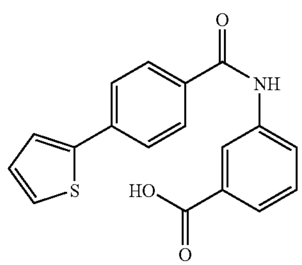 | 323.37 | 324.25 | 3.11 | 3.06 | 3.38 | |
| 625 | 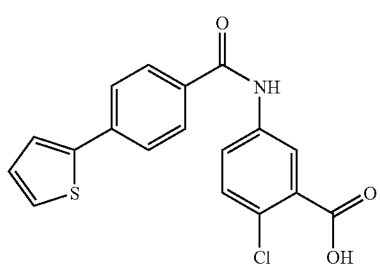 | 357.82 | | | | | |
| 626 | 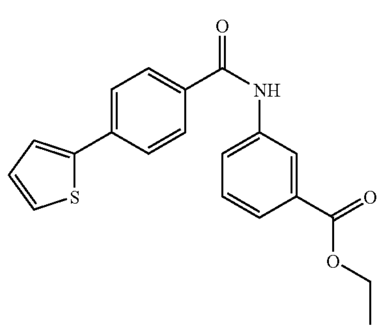 | 351.43 | | | | | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 627 | 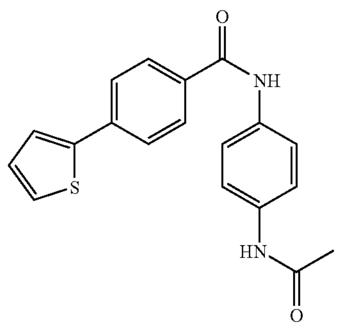 | 336.42 | | | | | |
| 628 | 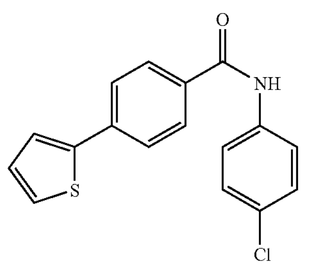 | 313.81 | | | | | |
| 629 | 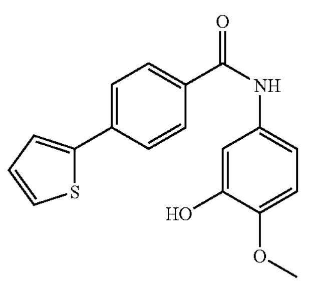 | 325.39 | | | | | |
| 630 | 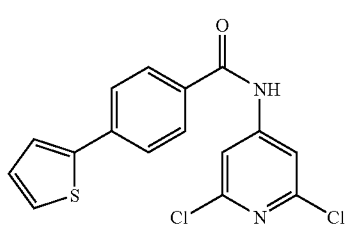 | 349.24 | 349.09 | 3.96 | 3.91 | 4.19 | |
| 631 | 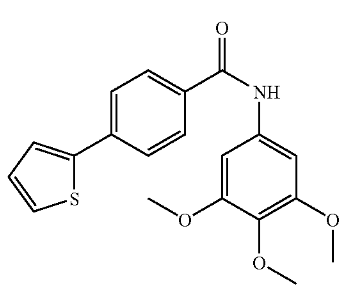 | 369.44 | 370.13 | 3.38 | 3.25 | 3.65 | + |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 632 | 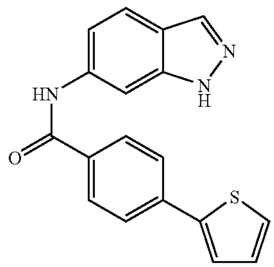 | 319.39 | 320.10 | 3.08 | 2.99 | 3.27 | + |
| 633 | 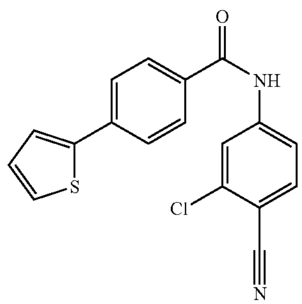 | 338.82 | | | | | |
| 634 | 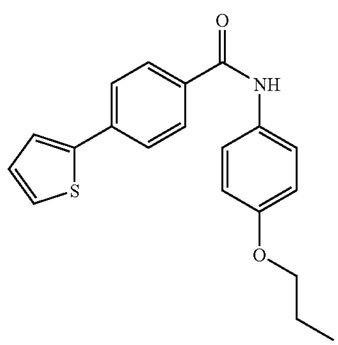 | 337.44 | 338.28 | 3.83 | 3.73 | 3.99 | |
| 635 | 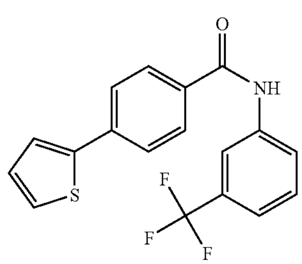 | 347.36 | 348.13 | 3.92 | 3.85 | 4.19 | + |
| 636 | 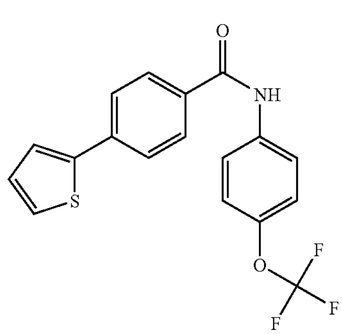 | 363.36 | | | | | |

-continued
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 637 | 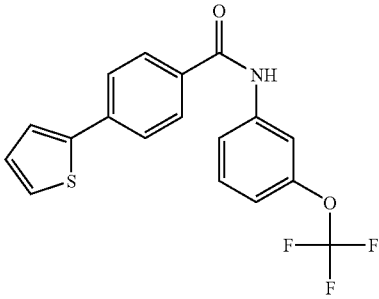 | 363.36 | 364.29 | 4.07 | 3.82 | 4.09 | + |
| 638 | 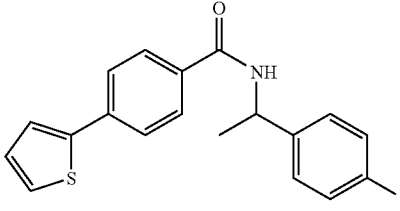 | 325.41 | | | | | |
| 639 | 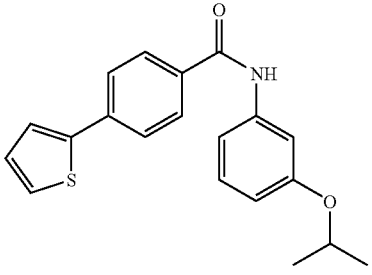 | 337.44 | | | | | + |
| 640 | 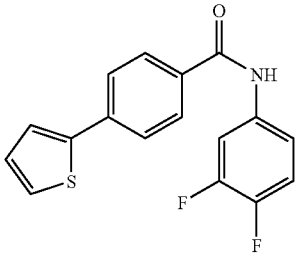 | 315.34 | 316.10 | 3.98 | 3.82 | 4.12 | + |
| 641 | 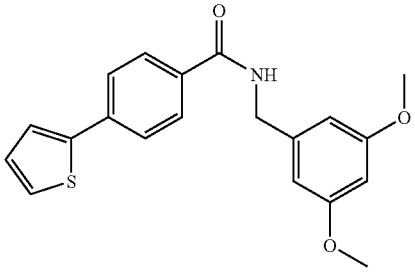 | 353.44 | | | | | |

-continued
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 642 | 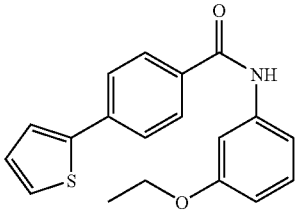 | 323.42 | 324.28 | 3.71 | 3.59 | 4.06 | |
| 643 | 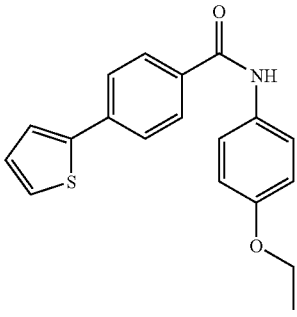 | 323.42 | 324.28 | 3.62 | 3.55 | 3.85 | ++ |
| 644 | 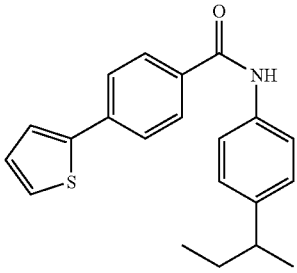 | 335.47 | 336.39 | 4.12 | 3.88 | 4.69 | |
| 645 | 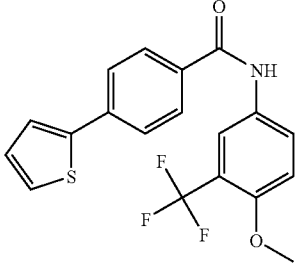 | 377.39 | 378.30 | 3.79 | 3.75 | 3.92 | |
| 646 | 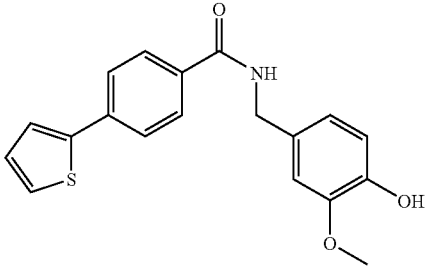 | 339.42 | | | | | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 647 | 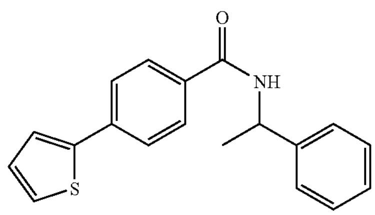 | 307.42 | 308.25 | 3.46 | 3.38 | 3.79 | |
| 648 | 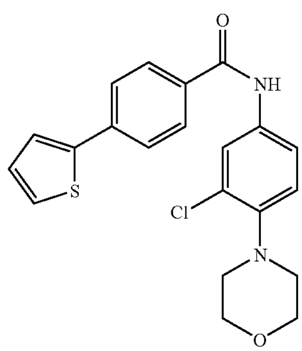 | 398.91 | 399.10 | 3.72 | 3.62 | 4.32 | |
| 649 | 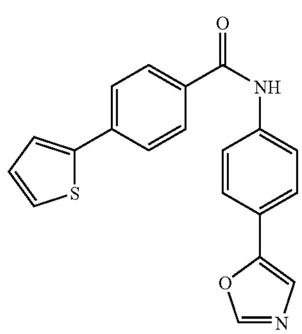 | 346.41 | | | | | |
| 650 | 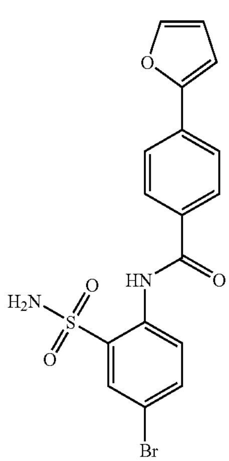 | 393.87 | | | | | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 651 | 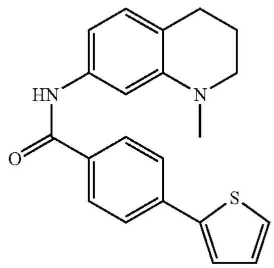 | 348.47 | | | | | |
| 652 | 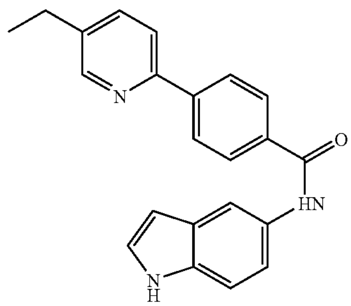 | 341.42 | 342.17 | 2.25 | 1.96 | 2.86 | |
| 653 | 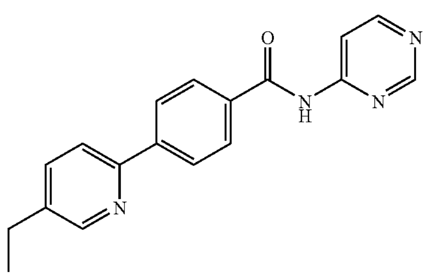 | 304.35 | 305.27 | 1.85 | 1.72 | 2.38 | |
| 654 | 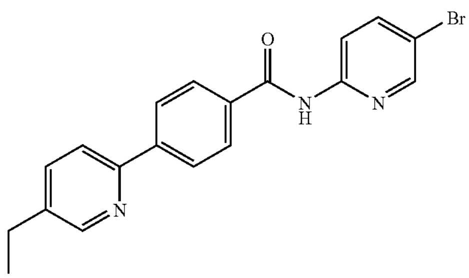 | 382.26 | 384.07 | 2.60 | 2.36 | 2.85 | + |
| 655 | 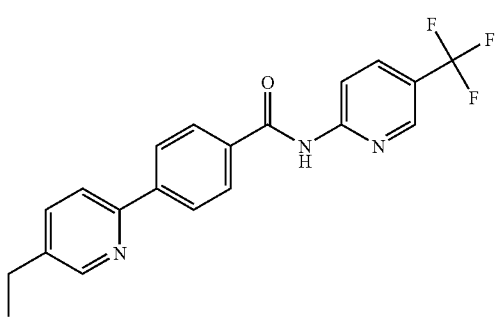 | 371.37 | | | | | |

-continued
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 656 | 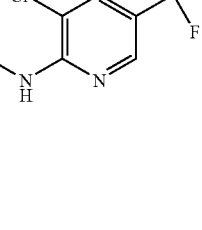 | 405.81 | 406.19 | 2.59 | 2.53 | 2.91 | + |
| 657 | 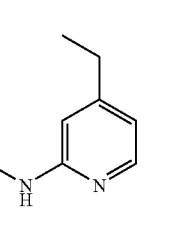 | 331.42 | 332.28 | 1.96 | 1.90 | 2.33 | |
| 658 | 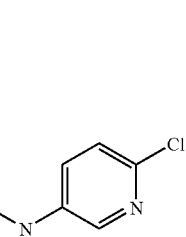 | 337.81 | | | | | |
| 659 | 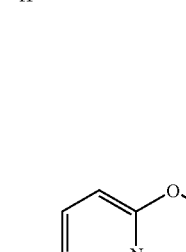 | 333.39 | | | | | |
| 660 | 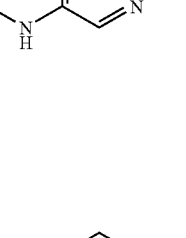 | 337.81 | 338.27 | 2.35 | 2.29 | 2.45 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 661 | 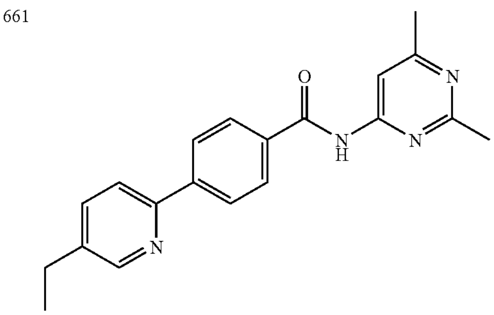 | 332.41 | 333.25 | 1.83 | 1.63 | 2.12 | |
| 662 | 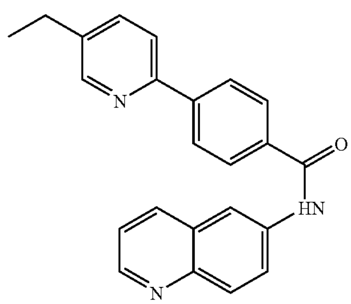 | 353.43 | 354.25 | 1.85 | 1.73 | 2.06 | |
| 663 | 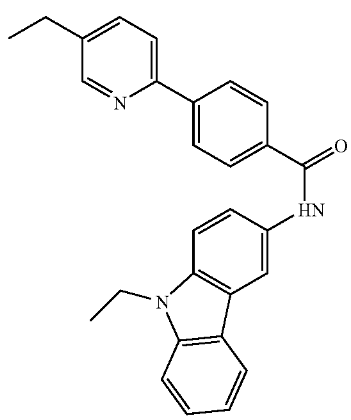 | 419.53 | | | | | |
| 664 | 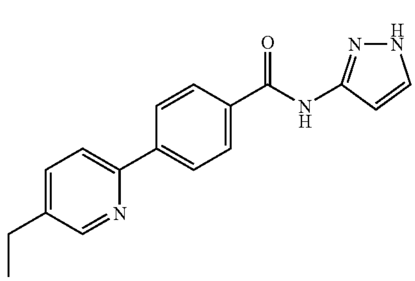 | 292.34 | 293.06 | 1.80 | 1.70 | 2.13 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 665 | 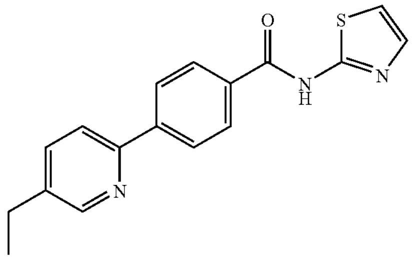 | 309.39 | 310.28 | 2.16 | 2.03 | 2.59 | |
| 666 | 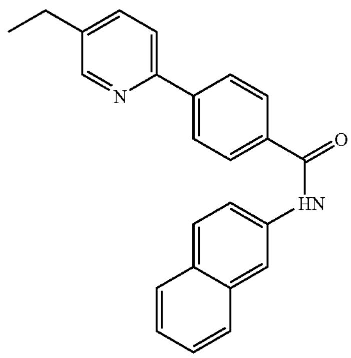 | 352.44 | 353.27 | 2.78 | 2.69 | 3.23 | |
| 667 | 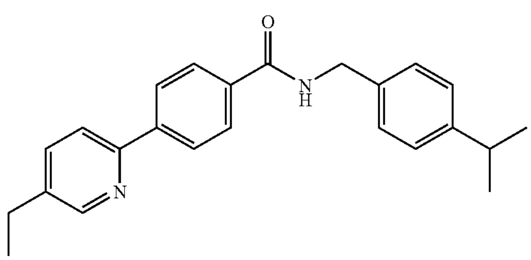 | 358.49 | 359.29 | 2.82 | 2.65 | 3.39 | |
| 668 | 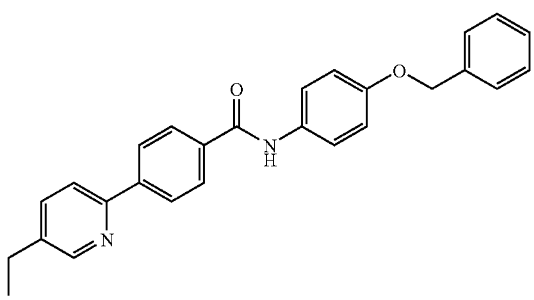 | 408.50 | | | | | |
| 669 | 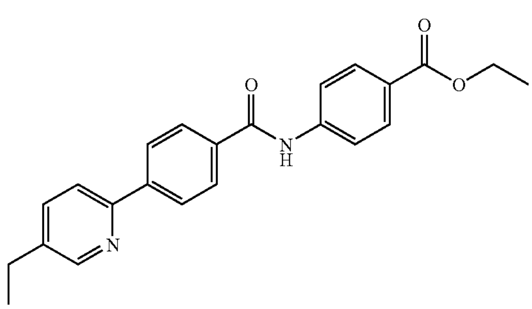 | 374.44 | 375.22 | 2.72 | 2.63 | 3.11 | |

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 670 | 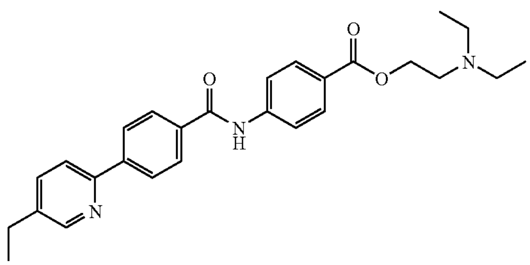 | 445.57 | 446.26 | 2.07 | 1.99 | 2.45 | |
| 671 | 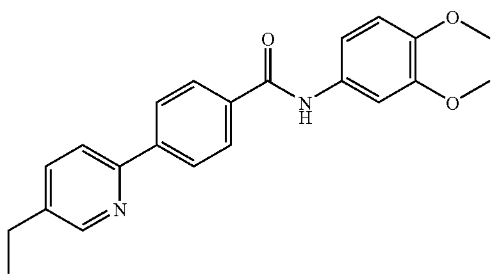 | 362.43 | 363.37 | 2.21 | 2.12 | 2.69 | |
| 672 | 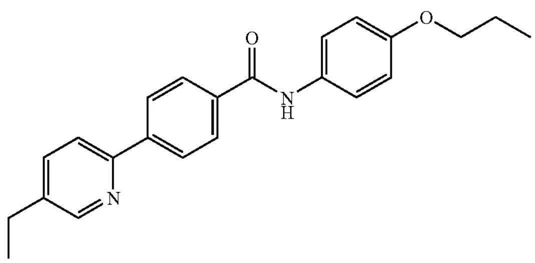 | 360.46 | 361.32 | 2.78 | 2.69 | 3.14 | |
| 673 | 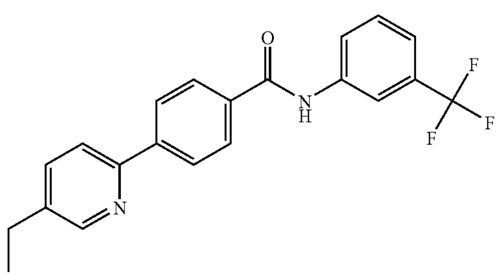 | 370.38 | 371.10 | 2.85 | 2.69 | 3.32 | |
| 674 | 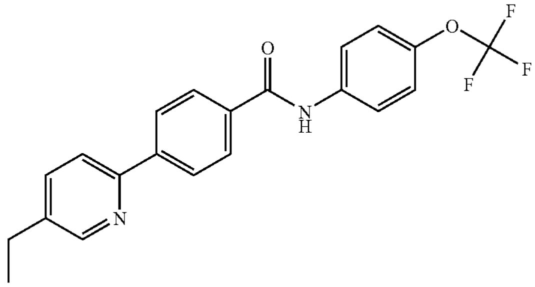 | 386.38 | 387.18 | 2.98 | 2.81 | 3.22 | ++ |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 675 | 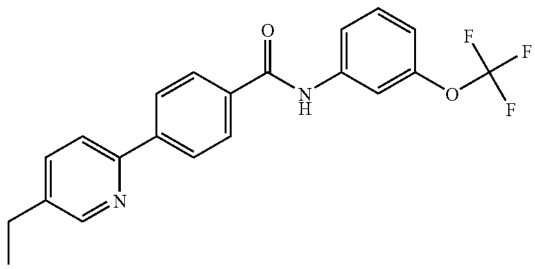 | 386.38 | 387.20 | 2.95 | 2.81 | 3.38 | + |
| 676 | 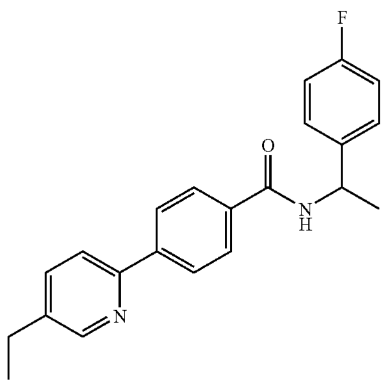 | 348.42 | 349.29 | 2.48 | 2.39 | 2.98 | + |
| 677 | 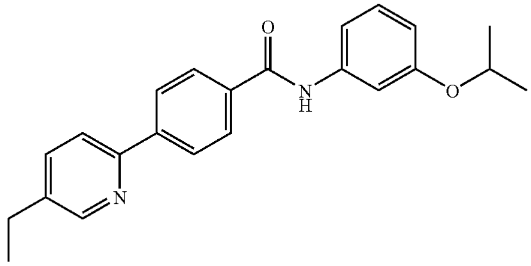 | 360.46 | 361.32 | 2.75 | 2.65 | 3.23 | |
| 678 | 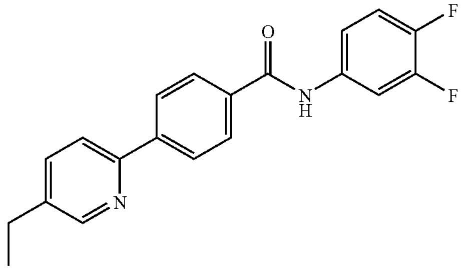 | 338.36 | 339.18 | 2.62 | 2.52 | 3.05 | |
| 679 | 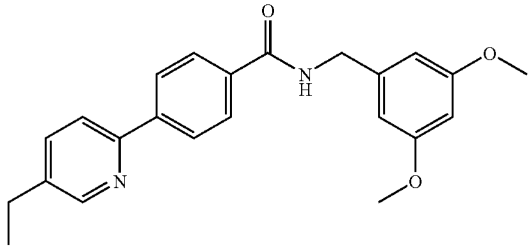 | 376.46 | 377.34 | 2.38 | 2.18 | 2.91 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 680 | 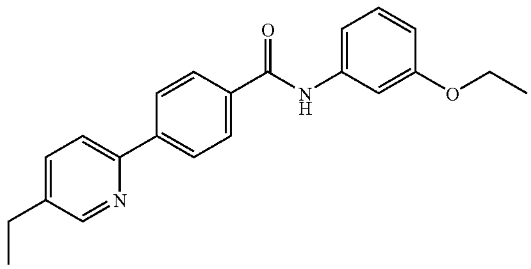 | 346.43 | 347.22 | 2.59 | 2.52 | 3.06 | |
| 681 | 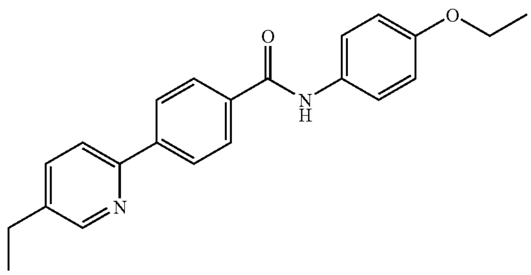 | 346.43 | 347.21 | 2.54 | 2.48 | 2.91 | |
| 682 | 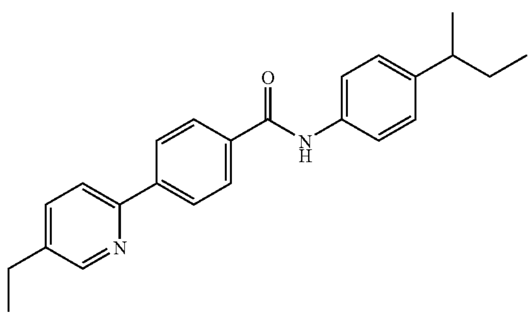 | 358.49 | 359.29 | 3.08 | 2.98 | 3.67 | |
| 683 | 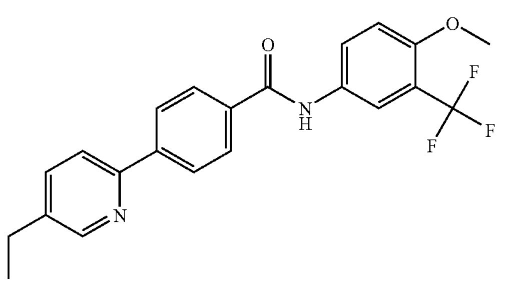 | 400.40 | 401.21 | 2.81 | 2.65 | 3.46 | |
| 684 | 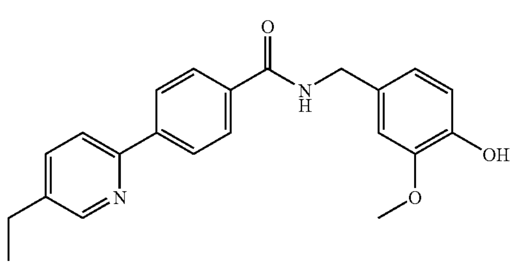 | 362.43 | 363.37 | 1.99 | 1.90 | 2.23 | |

-continued
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 685 | 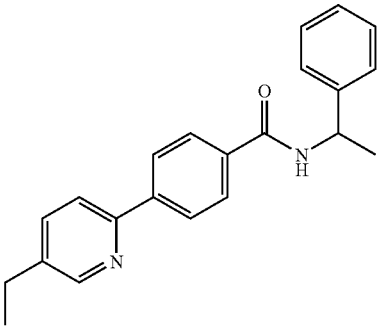 | 330.43 | 331.26 | 2.42 | 2.33 | 2.80 | +++ |
| 686 | 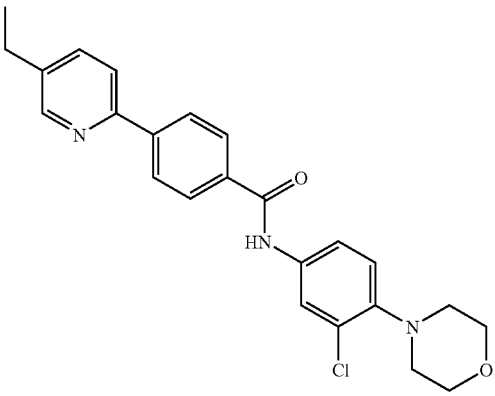 | 421.93 | 422.03 | 2.58 | 2.50 | 2.96 | + |
| 687 | 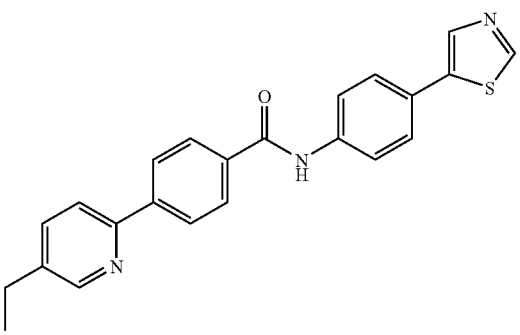 | 369.43 | 370.17 | 2.42 | 2.16 | 2.82 | |
| 688 | 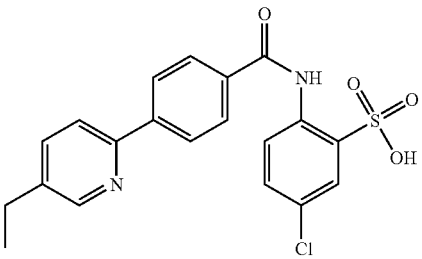 | 416.89 | | | | | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 689 | 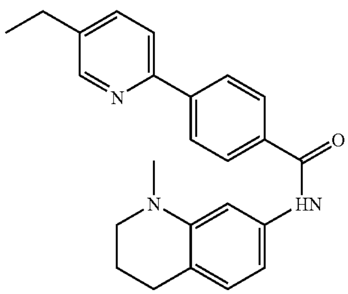 | 371.49 | 372.18 | 2.00 | 1.95 | 2.42 | |
| 690 | 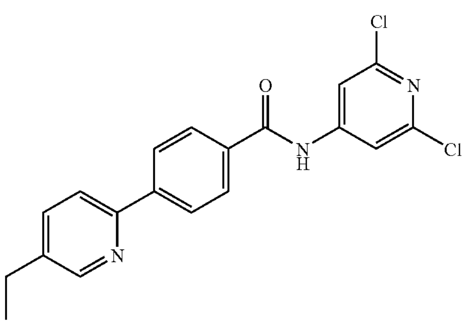 | 372.26 | | | | | |
| 691 | 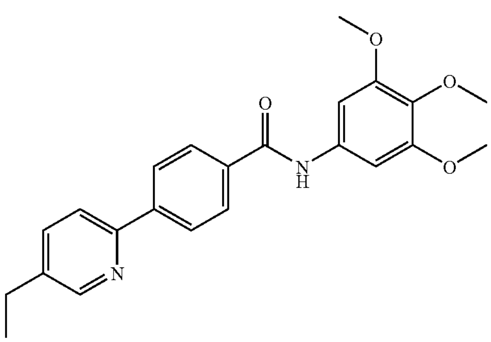 | 392.46 | 393.26 | 2.29 | 2.15 | 2.73 | |
| 692 | 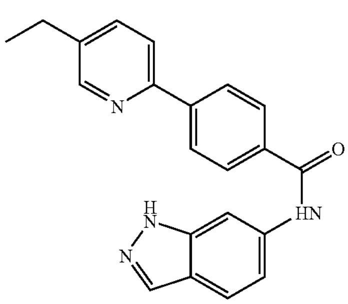 | 342.40 | 343.20 | 2.12 | 1.93 | 2.72 | |

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 693 | 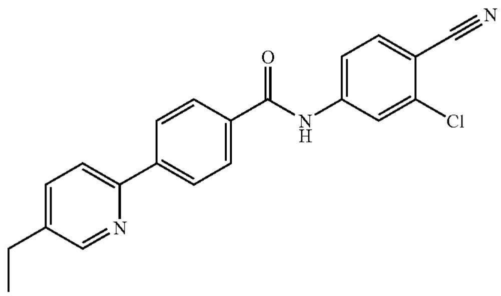 | 361.83 | 362.29 | 2.75 | 2.69 | 3.08 | |
| 694 | 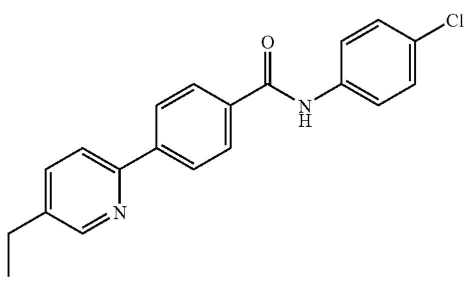 | 336.82 | 337.35 | 2.71 | 2.55 | 3.09 | |
| 695 | 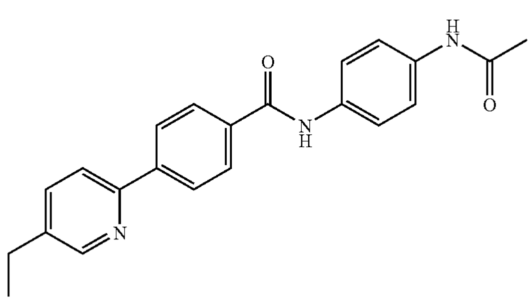 | 359.43 | 360.22 | 2.00 | 1.93 | 2.32 | |
| 696 | 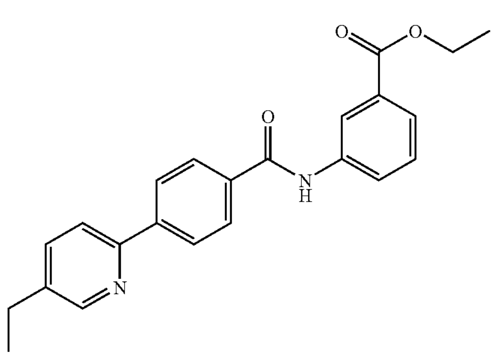 | 374.44 | 375.22 | 2.68 | 2.58 | 3.15 | ++++ |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 697 | 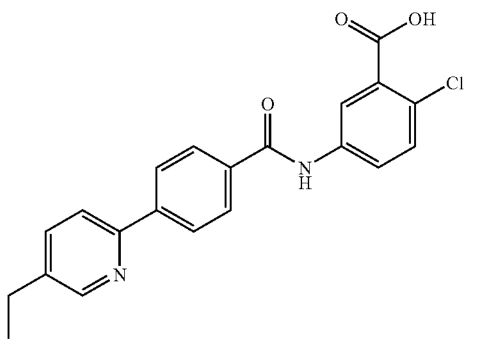 | 380.83 | | | | | |
| 698 | 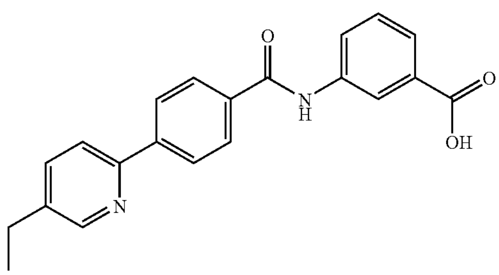 | 346.39 | 347.15 | 2.15 | 1.98 | 2.48 | |
| 699 | 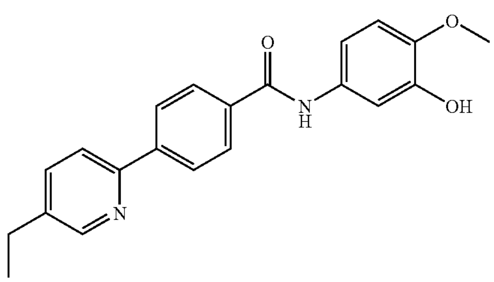 | 348.41 | 349.29 | 2.05 | 1.97 | 2.78 | |
| 700 | 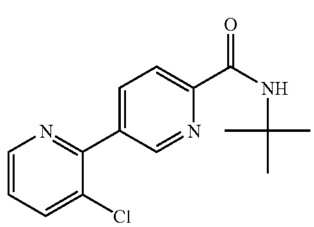 | 289.77 | | | | | |
| 701 | 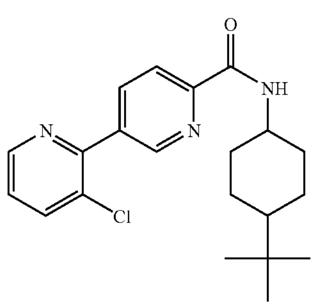 | 371.91 | 372.09 | 4.25 | 4.09 | 4.79 | |

-continued
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 702 | 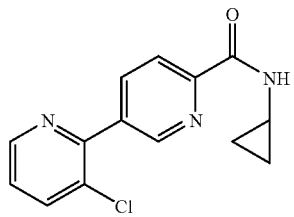 | 273.72 | 274.06 | 2.52 | 2.33 | 2.96 | |
| 703 | 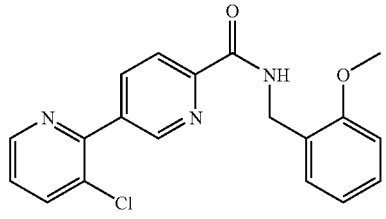 | 353.81 | 354.12 | 3.25 | 2.96 | 3.69 | + |
| 704 | 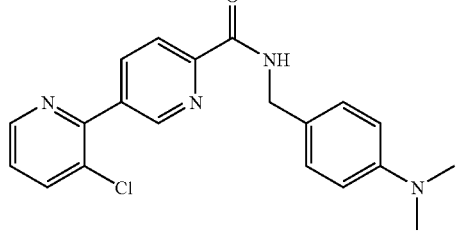 | 366.85 | 367.02 | 2.19 | 1.87 | 2.43 | |
| 705 | 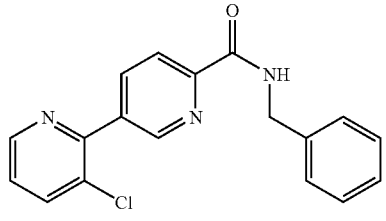 | 323.78 | 324.16 | 3.13 | 2.89 | 3.61 | |
| 706 | 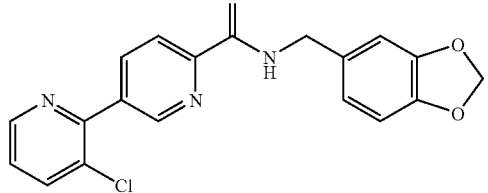 | 367.79 | 368.06 | 3.08 | 2.86 | 3.33 | |
| 707 | 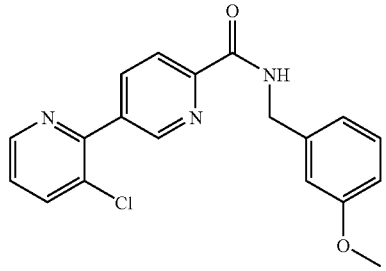 | 353.81 | 354.12 | 3.11 | 2.92 | 3.46 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 708 | 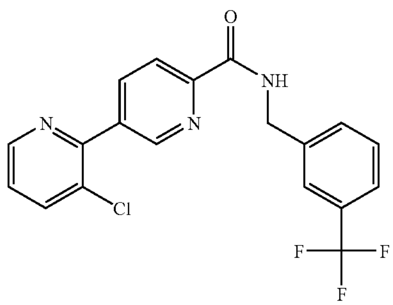 | 391.78 | | | | | |
| 709 | 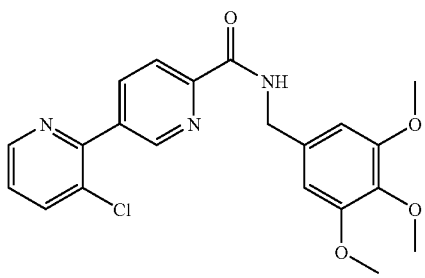 | 413.86 | 414.08 | 2.89 | 2.79 | 3.18 | |
| 710 | 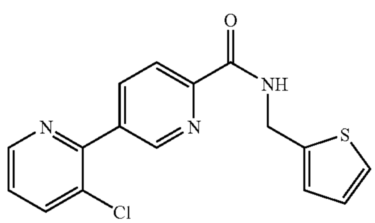 | 329.81 | 327.05 | 5.28 | 4.88 | 5.69 | + |
| 711 | 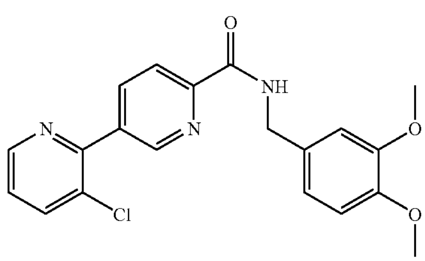 | 383.84 | 384.12 | 2.88 | 2.75 | 3.22 | ++ |
| 712 | 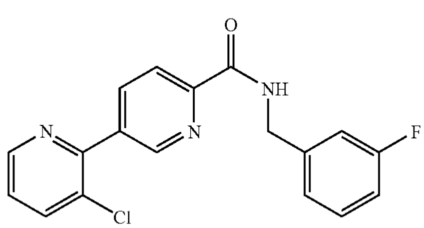 | 341.78 | 342.08 | 3.18 | 3.08 | 3.31 | ++++ |
| 713 | 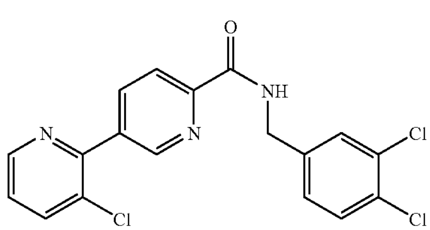 | 392.67 | 391.93 | 3.61 | 3.52 | 3.88 | |

-continued
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 714 | 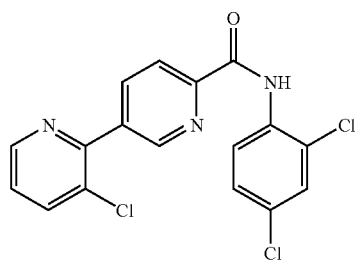 | 378.65 | | | | | |
| 715 | 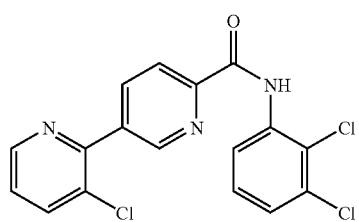 | 378.65 | | | | | |
| 716 | 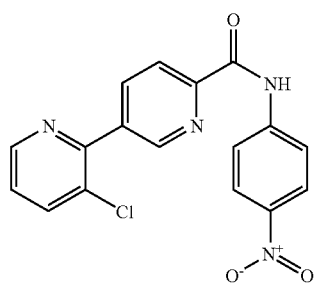 | 354.76 | | | | | |
| 717 | 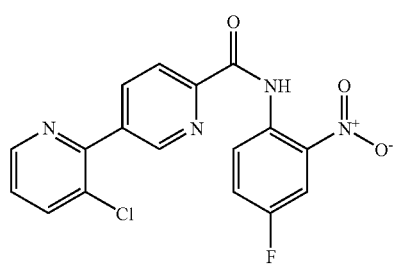 | 372.75 | | | | | |
| 718 | 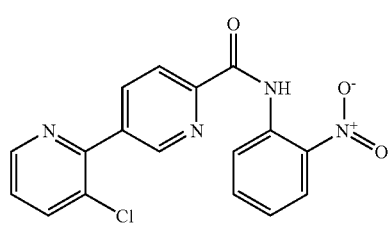 | 354.76 | | | | | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 719 | 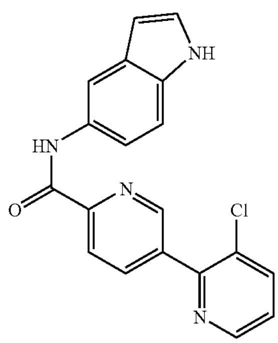 | 348.79 | | | | | |
| 720 | 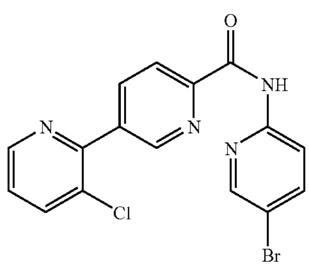 | 389.64 | | | | | |
| 721 | 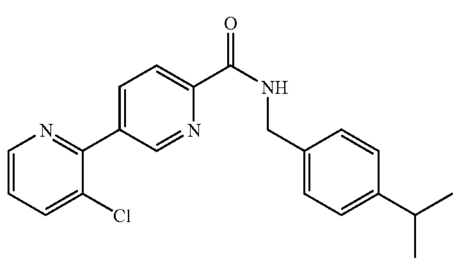 | 365.87 | 366.12 | 3.75 | 3.61 | 4.15 | + |
| 722 | 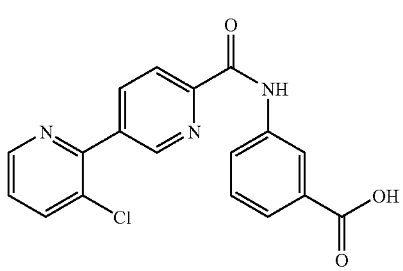 | 353.77 | | | | | |
| 723 | 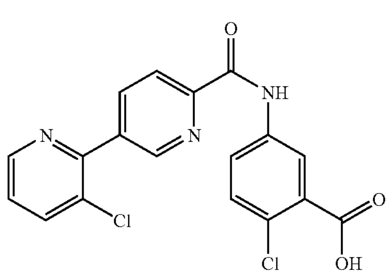 | 388.21 | | | | | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 724 | 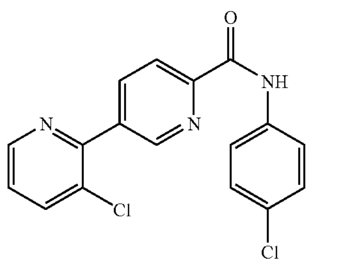 | 344.20 | | | | | |
| 725 | 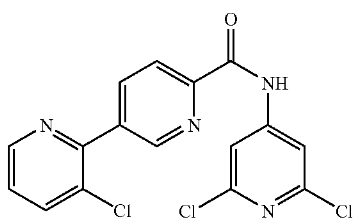 | 379.64 | | | | | |
| 726 | 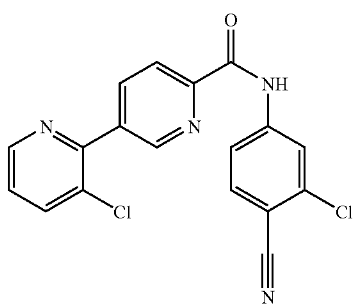 | 369.21 | | | | | |
| 727 | 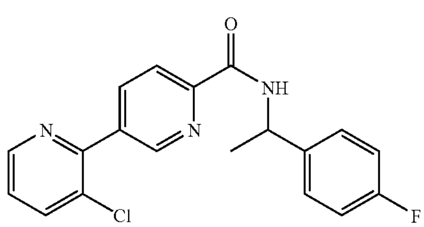 | 355.80 | 356.12 | 3.33 | 3.21 | 3.71 | |
| 728 | 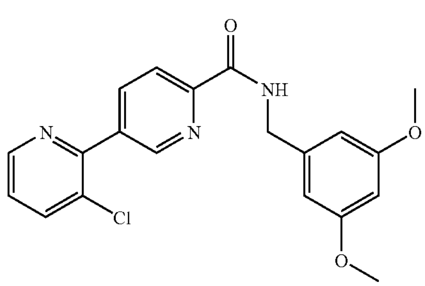 | 383.84 | 384.09 | 3.15 | 2.89 | 3.45 | |

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 729 | 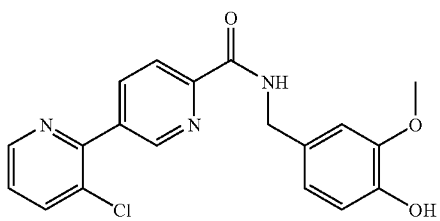 | 369.81 | 370.10 | 2.62 | 2.55 | 2.83 | ++++ |
| 730 | 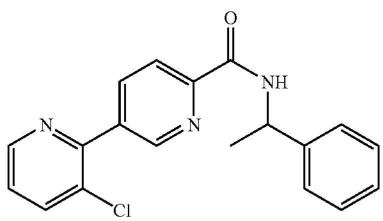 | 337.81 | | | | | |
| 731 | 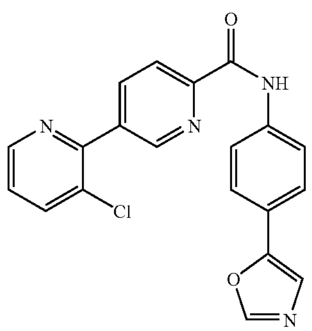 | 376.81 | | | | | |
| 732 | 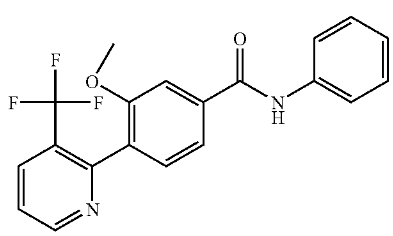 | 372.35 | | | | | |
| 733 | 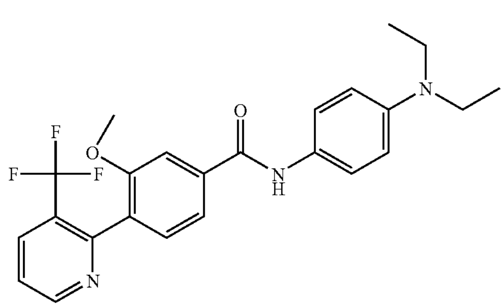 | 443.47 | 444.39 | 2.51 | 2.39 | 2.88 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 734 | 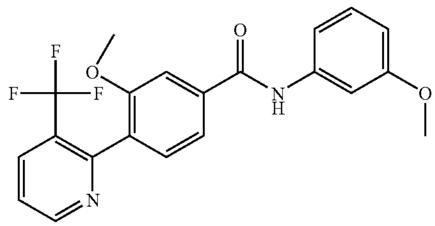 | 402.38 | 403.31 | 3.18 | 2.88 | 3.69 | |
| 735 | 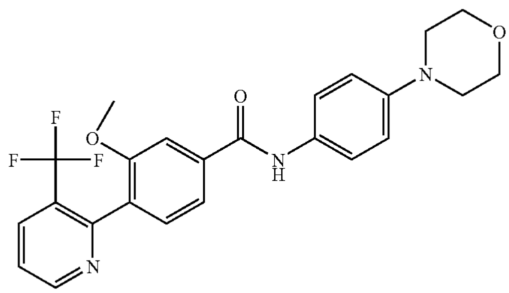 | 457.46 | 458.32 | 2.56 | 2.42 | 3.00 | |
| 736 | 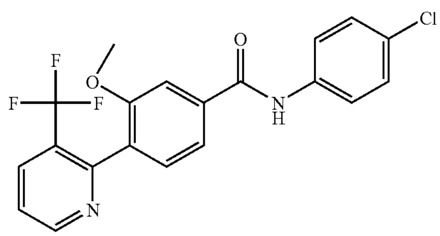 | 406.79 | 407.14 | 3.44 | 3.18 | 3.81 | |
| 737 | 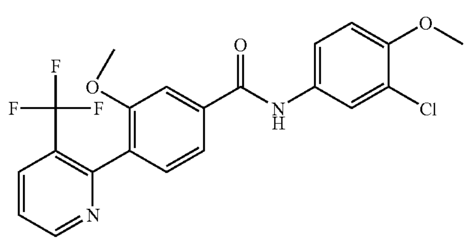 | 436.82 | 437.12 | 3.33 | 3.22 | 3.72 | |
| 738 | 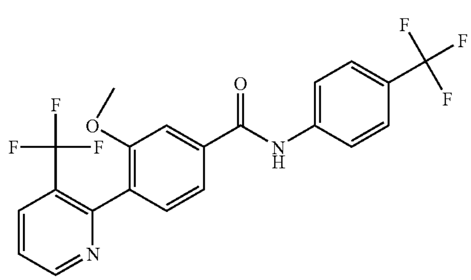 | 440.35 | 441.20 | 3.59 | 3.39 | 3.96 | |
| 739 | 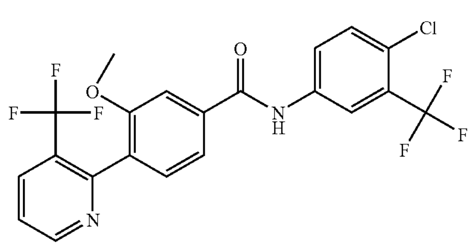 | 474.79 | 475.01 | 3.78 | 3.58 | 4.21 | |

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 740 | 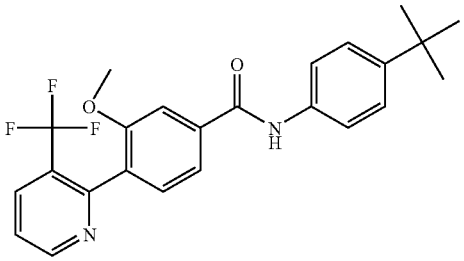 | 428.46 | 429.28 | 3.75 | 3.48 | 4.09 | |
| 741 | 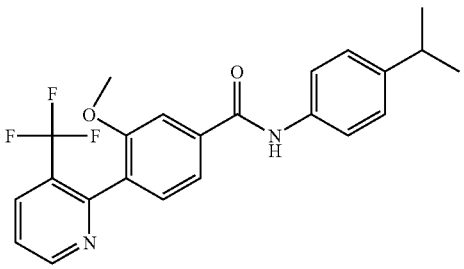 | 414.43 | 415.29 | 3.68 | 3.43 | 4.15 | |
| 742 | 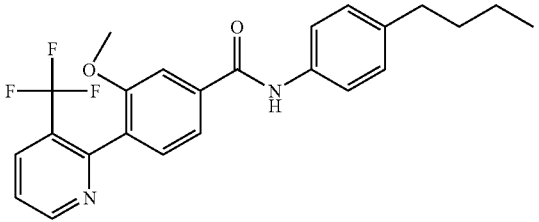 | 428.46 | 429.29 | 3.86 | 3.58 | 4.24 | |
| 743 | 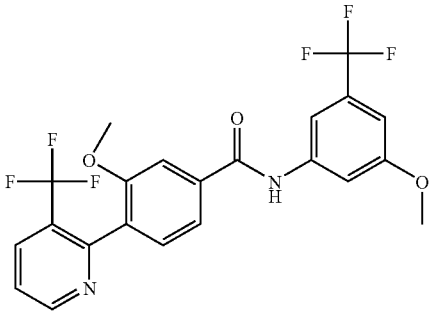 | 470.37 | 471.33 | 3.64 | 3.45 | 4.01 | |
| 744 | 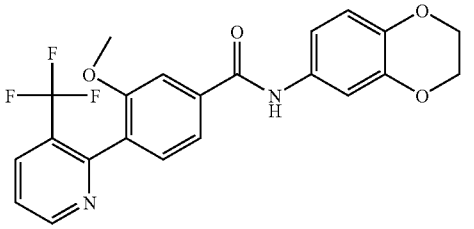 | 430.39 | 431.31 | 3.09 | 2.95 | 3.59 | |

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 745 | 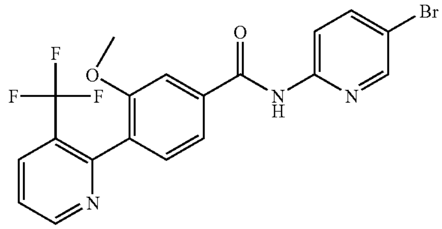 | 452.23 | 451.96 | 3.39 | 3.19 | 3.51 | |
| 746 | 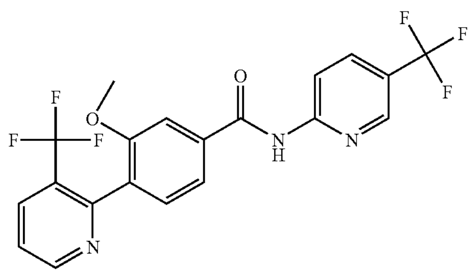 | 441.34 | 442.22 | 3.52 | 3.28 | 3.81 | |
| 747 | 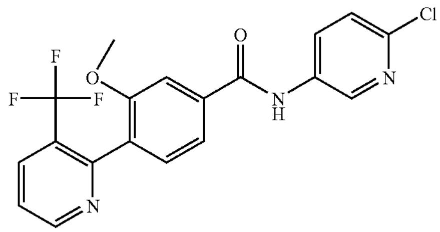 | 407.78 | 408.11 | 3.09 | 2.93 | 3.53 | |
| 748 | 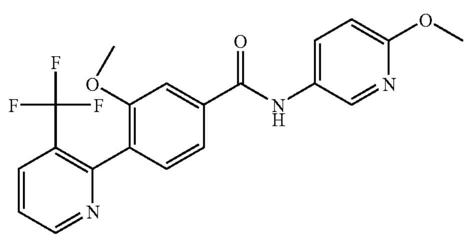 | 403.36 | 404.29 | 2.79 | 2.52 | 3.28 | |
| 749 | 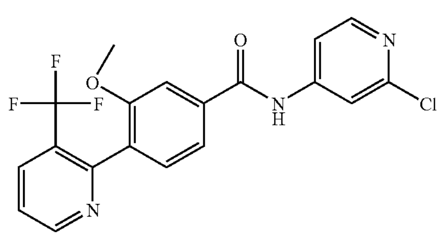 | 407.78 | 408.12 | 3.08 | 2.95 | 3.62 | |
| 750 | 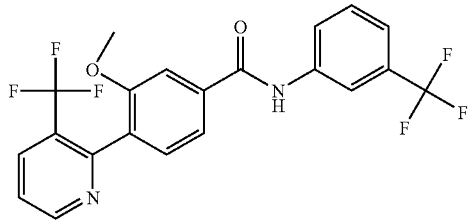 | 440.35 | 441.21 | 3.56 | 3.18 | 4.04 | |

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 751 | 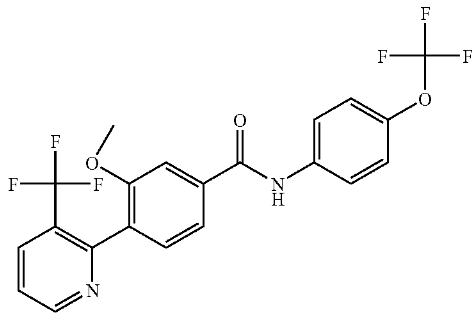 | 456.35 | 457.24 | 3.61 | 3.23 | 3.91 | |
| 752 | 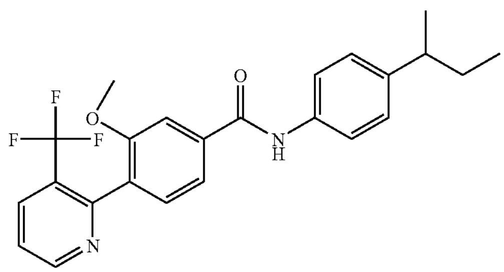 | 428.46 | 429.29 | 3.81 | 3.55 | 4.18 | |
| 753 | 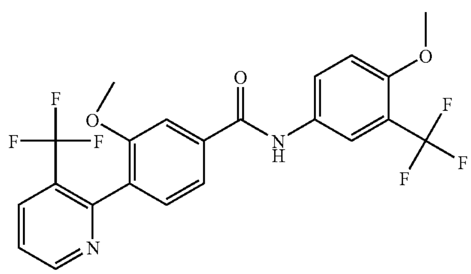 | 470.37 | 471.32 | 3.49 | 3.18 | 3.86 | |
| 754 | 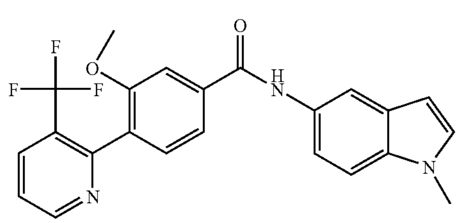 | 425.41 | 426.12 | 3.19 | 2.92 | 3.59 | |
| 755 | 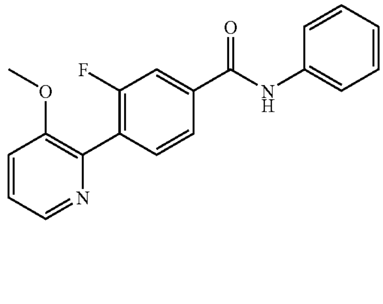 | 322.34 | 323.15 | 2.46 | 2.09 | 2.75 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 756 | 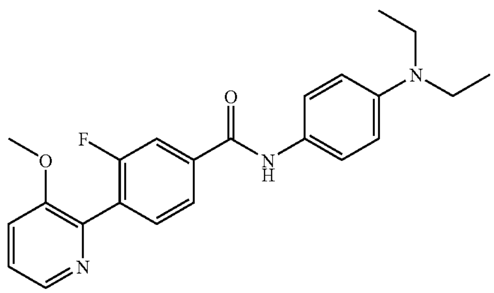 | 393.47 | 394.17 | 1.95 | 1.88 | 2.33 | |
| 757 | 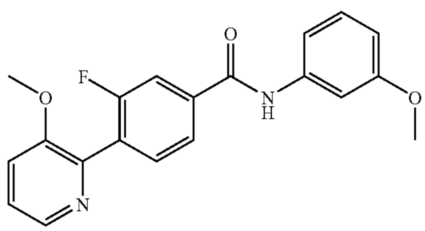 | 352.37 | 353.24 | 2.52 | 2.36 | 2.78 | |
| 758 | 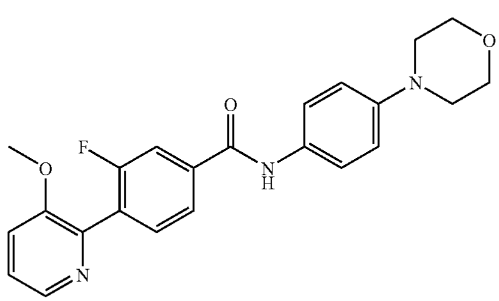 | 407.45 | 408.17 | 1.98 | 1.89 | 2.31 | |
| 759 | 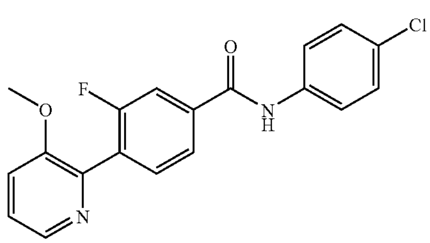 | 356.79 | 357.09 | 2.80 | 2.66 | 3.13 | |
| 760 | 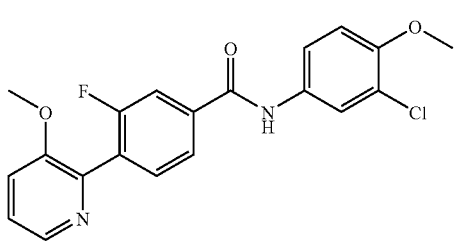 | 386.81 | 387.12 | 2.69 | 2.53 | 3.03 | |

-continued

| ID | STRUCTURE | MW (Calc) | MS (Obs) | HPLC RT (Min) | HPLC START TIME (Min) | HPLC END TIME (Min) | % Inhibition @ 1 uM |
|----|-----------|-----------|----------|---------------|----------------------|--------------------|---------------------|
| 761 | 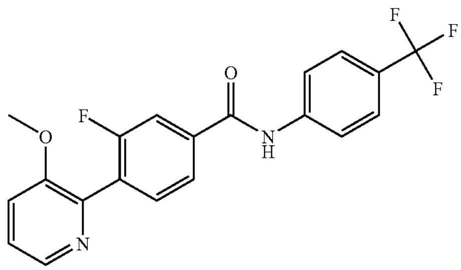 | 390.34 | 391.27 | 2.99 | 2.86 | 3.38 | |
| 762 | 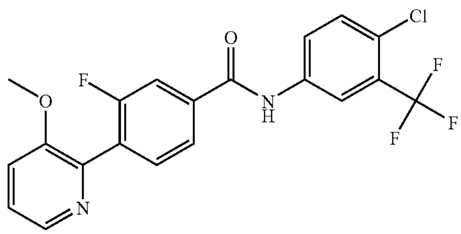 | 424.79 | 425.00 | 3.19 | 3.06 | 3.53 | |
| 763 | 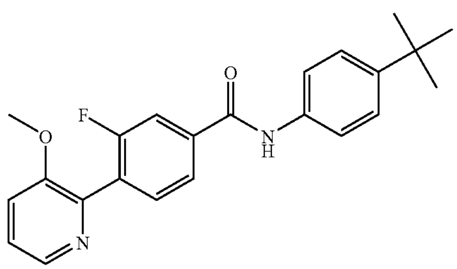 | 378.45 | 379.30 | 3.15 | 2.93 | 3.43 | |
| 764 | 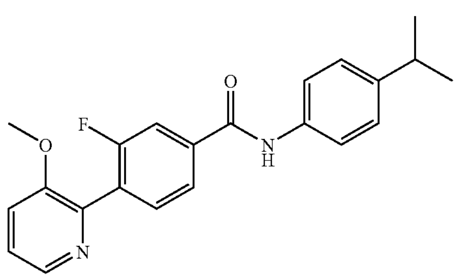 | 364.42 | 365.09 | 2.98 | 2.85 | 3.55 | |
| 765 | 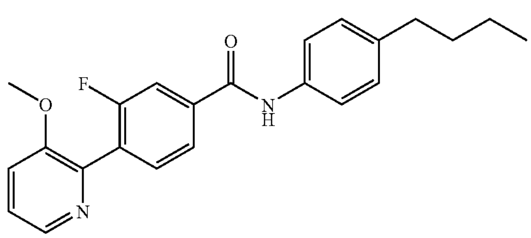 | 378.45 | 379.30 | 3.24 | 3.09 | 3.56 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 766 | 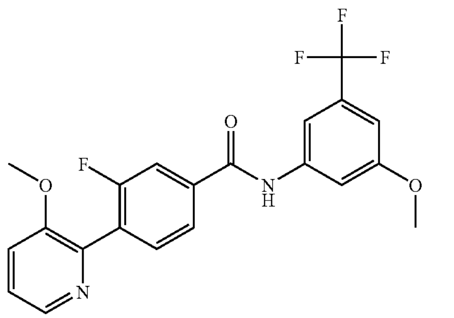 | 420.37 | 421.09 | 3.05 | 2.89 | 3.28 | |
| 767 | 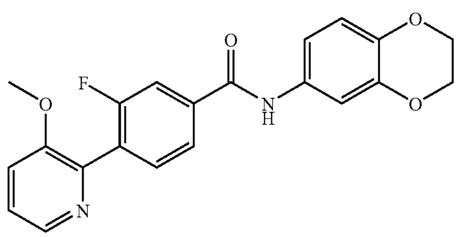 | 380.38 | 381.22 | 2.43 | 2.32 | 2.75 | |
| 768 | 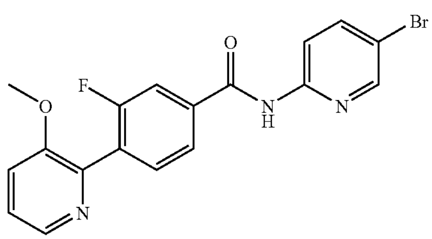 | 402.23 | 404.19 | 2.68 | 2.60 | 2.79 | |
| 769 | 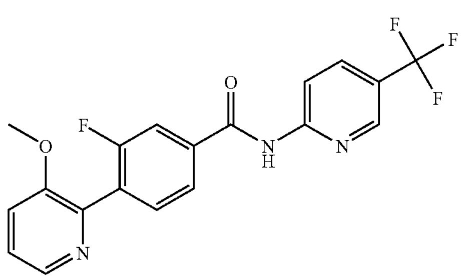 | 391.33 | 392.14 | 2.86 | 2.78 | 2.99 | |
| 770 | 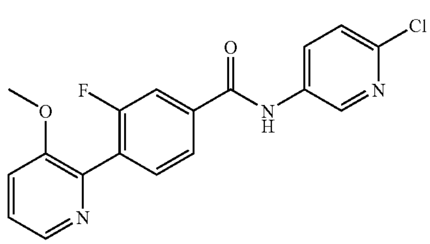 | 357.77 | 358.10 | 2.39 | 2.30 | 2.63 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 771 | 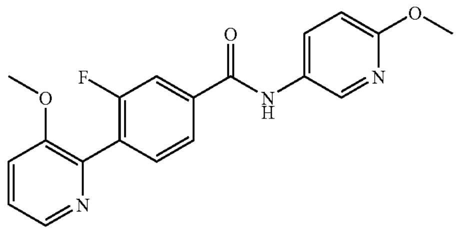 | 353.36 | 354.15 | 2.13 | 2.02 | 2.39 | |
| 772 | 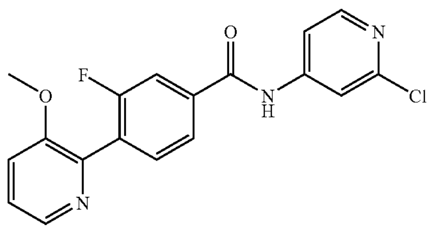 | 357.77 | | | | | |
| 773 | 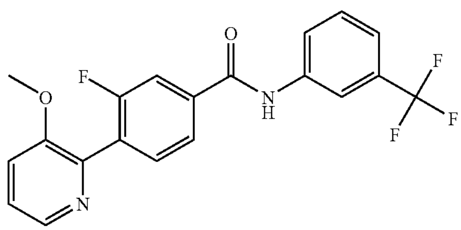 | 390.34 | 391.26 | 2.96 | 2.81 | 3.24 | |
| 774 | 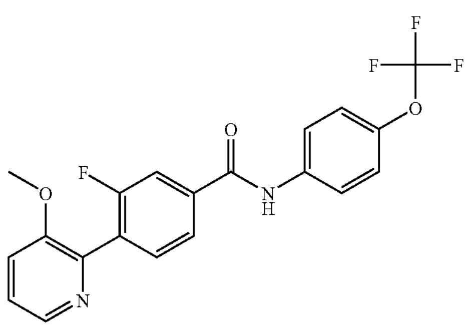 | 406.34 | 407.18 | 3.02 | 2.88 | 3.32 | |
| 775 | 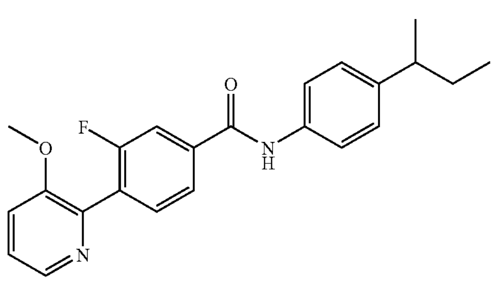 | 378.45 | 379.30 | 3.21 | 3.06 | 3.48 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 776 | 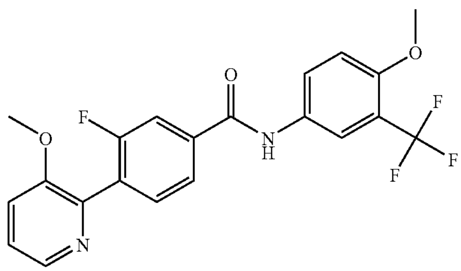 | 420.37 | 421.10 | 2.89 | 2.75 | 3.12 | |
| 777 | 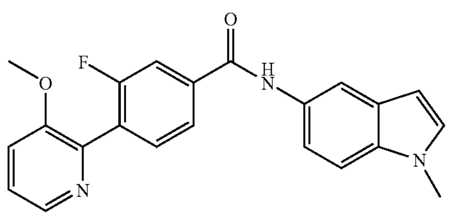 | 375.41 | 376.17 | 2.55 | 2.33 | 2.96 | |
| 778 | 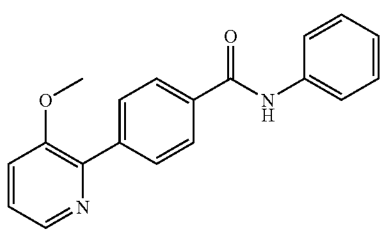 | 304.35 | 305.26 | 2.25 | 2.12 | 2.52 | |
| 779 | 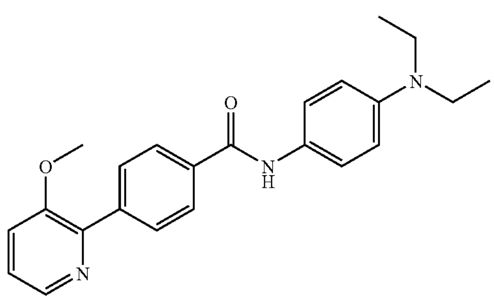 | 375.47 | 376.28 | 1.83 | 1.69 | 1.93 | |
| 780 | 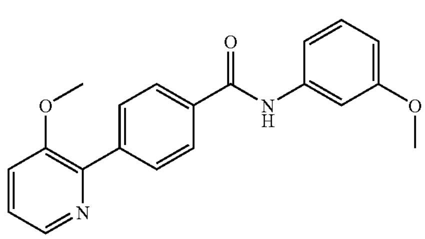 | 334.38 | 335.31 | 2.33 | 2.19 | 2.59 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 781 | 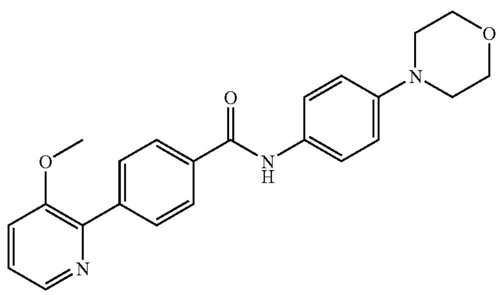 | 389.46 | 390.41 | 1.83 | 1.73 | 1.99 | |
| 782 | 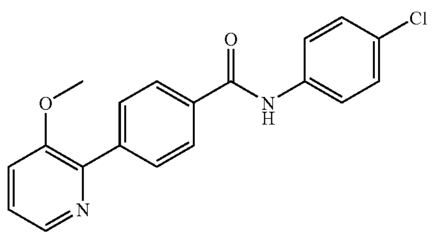 | 338.80 | 339.09 | 2.60 | 2.50 | 2.99 | |
| 783 | 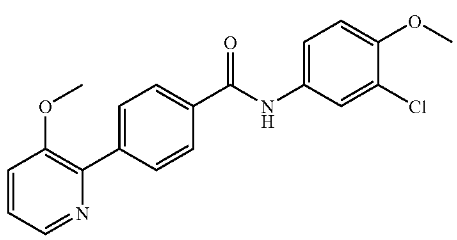 | 368.82 | 369.09 | 2.49 | 2.40 | 2.73 | |
| 784 | 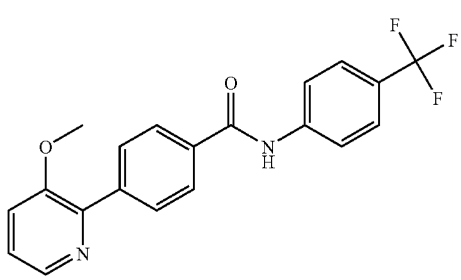 | 372.35 | 373.10 | 2.81 | 2.68 | 2.98 | |
| 785 | 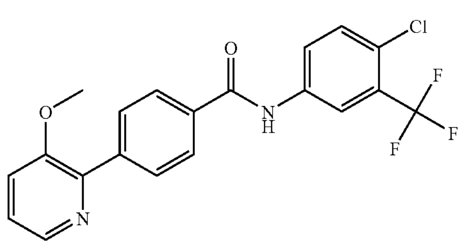 | 406.79 | 407.14 | 3.01 | 2.86 | 3.23 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 786 | 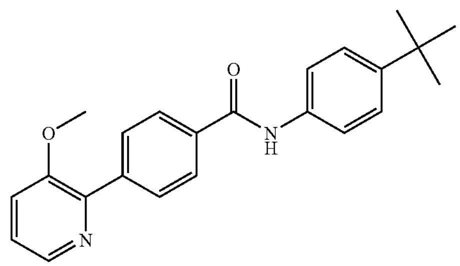 | 360.46 | 361.32 | 2.95 | 2.82 | 3.12 | |
| 787 | 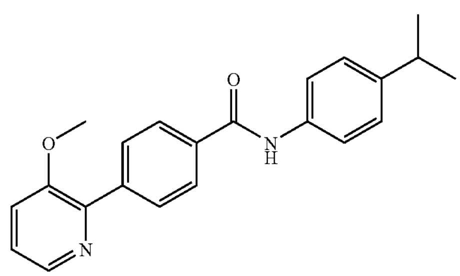 | 346.43 | 347.18 | 2.83 | 2.68 | 3.19 | |
| 788 | 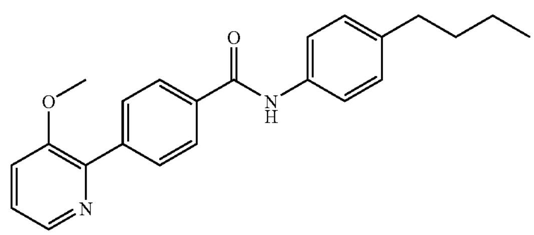 | 360.46 | 361.30 | 3.08 | 2.92 | 3.52 | |
| 789 | 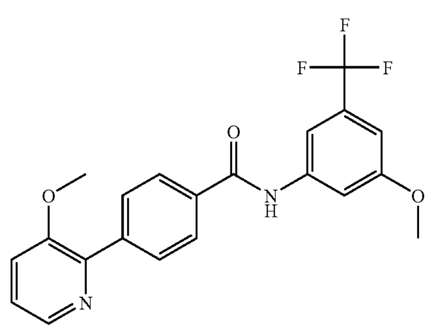 | 402.38 | 403.31 | 2.88 | 2.72 | 3.12 | |
| 790 | 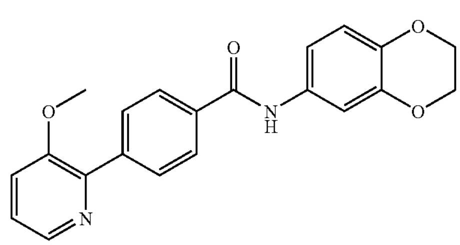 | 362.39 | 363.32 | 2.26 | 2.16 | 2.52 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 791 | 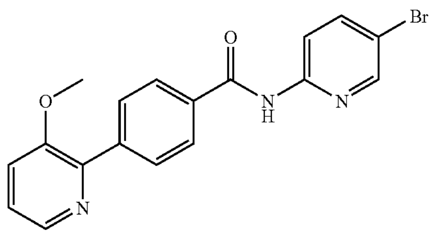 | 384.24 | | | | | |
| 792 | 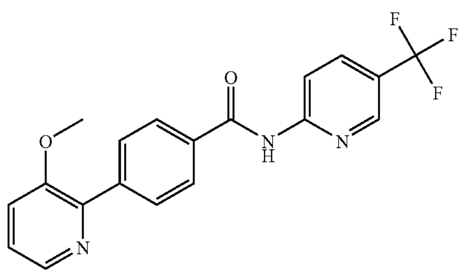 | 373.34 | | | | | |
| 793 | 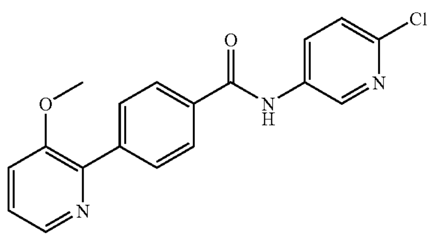 | 339.78 | 340.09 | 2.19 | 2.09 | 2.49 | |
| 794 | 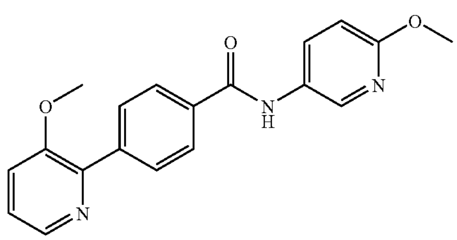 | 335.37 | 336.35 | 1.96 | 1.87 | 2.30 | |
| 795 | 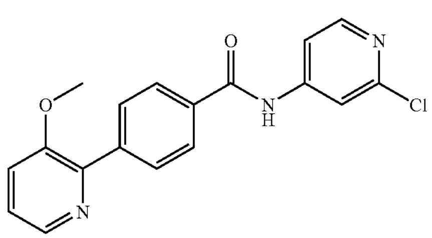 | 339.78 | 340.09 | 2.22 | 2.08 | 2.43 | |
| 796 | 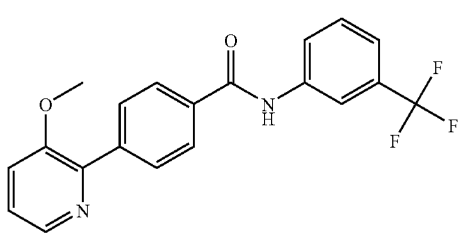 | 372.35 | 373.10 | 2.76 | 2.63 | 3.12 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 797 | 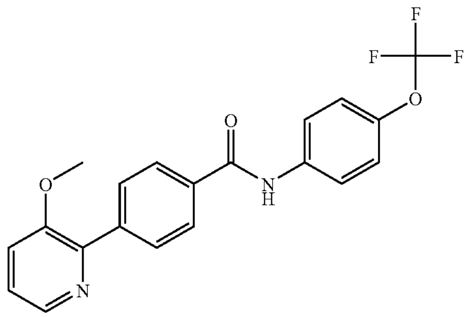 | 388.35 | 389.30 | 2.82 | 2.71 | 3.09 | |
| 798 | 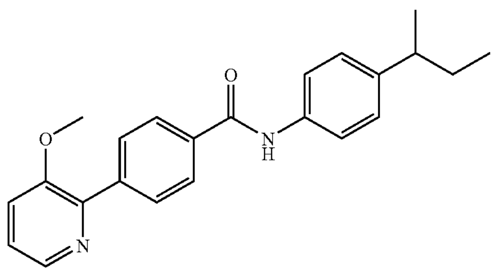 | 360.46 | 361.30 | 2.99 | 2.85 | 3.36 | |
| 799 | 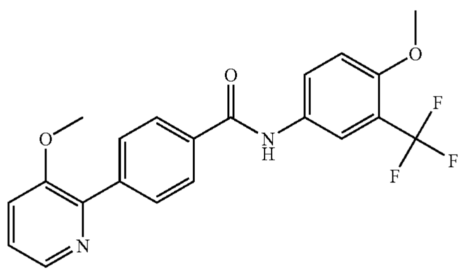 | 402.38 | 403.31 | 2.70 | 2.53 | 2.99 | |
| 800 | 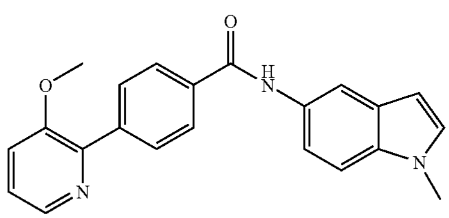 | 357.42 | 358.19 | 2.39 | 2.25 | 2.52 | |
| 801 | 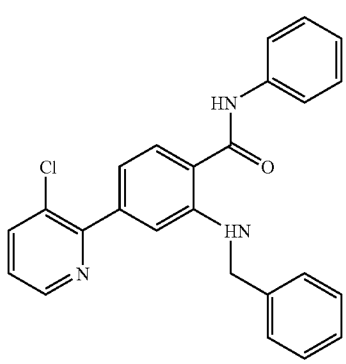 | 413.91 | 414.13 | 3.75 | 3.51 | 4.04 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 802 | 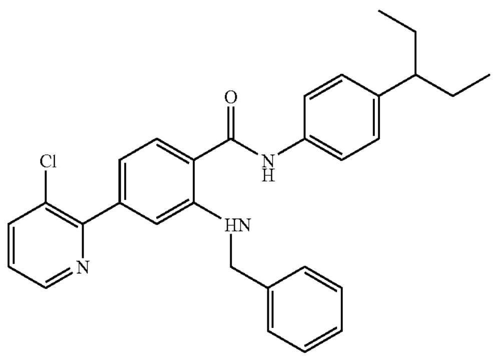 | 485.03 | 485.36 | 2.99 | 2.85 | 3.32 | |
| 803 | 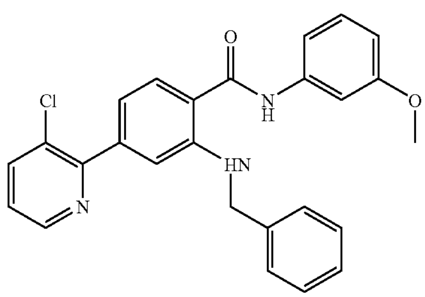 | 443.94 | 444.32 | 3.76 | 3.49 | 4.15 | |
| 804 | 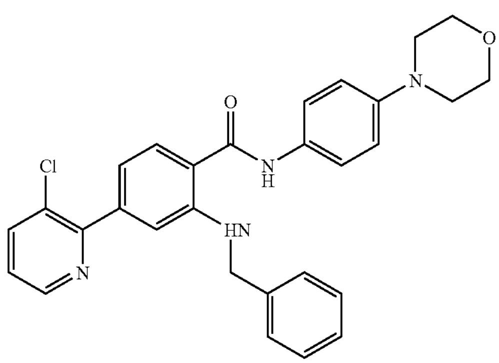 | 499.02 | 499.19 | 3.08 | 2.91 | 3.56 | |
| 805 | 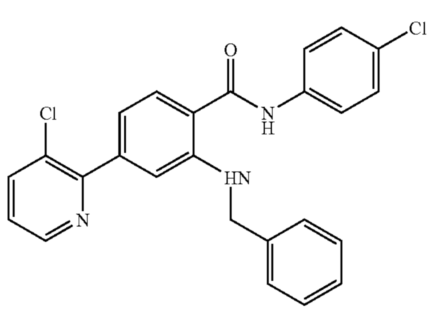 | 448.36 | 448.07 | 4.04 | 3.89 | 4.41 | |

-continued
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 806 | 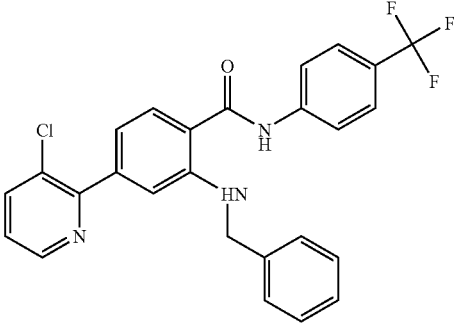 | 481.91 | 482.15 | 4.12 | 3.79 | 4.45 | |
| 807 | 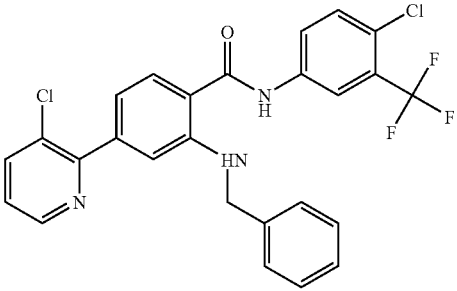 | 516.35 | 516.14 | 4.31 | 4.02 | 4.62 | |
| 808 | 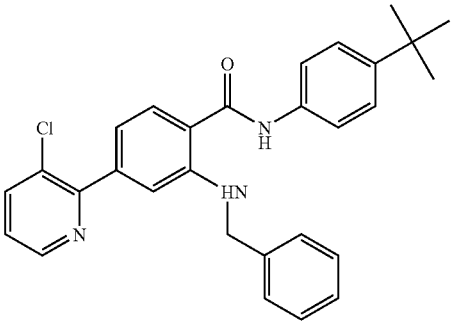 | 470.02 | 470.30 | 4.28 | 4.18 | 4.85 | |
| 809 | 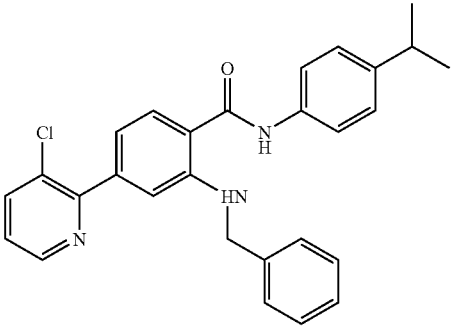 | 455.99 | 456.26 | 4.18 | 4.06 | 4.68 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 810 | 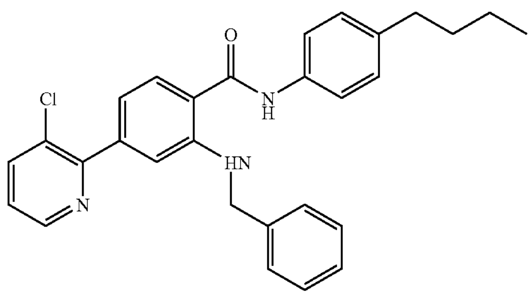 | 470.02 | 470.31 | 4.39 | 4.19 | 4.87 | |
| 811 | 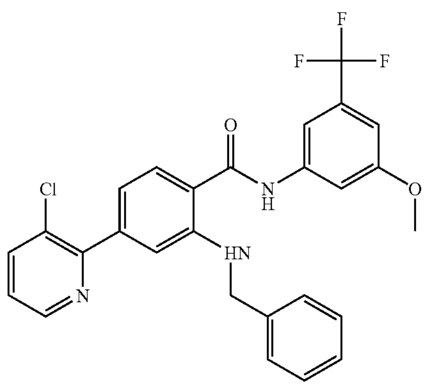 | 511.94 | 512.34 | 4.15 | 3.99 | 4.42 | |
| 812 | 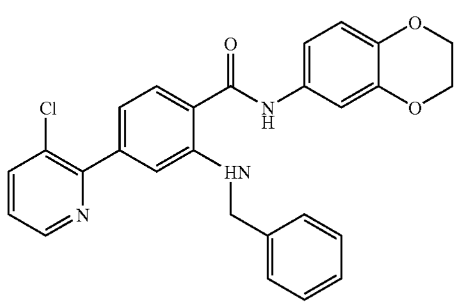 | 471.95 | 472.32 | 3.63 | 3.43 | 4.05 | |
| 813 | 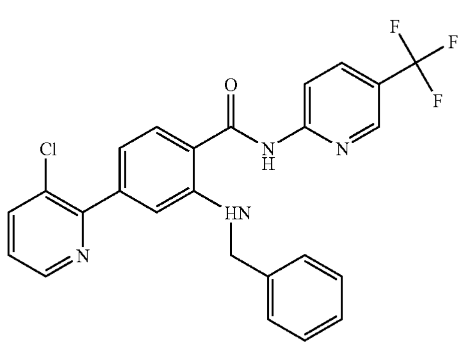 | 482.90 | 483.25 | 4.06 | 3.88 | 4.31 | |

-continued
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 814 | 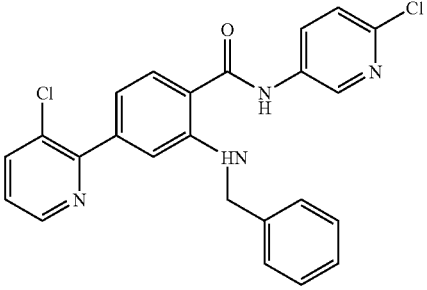 | 449.34 | 448.93 | 3.71 | 3.51 | 3.99 | |
| 815 | 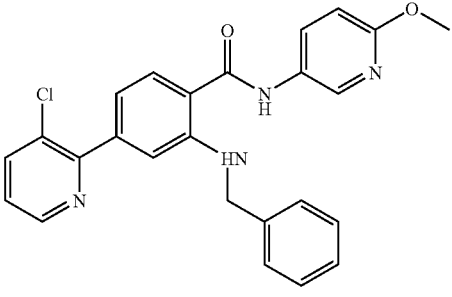 | 444.92 | 445.27 | 3.41 | 3.16 | 3.71 | |
| 816 | 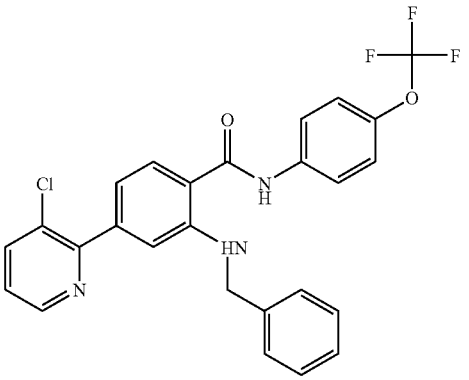 | 497.91 | 498.33 | 4.11 | 3.96 | 4.52 | |
| 817 | 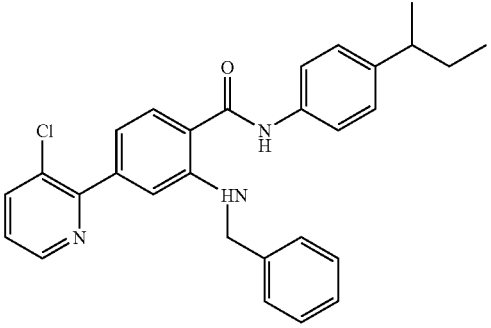 | 470.02 | 470.34 | 4.32 | 4.21 | 4.71 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 818 | 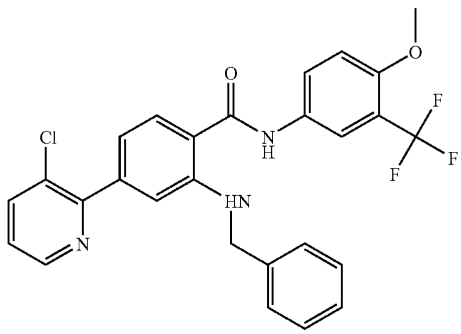 | 511.94 | 512.34 | 3.99 | 3.78 | 4.38 | |
| 819 | 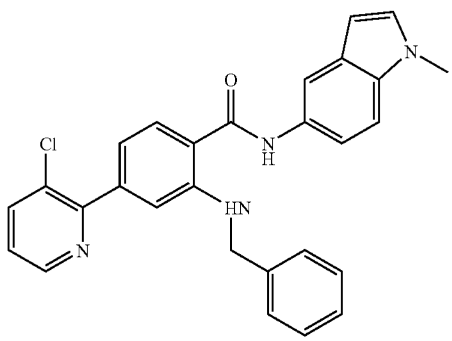 | 466.97 | 467.21 | 3.72 | 3.48 | 4.19 | |
| 820 | 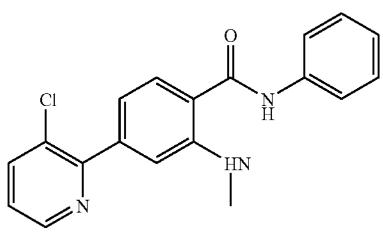 | 337.81 | 338.29 | 3.15 | 2.96 | 3.71 | |
| 821 | 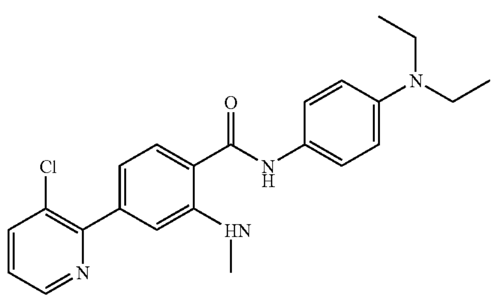 | 408.93 | 409.26 | 2.49 | 2.32 | 2.70 | |
| 822 | 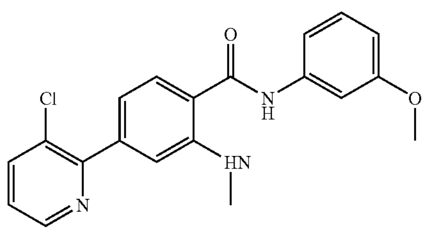 | 367.84 | 368.14 | 3.19 | 2.99 | 3.76 | |

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 823 | 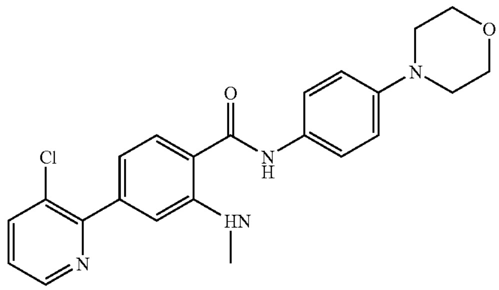 | 422.92 | 423.05 | 2.52 | 2.35 | 2.75 | |
| 824 | 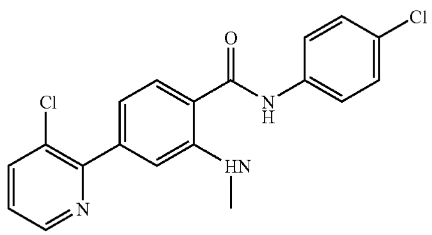 | 372.26 | 371.98 | 3.51 | 3.16 | 3.99 | |
| 825 | 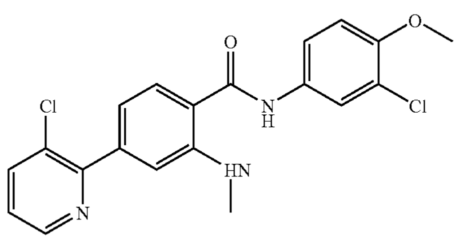 | 402.28 | 402.14 | 3.39 | 3.06 | 3.96 | |
| 826 | 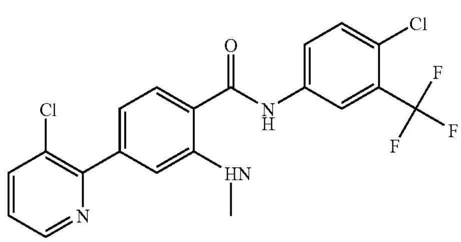 | 440.26 | 440.13 | 3.92 | 3.82 | 4.32 | |
| 827 | 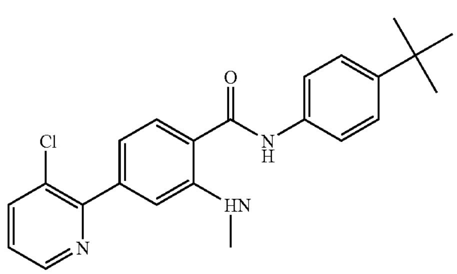 | 393.92 | 394.16 | 3.81 | 3.65 | 4.45 | |

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 828 | 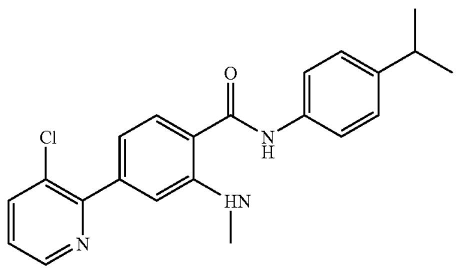 | 379.89 | 380.24 | 3.68 | 3.41 | 3.96 | |
| 829 | 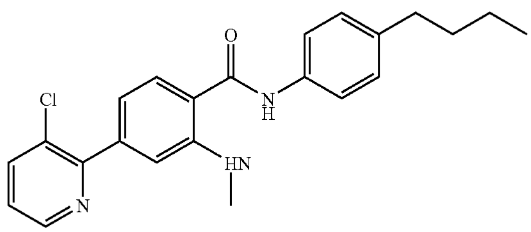 | 393.92 | 394.16 | 3.96 | 3.56 | 4.58 | |
| 830 | 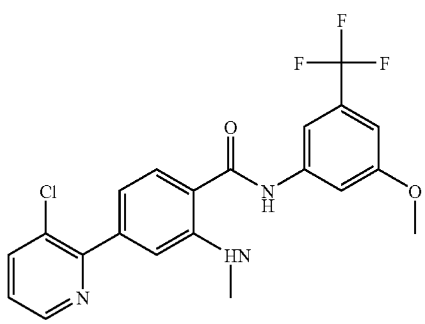 | 435.84 | 436.24 | 3.72 | 3.61 | 4.04 | |
| 831 | 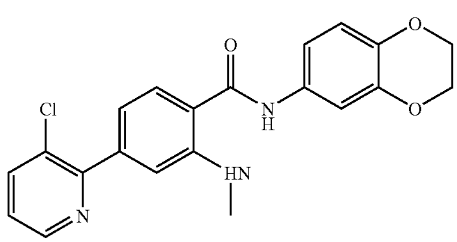 | 395.85 | 396.11 | 3.05 | 2.91 | 3.38 | |
| 832 | 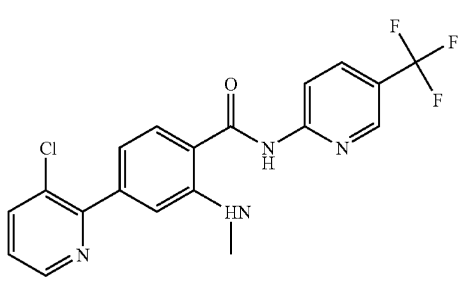 | 406.80 | 407.17 | 3.61 | 3.32 | 3.99 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 833 | 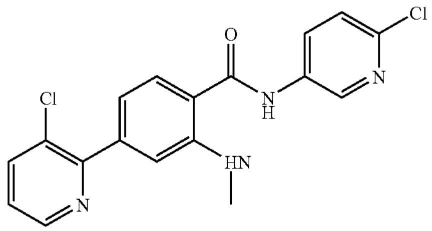 | 373.24 | 373.02 | 3.12 | 2.86 | 3.51 | |
| 834 | 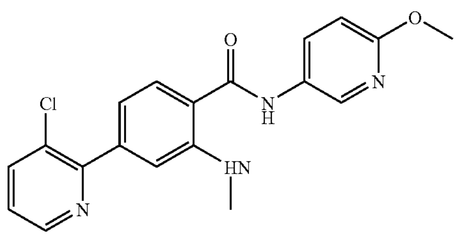 | 368.83 | 369.09 | 2.75 | 2.58 | 2.95 | |
| 835 | 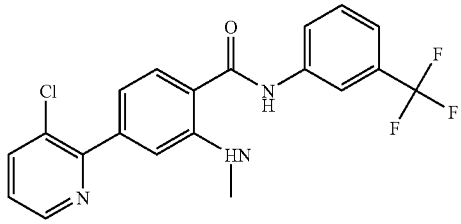 | 405.81 | 406.21 | 3.69 | 3.49 | 4.14 | |
| 836 | 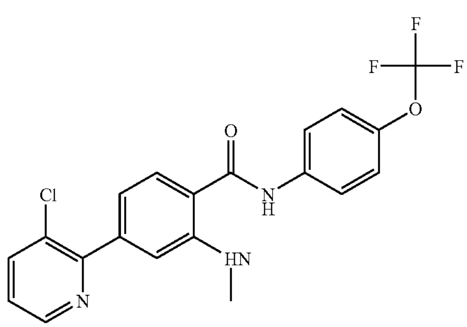 | 421.81 | 421.98 | 3.71 | 3.49 | 4.21 | |
| 837 | 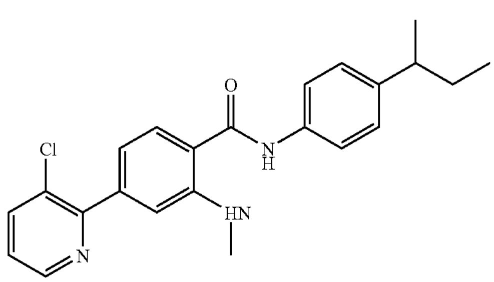 | 393.92 | 394.19 | 3.89 | 3.53 | 4.12 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 838 | 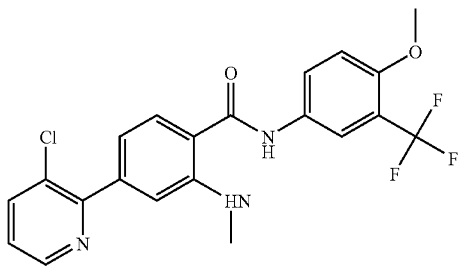 | 435.84 | 436.22 | 3.55 | 3.16 | 4.01 | |
| 839 | 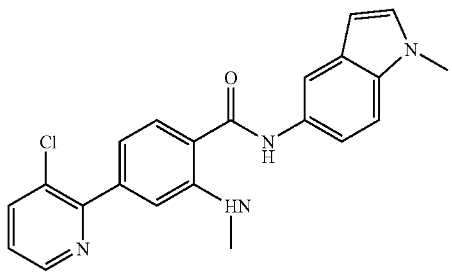 | 390.88 | 391.31 | 3.13 | 2.78 | 3.79 | |
| 840 | 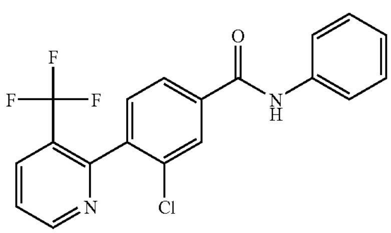 | 376.77 | 377.24 | 3.41 | 3.26 | 3.71 | |
| 841 | 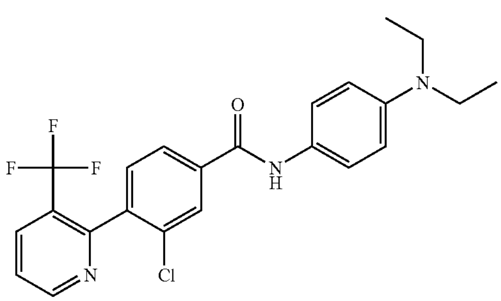 | 447.89 | 448.10 | 2.66 | 2.32 | 3.12 | |
| 842 | 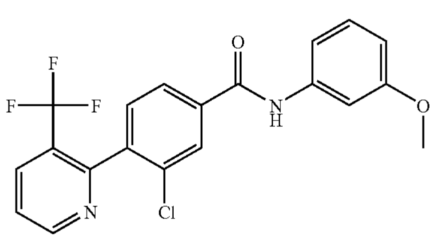 | 406.79 | 407.14 | 3.45 | 3.00 | 3.83 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 843 | 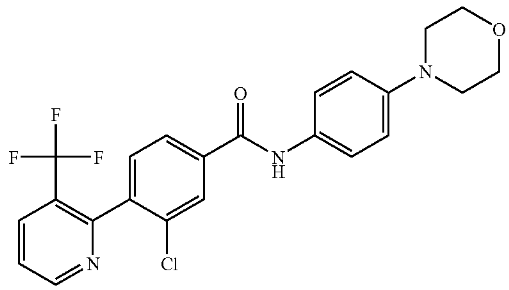 | 461.87 | 462.22 | 2.78 | 2.63 | 3.22 | |
| 844 | 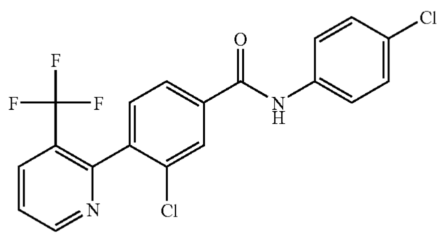 | 411.21 | 410.98 | 3.68 | 3.36 | 4.11 | |
| 845 | 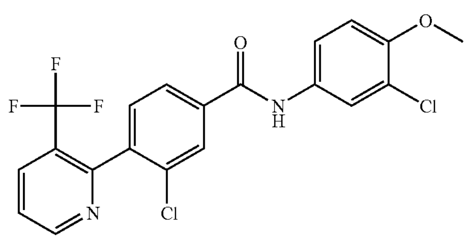 | 441.24 | 441.08 | 3.56 | 3.16 | 3.85 | |
| 846 | 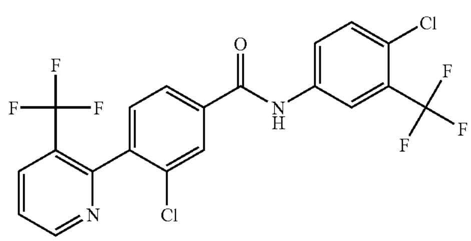 | 479.21 | 478.96 | 3.99 | 3.62 | 4.34 | |
| 847 | 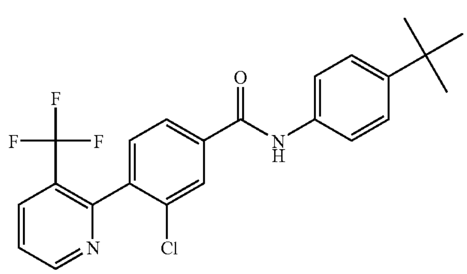 | 432.88 | 433.22 | 3.96 | 3.72 | 4.44 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 848 | 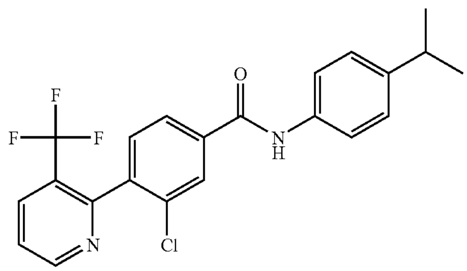 | 418.85 | 419.13 | 3.85 | 3.58 | 4.25 | |
| 849 | 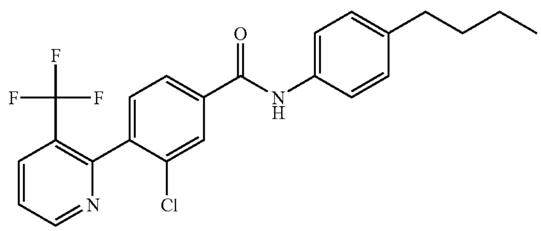 | 432.88 | 433.22 | 4.12 | 3.78 | 4.61 | |
| 850 | 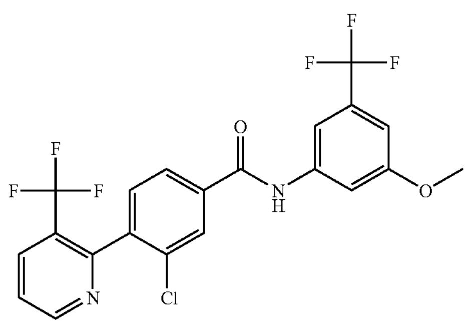 | 474.79 | 475.01 | 3.83 | 3.59 | 4.19 | |
| 851 | 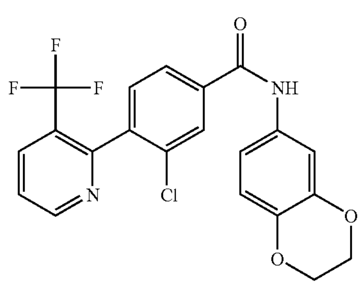 | 434.81 | 435.12 | 3.32 | 2.92 | 3.82 | |
| 852 | 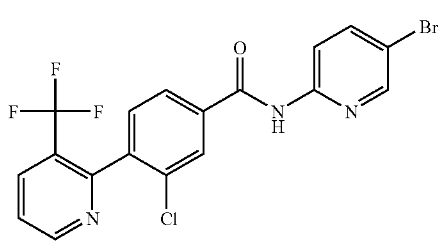 | 456.65 | 458.13 | 3.63 | 3.35 | 4.15 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 853 | 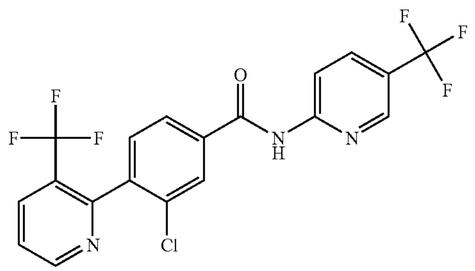 | 445.75 | 446.10 | 3.71 | 3.48 | 4.06 | |
| 854 | 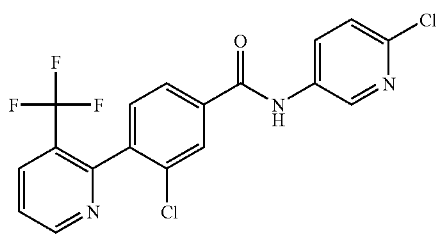 | 412.20 | 412.09 | 3.32 | 3.18 | 3.63 | |
| 855 | 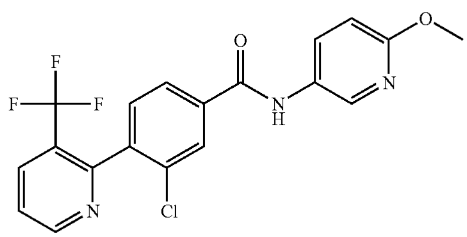 | 407.78 | 408.11 | 3.05 | 2.90 | 3.36 | |
| 856 | 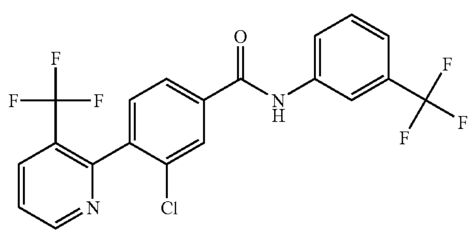 | 444.77 | 445.16 | 3.78 | 3.34 | 4.18 | |
| 857 | 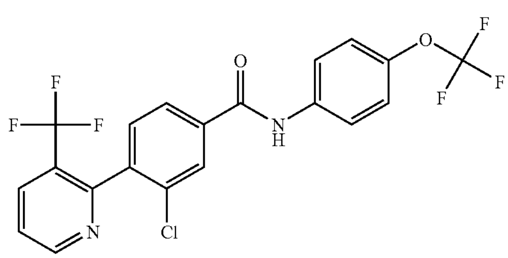 | 460.77 | 461.12 | 3.85 | 3.55 | 4.14 | |
| 858 | 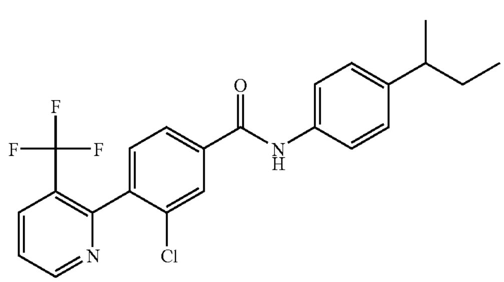 | 432.88 | 433.22 | 4.05 | 3.65 | 4.58 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 859 | 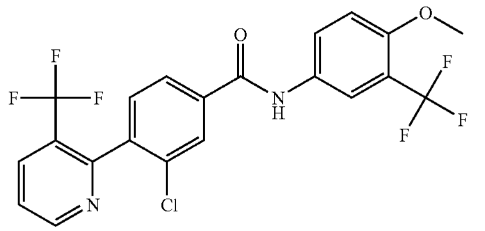 | 474.79 | 475.01 | 3.68 | 3.42 | 3.98 | |
| 860 | 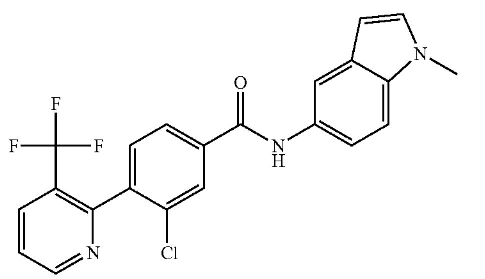 | 429.83 | 430.18 | 3.41 | 3.13 | 3.95 | |
| 861 | 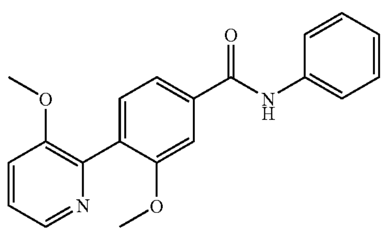 | 334.38 | 335.32 | 2.30 | 2.13 | 2.78 | |
| 862 | 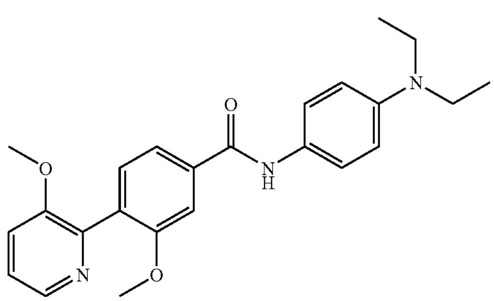 | 405.50 | 406.38 | 1.85 | 1.63 | 2.09 | |
| 863 | 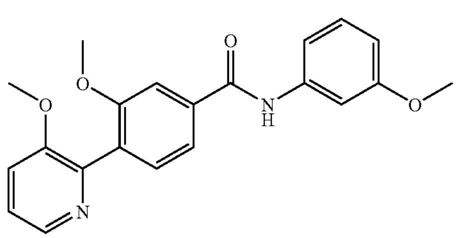 | 364.40 | 365.09 | 2.36 | 2.17 | 2.78 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 864 | 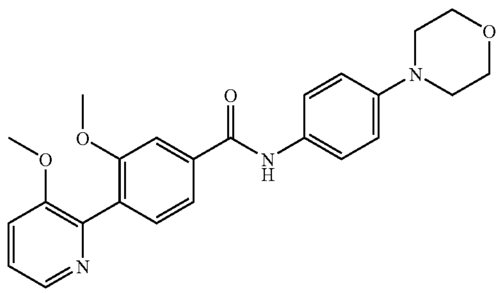 | 419.48 | 420.22 | 1.87 | 1.80 | 2.15 | |
| 865 | 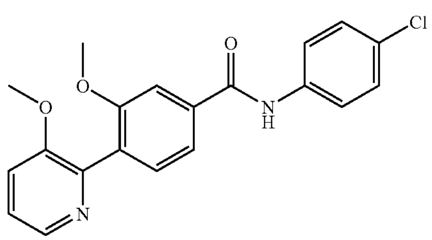 | 368.82 | 369.10 | 2.65 | 2.49 | 2.93 | |
| 866 | 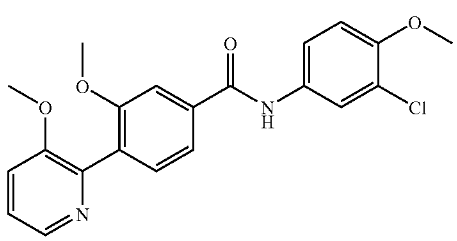 | 398.85 | 399.10 | 2.50 | 2.36 | 2.70 | |
| 867 | 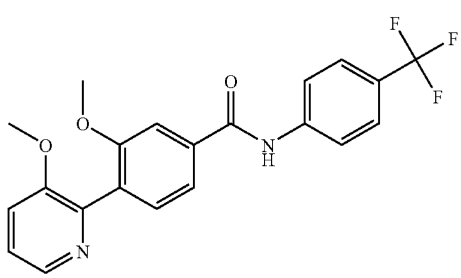 | 402.38 | 403.31 | 2.80 | 2.69 | 3.09 | |
| 868 | 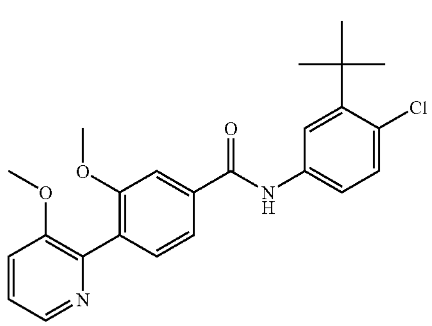 | 436.82 | 437.12 | 2.99 | 2.70 | 3.25 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 869 | 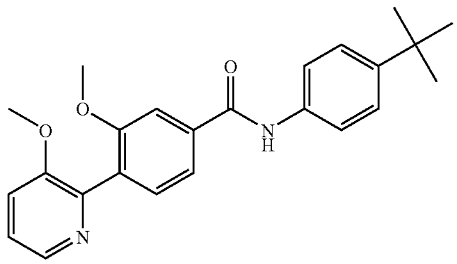 | 390.49 | 391.35 | 2.95 | 2.69 | 3.15 | |
| 870 | 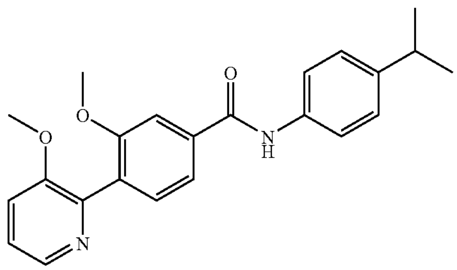 | 376.46 | 377.35 | 2.82 | 2.66 | 3.08 | |
| 871 | 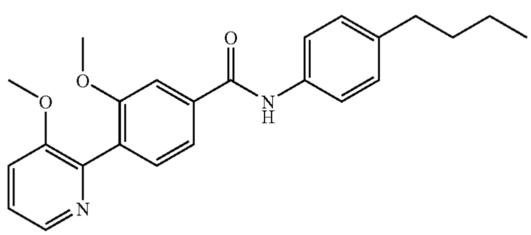 | 390.49 | 391.35 | 3.02 | 2.93 | 3.29 | |
| 872 | 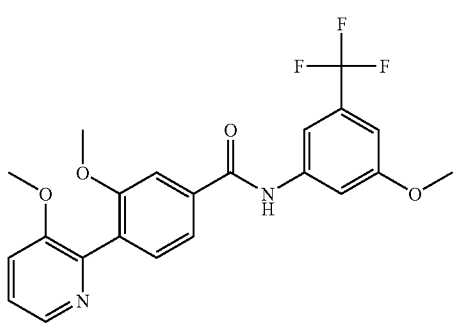 | 432.40 | 433.25 | 2.86 | 2.69 | 3.16 | |
| 873 | 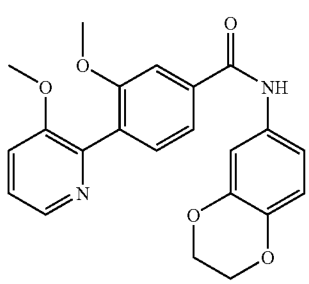 | 392.42 | 393.21 | 2.28 | 2.10 | 2.46 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 874 | 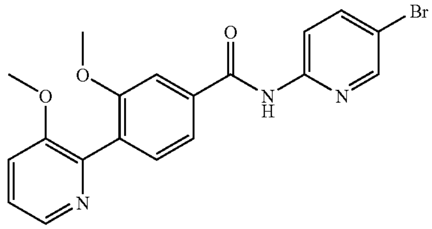 | 414.26 | 414.09 | 2.52 | 2.41 | 2.82 | |
| 875 | 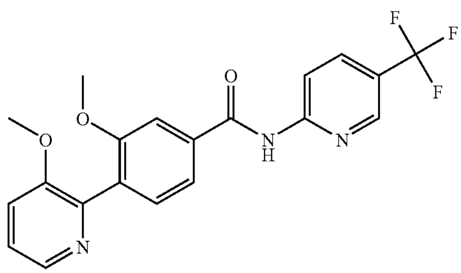 | 403.36 | 404.34 | 2.63 | 2.49 | 2.88 | |
| 876 | 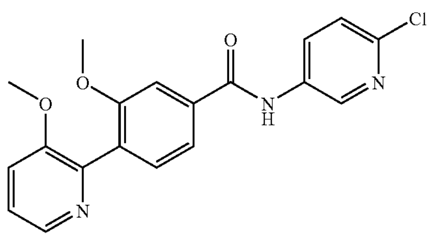 | 369.81 | 370.11 | 2.23 | 2.10 | 2.49 | |
| 877 | 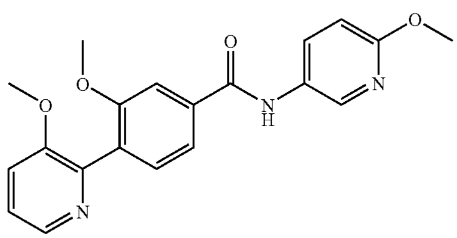 | 365.39 | 366.18 | 2.02 | 1.66 | 2.23 | |
| 878 | 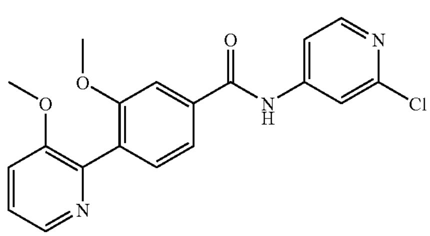 | 369.81 | 370.12 | 2.25 | 2.02 | 2.43 | |
| 879 | 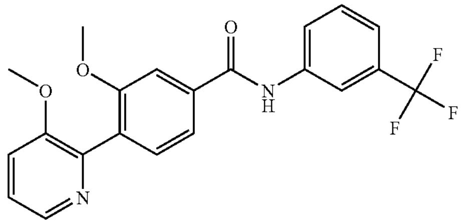 | 402.38 | 403.32 | 2.79 | 2.65 | 2.99 | |

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 880 | 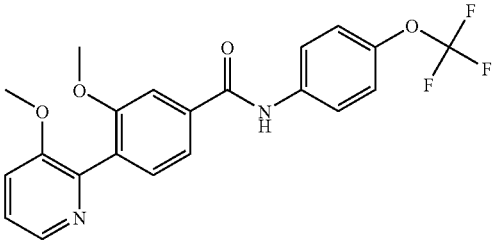 | 418.38 | 419.17 | 2.83 | 2.69 | 3.09 | |
| 881 | 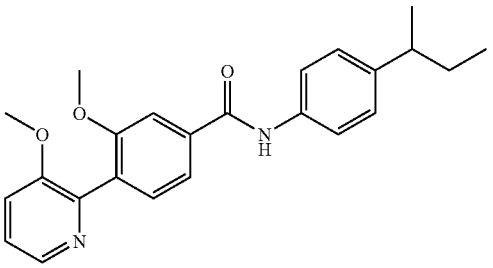 | 390.49 | 391.35 | 3.02 | 2.88 | 3.26 | |
| 882 | 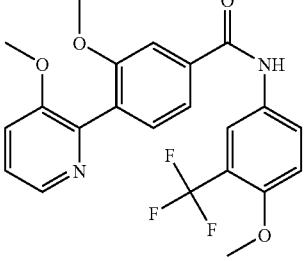 | 432.40 | 433.23 | 2.72 | 2.59 | 2.99 | |
| 883 | 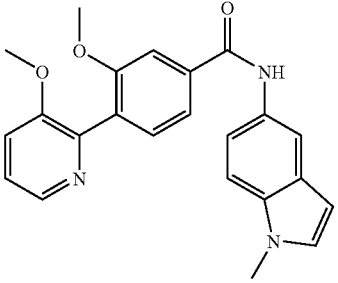 | 387.44 | 388.28 | 2.42 | 2.16 | 2.82 | |
| 884 | 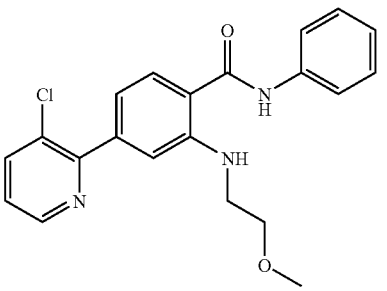 | 381.87 | 382.19 | 3.15 | 2.93 | 3.52 | |

-continued
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 885 | 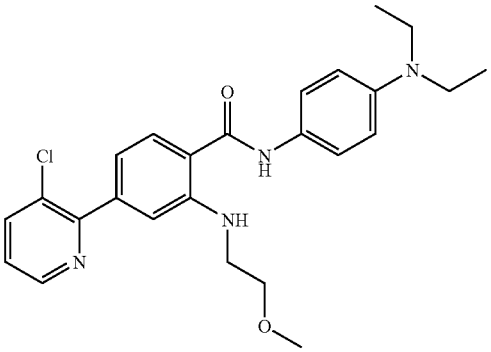 | 452.99 | 453.12 | 2.52 | 2.35 | 2.92 | |
| 886 | 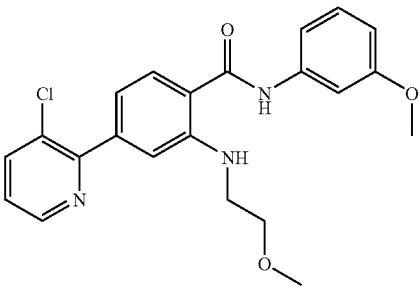 | 411.89 | 412.12 | 3.18 | 2.96 | 3.86 | |
| 887 | 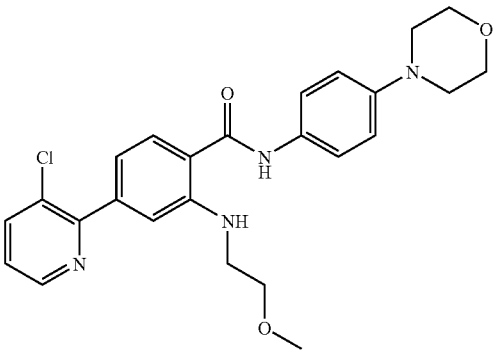 | 466.97 | | | | | |
| 888 | 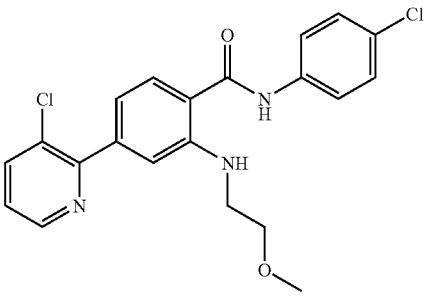 | 416.31 | 416.25 | 3.46 | 3.23 | 3.86 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 889 | 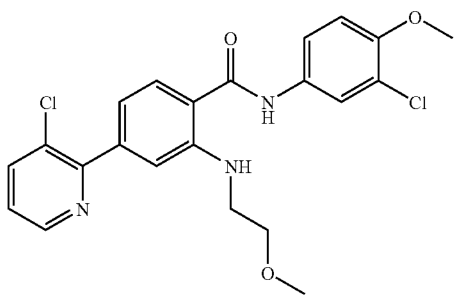 | 446.34 | 446.15 | 3.34 | 3.21 | 3.96 | |
| 890 | 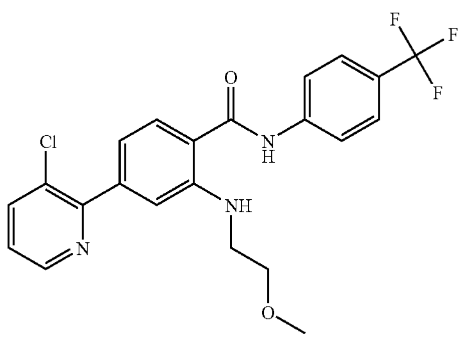 | 449.86 | 450.13 | 3.62 | 3.42 | 4.06 | |
| 891 | 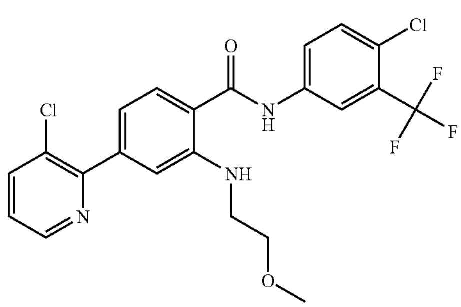 | 484.31 | 484.14 | 3.79 | 3.59 | 4.15 | |
| 892 | 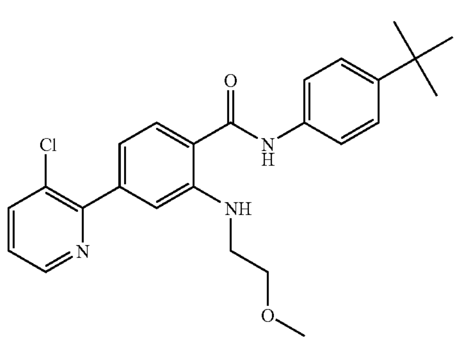 | 437.97 | | | | | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 893 | 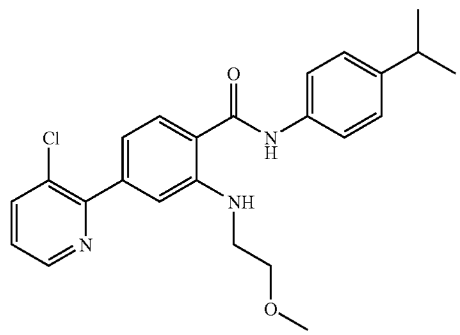 | 423.95 | 424.16 | 3.66 | 3.45 | 4.04 | |
| 894 | 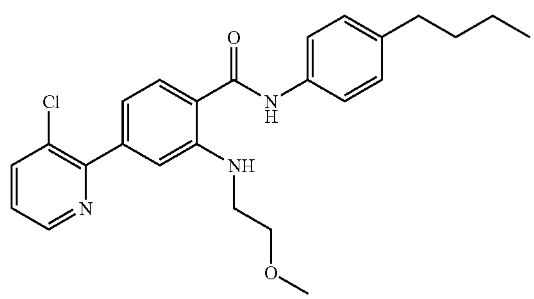 | 437.97 | 438.20 | 3.88 | 3.73 | 4.19 | |
| 895 | 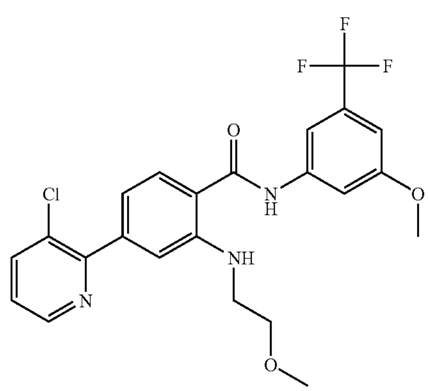 | 479.89 | 480.09 | 3.66 | 3.46 | 4.05 | |
| 896 | 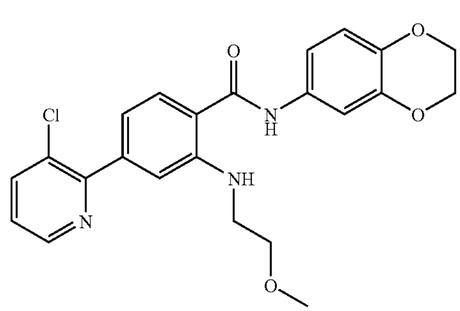 | 439.90 | 440.22 | 3.09 | 2.93 | 3.49 | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 897 | 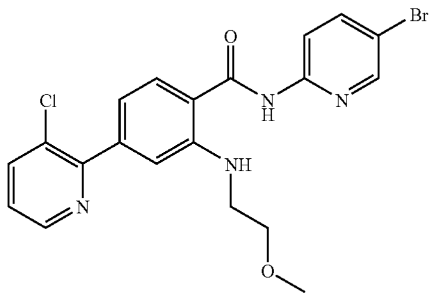 | 461.75 | | | | | |
| 898 | 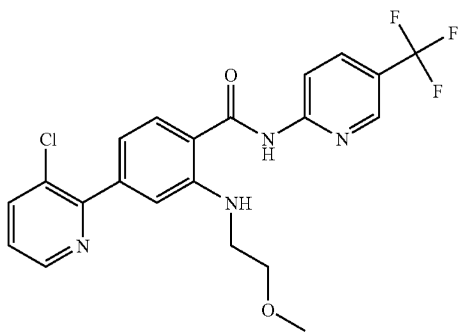 | 450.85 | | | | | |
| 899 | 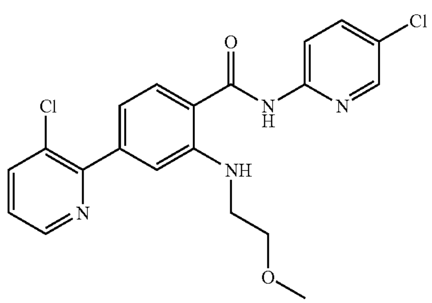 | 417.30 | 417.27 | 3.06 | 2.93 | 3.52 | |
| 900 | 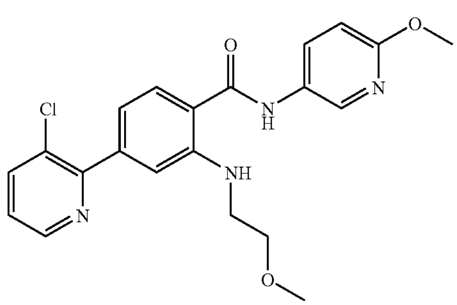 | 412.88 | 413.24 | 2.78 | 2.65 | 3.25 | |
| 901 | 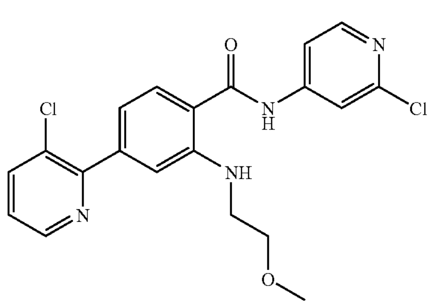 | 417.30 | | | | | |

|  |  |  |  | HPLC | HPLC |  |
|---|---|---|---|---|---|---|
|  |  |  | HPLC | START | END | % |
|  |  | MW | MS | RT | TIME | TIME | Inhibition |
| ID | STRUCTURE | (Calc) | (Obs) | (Min) | (Min) | (Min) | @ 1 uM |
| 902 | | 449.86 | 450.12 | 3.61 | 3.36 | 4.12 | |
| 903 | | 465.86 | 466.25 | 3.62 | 3.43 | 4.11 | |
| 904 | | 437.97 | 438.18 | 3.79 | 3.49 | 4.22 | |
| 905 | | 479.89 | 480.08 | 3.52 | 3.38 | 3.98 | |

-continued
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 906 | 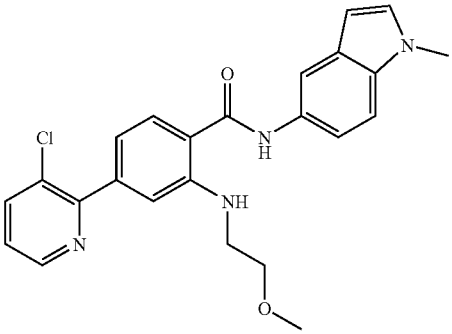 | 434.93 | 435.28 | 3.18 | 3.03 | 3.59 | |
| 907 | 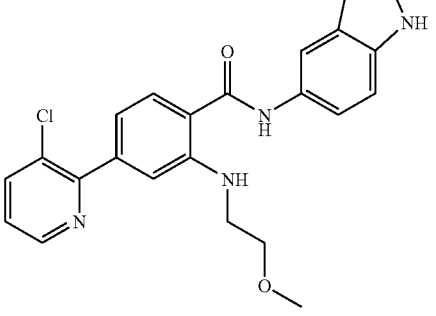 | 421.89 | | | | | |
| 908 | 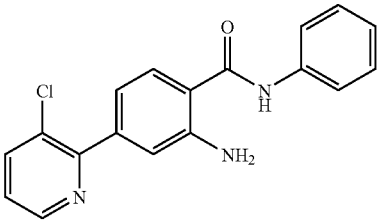 | 323.78 | | | | | |
| 909 | 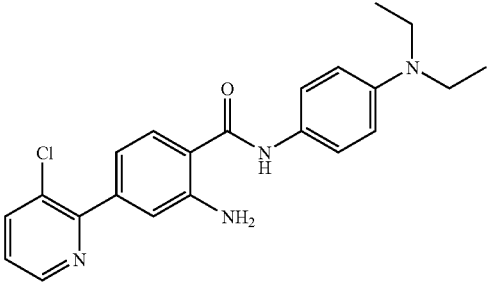 | 394.91 | 395.15 | 2.21 | 2.12 | 2.52 | |
| 910 | 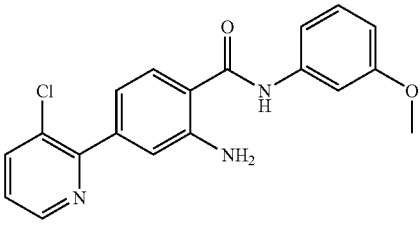 | 353.81 | | | | | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 911 | 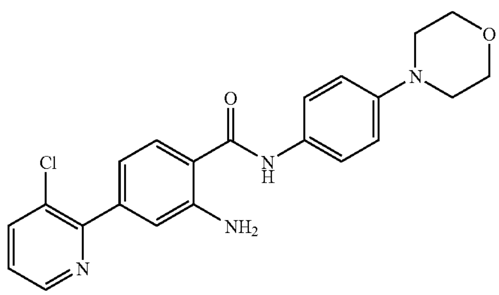 | 408.89 | | | | | |
| 912 | 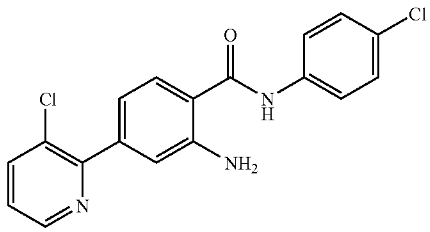 | 358.23 | 358.11 | 3.18 | 2.99 | 3.36 | |
| 913 | 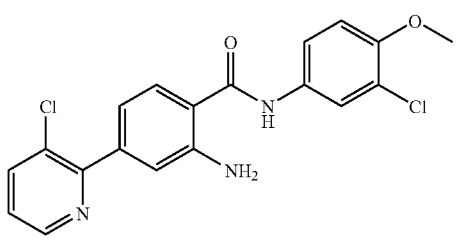 | 388.26 | 388.17 | 3.01 | 2.93 | 3.29 | |
| 914 | 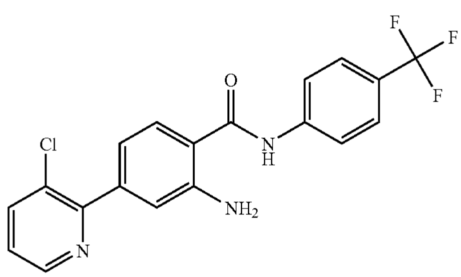 | 391.78 | 392.10 | 3.35 | 3.15 | 3.58 | |
| 915 | 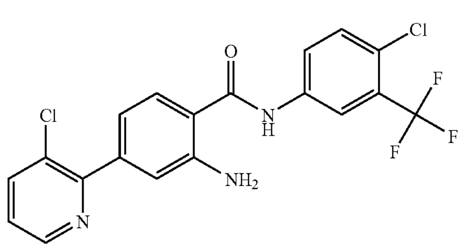 | 426.23 | 426.03 | 3.54 | 3.42 | 3.87 | |

| ID | STRUCTURE | MW (Calc) | MS (Obs) | HPLC RT (Min) | HPLC START TIME (Min) | HPLC END TIME (Min) | % Inhibition @ 1 uM |
|----|-----------|-----------|----------|---------------|------------------------|----------------------|---------------------|
| 916 | 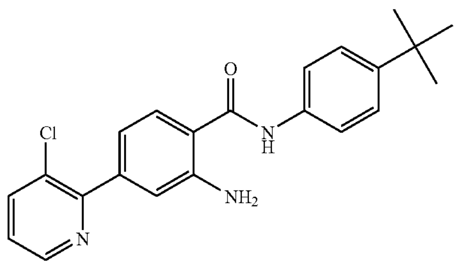 | 379.89 | | | | | |
| 917 | 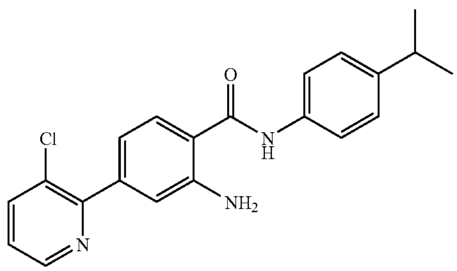 | 365.87 | 366.14 | 3.35 | 3.25 | 3.63 | |
| 918 | 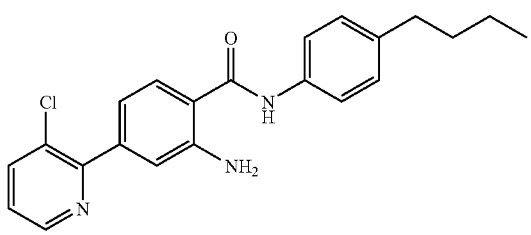 | 379.89 | 380.30 | 3.59 | 3.51 | 3.78 | |
| 919 | 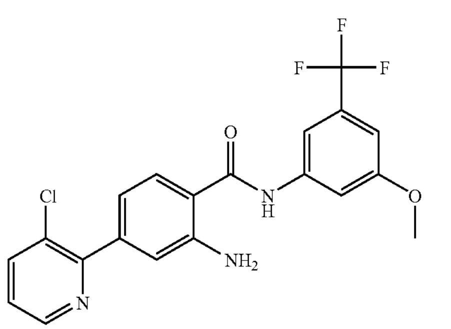 | 421.81 | 421.98 | 3.41 | 3.32 | 3.71 | |
| 920 | 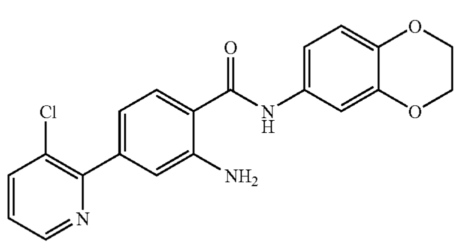 | 381.82 | 382.13 | 2.73 | 2.59 | 2.99 | |

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 921 | 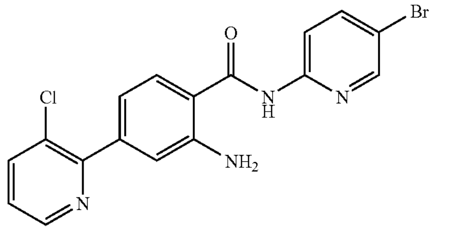 | 403.67 | | | | | |
| 922 | 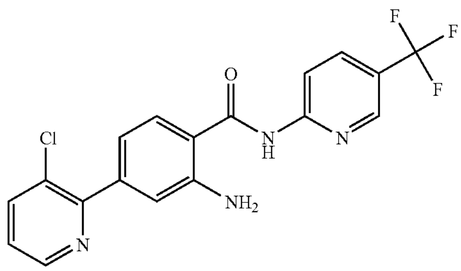 | 392.77 | | | | | |
| 923 | 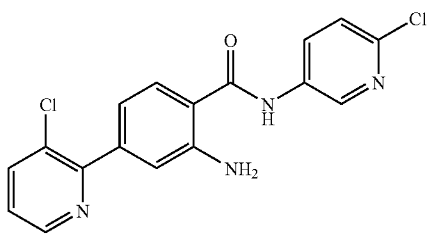 | 359.22 | 359.09 | 2.72 | 2.65 | 3.05 | |
| 924 | 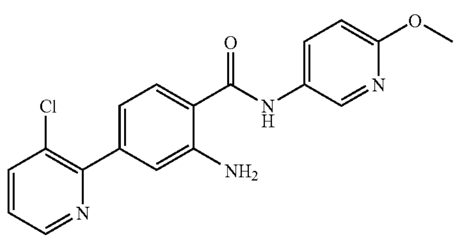 | 354.80 | 355.16 | 2.38 | 2.29 | 2.48 | |
| 925 | 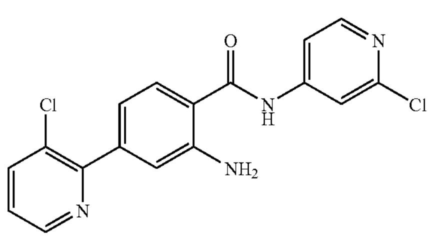 | 359.22 | | | | | |
| 926 | 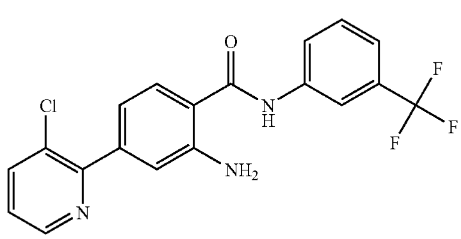 | 391.78 | 392.11 | 3.31 | 3.22 | 3.62 | |

-continued
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 927 | 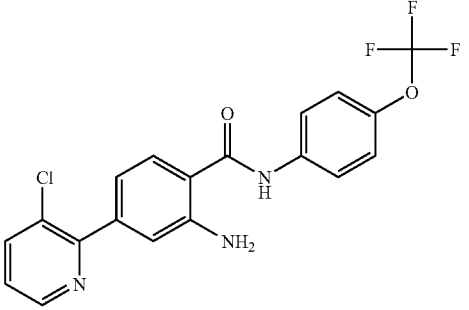 | 407.78 | 408.12 | 3.33 | 3.22 | 3.49 | |
| 928 | 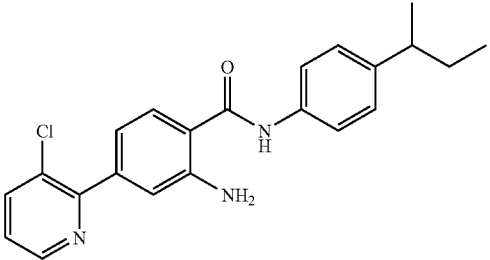 | 379.89 | 380.25 | 3.53 | 3.35 | 3.79 | |
| 929 | 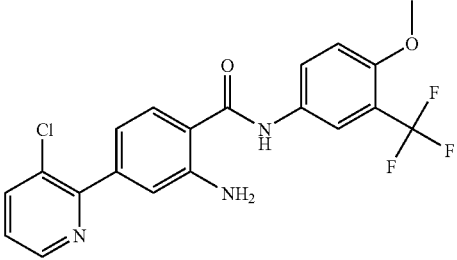 | 421.81 | 421.97 | 3.19 | 2.99 | 3.39 | |
| 930 | 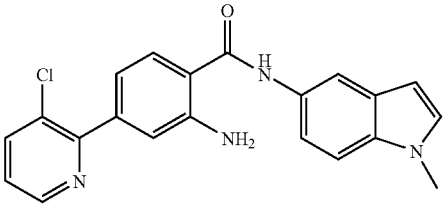 | 376.85 | 377.27 | 2.83 | 2.75 | 3.12 | |
| 931 | 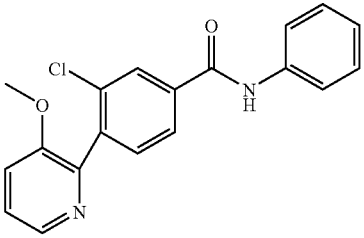 | 338.80 | 339.10 | 2.55 | | | |

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 932 | 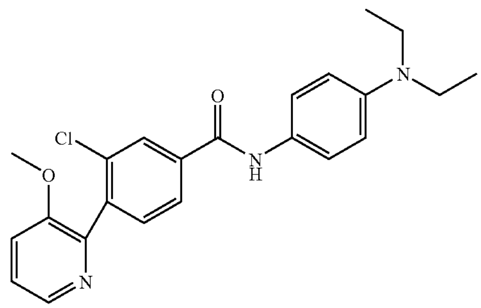 | 409.92 | 410.23 | 2.03 | | | |
| 933 | 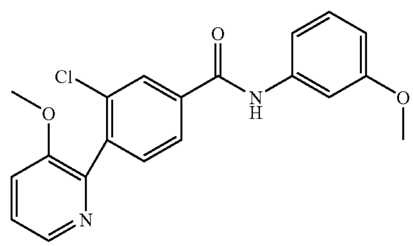 | 368.82 | 369.10 | 2.62 | | | |
| 934 | 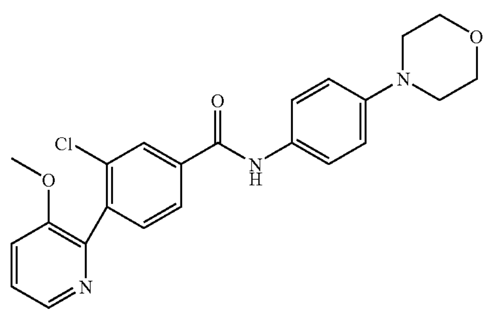 | 423.90 | 424.11 | 2.05 | | | |
| 935 | 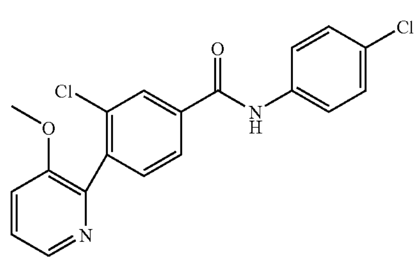 | 373.24 | 373.01 | 2.88 | | | |
| 936 | 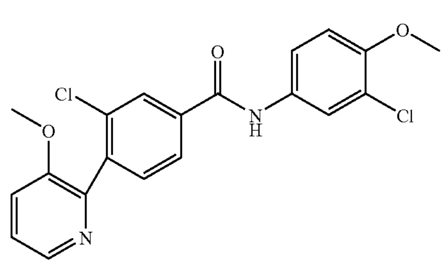 | 403.27 | 403.27 | 2.73 | | | |

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 937 | 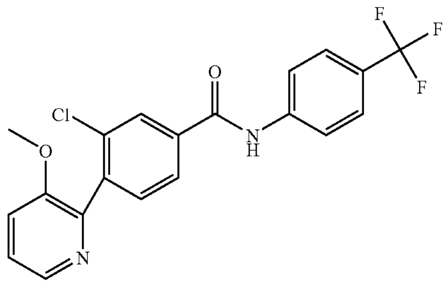 | 406.79 | 407.14 | 3.05 | | | |
| 938 | 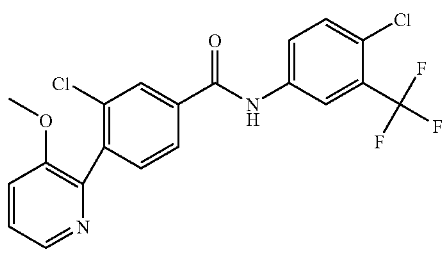 | 441.24 | 441.10 | 3.25 | | | |
| 939 | 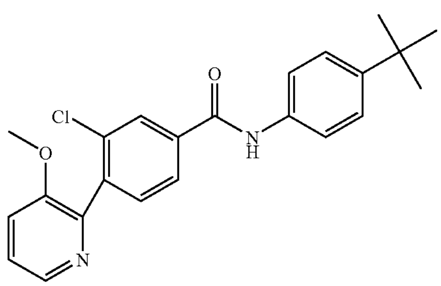 | 394.90 | 395.14 | 3.19 | | | |
| 940 | 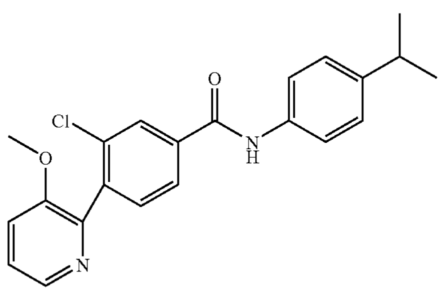 | 380.88 | 381.24 | 3.06 | | | |
| 941 | 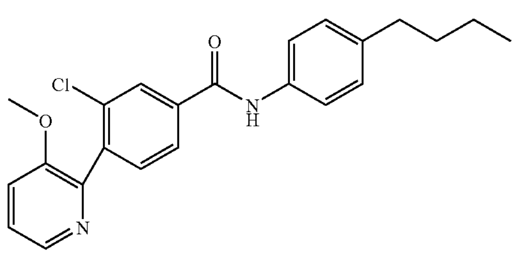 | 394.90 | 395.16 | 3.33 | | | |

-continued
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 942 | 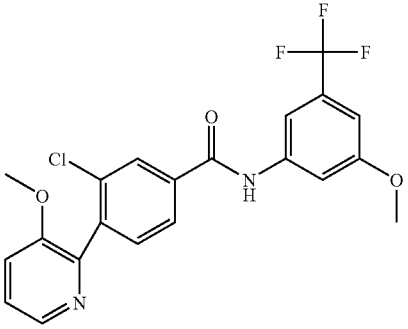 | 436.82 | 437.12 | 3.12 | | | |
| 943 | 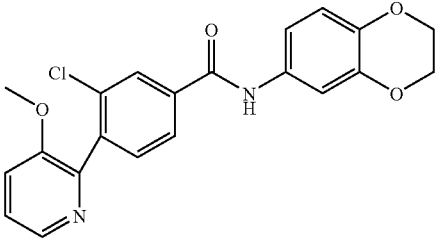 | 396.83 | 397.08 | 2.52 | | | |
| 944 | 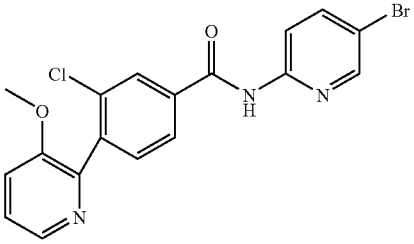 | 418.68 | 420.02 | 2.76 | | | |
| 945 | 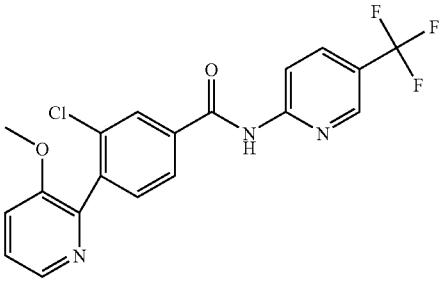 | 407.78 | 407.51 | 3.25 | | | |
| 946 | 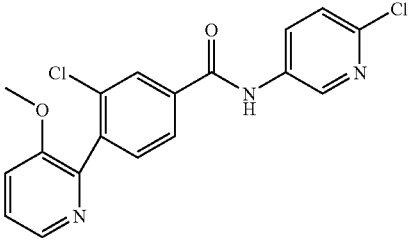 | 374.23 | 374.08 | 2.45 | | | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 947 | 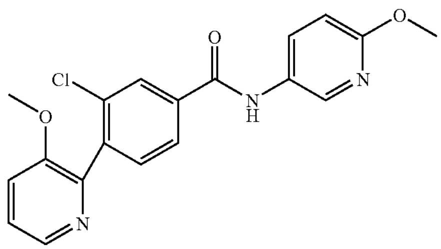 | 369.81 | 370.10 | 2.22 | | | |
| 948 | 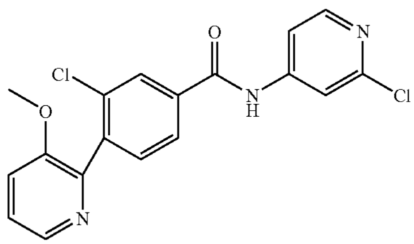 | 374.23 | 374.08 | 2.51 | | | |
| 949 | 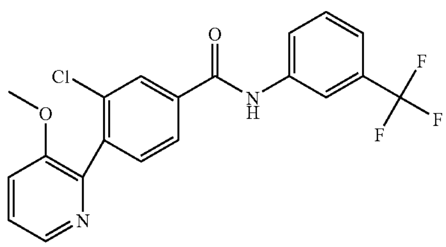 | 406.79 | 407.13 | 3.02 | | | |
| 950 | 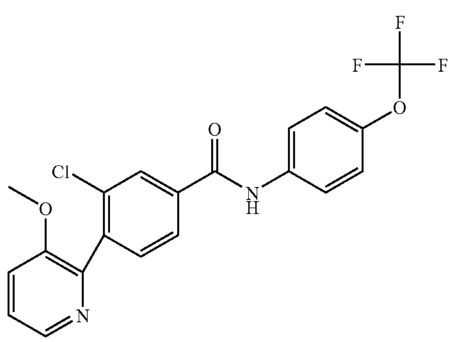 | 422.79 | 422.96 | 3.08 | | | |
| 951 | 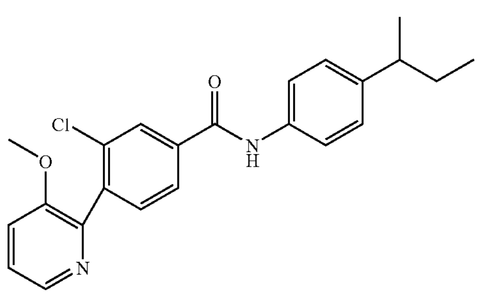 | 394.90 | 395.17 | 3.26 | | | |

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 952 | 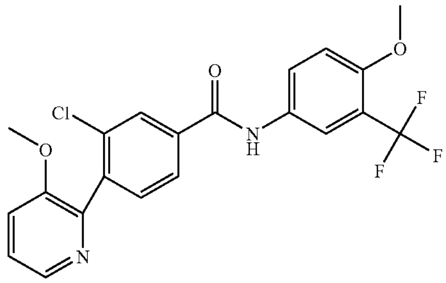 | 436.82 | 437.12 | 2.95 | | | |
| 953 | 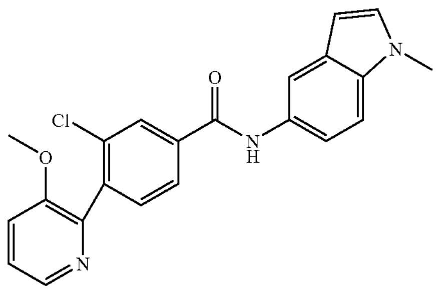 | 391.86 | | | | | |
| 954 | 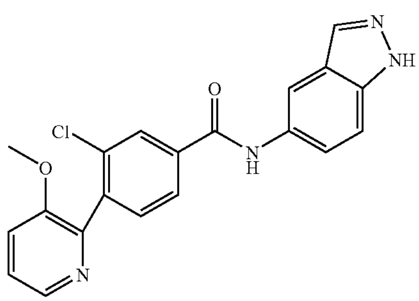 | 378.82 | | | | | |
| 955 | 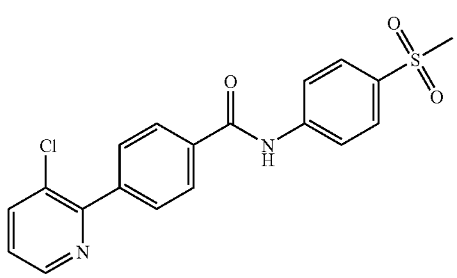 | 386.86 | | | | | |
| 956 | 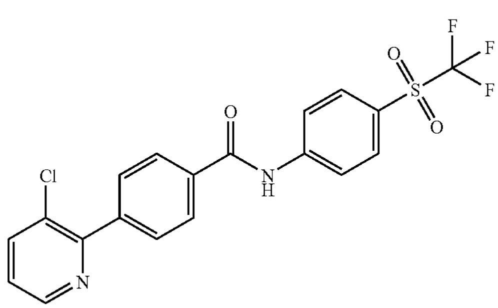 | 440.83 | | | | | |

-continued
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 957 | 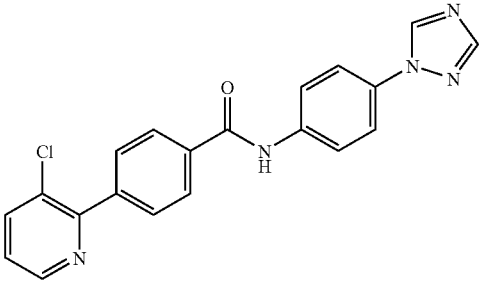 | 375.82 | | | | | |
| 958 | 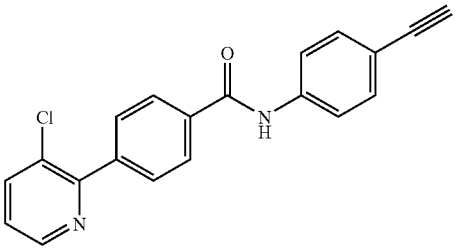 | 332.79 | | | | | |
| 959 | 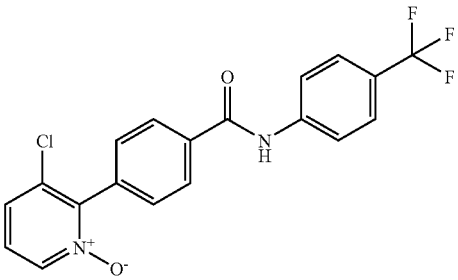 | 392.77 | | | | | |
| 960 | 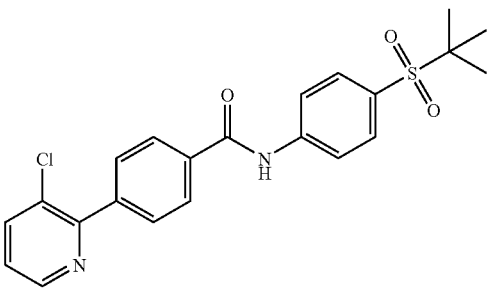 | 428.94 | | | | | |
| 961 | 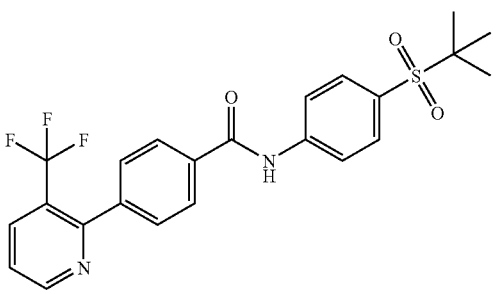 | 448.47 | | | | | |

-continued

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 962 | 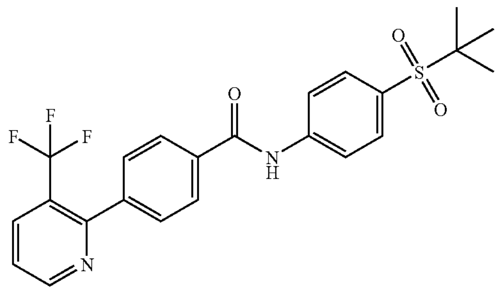 | 462.49 | | | | | |
| 963 | 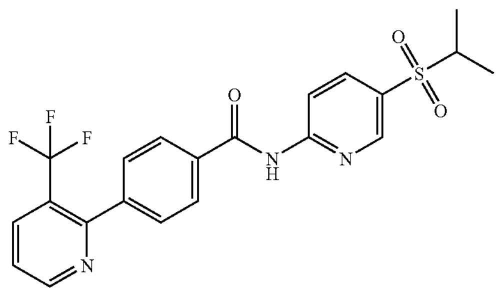 | 449.46 | | | | | |
| 964 | 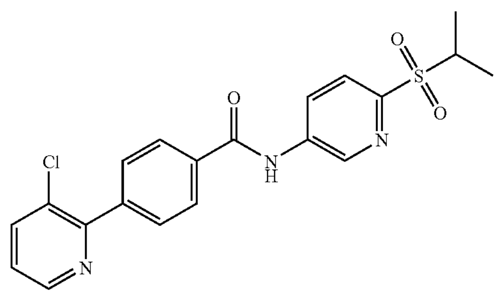 | 415.90 | | | | | |
| 965 | 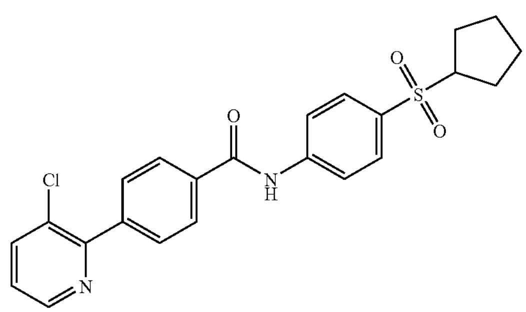 | 440.95 | | | | | |
| 966 | 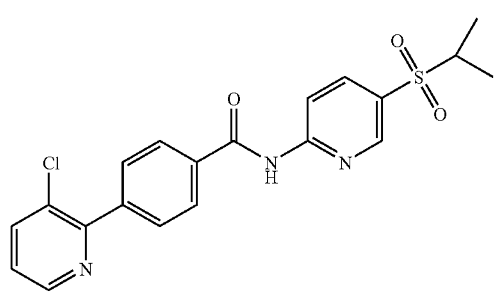 | 415.90 | | | | | |

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 967 | 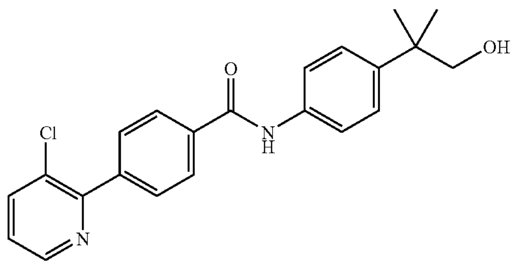 | 380.88 | | | | | |
| 968 | 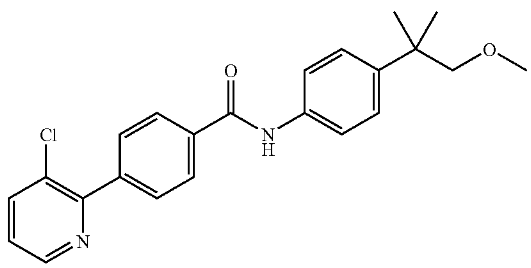 | 394.90 | | | | | |
| 969 | 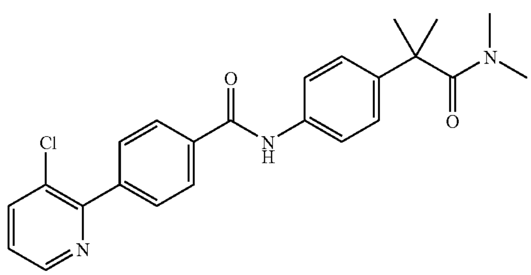 | 421.93 | | | | | |
| 970 | 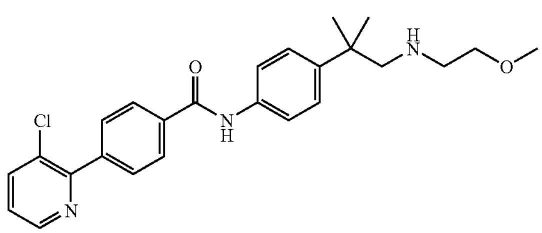 | 437.97 | | | | | |
| 971 | 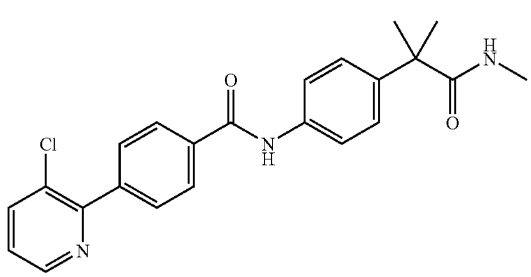 | 407.90 | | | | | |

| | AMIDE COMPOUNDS | | | | | |
|---|---|---|---|---|---|---|
| ID | STRUCTURE | MW (Calc) | MS (Obs) | HPLC RT (Min) | HPLC START TIME (Min) | HPLC END TIME (Min) | % Inhibition @ 1 uM |
| 972 | | 393.88 | | | | | |
| 973 | | 377.76 | | | | | |
| 974 | | 400.89 | | | | | |
| 975 | | 414.91 | | | | | |
| 976 | | 378.74 | | | | | |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 977 | 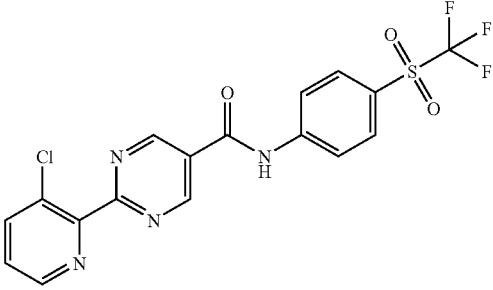 | 442.81 | | | | | |
| 978 | 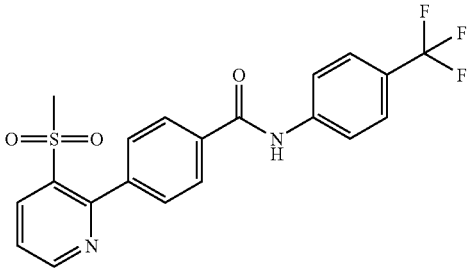 | 420.41 | 421.10 | 3.05 | 2.95 | 3.23 | |
| 979 | 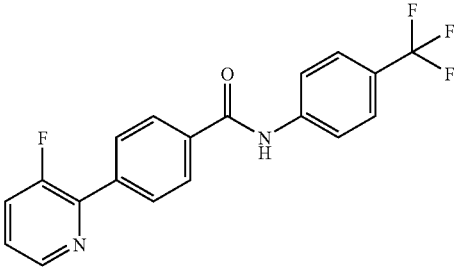 | 360.31 | 361.23 | 3.43 | 3.33 | 3.72 | |
| 980 | 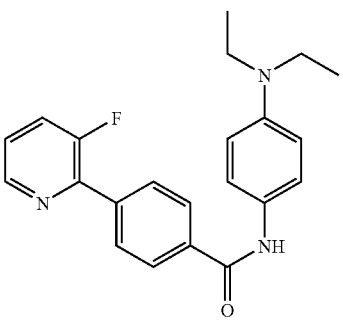 | 363.44 | 364.33 | 2.26 | 2.16 | 2.69 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 981 | 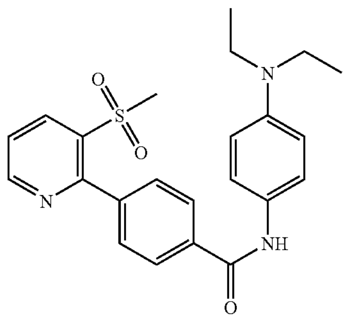 | 423.54 | 424.16 | 1.98 | 1.76 | 2.34 | |
| 982 | 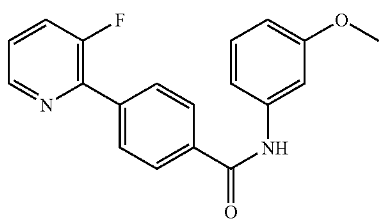 | 322.34 | 323.15 | 2.98 | 2.85 | 3.28 | |
| 983 | 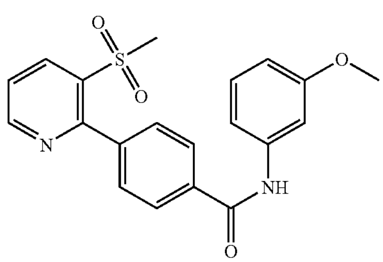 | 382.44 | 383.12 | 2.58 | 2.18 | 2.78 | |
| 984 | 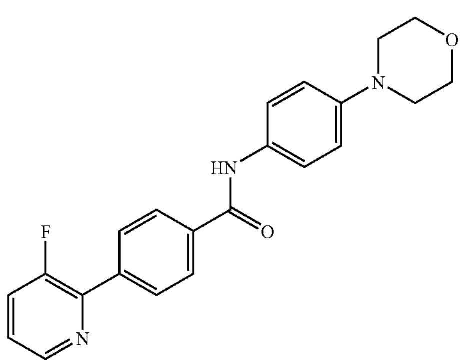 | 377.42 | 378.28 | 2.32 | 2.19 | 2.72 | |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 985 | 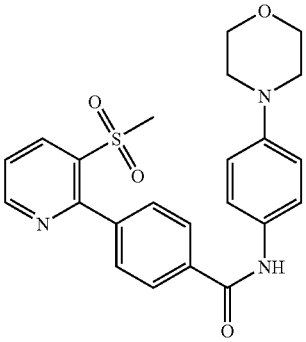 | 437.52 | 438.15 | 1.98 | 1.79 | 2.19 | |
| 986 | 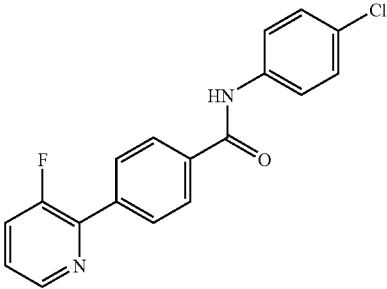 | 326.76 | 327.10 | 3.26 | 3.15 | 3.54 | |
| 987 | 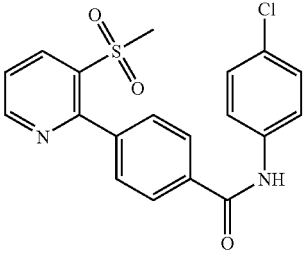 | 386.86 | 387.09 | 2.85 | 2.73 | 3.12 | |
| 988 | 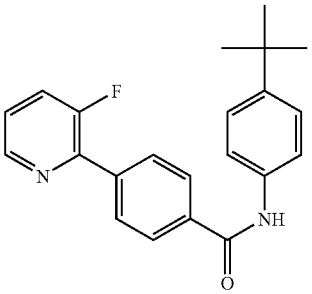 | 348.42 | 349.28 | 3.59 | 3.36 | 4.12 | |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 989 | 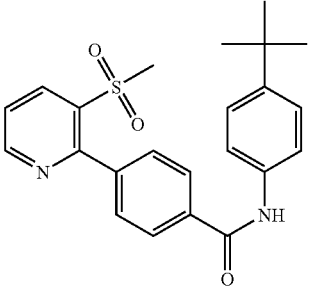 | 408.52 | 409.25 | 3.22 | 3.09 | 3.53 | |
| 990 | 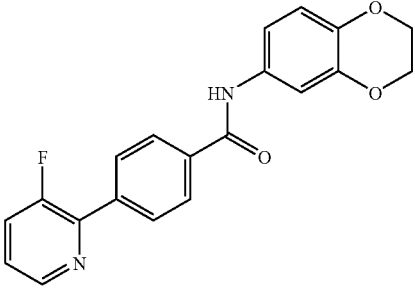 | 350.35 | 351.27 | 2.88 | 2.72 | 3.29 | |
| 991 | 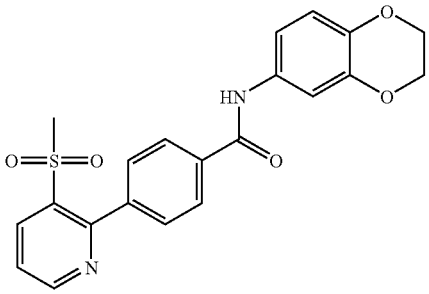 | 410.45 | 411.14 | 2.46 | 2.29 | 2.76 | |
| 992 | 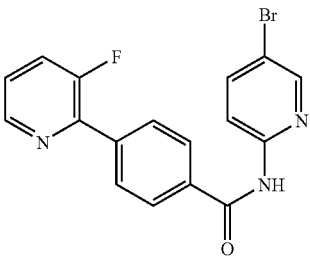 | 372.20 | | | | | |
| 993 | 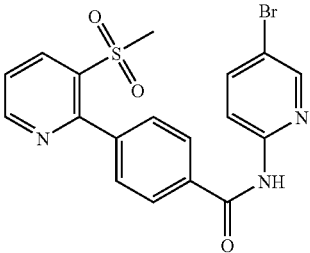 | 432.30 | | | | | |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 994 | 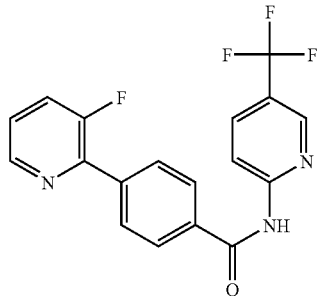 | 361.30 | 362.22 | 3.35 | 3.22 | 3.68 | |
| 995 | 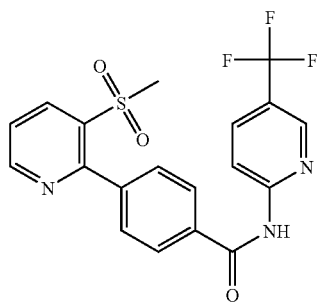 | 421.40 | 421.97 | 2.88 | 2.73 | 3.09 | |
| 996 | 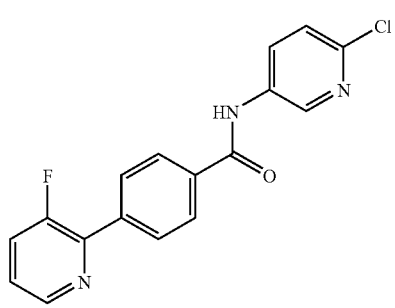 | 327.75 | 328.23 | 2.86 | 2.68 | 3.15 | |
| 997 | 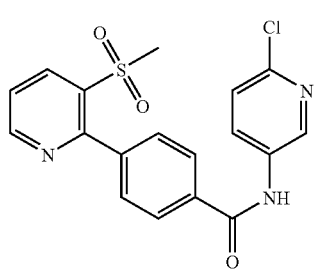 | 387.85 | 388.15 | 2.42 | 2.29 | 2.75 | |
| 998 | 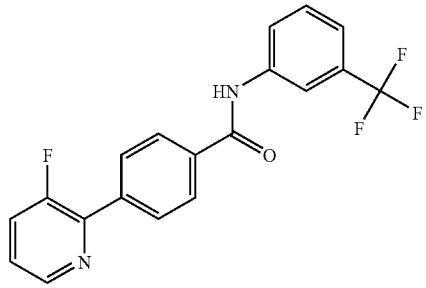 | 360.31 | 361.23 | 3.41 | 3.18 | 3.69 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 999 | 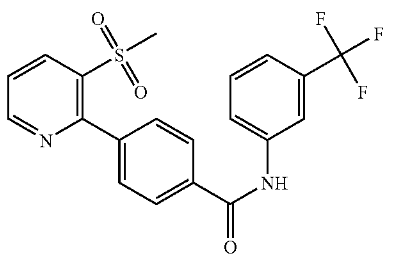 | 420.41 | 421.08 | 3.02 | 2.78 | 3.25 | |
| 1000 | 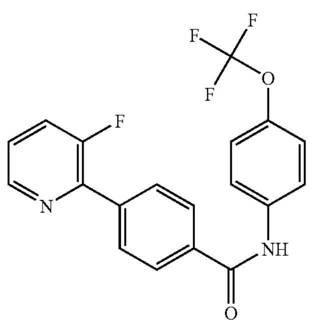 | 376.31 | 377.27 | 3.44 | 3.32 | 3.67 | |
| 1001 | 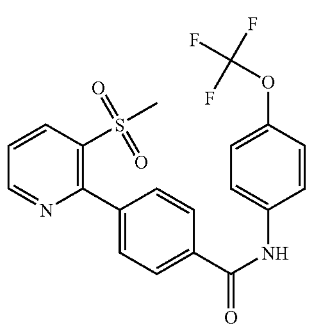 | 436.41 | 437.12 | 3.08 | 2.86 | 3.36 | |
| 1002 | 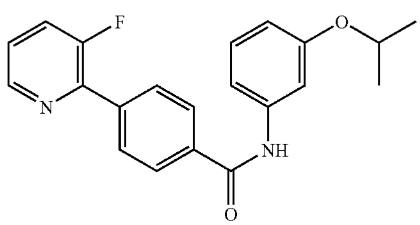 | 350.40 | 351.30 | 3.31 | 3.07 | 3.62 | |
| 1003 | 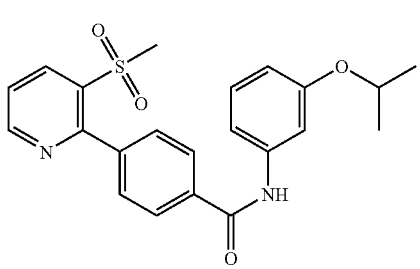 | 410.50 | 411.20 | 2.93 | 2.75 | 3.28 | |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1004 | 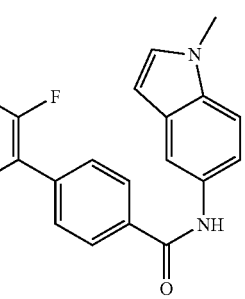 | 345.38 | 346.10 | 2.96 | 2.76 | 3.33 | |
| 1005 | 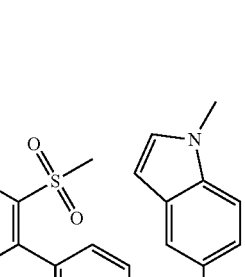 | 405.48 | | | | | |
| 1006 | 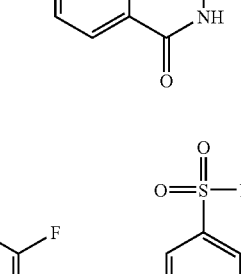 | 371.39 | | | | | |
| 1007 | 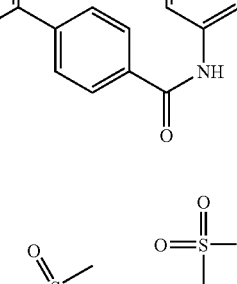 | 431.49 | | | | | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1008 | | 361.30 | 362.21 | 3.12 | 2.96 | 3.51 | |
| 1009 | | 421.40 | 421.96 | 2.71 | 2.52 | 2.98 | |
| 1010 | | 424.38 | 425.02 | 3.49 | 3.39 | 3.64 | |
| 1011 | | 484.48 | 485.21 | 3.11 | 2.99 | 3.28 | |

-continued

| | AMIDE COMPOUNDS | | | | | | |
|---|---|---|---|---|---|---|---|
| ID | STRUCTURE | MW (Calc) | MS (Obs) | HPLC RT (Min) | HPLC START TIME (Min) | HPLC END TIME (Min) | % Inhibition @ 1 uM |
| 1012 | | 370.41 | 371.04 | 2.66 | 2.56 | 2.96 | |
| 1013 | | 430.50 | 431.29 | 2.23 | 2.15 | 2.33 | |
| 1014 | | 384.43 | 385.22 | 2.79 | 2.69 | 3.15 | |
| 1015 | | 444.53 | 445.23 | 2.40 | 2.32 | 2.85 | |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1016 | 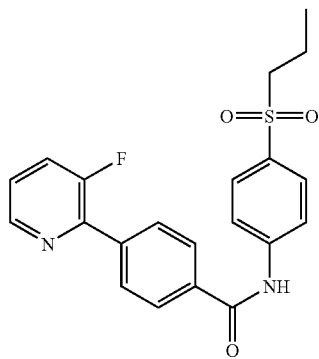 | 398.46 | 399.10 | 2.99 | 2.80 | 3.25 | |
| 1017 | 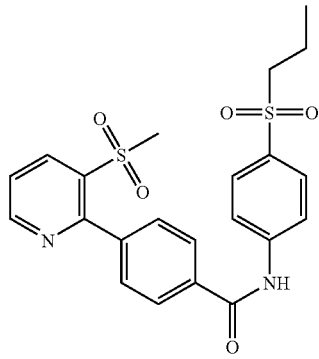 | 458.56 | 459.23 | 2.59 | 2.35 | 2.95 | |
| 1018 | 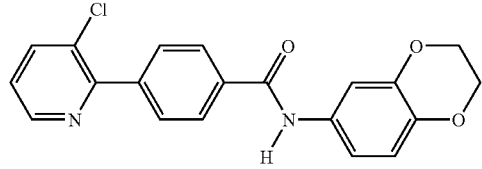 | 366.81 | 367.09 | 3.04 | 2.95 | 3.62 | ++ |
| 1019 | 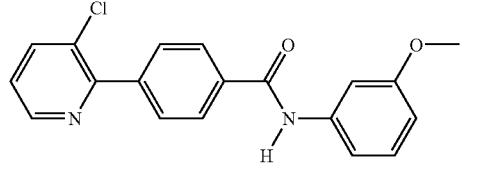 | 338.80 | 339.09 | 3.18 | 3.09 | 3.59 | + |
| 1020 | 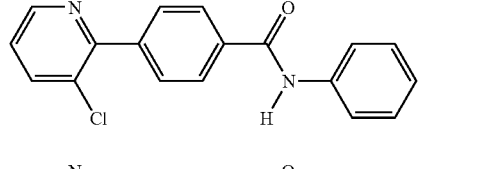 | 308.77 | 309.28 | 3.12 | 3.05 | 3.58 | + |
| 1021 | 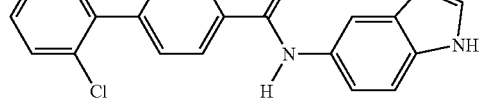 | 347.81 | 348.15 | 2.90 | 2.83 | 3.18 | ++++ |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1022 | 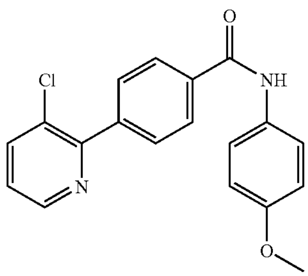 | 338.80 | 339.11 | 3.05 | 2.92 | 3.43 | ++ |
| 1023 | 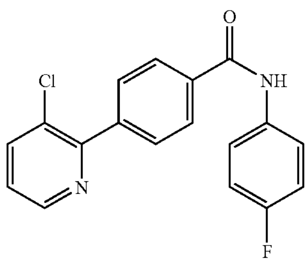 | 326.76 | 327.11 | 3.19 | 3.12 | 3.47 | |
| 1024 | 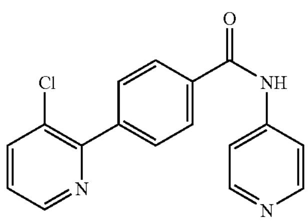 | 309.76 | 310.28 | 2.21 | 2.09 | 2.61 | ++++ |
| 1025 | 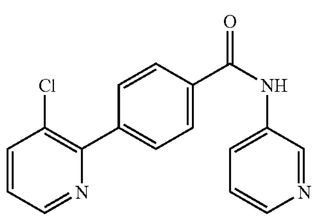 | 309.76 | 310.28 | 2.09 | 2.02 | 2.46 | ++++ |
| 1026 | 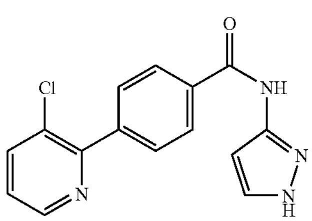 | 298.73 | 299.17 | 2.29 | 2.19 | 2.53 | + |
| 1027 | 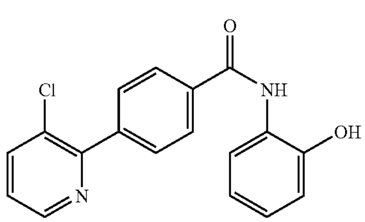 | 324.77 | 325.23 | 2.93 | 2.85 | 3.18 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1028 | 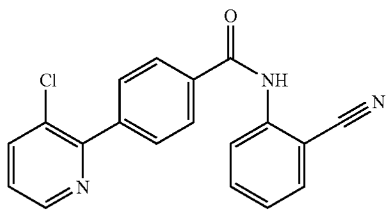 | 333.78 | 334.18 | 2.93 | 2.78 | 3.32 | + |
| 1029 | 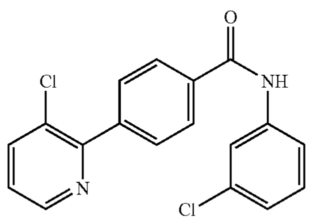 | 343.22 | 343.09 | 3.52 | 3.42 | 3.81 | + |
| 1030 | 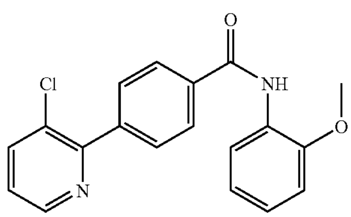 | 338.80 | 339.12 | 3.34 | 3.22 | 3.68 | ++++ |
| 1031 | 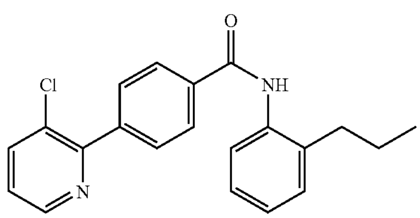 | 350.85 | 351.29 | 3.45 | 3.34 | 3.91 | |
| 1032 | 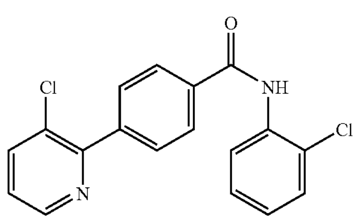 | 343.22 | 343.09 | 3.41 | 3.33 | 3.81 | + |
| 1033 | 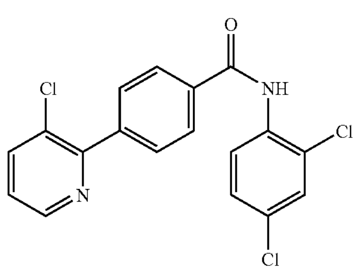 | 377.66 | 377.16 | 3.79 | 3.71 | 4.14 | + |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1034 | 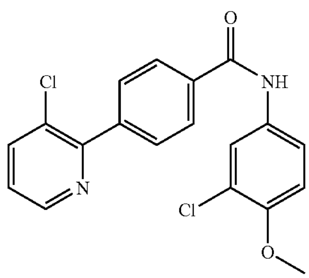 | 373.24 | 373.03 | 3.33 | 3.22 | 3.66 | + |
| 1035 | 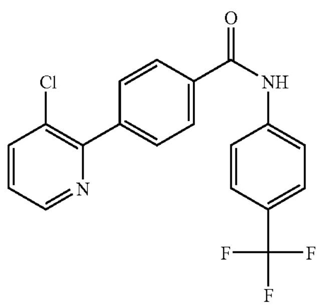 | 376.77 | 377.26 | 3.67 | 3.54 | 3.89 | ++++ |
| 1036 | 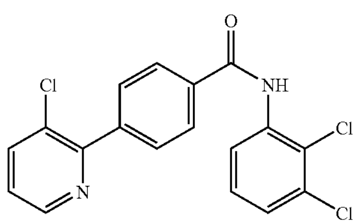 | 377.66 | 377.17 | 3.74 | 3.61 | 4.05 | |
| 1037 | 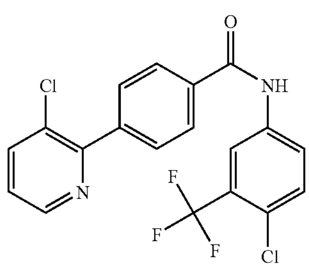 | 411.21 | 411.00 | 3.89 | 3.78 | 4.24 | +++ |
| 1038 | 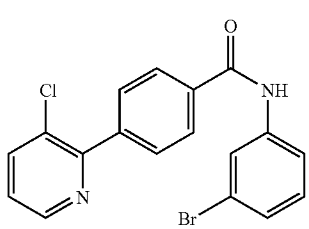 | 387.67 | 389.18 | 3.57 | 3.48 | 3.91 | + |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1039 | 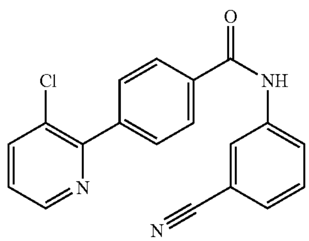 | 333.78 | 334.15 | 3.16 | 3.09 | 3.48 | + |
| 1040 | 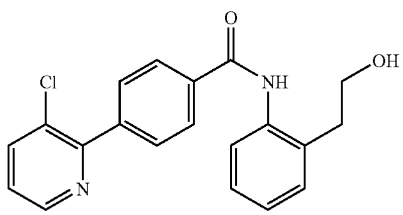 | 352.82 | 353.22 | 2.78 | 2.71 | 3.15 | +++ |
| 1041 | 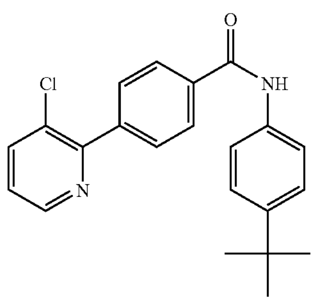 | 364.88 | 365.09 | 3.85 | 3.75 | 4.31 | ++++ |
| 1042 | 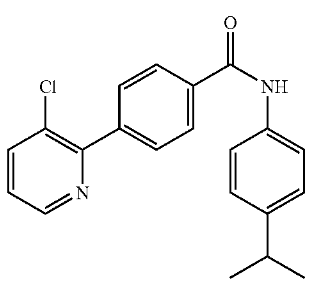 | 350.85 | 351.29 | 3.71 | 3.62 | 4.05 | ++++ |
| 1043 | 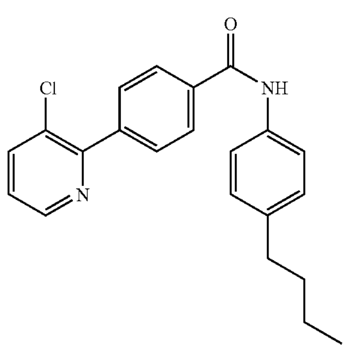 | 364.88 | 365.09 | 3.96 | 3.85 | 4.68 | ++ |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1044 | 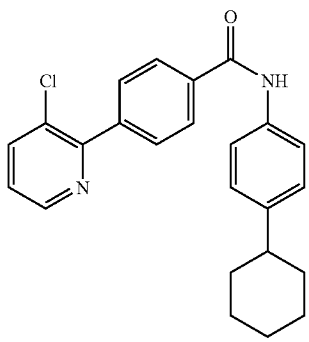 | 390.92 | 391.32 | 4.19 | 3.99 | 4.57 | ++++ |
| 1045 | 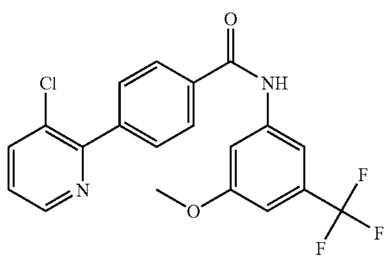 | 406.79 | 407.15 | 3.73 | 3.65 | 4.14 | ++ |
| 1046 | 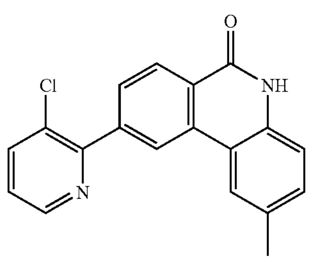 | 336.82 | 337.34 | 3.29 | 3.16 | 3.59 | + |
| 1047 | 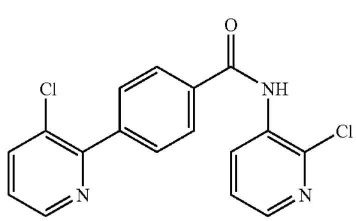 | 344.20 | 344.08 | 2.90 | 2.83 | 3.32 | ++ |
| 1048 | 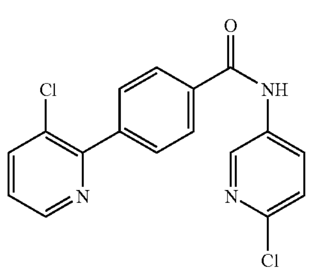 | 344.20 | 344.08 | 3.02 | 2.92 | 3.31 | + |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1049 | 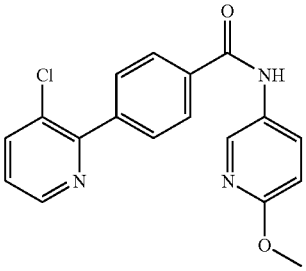 | 339.78 | 340.10 | 2.66 | 2.58 | 2.98 | + |
| 1050 | 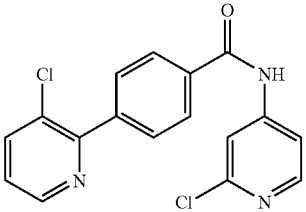 | 344.20 | 344.08 | 3.05 | 2.88 | 3.36 | ++++ |
| 1051 | 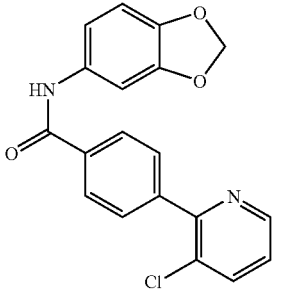 | 352.78 | 353.15 | 3.05 | 2.90 | 3.48 | + |
| 1052 | 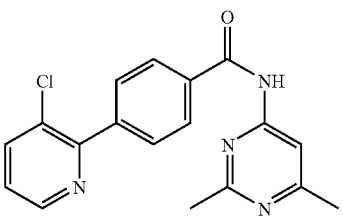 | 338.80 | 339.13 | 2.29 | 2.22 | 2.51 | + |
| 1053 | 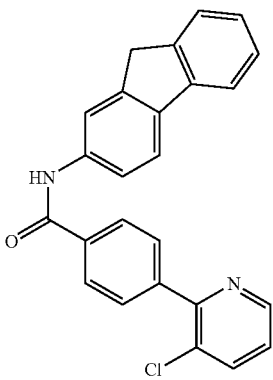 | 396.88 | 397.10 | 3.83 | 3.53 | 4.24 | ++ |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1054 | 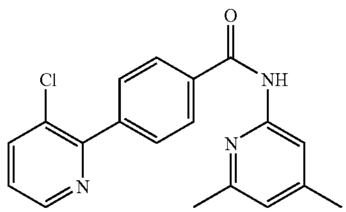 | 337.81 | 338.29 | 2.40 | 2.25 | 2.80 | + |
| 1055 | 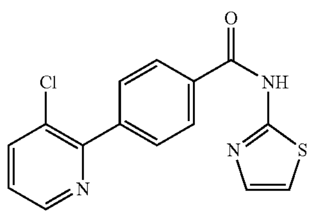 | 315.78 | 316.06 | 2.82 | 2.72 | 3.16 | + |
| 1056 | 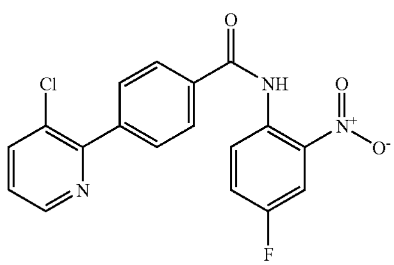 | 371.76 | 371.96 | 3.56 | 3.48 | 3.83 | |
| 1057 | 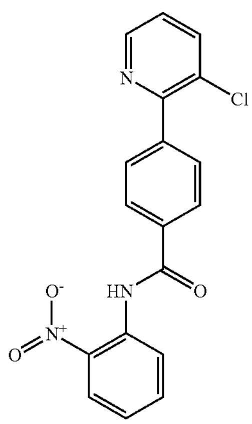 | 353.77 | 354.12 | 3.53 | 3.46 | 3.78 | |
| 1058 | 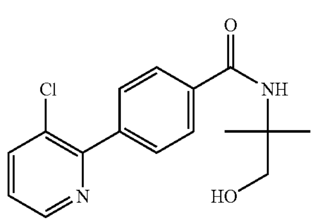 | 304.78 | 305.24 | 2.33 | 2.29 | 2.61 | + |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1059 | 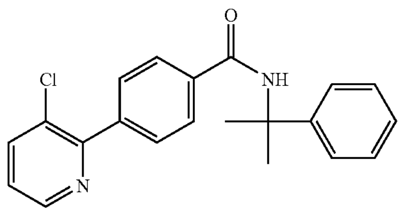 | 350.85 | 351.30 | 3.29 | 3.21 | 3.66 | |
| 1060 | 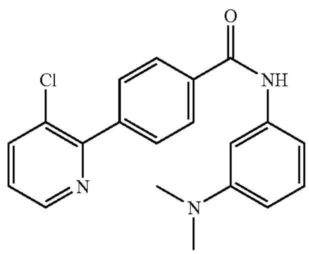 | 351.84 | 352.29 | 2.28 | 2.16 | 2.62 | ++++ |
| 1061 | 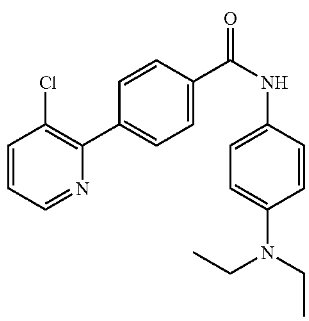 | 379.89 | 380.27 | 2.39 | 2.19 | 2.82 | ++++ |
| 1062 | 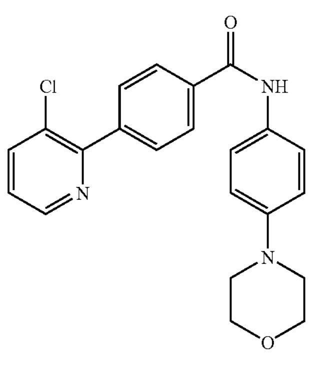 | 393.88 | 394.15 | 2.43 | 2.36 | 2.89 | + |
| 1063 | 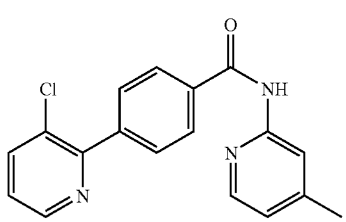 | 323.78 | 324.28 | 2.28 | 2.17 | 2.59 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1064 | 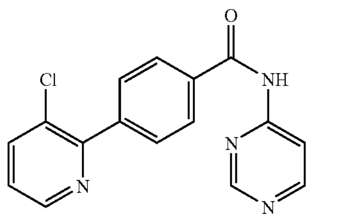 | 310.75 | 311.25 | 2.35 | 2.23 | 2.53 | |
| 1065 | 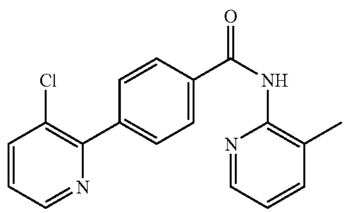 | 323.78 | 324.28 | 2.19 | 2.12 | 2.39 | ++ |
| 1066 | 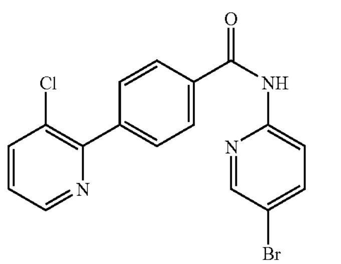 | 388.65 | 390.14 | 3.42 | 3.35 | 3.63 | ++ |
| 1067 | 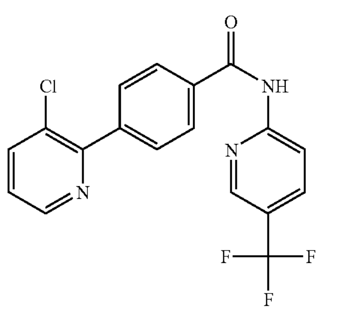 | 377.76 | 378.19 | 3.56 | 3.51 | 3.82 | ++ |
| 1068 | 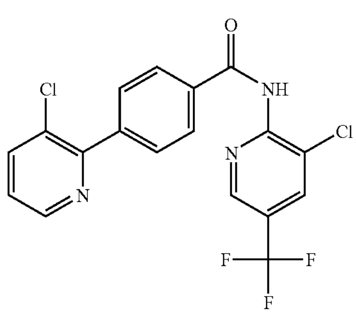 | 412.20 | 412.11 | 3.32 | 3.13 | 3.63 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1069 | 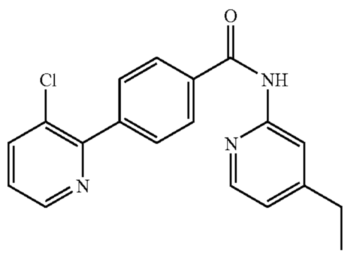 | 337.81 | 338.29 | 2.42 | 2.36 | 2.64 | |
| 1070 | 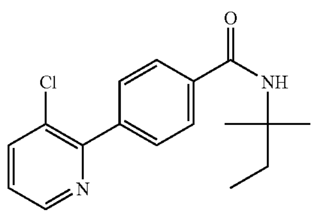 | 302.81 | 303.08 | 3.15 | 3.06 | 3.59 | + |
| 1071 | 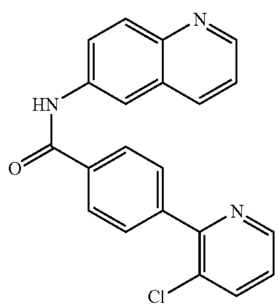 | 359.82 | 360.14 | 2.33 | 2.22 | 2.59 | + |
| 1072 | 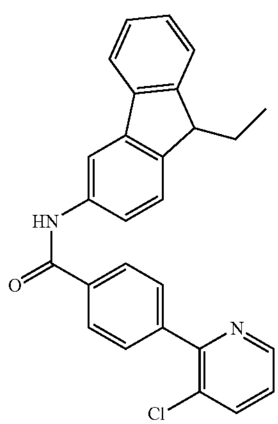 | 425.92 | 426.12 | 3.78 | 3.68 | 4.49 | ++ |
| 1073 | 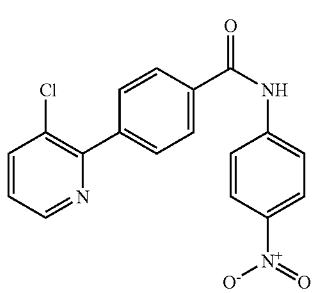 | 353.77 | 354.15 | 3.39 | 3.31 | 3.56 | ++++ |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1074 | 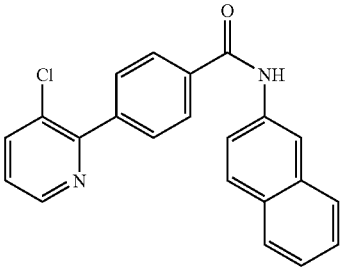 | 358.83 | 359.15 | 3.58 | 3.48 | 3.92 | ++++ |
| 1075 | 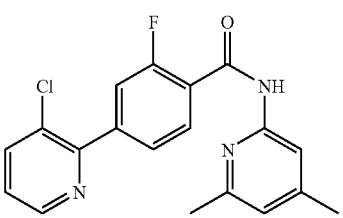 | 355.80 | 356.12 | 2.50 | 2.38 | 2.93 | |
| 1076 | 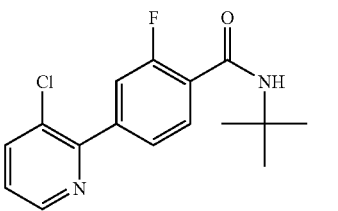 | 306.77 | 307.22 | 3.25 | 3.18 | 3.46 | |
| 1077 | 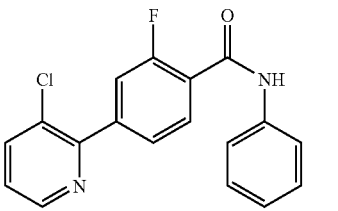 | 326.76 | 327.10 | 3.35 | 3.28 | 3.59 | |
| 1078 | 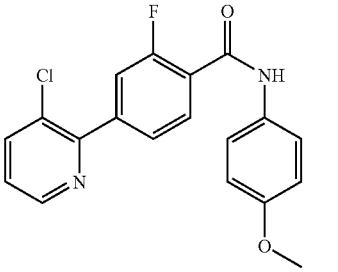 | 356.79 | 357.01 | 3.28 | 3.19 | 3.75 | |
| 1079 | 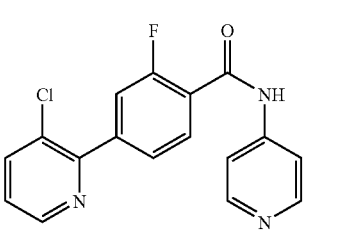 | 327.75 | 328.19 | 2.25 | 2.13 | 2.58 | + |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1080 | 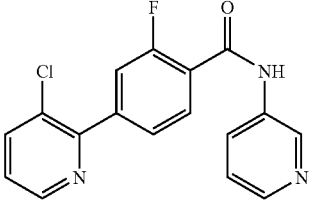 | 327.75 | 328.21 | 2.18 | 2.12 | 2.53 | + |
| 1081 | 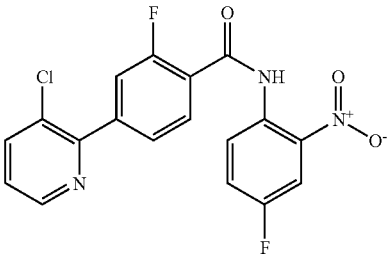 | 389.75 | 390.15 | 3.82 | 3.66 | 4.21 | |
| 1082 | 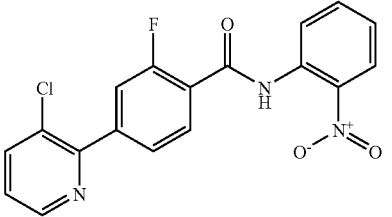 | 371.76 | 371.94 | 3.78 | 3.71 | 4.16 | |
| 1083 | 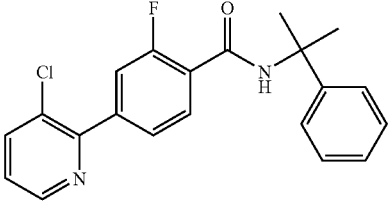 | 368.84 | 369.07 | 3.56 | 3.46 | 3.96 | + |
| 1084 | 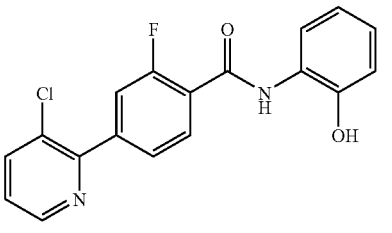 | 342.76 | 343.09 | 3.18 | 3.08 | 3.49 | + |
| 1085 | 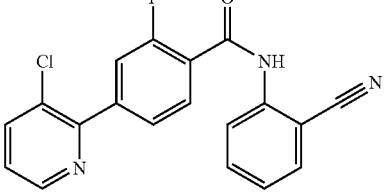 | 351.77 | 352.15 | 3.31 | 3.12 | 3.61 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1086 | 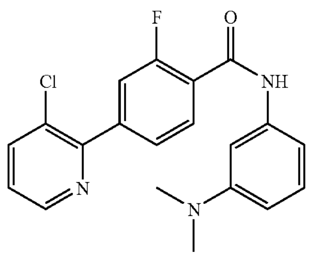 | 369.83 | 370.11 | 2.39 | 2.29 | 2.76 | + |
| 1087 | 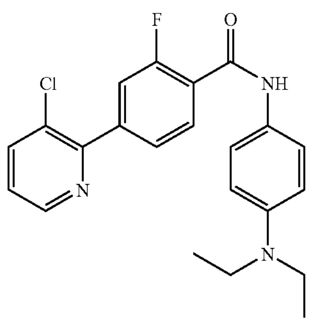 | 397.88 | 398.10 | 2.48 | 2.26 | 2.99 | |
| 1088 | 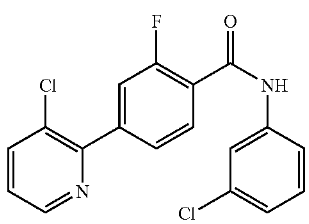 | 361.21 | 361.02 | 3.69 | 3.58 | 3.96 | + |
| 1089 | 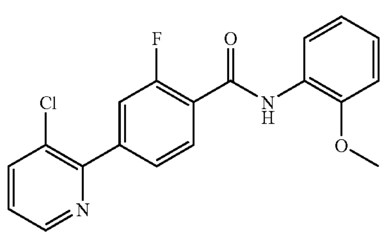 | 356.79 | 357.00 | 3.76 | 3.69 | 4.05 | |
| 1090 | 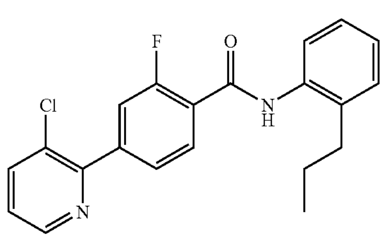 | 368.84 | 369.04 | 3.83 | 3.66 | 4.26 | |

-continued

| | AMIDE COMPOUNDS | | | | | | |
|---|---|---|---|---|---|---|---|
| ID | STRUCTURE | MW (Calc) | MS (Obs) | HPLC RT (Min) | HPLC START TIME (Min) | HPLC END TIME (Min) | % Inhibition @ 1 uM |
| 1091 | | 356.79 | 357.00 | 3.38 | 3.29 | 3.85 | + |
| 1092 | | 411.87 | 412.10 | 2.61 | 2.46 | 3.19 | |
| 1093 | | 361.21 | | | | | |
| 1094 | | 341.78 | 342.07 | 2.40 | 2.26 | 2.73 | |
| 1095 | | 395.65 | 394.97 | 4.45 | 4.31 | 4.51 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1096 | 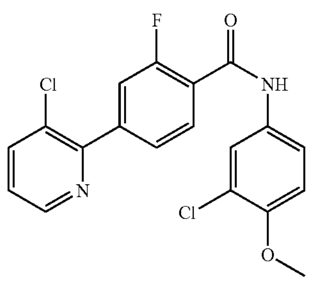 | 391.23 | 391.22 | 3.52 | 3.41 | 3.81 | ++ |
| 1097 | 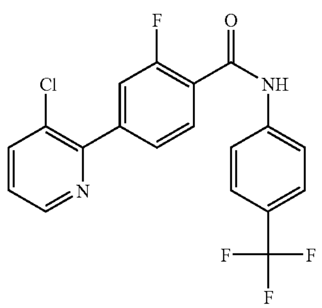 | 394.76 | 395.00 | 3.81 | 3.68 | 4.05 | |
| 1098 | 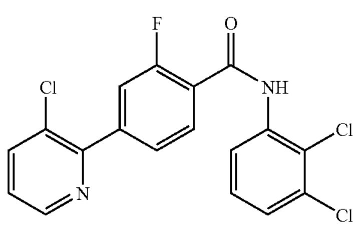 | 395.65 | 396.95 | 4.34 | 4.24 | 4.61 | |
| 1099 | 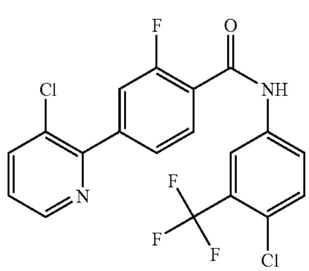 | 429.20 | 428.97 | 4.02 | 3.88 | 4.31 | |
| 1100 | 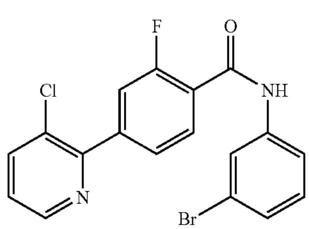 | 405.66 | 406.99 | 3.75 | 3.66 | 4.09 | ++++ |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1101 | 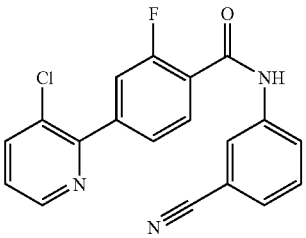 | 351.77 | 352.14 | 3.31 | 3.22 | 3.59 | ++++ |
| 1102 | 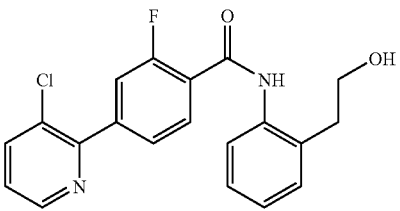 | 370.81 | 371.01 | 2.89 | 2.82 | 3.22 | |
| 1103 | 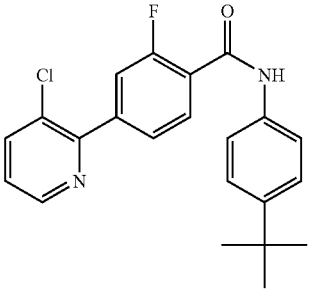 | 382.87 | 383.16 | 4.05 | 3.95 | 4.26 | + |
| 1104 | 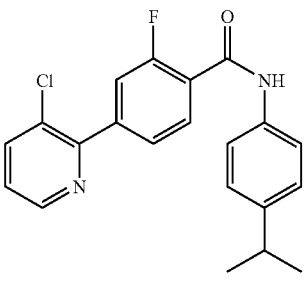 | 368.84 | 369.07 | 3.91 | 3.82 | 4.30 | |
| 1105 | 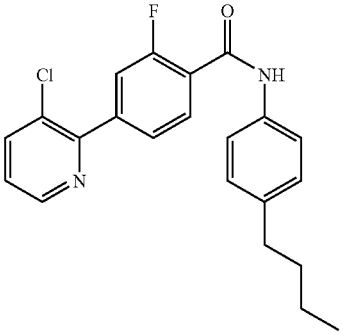 | 382.87 | | | | | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1106 | 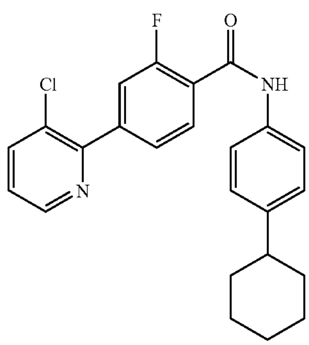 | 408.91 | 409.21 | 4.44 | 4.31 | 4.85 | |
| 1107 | 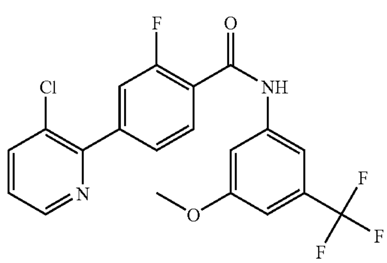 | 424.79 | 424.96 | 3.86 | 3.76 | 4.21 | |
| 1108 | 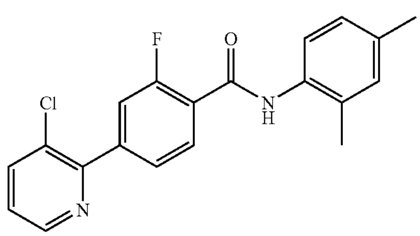 | 354.81 | 355.19 | 3.63 | 3.56 | 3.95 | |
| 1109 | 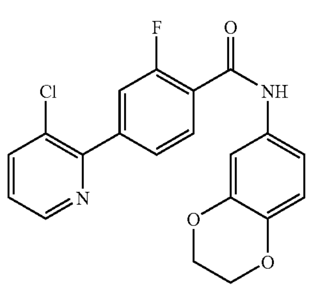 | 384.80 | 385.11 | 3.22 | 3.15 | 3.55 | |
| 1110 | 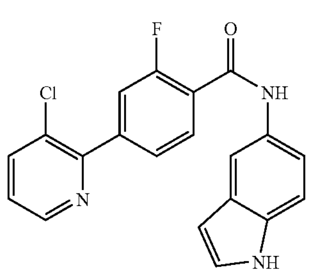 | 365.80 | 366.10 | 3.09 | 3.02 | 3.59 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1111 | | 328.74 | 329.16 | 2.60 | 2.50 | 2.85 | |
| 1112 | | 341.78 | 342.06 | 2.32 | 2.23 | 2.70 | + |
| 1113 | | 406.64 | 408.06 | 3.76 | 3.69 | 3.99 | |
| 1114 | | 395.75 | 396.06 | 3.84 | 3.71 | 4.07 | + |
| 1115 | | 430.19 | 430.12 | 3.55 | 3.49 | 3.88 | + |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1116 | 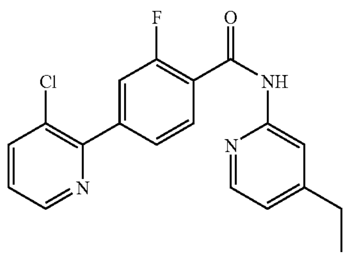 | 355.80 | 356.13 | 2.58 | 2.46 | 2.76 | |
| 1117 | 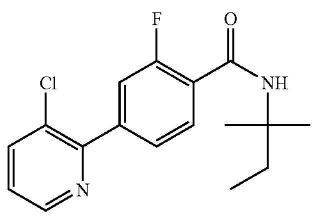 | 320.80 | 321.12 | 3.46 | 3.36 | 4.02 | |
| 1118 | 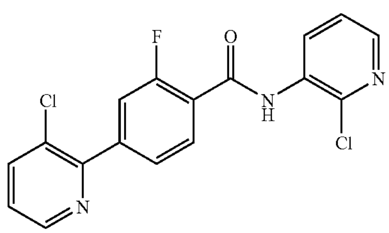 | 362.19 | 362.15 | 3.44 | 3.11 | 3.62 | + |
| 1119 | 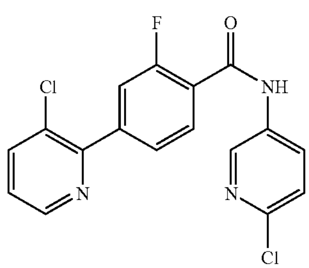 | 362.19 | 362.14 | 3.18 | 3.11 | 3.45 | |
| 1120 | 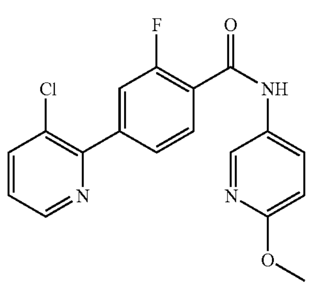 | 357.77 | 358.10 | 2.88 | 2.79 | 3.23 | + |
| 1121 | 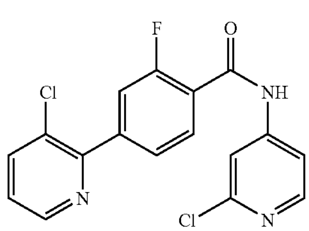 | 362.19 | | | | | |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1122 | 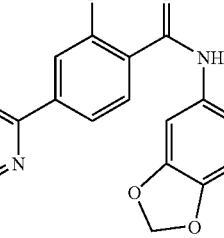 | 370.77 | 370.99 | 3.23 | 3.15 | 3.49 | |
| 1123 | 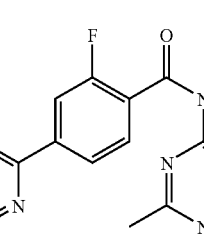 | 356.79 | 357.07 | 2.40 | 2.29 | 2.73 | +++ |
| 1124 | 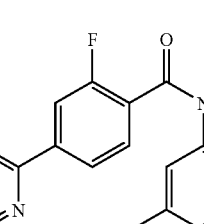 | 377.81 | 378.17 | 2.40 | 2.32 | 2.78 | ++ |
| 1125 | 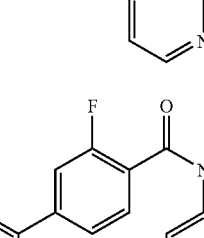 | 414.87 | 415.24 | 4.05 | 3.89 | 4.38 | |
| 1126 | 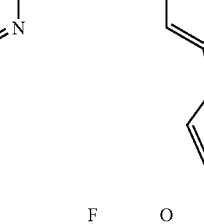 | 376.82 | 377.27 | 3.75 | 3.66 | 4.11 | ++ |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1127 | 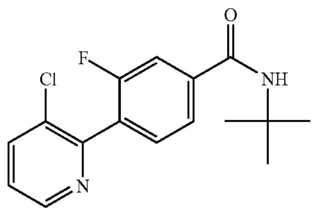 | 306.77 | 307.22 | 3.06 | 2.95 | 3.46 | + |
| 1128 | 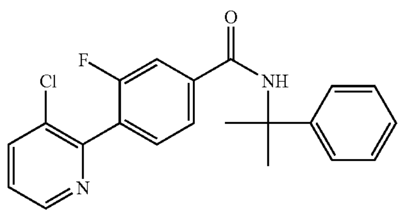 | 368.84 | 369.10 | 3.36 | 3.28 | 3.73 | |
| 1129 | 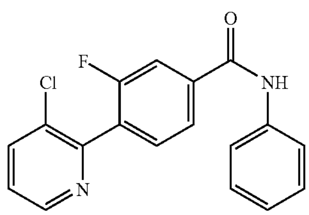 | 326.76 | 327.10 | 3.21 | 3.12 | 3.52 | |
| 1130 | 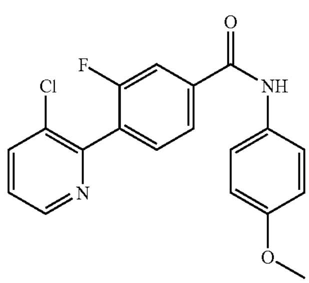 | 356.79 | 357.09 | 3.13 | 3.03 | 3.63 | |
| 1131 | 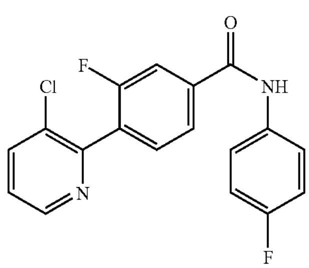 | 344.75 | 344.97 | 3.28 | 3.12 | 3.53 | + |
| 1132 | 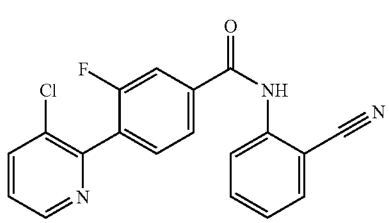 | 351.77 | 352.22 | 2.99 | 2.86 | 3.29 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1133 | | 361.21 | 361.13 | 3.53 | 3.41 | 3.88 | + |
| 1134 | | 356.79 | 357.04 | 3.35 | 3.09 | 3.73 | |
| 1135 | | 368.84 | 369.10 | 3.49 | 3.35 | 4.02 | + |
| 1136 | | 356.79 | 357.09 | 3.24 | 2.89 | 3.79 | + |
| 1137 | | 361.21 | 361.09 | 3.39 | 3.12 | 3.79 | |
| 1138 | | 395.65 | 394.98 | 3.74 | 3.49 | 4.12 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1139 | 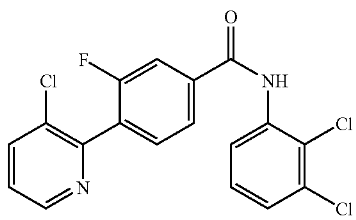 | 395.65 | 394.97 | 3.66 | 3.46 | 4.06 | ++++ |
| 1140 | 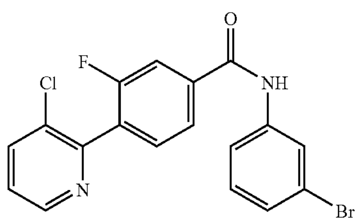 | 405.66 | 407.03 | 3.61 | 3.48 | 4.09 | |
| 1141 | 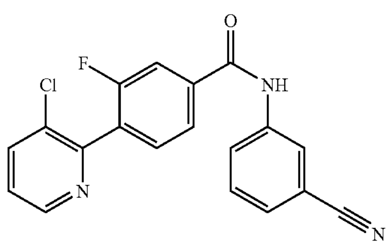 | 351.77 | 352.18 | 3.21 | 3.13 | 3.42 | ++++ |
| 1142 | 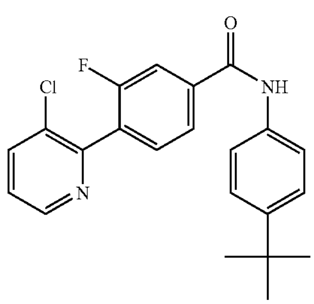 | 382.87 | 383.17 | 3.87 | 3.77 | 4.24 | ++++ |
| 1143 | 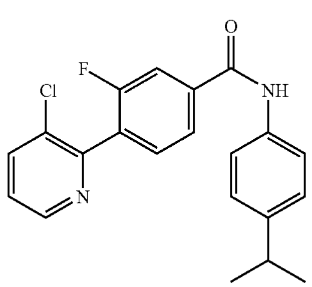 | 368.84 | 369.08 | 3.72 | 3.48 | 4.11 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1144 | 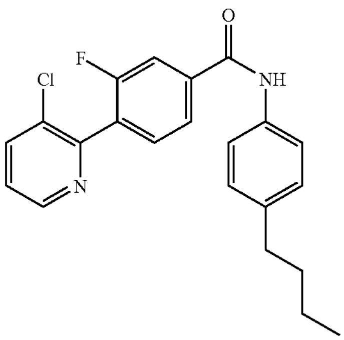 | 382.87 | 383.18 | 3.99 | 3.79 | 4.56 | ++++ |
| 1145 | 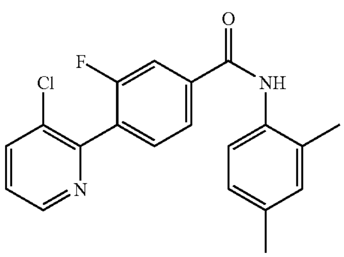 | 354.81 | 355.20 | 3.33 | 3.22 | 3.79 | ++++ |
| 1146 | 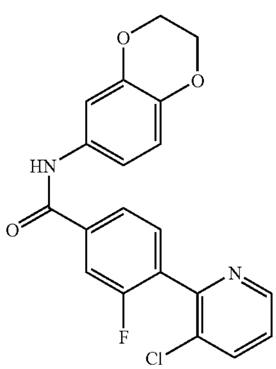 | 384.80 | 385.18 | 3.12 | 3.03 | 349 | |
| 1147 | 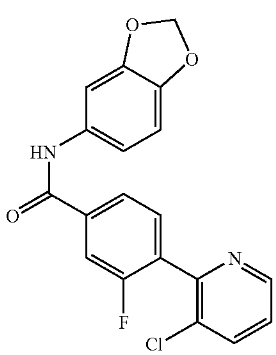 | 370.77 | 370.99 | 3.14 | 2.99 | 3.59 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1148 | | 371.76 | 371.94 | 3.42 | 3.33 | 3.69 | |
| 1149 | | 389.75 | 390.22 | 3.49 | 3.41 | 3.83 | ++++ |
| 1150 | | 371.76 | 372.00 | 3.49 | 3.41 | 3.92 | |
| 1151 | | 391.23 | 391.22 | 3.38 | 3.21 | 3.73 | ++++ |
| 1152 | | 394.76 | 395.03 | 3.68 | 3.51 | 3.91 | ++ |

AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1153 | 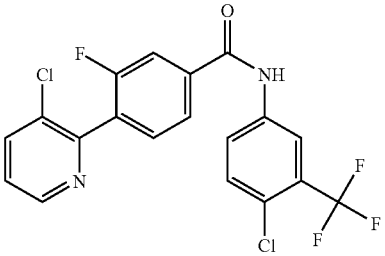 | 429.20 | 428.99 | 3.91 | 3.79 | 4.19 | |
| 1154 | 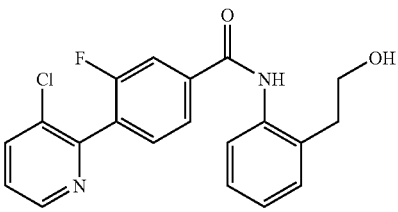 | 370.81 | 371.04 | 2.90 | 2.78 | 3.19 | |
| 1155 | 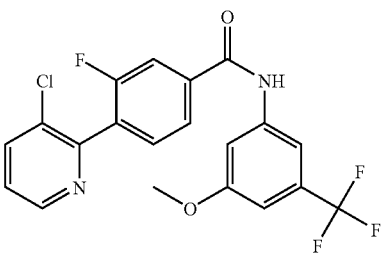 | 424.79 | 425.01 | 3.76 | 3.63 | 3.95 | |
| 1156 | 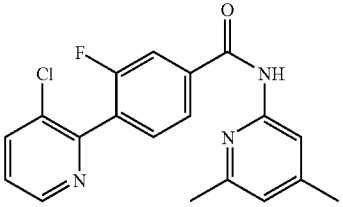 | 355.80 | 356.13 | 2.45 | 2.28 | 2.82 | + |
| 1157 | 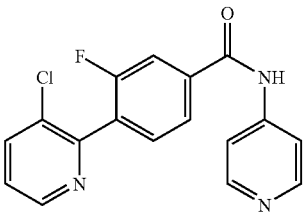 | 327.75 | 328.21 | 2.28 | 2.15 | 2.59 | ++++ |
| 1158 | 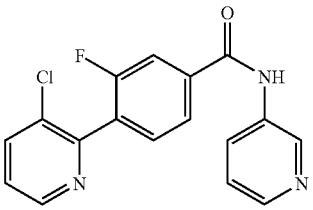 | 327.75 | 328.23 | 2.17 | 2.07 | 2.49 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1159 | 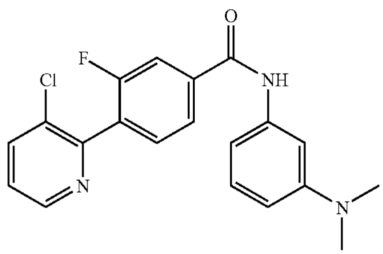 | 369.83 | 370.13 | 2.39 | 2.25 | 2.63 | |
| 1160 | 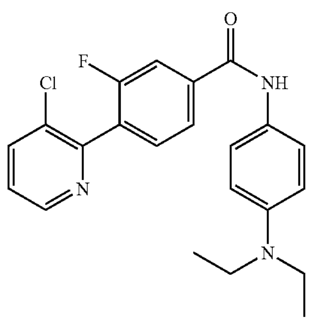 | 397.88 | 398.14 | 2.43 | 2.30 | 2.99 | |
| 1161 | 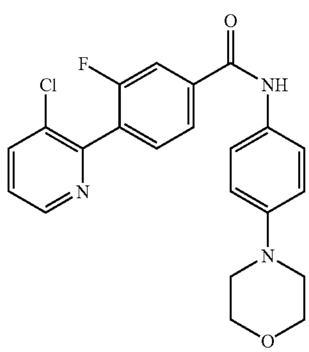 | 411.87 | 412.11 | 2.56 | 2.35 | 2.98 | |
| 1162 | 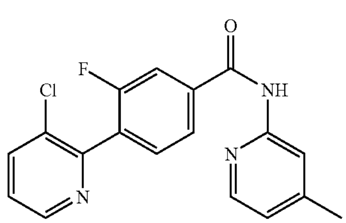 | 341.78 | 342.08 | 2.33 | 2.15 | 2.60 | ++++ |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1163 | 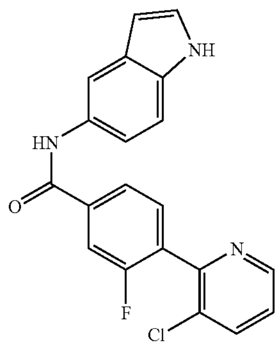 | 365.80 | 366.10 | 2.99 | 2.86 | 3.53 | |
| 1164 | 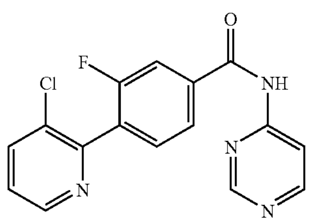 | 328.74 | 329.18 | 2.46 | 2.39 | 2.78 | |
| 1165 | 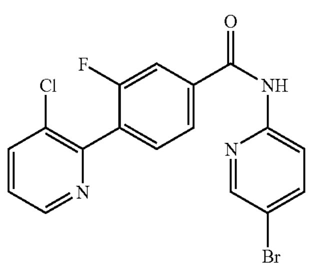 | 406.64 | 408.06 | 3.46 | 3.38 | 3.81 | |
| 1166 | 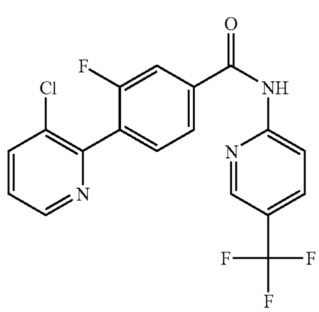 | 395.75 | 396.10 | 3.58 | 3.48 | 3.85 | ++ |
| 1167 | 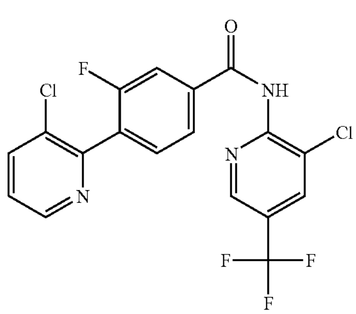 | 430.19 | 430.13 | 3.35 | 3.15 | 3.75 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1168 | 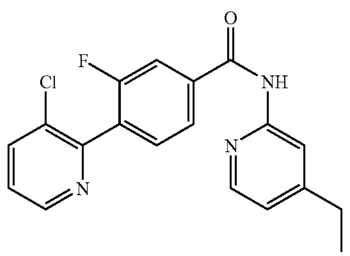 | 355.80 | 356.14 | 2.48 | 2.26 | 2.85 | |
| 1169 | 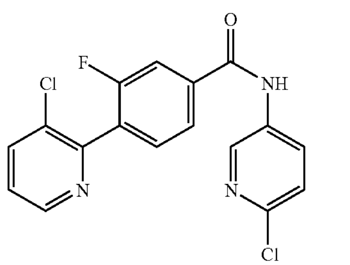 | 362.19 | 362.16 | 3.12 | 2.95 | 3.46 | + |
| 1170 | 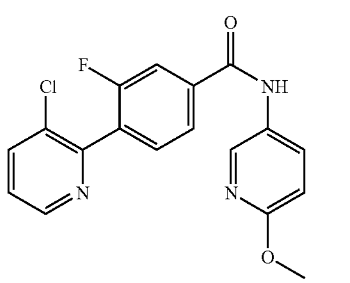 | 357.77 | 358.11 | 2.79 | 2.65 | 3.18 | ++ |
| 1171 | 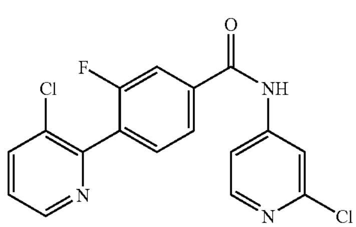 | 362.19 | 362.19 | 3.12 | 3.07 | 3.45 | |
| 1172 | 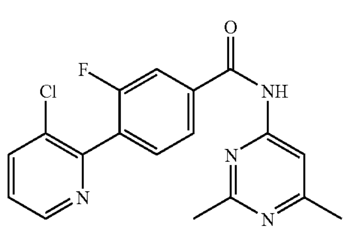 | 356.79 | 357.09 | 2.36 | 2.30 | 2.55 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1173 | 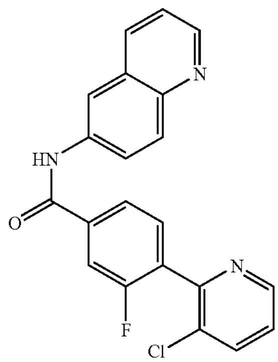 | 377.81 | 378.19 | 2.40 | 2.12 | 2.78 | ++++ |
| 1174 | 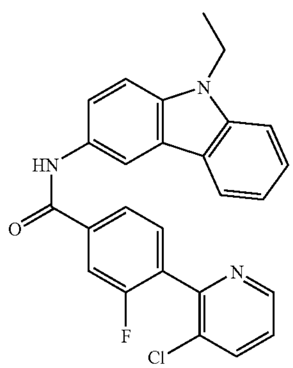 | 443.91 | | | | | |
| 1175 | 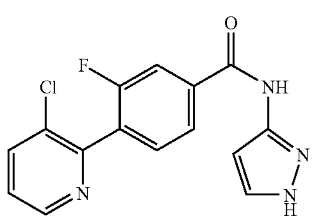 | 316.72 | 317.08 | 2.42 | 2.33 | 2.83 | + |
| 1176 | 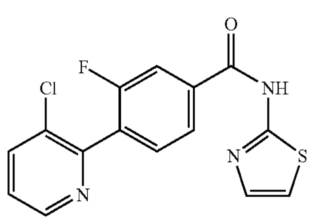 | 333.77 | 334.13 | 2.91 | 2.84 | 3.29 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1177 | 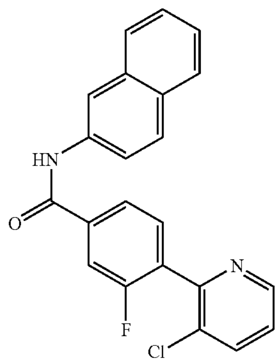 | 376.82 | 377.26 | 3.61 | 3.45 | 4.12 | ++++ |
| 1178 | 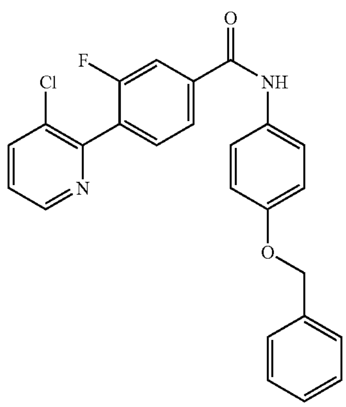 | 432.89 | 433.22 | 3.72 | 3.48 | 4.02 | |
| 1179 | 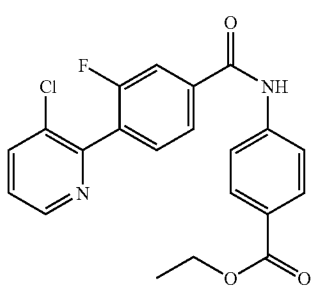 | 398.82 | 399.10 | 3.51 | 3.31 | 3.82 | |
| 1180 | 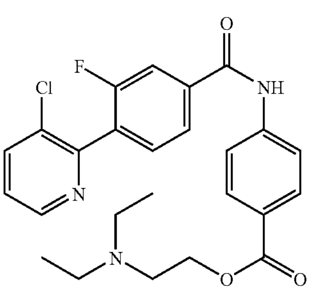 | 469.95 | 470.32 | 2.66 | 2.56 | 2.98 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1181 | 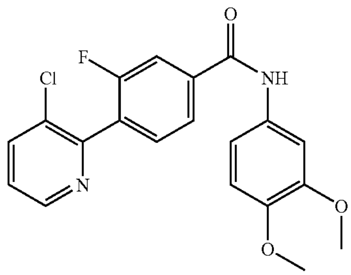 | 386.81 | 387.15 | 2.98 | 2.80 | 3.38 | |
| 1182 | 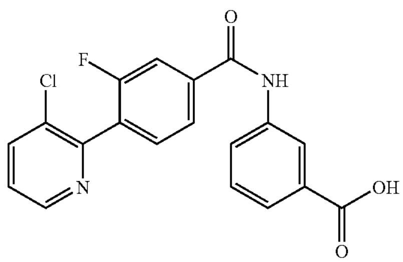 | 370.77 | 371.04 | 2.85 | 2.78 | 3.21 | + |
| 1183 | 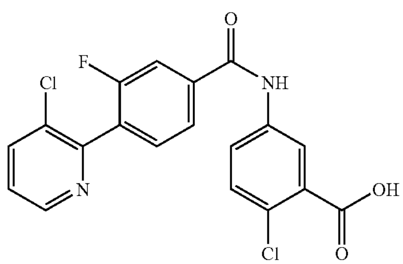 | 405.22 | 405.21 | 2.99 | 2.80 | 3.26 | ++++ |
| 1184 | 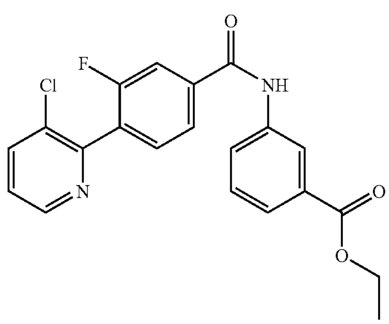 | 398.82 | 399.10 | 3.45 | 3.36 | 3.91 | |
| 1185 | 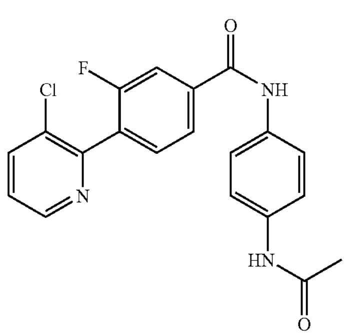 | 383.81 | 384.11 | 2.65 | 2.52 | 3.03 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1186 | 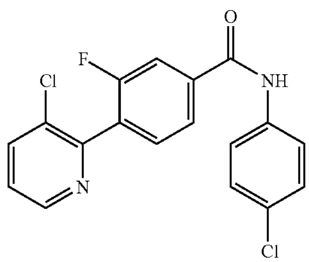 | 361.21 | 361.12 | 3.52 | 3.41 | 3.78 | |
| 1187 | 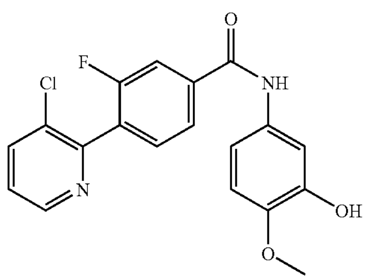 | 372.79 | 373.05 | 2.78 | 2.68 | 3.06 | ++ |
| 1188 | 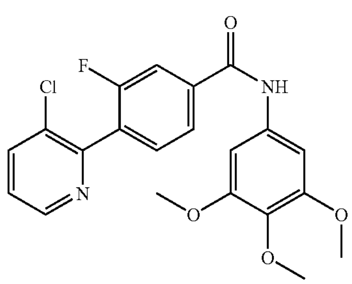 | 416.84 | 417.30 | 3.08 | 2.96 | 3.61 | |
| 1189 | 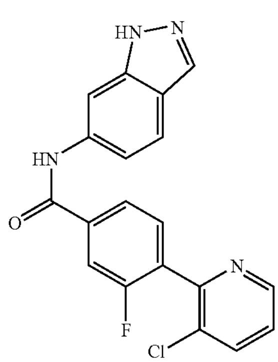 | 366.79 | 367.07 | 2.79 | 2.66 | 3.31 | +++ |

US 7,338,950 B2

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1190 | 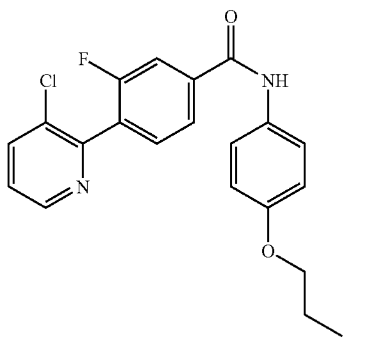 | 384.84 | 385.21 | 3.56 | 3.48 | 3.92 | ++ |
| 1191 | 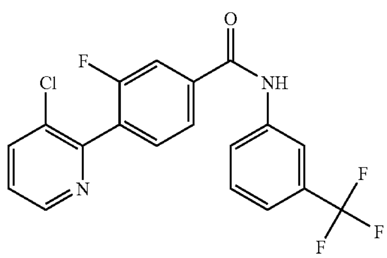 | 394.76 | 395.06 | 3.65 | 3.51 | 3.96 | |
| 1192 | 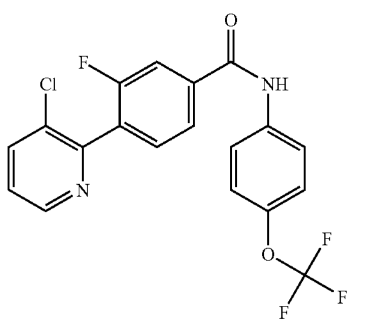 | 410.76 | 411.04 | 3.71 | 3.62 | 3.96 | ++ |
| 1193 | 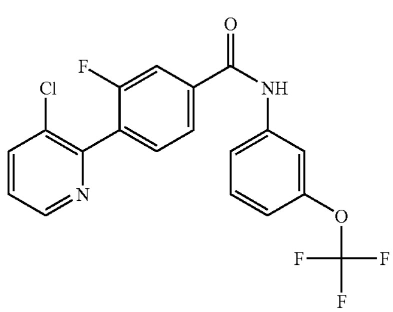 | 410.76 | 411.01 | 3.73 | 3.62 | 4.12 | + |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1194 | 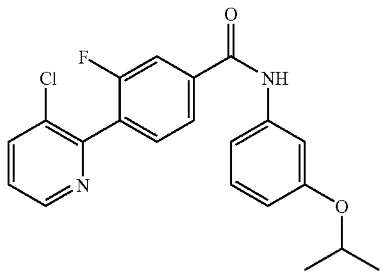 | 384.84 | 385.22 | 3.58 | 3.46 | 3.82 | + |
| 1195 | 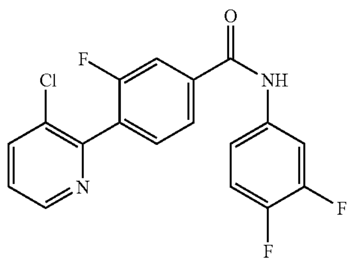 | 362.74 | 363.29 | 3.43 | 3.33 | 3.72 | +++ |
| 1196 | 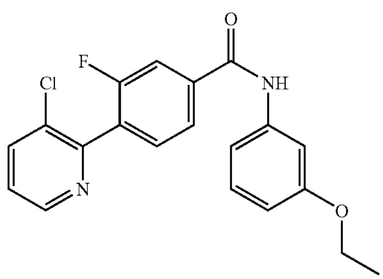 | 370.81 | 371.10 | 3.42 | 3.31 | 3.76 | |
| 1197 | 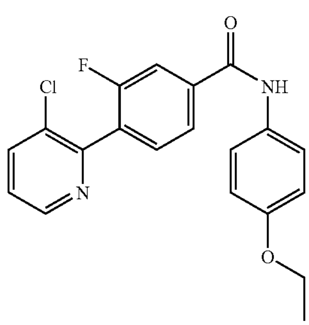 | 370.81 | 371.06 | 3.32 | 3.21 | 3.71 | |
| 1198 | 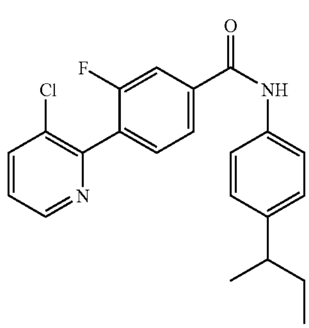 | 382.87 | 383.20 | 3.91 | 3.75 | 4.14 | |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1199 | 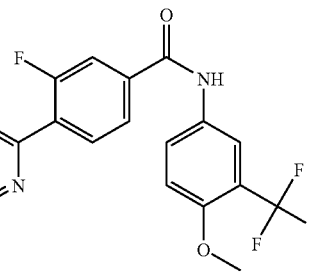 | 424.79 | 425.00 | 3.55 | 3.46 | 3.72 | |
| 1200 | 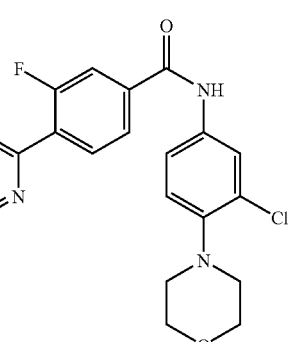 | 446.31 | 446.12 | 3.38 | 3.28 | 3.61 | ++++ |
| 1201 | 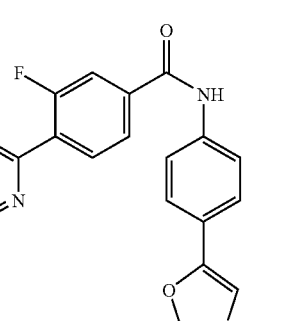 | 393.81 | 394.10 | 3.16 | 3.08 | 3.48 | |
| 1202 | 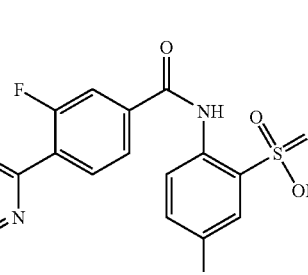 | 441.27 | 441.01 | 2.26 | 2.20 | 2.56 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1203 | 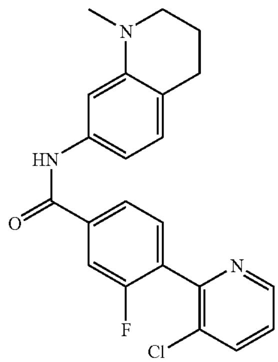 | 395.87 | 396.11 | 2.61 | 2.11 | 3.01 | + |
| 1204 | 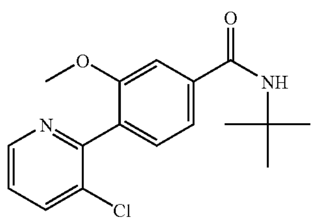 | 318.81 | 319.00 | 2.76 | 2.68 | 3.26 | + |
| 1205 | 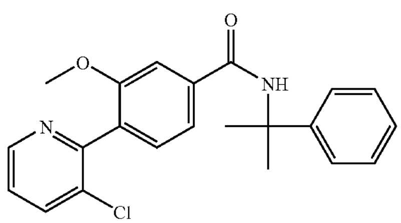 | 380.88 | 381.24 | 3.11 | 2.98 | 3.46 | |
| 1206 | 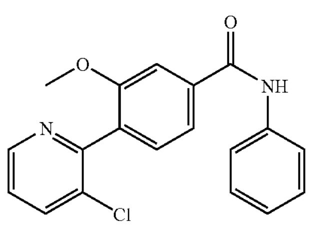 | 338.80 | 339.12 | 2.95 | 2.79 | 3.33 | + |
| 1207 | 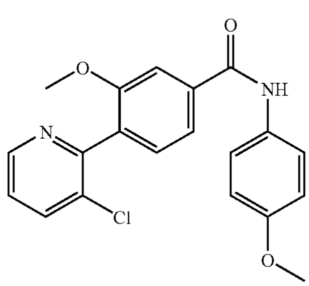 | 368.82 | 369.09 | 2.89 | 2.75 | 3.36 | + |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1208 | 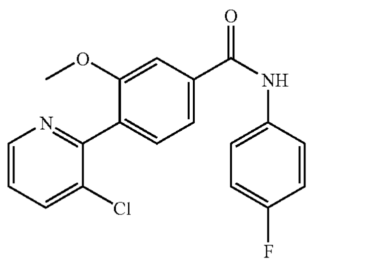 | 356.79 | 357.09 | 3.02 | 2.95 | 3.26 | |
| 1209 | 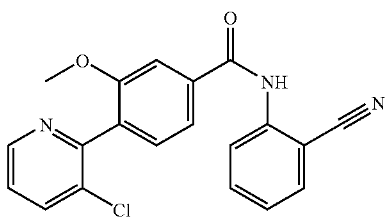 | 363.81 | 364.29 | 2.76 | 2.65 | 2.90 | + |
| 1210 | 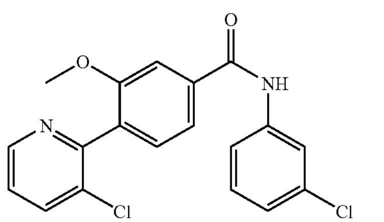 | 373.24 | 373.02 | 3.31 | 3.19 | 3.69 | + |
| 1211 | 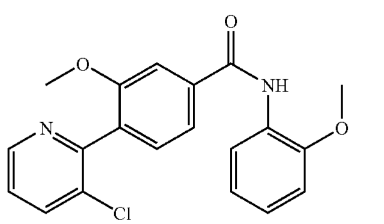 | 368.82 | 369.10 | 3.09 | 2.96 | 3.51 | ++ |
| 1212 | 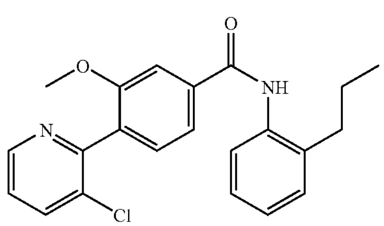 | 380.88 | 381.25 | 3.23 | 3.11 | 3.75 | ++ |
| 1213 | 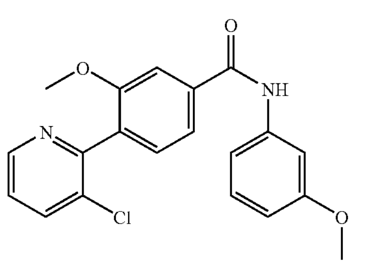 | 368.82 | 369.09 | 2.98 | 2.86 | 3.35 | ++ |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1214 | 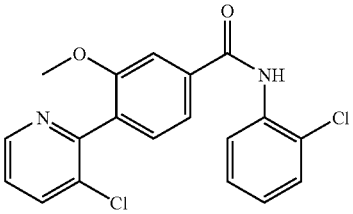 | 373.24 | 373.01 | 3.14 | 2.95 | 3.65 | |
| 1215 | 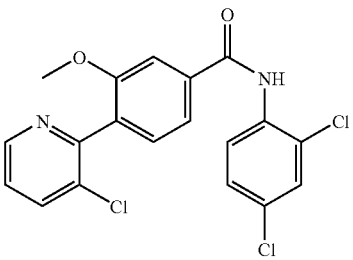 | 407.69 | 407.09 | 3.49 | 3.39 | 3.93 | |
| 1216 | 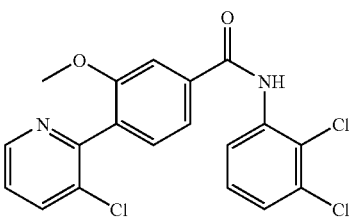 | 407.69 | 409.01 | 3.42 | 3.36 | 3.83 | ++++ |
| 1217 | 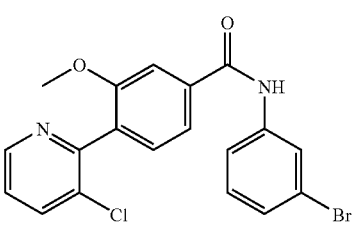 | 417.69 | 419.04 | 3.35 | 3.19 | 3.85 | |
| 1218 | 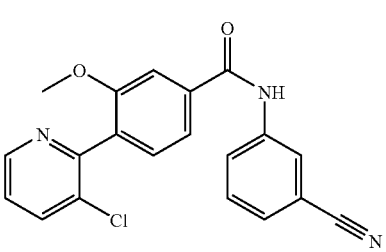 | 363.81 | 364.29 | 2.99 | 2.92 | 3.32 | ++++ |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1219 | 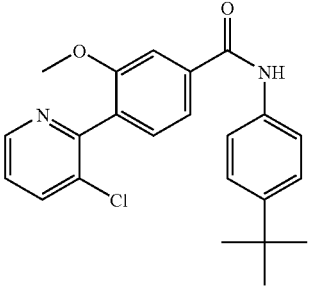 | 394.90 | 395.14 | 3.61 | 3.46 | 4.08 | |
| 1220 | 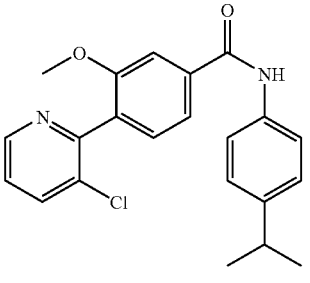 | 380.88 | 381.26 | 3.49 | 3.38 | 3.95 | |
| 1221 | 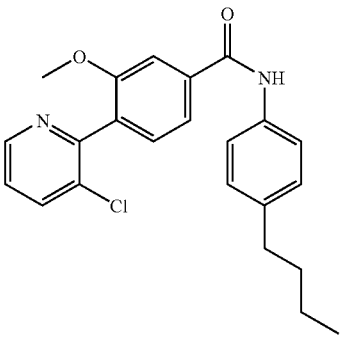 | 394.90 | 395.14 | 3.73 | 3.58 | 4.15 | ++ |
| 1222 | 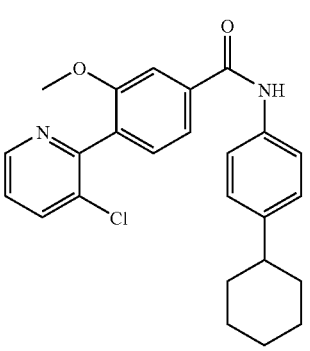 | 420.94 | 421.17 | 3.96 | 3.73 | 4.35 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1223 | 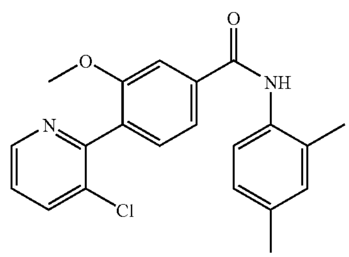 | 366.85 | 367.09 | 3.09 | 2.95 | 3.51 | ++++ |
| 1224 | 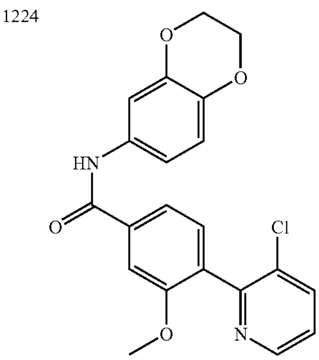 | 396.83 | 397.07 | 2.88 | 2.72 | 3.26 | |
| 1225 | 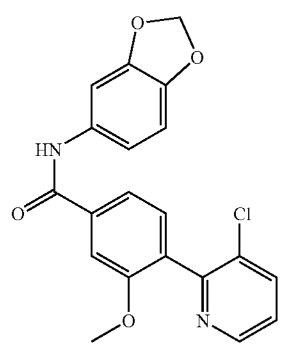 | 382.81 | 383.10 | 2.90 | 2.69 | 3.39 | |
| 1226 | 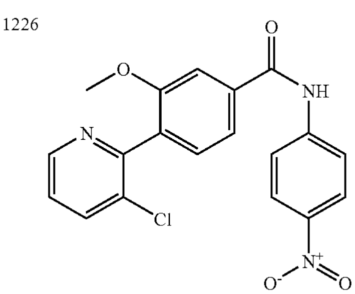 | 383.79 | 384.08 | 3.19 | 3.12 | 3.41 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|----|-----------|-----------|----------|---------------|-----------------------|---------------------|---------------------|
| 1227 | 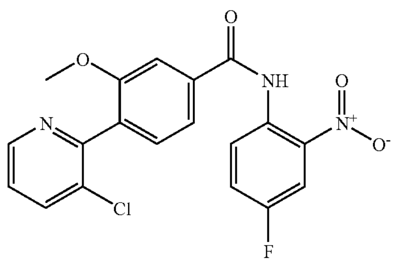 | 401.78 | 402.12 | 3.31 | 3.16 | 3.65 | ++++ |
| 1228 | 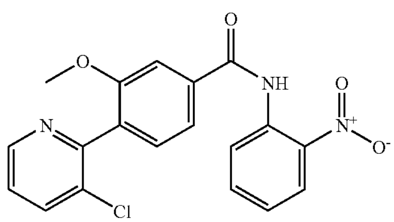 | 383.79 | 384.09 | 3.29 | 3.18 | 3.56 | |
| 1229 | 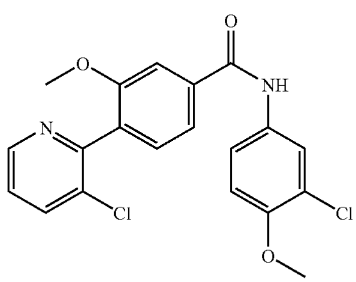 | 403.27 | 403.27 | 3.15 | 3.06 | 3.45 | +++ |
| 1230 | 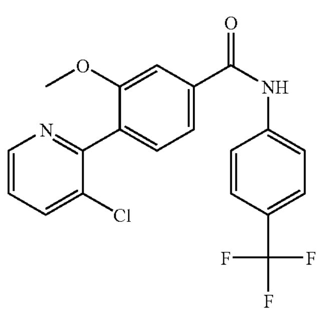 | 406.79 | 407.15 | 3.46 | 3.36 | 3.93 | ++ |
| 1231 | 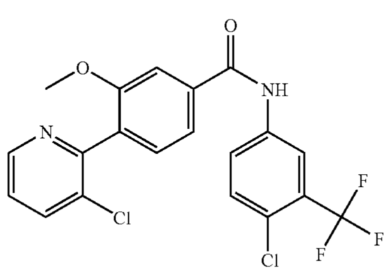 | 441.24 | 441.09 | 3.69 | 3.56 | 4.01 | + |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1232 | 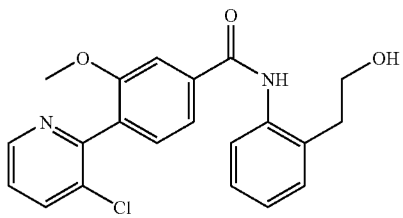 | 382.85 | 383.14 | 2.65 | 2.49 | 3.01 | |
| 1233 | 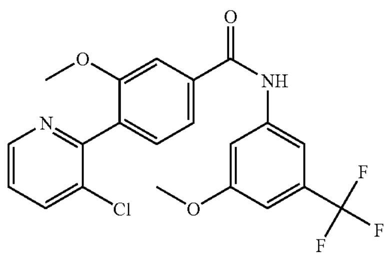 | 436.82 | 437.12 | 3.54 | 3.42 | 3.89 | |
| 1234 | 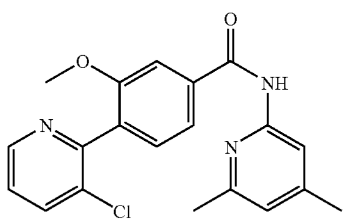 | 367.84 | 368.13 | 2.36 | 2.28 | 2.70 | + |
| 1235 | 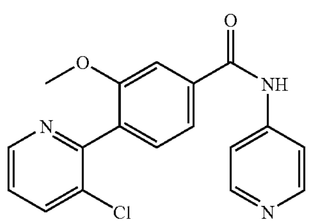 | 339.78 | 340.09 | 2.16 | 2.03 | 2.55 | ++++ |
| 1236 | 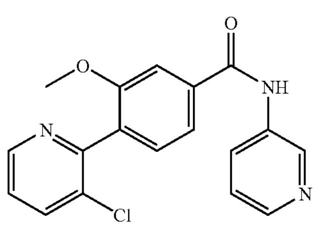 | 339.78 | 340.11 | 2.09 | 2.03 | 2.42 | + |
| 1237 | 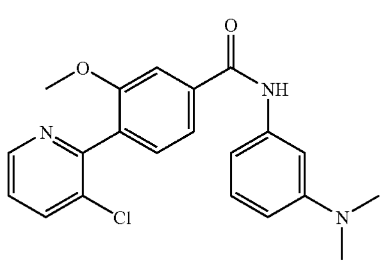 | 381.87 | 382.16 | 2.22 | 2.16 | 2.63 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1238 | 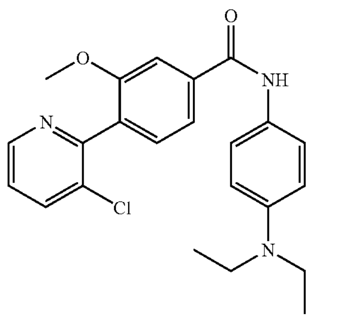 | 409.92 | 410.21 | 2.32 | 2.26 | 2.69 | |
| 1239 | 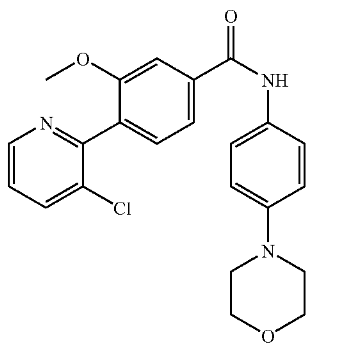 | 423.90 | 424.12 | 2.36 | 2.29 | 2.69 | |
| 1240 | 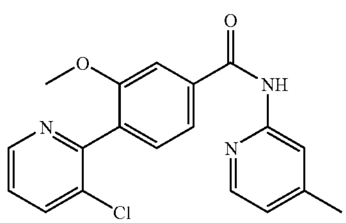 | 353.81 | 354.15 | 2.23 | 2.13 | 2.51 | ++++ |
| 1241 | 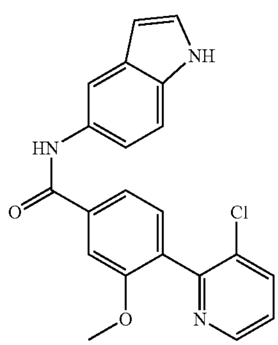 | 377.83 | 378.20 | 2.76 | 2.68 | 3.31 | |
| 1242 | 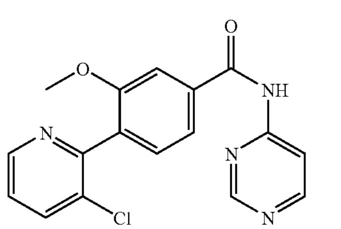 | 340.77 | 340.96 | 2.32 | 2.13 | 2.70 | ++ |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1243 | 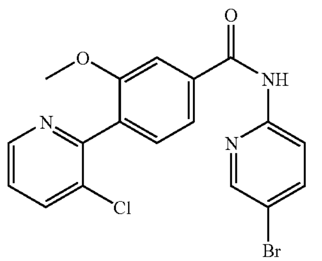 | 418.68 | 420.00 | 3.23 | 3.15 | 3.63 | + |
| 1244 | 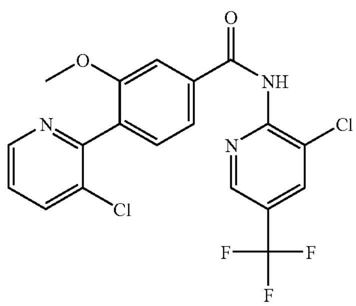 | 442.23 | 442.16 | 3.15 | 2.96 | 3.39 | |
| 1245 | 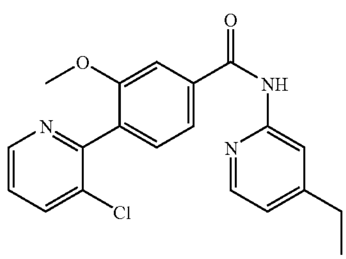 | 367.84 | 368.15 | 2.39 | 2.13 | 2.66 | |
| 1246 | 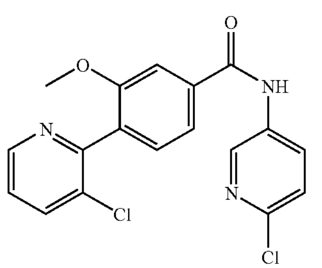 | 374.23 | 374.08 | 2.86 | 2.76 | 3.25 | |
| 1247 | 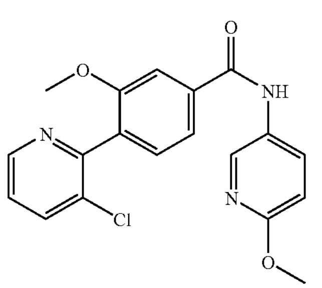 | 369.81 | 370.12 | 2.56 | 2.49 | 2.93 | ++ |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1248 | 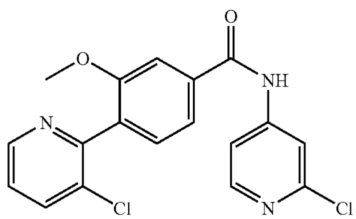 | 374.23 | 374.09 | 2.89 | 2.70 | 3.38 | + |
| 1249 | 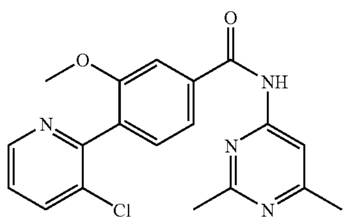 | 368.83 | 369.14 | 2.23 | 2.12 | 2.46 | + |
| 1250 | 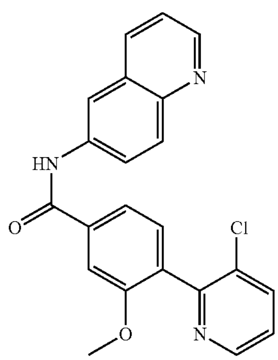 | 389.84 | 390.25 | 2.26 | 2.20 | 2.83 | ++++ |
| 1251 | 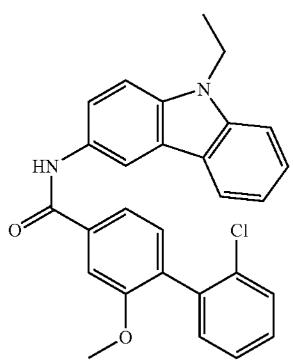 | 455.95 | 456.21 | 3.58 | 3.43 | 3.95 | + |
| 1252 | 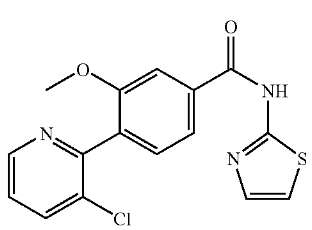 | 345.81 | 345.95 | 2.70 | 2.63 | 2.98 | + |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1253 | 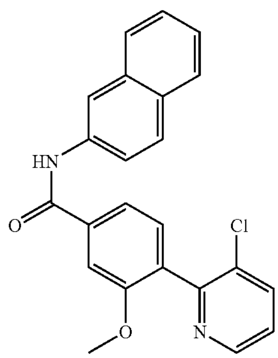 | 388.86 | 389.31 | 3.35 | 3.23 | 3.79 | ++++ |
| 1254 | 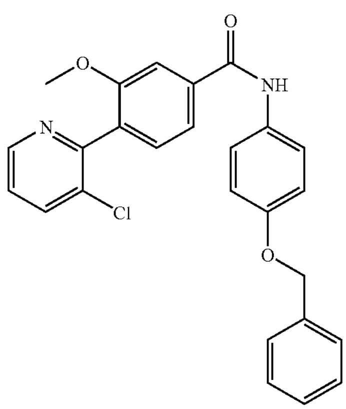 | 444.92 | 445.29 | 3.49 | 3.32 | 3.99 | |
| 1255 | 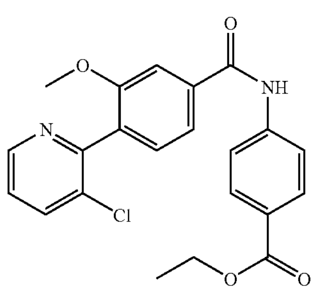 | 410.86 | 411.14 | 3.26 | 3.16 | 3.45 | |
| 1256 | 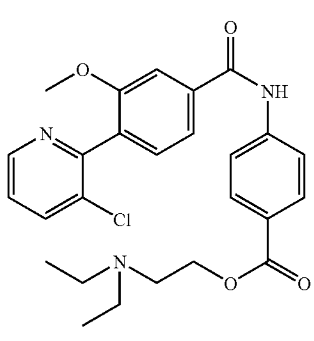 | 481.98 | 482.22 | 2.50 | 2.39 | 2.66 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1257 | 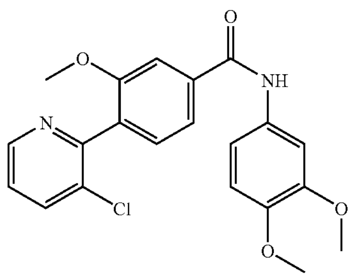 | 398.85 | 399.10 | 2.73 | 2.55 | 3.16 | + |
| 1258 | 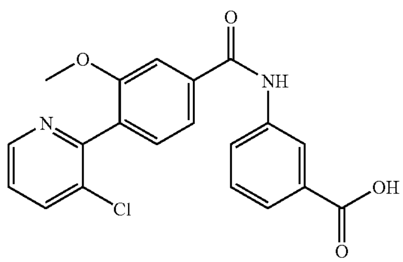 | 382.81 | 383.10 | 2.63 | 2.52 | 3.03 | + |
| 1259 | 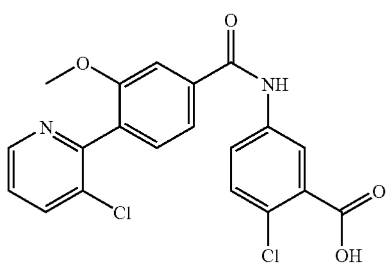 | 417.25 | 417.27 | 2.79 | 2.69 | 3.29 | ++++ |
| 1260 | 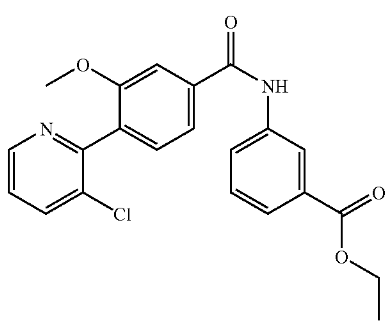 | 410.86 | 411.14 | 3.22 | 3.13 | 3.61 | |
| 1261 | 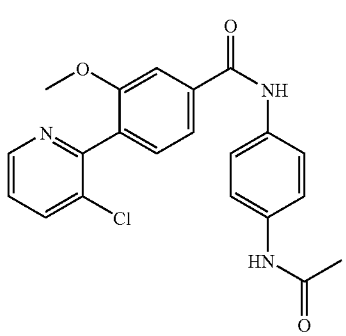 | 395.85 | 396.09 | 2.46 | 2.39 | 2.83 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1262 | 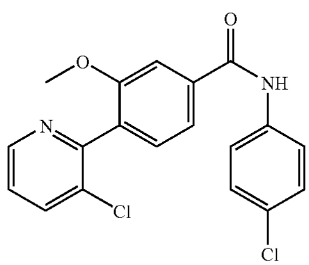 | 373.24 | 373.04 | 3.28 | 3.13 | 3.75 | |
| 1263 | 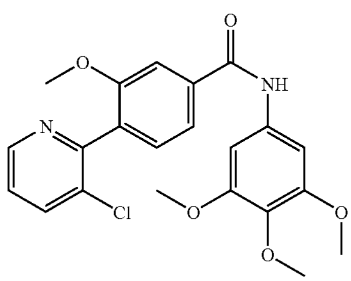 | 428.88 | 429.25 | 2.85 | 2.73 | 3.19 | ++++ |
| 1264 | 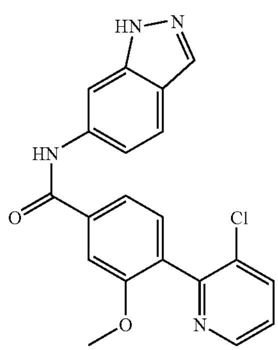 | 378.82 | 379.25 | 2.59 | 2.36 | 3.06 | ++ |
| 1265 | 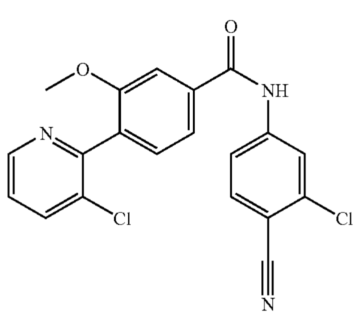 | 398.25 | 398.03 | 3.31 | 3.22 | 3.72 | ++++ |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1266 | 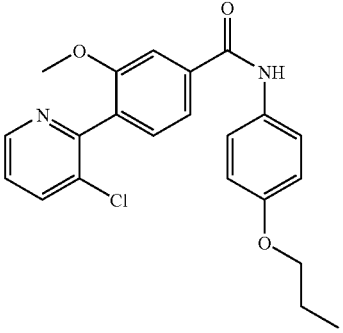 | 396.88 | 397.14 | 3.33 | 3.22 | 3.92 | |
| 1267 | 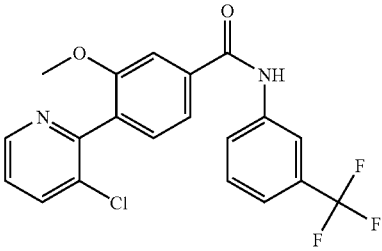 | 406.79 | 407.15 | 3.44 | 3.21 | 3.82 | ++ |
| 1268 | 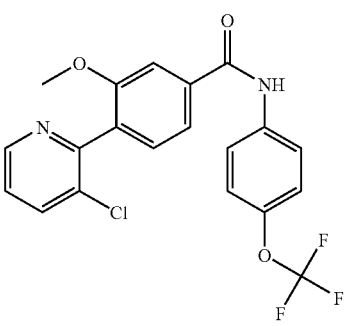 | 422.79 | 422.95 | 3.48 | 3.39 | 3.85 | |
| 1269 | 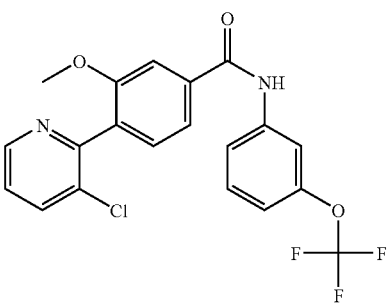 | 422.79 | 422.95 | 3.52 | 3.42 | 3.92 | + |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1270 | 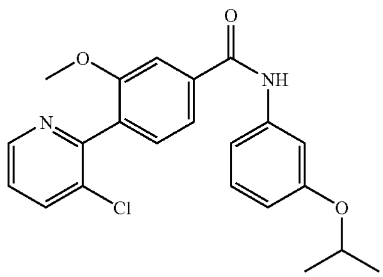 | 396.88 | 397.14 | 3.32 | 3.22 | 3.82 | + |
| 1271 | 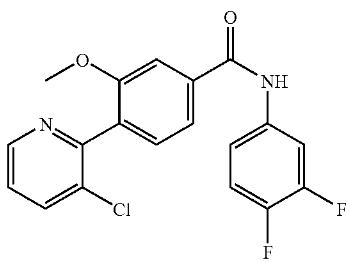 | 374.78 | 375.08 | 3.19 | 3.08 | 3.59 | +++ |
| 1272 | 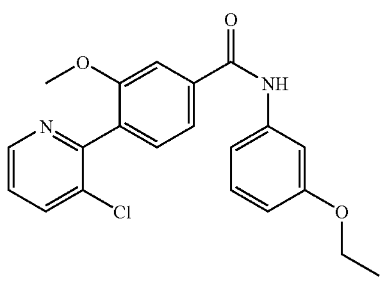 | 382.85 | 383.14 | 3.18 | 3.09 | 3.62 | |
| 1273 | 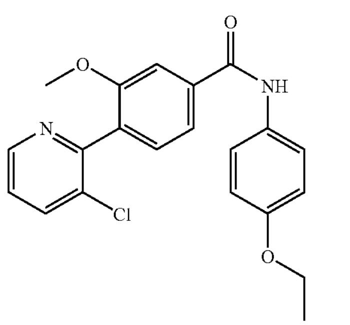 | 382.85 | 383.15 | 3.09 | 2.96 | 3.56 | + |
| 1274 | 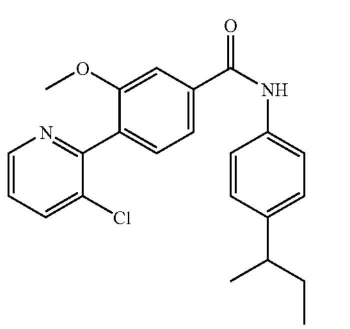 | 394.90 | 395.15 | 3.68 | 3.58 | 4.18 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1275 | 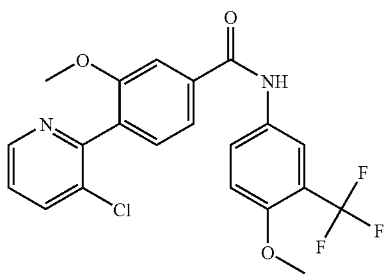 | 436.82 | 437.12 | 3.35 | 3.25 | 3.79 | ++ |
| 1276 | 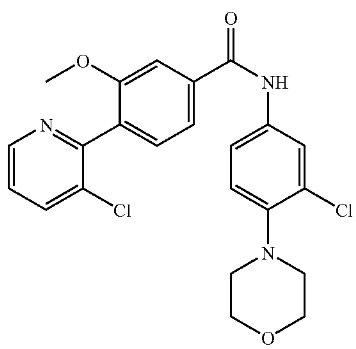 | 458.35 | 458.26 | 3.18 | 3.03 | 3.63 | + |
| 1277 | 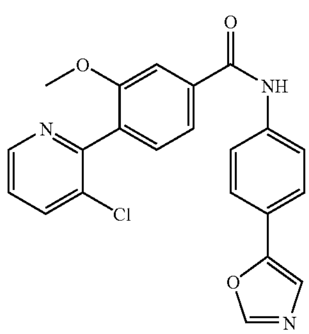 | 405.84 | 406.22 | 2.90 | 2.55 | 3.25 | +++ |
| 1278 | 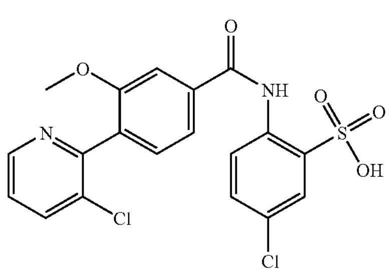 | 453.30 | 452.96 | 2.09 | 1.94 | 2.38 | + |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1279 | 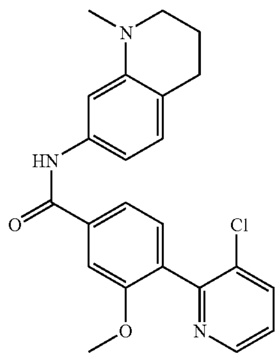 | 407.90 | 408.13 | 2.32 | 2.13 | 2.39 | |
| 1280 | 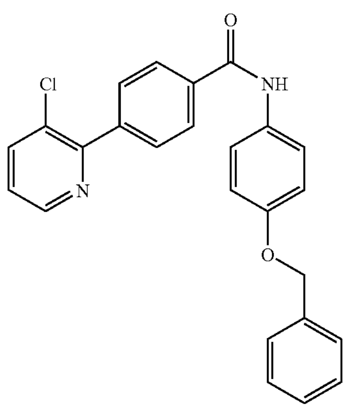 | 414.90 | 415.27 | 3.59 | 3.51 | 4.22 | |
| 1281 | 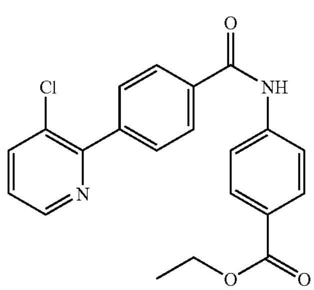 | 380.83 | 381.22 | 3.41 | 3.25 | 4.02 | |
| 1282 | 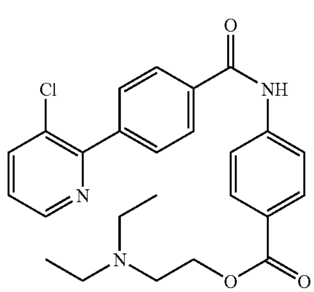 | 451.96 | 452.15 | 2.53 | 2.36 | 2.88 | + |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1283 | 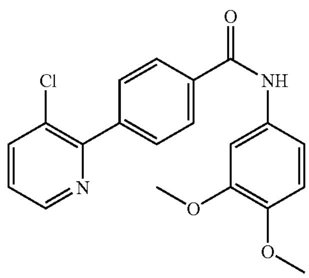 | 368.82 | 369.10 | 2.83 | 2.72 | 3.34 | |
| 1284 | 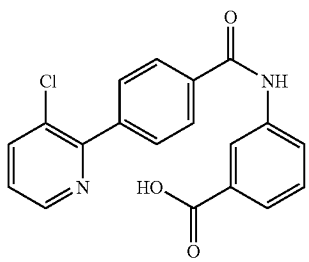 | 352.78 | 353.17 | 2.71 | 2.63 | 2.83 | |
| 1285 | 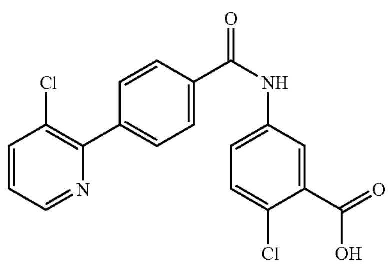 | 387.23 | 387.06 | 2.85 | 2.79 | 3.06 | |
| 1286 | 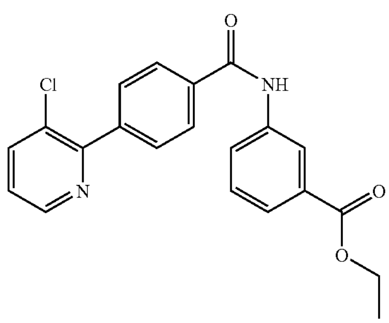 | 380.83 | 381.22 | 3.33 | 3.23 | 3.99 | + |
| 1287 | 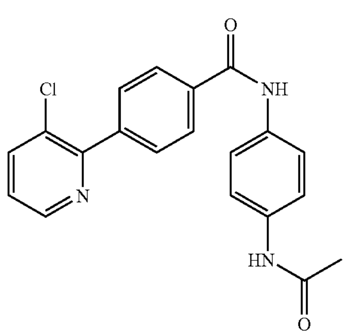 | 365.82 | 366.14 | 2.52 | 2.45 | 2.89 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1288 | 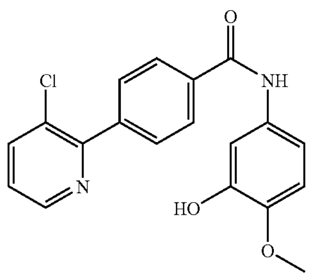 | 354.80 | 355.20 | 2.61 | 2.51 | 2.84 | + |
| 1289 | 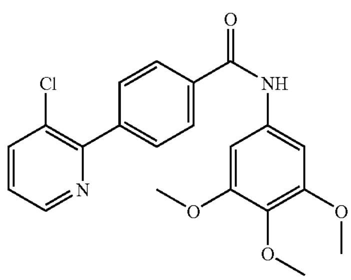 | 398.85 | 399.10 | 2.93 | 2.82 | 3.39 | |
| 1290 | 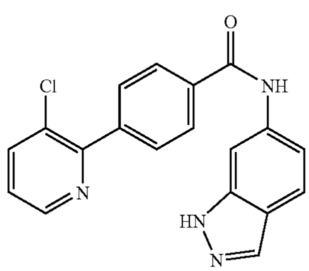 | 348.79 | 349.24 | 2.66 | 2.52 | 3.03 | ++ |
| 1291 | 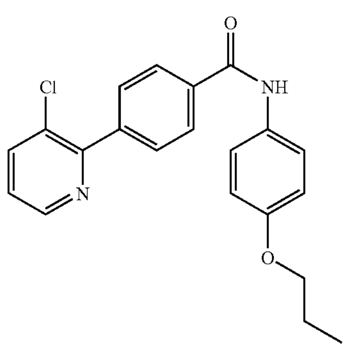 | 366.85 | 367.09 | 3.45 | 3.35 | 4.01 | + |
| 1292 | 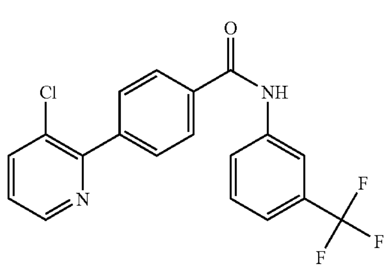 | 376.77 | 377.26 | 3.55 | 3.42 | 4.18 | |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1293 | 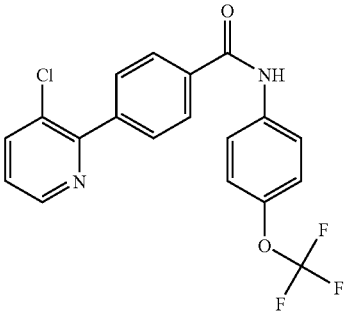 | 392.77 | 393.09 | 3.58 | 3.48 | 4.01 | + |
| 1294 | 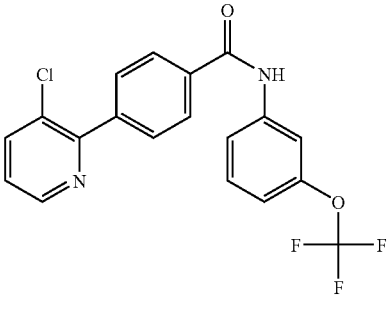 | 392.77 | 393.06 | 3.64 | 3.37 | 4.20 | + |
| 1295 | 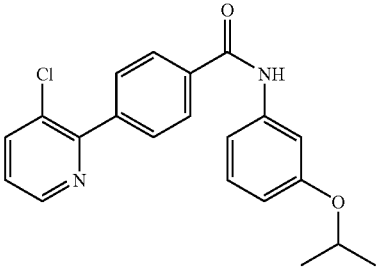 | 366.85 | 367.10 | 3.45 | 3.25 | 4.08 | + |
| 1296 | 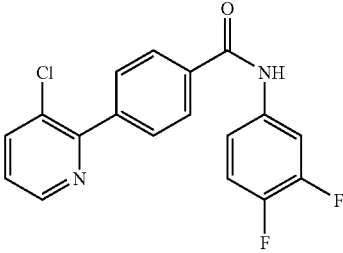 | 344.75 | 345.01 | 3.32 | 3.08 | 3.86 | + |
| 1297 | 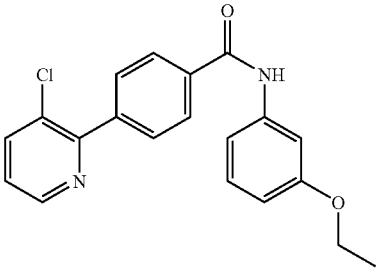 | 352.82 | 353.23 | 3.31 | 3.11 | 3.75 | |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1298 | 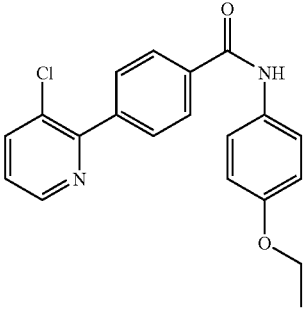 | 352.82 | 353.21 | 3.16 | 3.09 | 3.36 | + |
| 1299 | 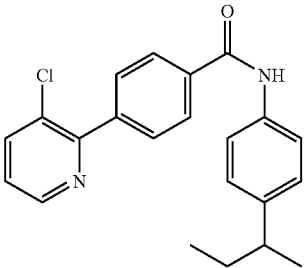 | 364.88 | 365.09 | 3.81 | 3.66 | 4.34 | |
| 1300 | 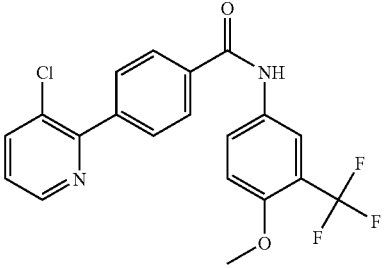 | 406.79 | 407.17 | 3.46 | 3.35 | 3.84 | |
| 1301 | 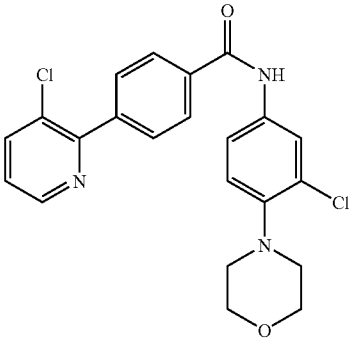 | 428.32 | 428.12 | 3.26 | 3.16 | 4.17 | +++ |

-continued

| | AMIDE COMPOUNDS | | | | | | |
|---|---|---|---|---|---|---|---|
| ID | STRUCTURE | MW (Calc) | MS (Obs) | HPLC RT (Min) | HPLC START TIME (Min) | HPLC END TIME (Min) | % Inhibition @ 1 uM |
| 1302 | | 375.82 | 376.16 | 3.02 | 2.95 | 3.29 | |
| 1303 | | 423.28 | 422.93 | 2.10 | 2.03 | 2.42 | |
| 1304 | | 377.88 | 378.24 | 2.29 | 2.07 | 2.49 | + |
| 1305 | | 351.84 | 352.18 | 3.51 | 3.44 | 3.72 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1306 | 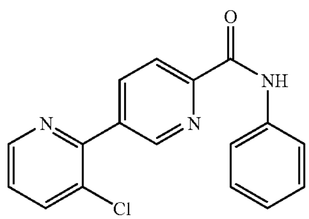 | 309.76 | 310.14 | 3.35 | 3.26 | 3.54 | ++++ |
| 1307 | 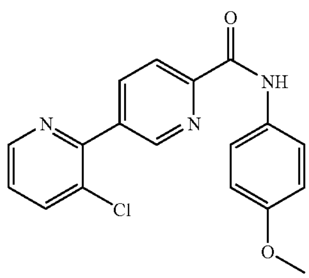 | 339.78 | 340.07 | 3.31 | 3.21 | 3.39 | |
| 1308 | 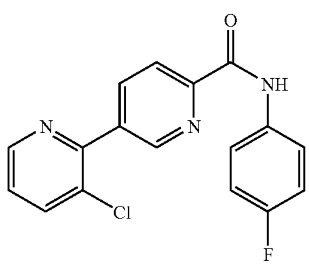 | 327.75 | 328.18 | 3.41 | 3.29 | 3.65 | + |
| 1309 | 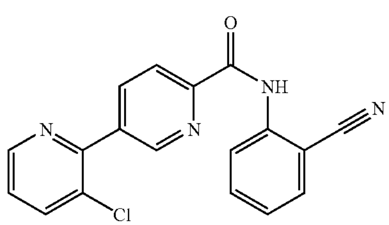 | 334.77 | 335.24 | 3.41 | 3.25 | 3.75 | + |
| 1310 | 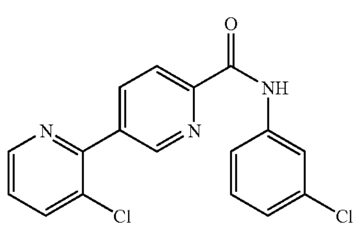 | 344.20 | 344.05 | 3.72 | 3.66 | 3.91 | |
| 1311 | 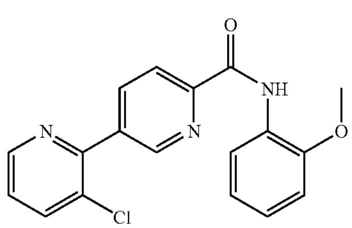 | 339.78 | 340.07 | 3.58 | 3.45 | 3.75 | |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1312 | 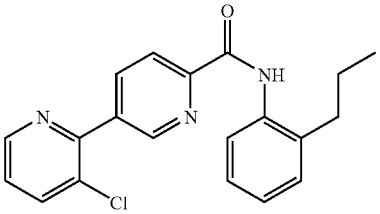 | 351.84 | 352.16 | 3.98 | 3.88 | 4.48 | |
| 1313 | 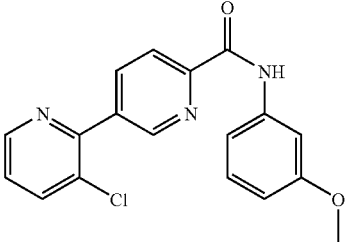 | 339.78 | 340.08 | 3.38 | 3.29 | 3.63 | |
| 1314 | 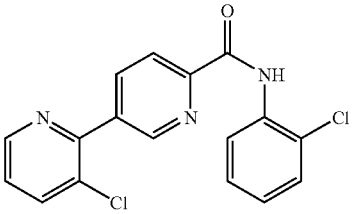 | 344.20 | 344.04 | 3.95 | 3.86 | 4.22 | ++++ |
| 1315 | 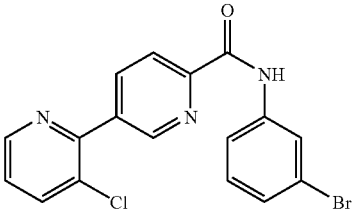 | 388.65 | 390.11 | 3.79 | 3.71 | 4.01 | |
| 1316 | 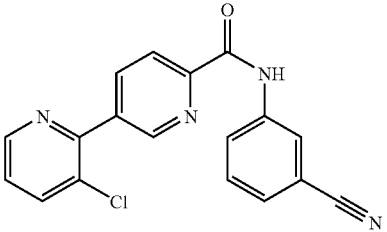 | 334.77 | 335.24 | 3.28 | 3.19 | 3.51 | ++++ |
| 1317 | 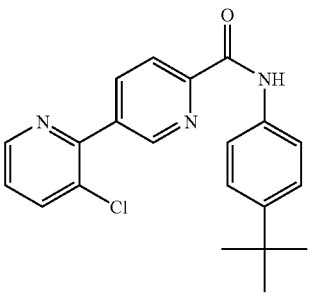 | 365.87 | | | | | |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1318 | 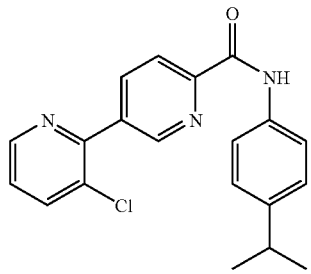 | 351.84 | 352.15 | 3.98 | 3.78 | 4.28 | |
| 1319 | 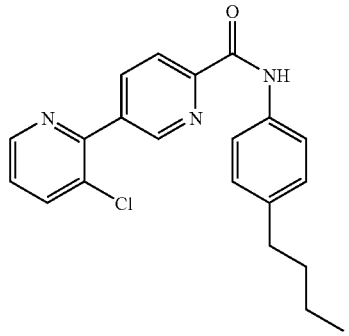 | 365.87 | 366.11 | 4.11 | 3.99 | 4.44 | +++ |
| 1320 | 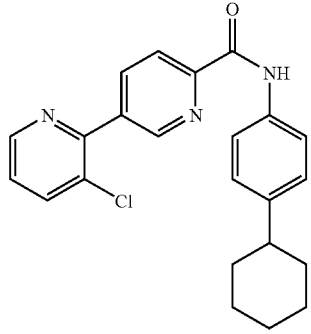 | 391.90 | 392.13 | 4.52 | 4.36 | 4.89 | ++++ |
| 1321 | 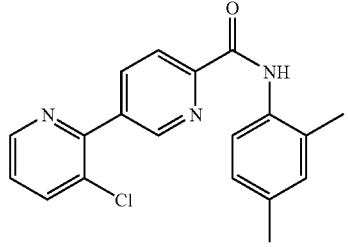 | 337.81 | 338.21 | 3.73 | 3.68 | 3.95 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1322 | 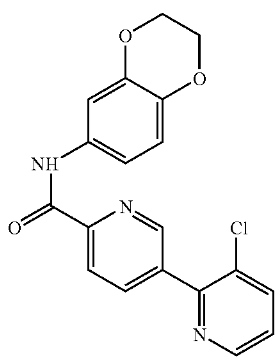 | 367.79 | 368.07 | 3.23 | 3.16 | 3.53 | |
| 1323 | 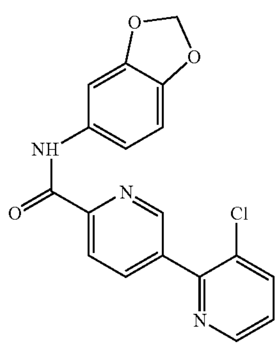 | 353.77 | | | | | |
| 1324 | 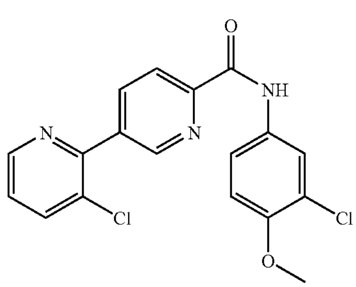 | 374.23 | 374.05 | 3.53 | 3.41 | 3.73 | |
| 1325 | 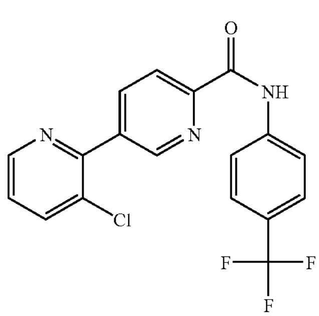 | 377.76 | 378.12 | 3.82 | 3.75 | 4.02 | + |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1326 | 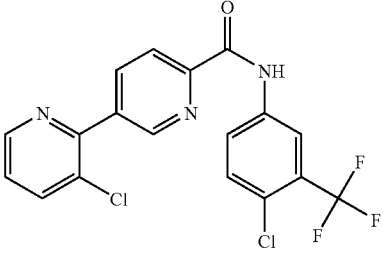 | 412.20 | 414.31 | 3.56 | 3.51 | 3.78 | |
| 1327 | 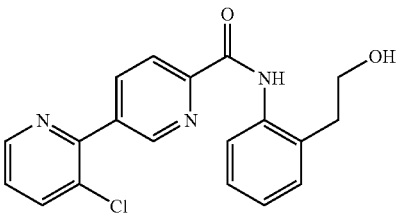 | 353.81 | | | | | |
| 1328 | 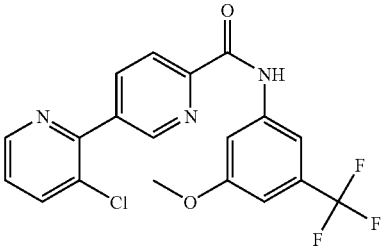 | 407.78 | 408.13 | 3.86 | 3.79 | 4.06 | + |
| 1329 | 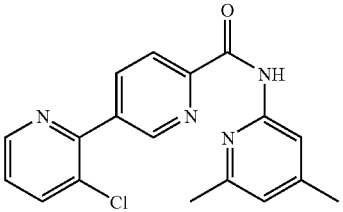 | 338.80 | 339.10 | 2.43 | 2.15 | 2.79 | + |
| 1330 | 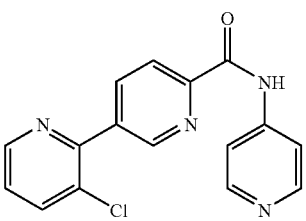 | 310.75 | 311.21 | 2.15 | 2.10 | 2.26 | +++ |
| 1331 | 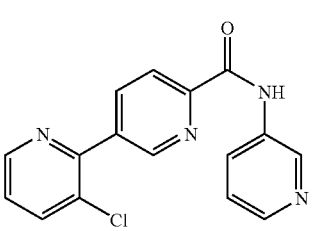 | 310.75 | 311.20 | 2.09 | 2.00 | 2.45 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1332 | 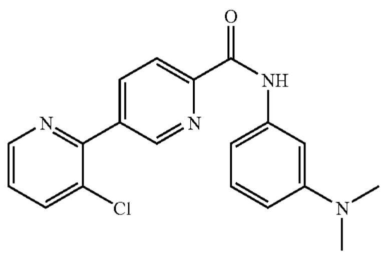 | 352.83 | 353.20 | 2.36 | 2.19 | 2.63 | |
| 1333 | 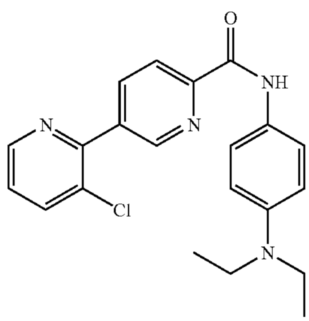 | 380.88 | 381.22 | 2.48 | 2.36 | 2.66 | |
| 1334 | 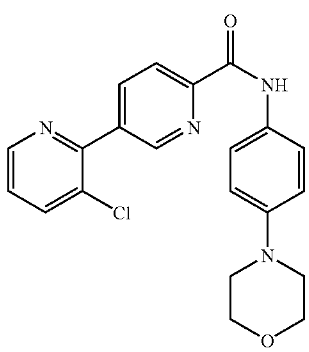 | 394.86 | 395.04 | 2.55 | 2.35 | 2.86 | + |
| 1335 | 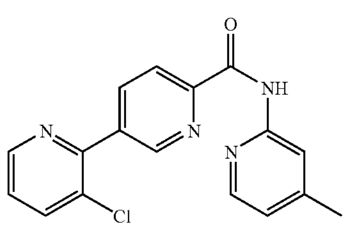 | 324.77 | 325.23 | 2.30 | 2.23 | 2.70 | + |
| 1336 | 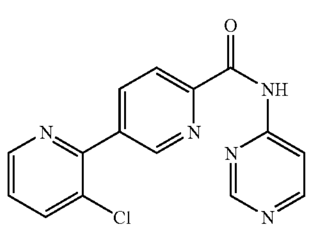 | 311.73 | 312.08 | 2.64 | 2.52 | 2.79 | ++++ |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1337 | 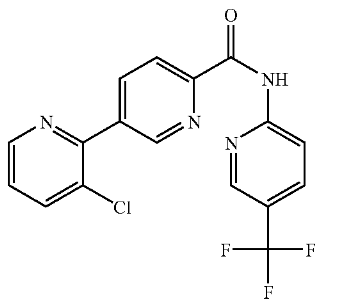 | 378.74 | 379.16 | 3.92 | 3.84 | 4.11 | |
| 1338 | 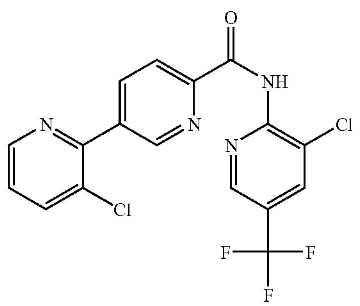 | 413.19 | 412.97 | 3.58 | 3.49 | 3.89 | |
| 1339 | 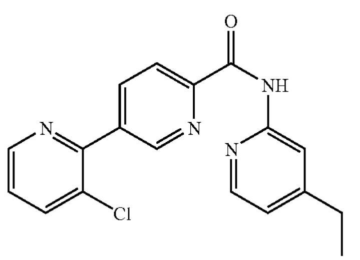 | 338.80 | 339.06 | 2.51 | 2.25 | 2.63 | |
| 1340 | 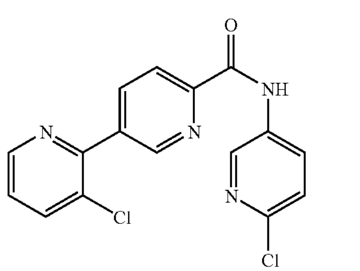 | 345.19 | 344.94 | 3.12 | 2.86 | 3.36 | |
| 1341 | 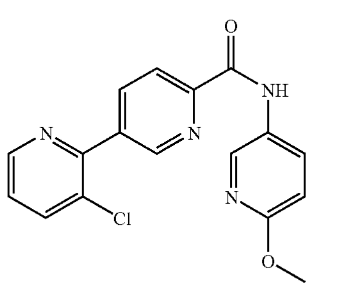 | 340.77 | 340.95 | 2.82 | 2.61 | 3.23 | ++ |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1342 | 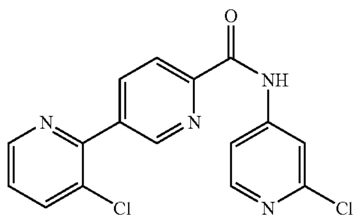 | 345.19 | 344.92 | 3.18 | 2.98 | 3.41 | + |
| 1343 | 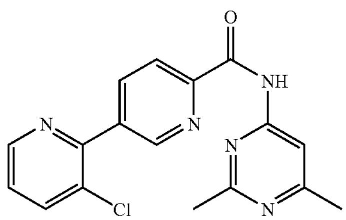 | 339.79 | 340.08 | 2.36 | 2.13 | 2.79 | + |
| 1344 | 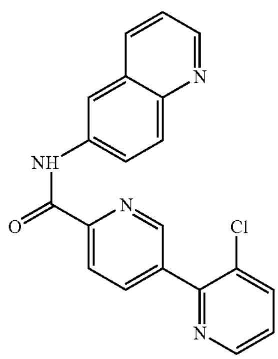 | 360.81 | 361.08 | 2.38 | 2.07 | 2.66 | + |
| 1345 | 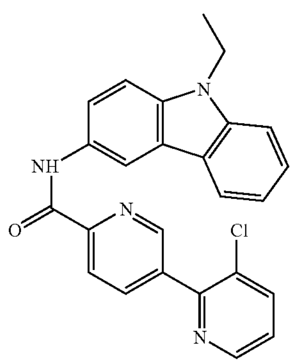 | 426.91 | 426.98 | 4.08 | 3.99 | 4.49 | ++++ |
| 1346 | 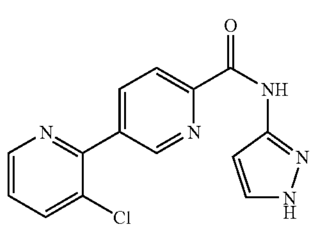 | 299.72 | 300.05 | 2.35 | 2.22 | 2.70 | |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1347 | 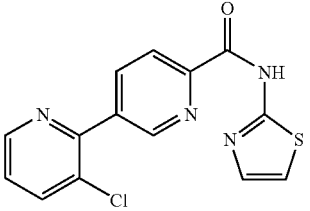 | 316.77 | 316.95 | 2.86 | 2.76 | 3.11 | |
| 1348 | 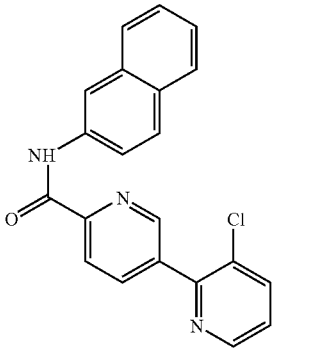 | 359.82 | 360.09 | 3.85 | 3.71 | 4.24 | ++ |
| 1349 | 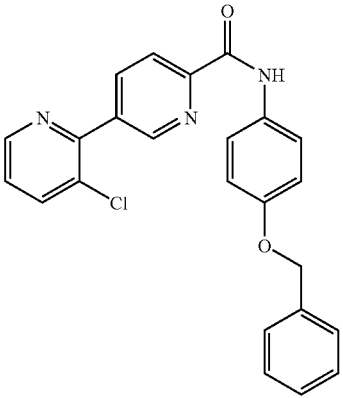 | 415.88 | 416.23 | 3.88 | 3.78 | 4.28 | + |
| 1350 | 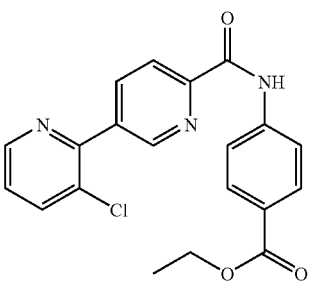 | 381.82 | 382.10 | 3.65 | 3.55 | 3.86 | + |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1351 | 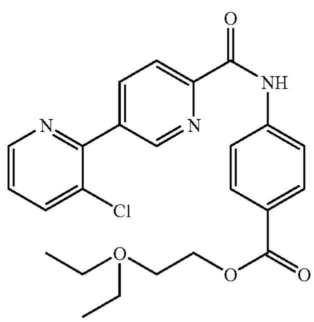 | 452.94 | 453.04 | 2.69 | 2.52 | 2.78 | |
| 1352 | 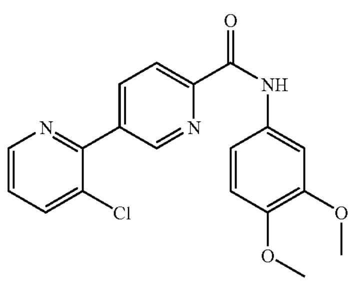 | 369.81 | 370.08 | 3.08 | 2.88 | 3.79 | |
| 1353 | 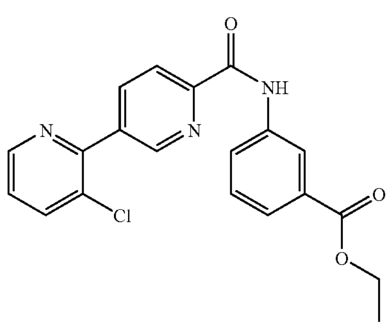 | 381.82 | 382.11 | 3.59 | 3.48 | 3.88 | |
| 1354 | 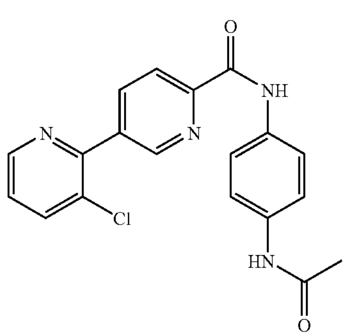 | 366.81 | 366.98 | 2.69 | 2.49 | 3.12 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1355 | 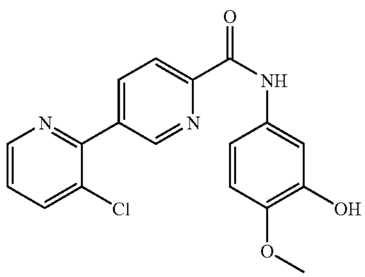 | 355.78 | 356.10 | 2.82 | 2.55 | 3.12 | ++ |
| 1356 | 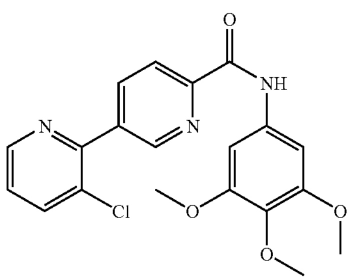 | 399.84 | 400.09 | 3.15 | 2.89 | 3.36 | + |
| 1357 | 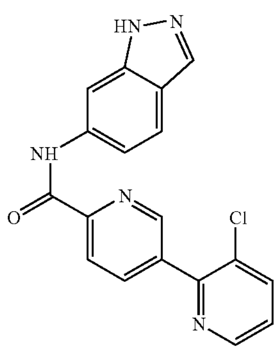 | 349.78 | 350.17 | 2.89 | 2.55 | 3.13 | ++++ |
| 1358 | 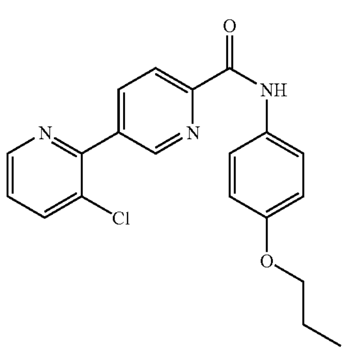 | 367.84 | 368.10 | 3.75 | 3.58 | 4.08 | + |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1359 | 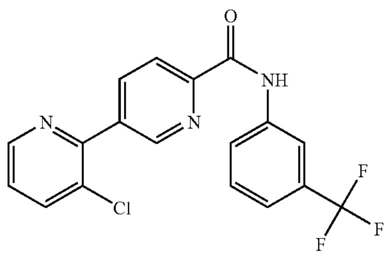 | 377.76 | 378.12 | 3.79 | 3.51 | 4.02 | |
| 1360 | 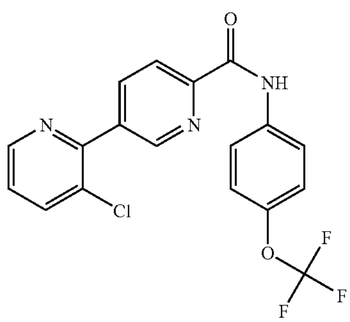 | 393.76 | 394.08 | 3.83 | 3.73 | 4.05 | + |
| 1361 | 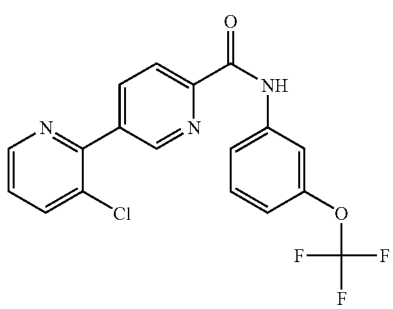 | 393.76 | 394.06 | 3.86 | 3.73 | 4.24 | ++ |
| 1362 | 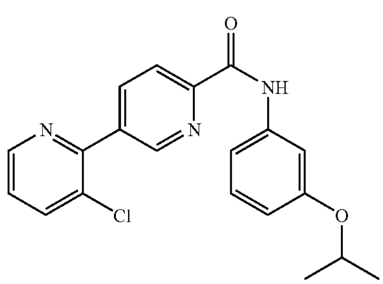 | 367.84 | 368.08 | 3.74 | 3.45 | 4.04 | + |
| 1363 | 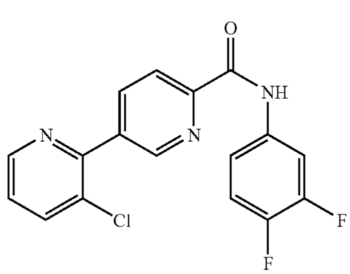 | 345.74 | 345.86 | 3.55 | 3.41 | 3.79 | ++++ |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1364 | 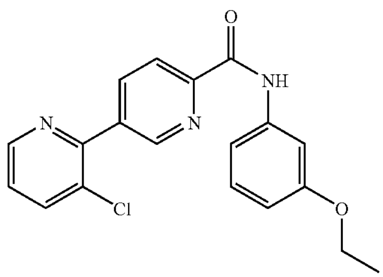 | 353.81 | 354.12 | 3.61 | 3.45 | 3.95 | ++++ |
| 1365 | 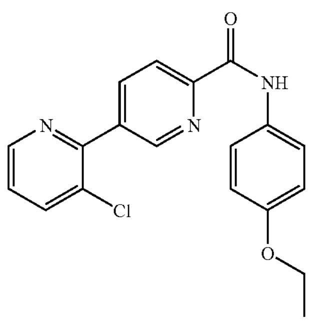 | 353.81 | 354.11 | 3.51 | 3.36 | 3.85 | |
| 1366 | 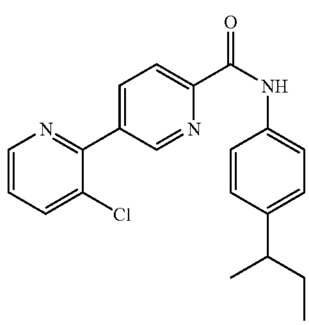 | 365.87 | 366.11 | 4.16 | 3.95 | 4.51 | |
| 1367 | 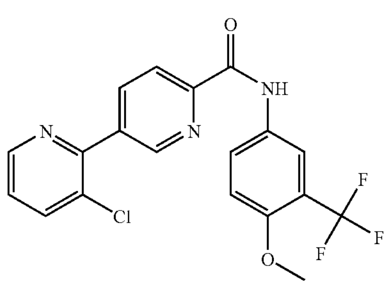 | 407.78 | 408.09 | 3.66 | 3.43 | 3.95 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1368 | 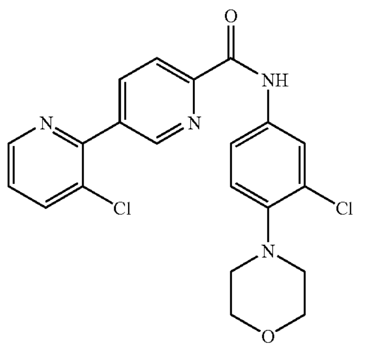 | 429.31 | 429.06 | 3.58 | 3.39 | 3.79 | |
| 1369 | 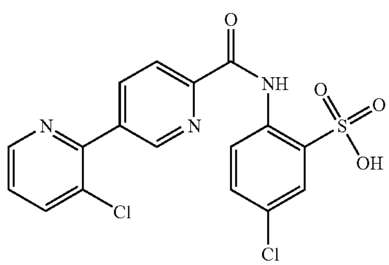 | 424.26 | 423.90 | 2.20 | 2.12 | 2.39 | |
| 1370 | 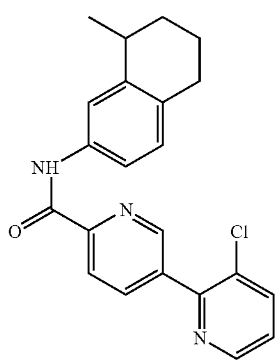 | 378.86 | 379.24 | 2.68 | 2.28 | 3.03 | |
| 1371 | 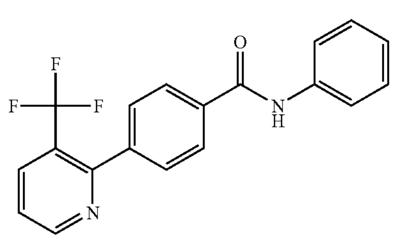 | 342.32 | 343.10 | 3.19 | 2.99 | 3.58 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1372 | 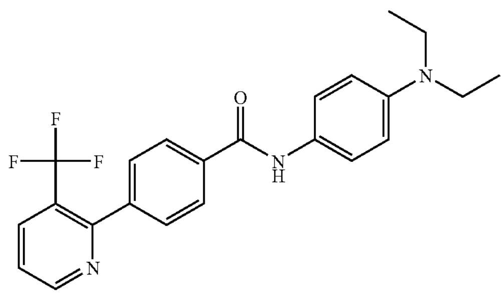 | 413.45 | 414.14 | 2.49 | 2.20 | 2.96 | |
| 1373 | 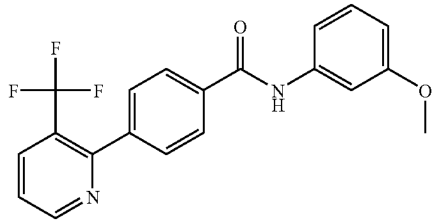 | 372.35 | 373.06 | 3.22 | 3.01 | 3.75 | |
| 1374 | 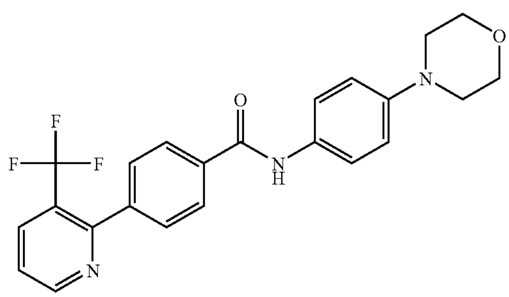 | 427.43 | 428.13 | 2.53 | 2.38 | 2.93 | |
| 1375 | 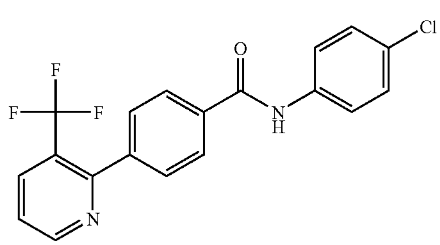 | 376.77 | 377.25 | 3.51 | 3.25 | 3.92 | |
| 1376 | 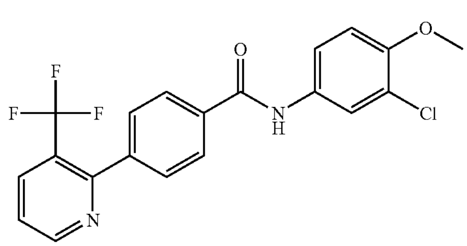 | 406.79 | 407.16 | 3.38 | 3.21 | 3.88 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1377 | 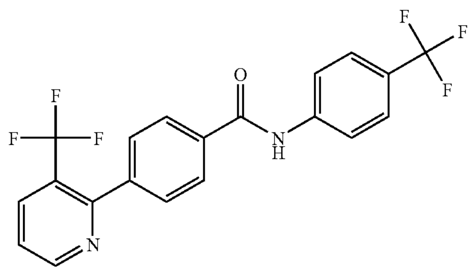 | 410.32 | 411.07 | 3.65 | 3.51 | 3.95 | |
| 1378 | 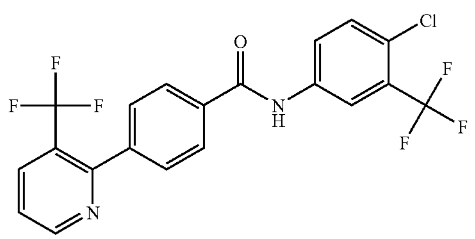 | 444.77 | 445.18 | 3.83 | 3.56 | 4.26 | |
| 1379 | 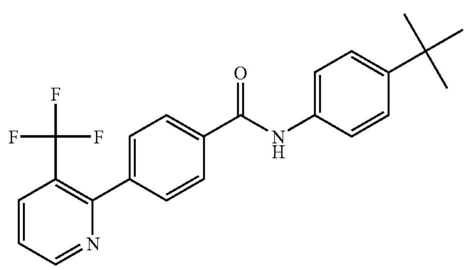 | 398.43 | 399.18 | 3.79 | 3.59 | 4.15 | |
| 1380 | 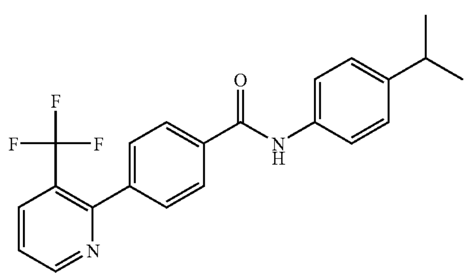 | 384.40 | 385.26 | 3.68 | 3.55 | 4.15 | |
| 1381 | 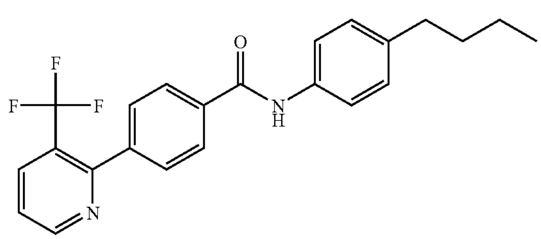 | 398.43 | 399.17 | 3.91 | 3.78 | 4.35 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1382 | 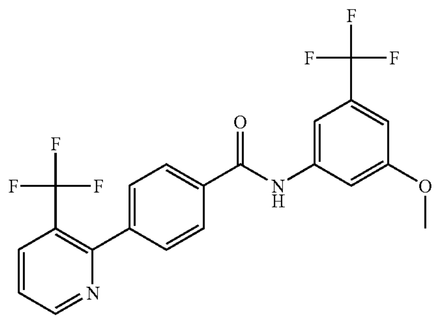 | 440.35 | 441.22 | 3.70 | 3.55 | 4.07 | |
| 1383 | 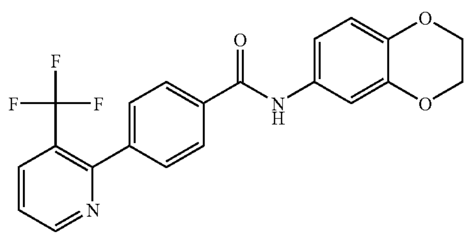 | 400.36 | 401.10 | 3.13 | 3.00 | 3.66 | |
| 1384 | 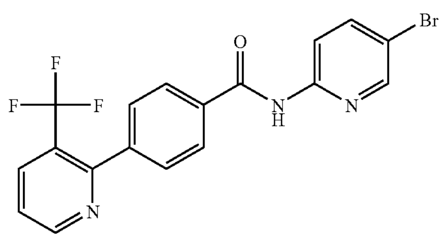 | 422.21 | 421.94 | 3.43 | 3.19 | 3.82 | |
| 1385 | 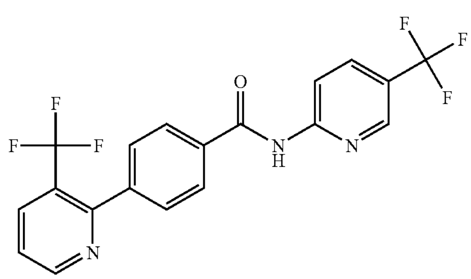 | 411.31 | 412.10 | 3.53 | 3.31 | 3.91 | |
| 1386 | 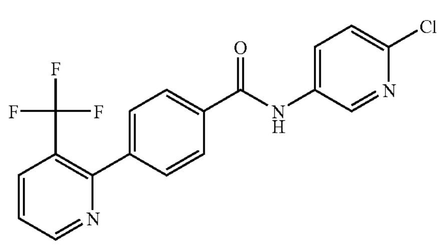 | 377.76 | 378.16 | 3.11 | 2.98 | 3.52 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1387 | 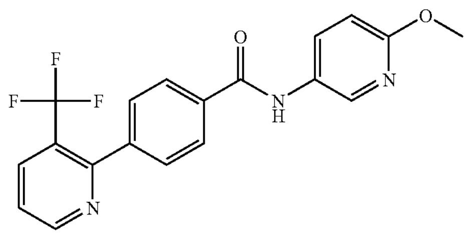 | 373.34 | 374.11 | 2.78 | 2.55 | 3.19 | |
| 1388 | 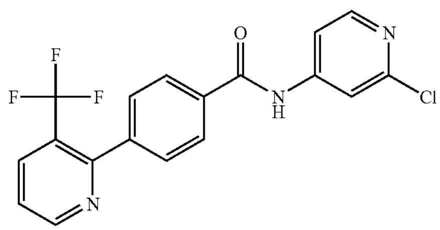 | 377.76 | 378.15 | 3.15 | 2.93 | 3.65 | |
| 1389 | 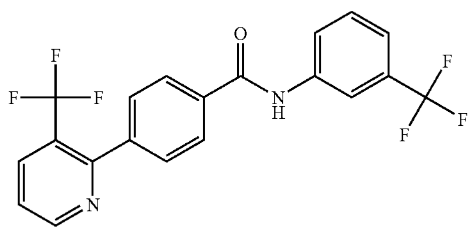 | 410.32 | 411.07 | 3.63 | 3.42 | 3.96 | |
| 1390 | 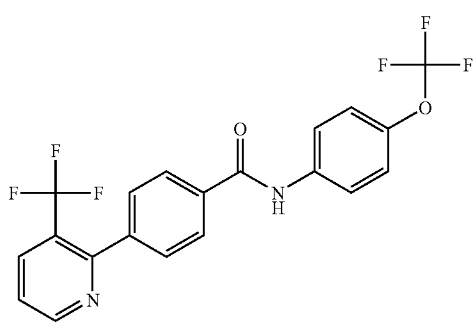 | 426.32 | 426.99 | 3.67 | 3.52 | 4.01 | |
| 1391 | 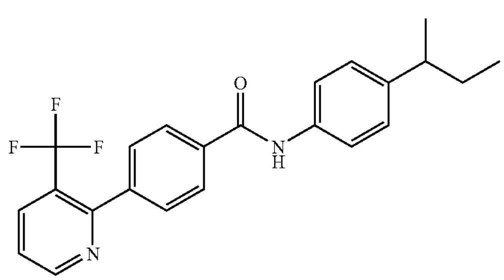 | 398.43 | 399.16 | 3.86 | 3.55 | 4.38 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1392 | 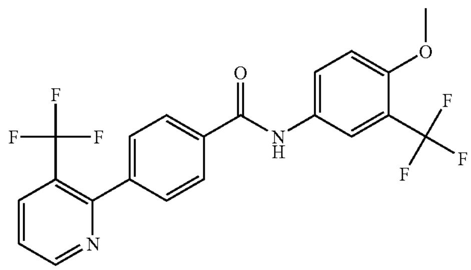 | 440.35 | 441.20 | 3.53 | 3.33 | 3.99 | |
| 1393 | 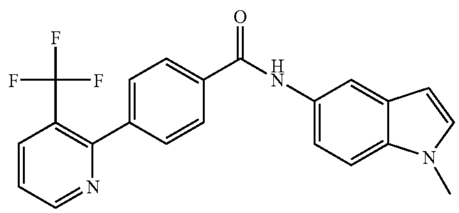 | 395.39 | | | | | |
| 1394 | 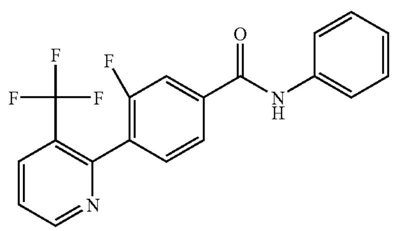 | 360.31 | 361.22 | 3.31 | 3.11 | 3.62 | |
| 1395 | 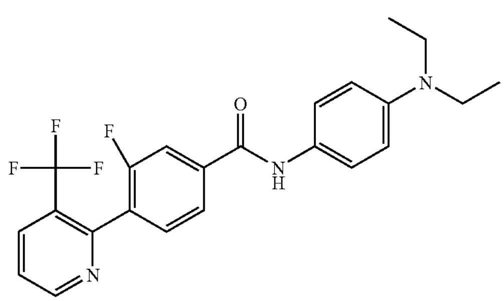 | 431.44 | 432.27 | 2.59 | 2.17 | 2.99 | |
| 1396 | 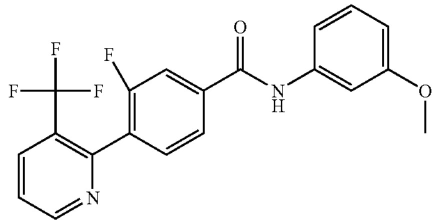 | 390.34 | 391.27 | 3.35 | 3.23 | 3.53 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|----|-----------|-----------|----------|---------------|-----------------------|---------------------|---------------------|
| 1397 | 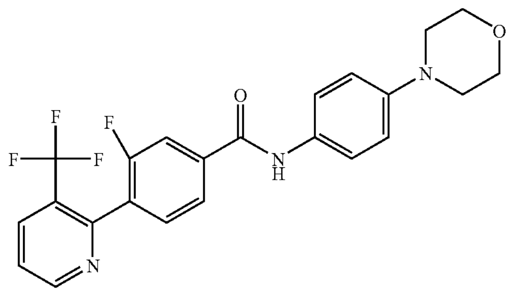 | 445.42 | 446.16 | 2.66 | 2.53 | 3.08 | |
| 1398 | 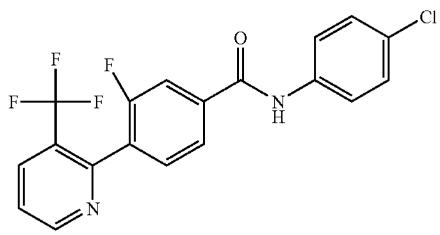 | 394.76 | 395.03 | 3.58 | 3.45 | 3.91 | |
| 1399 | 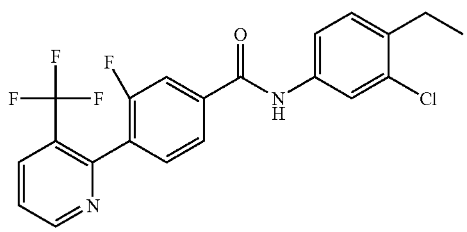 | 424.79 | 424.99 | 3.45 | 3.11 | 3.92 | |
| 1400 | 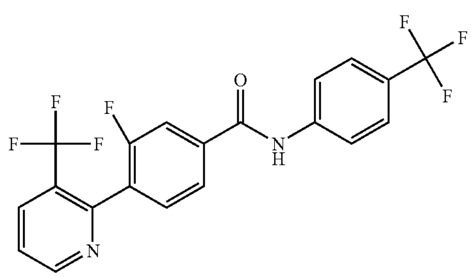 | 428.31 | 429.13 | 3.72 | 3.33 | 4.01 | |
| 1401 | 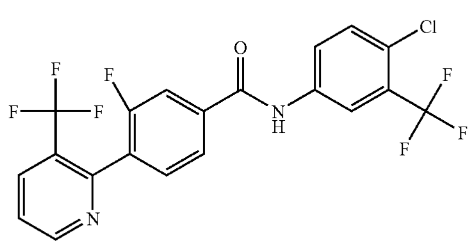 | 462.76 | 463.12 | 3.93 | 3.66 | 4.19 | |

-continued
AMIDE COMPOUNDS
| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1402 | 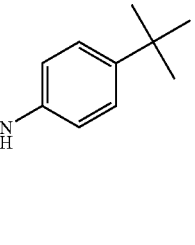 | 416.42 | 417.32 | 3.86 | 3.65 | 4.42 | |
| 1403 | 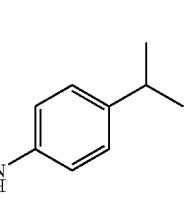 | 402.40 | 403.31 | 3.78 | 3.62 | 4.26 | |
| 1404 | 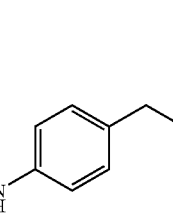 | 416.42 | 417.32 | 4.01 | 3.85 | 4.68 | |
| 1405 | 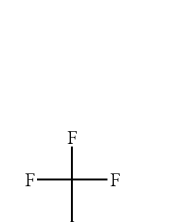 | 458.34 | 459.23 | 3.78 | 3.59 | 4.21 | |
| 1406 | 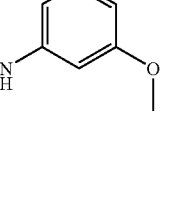 | 418.35 | 419.13 | 3.21 | 3.08 | 3.42 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1407 | 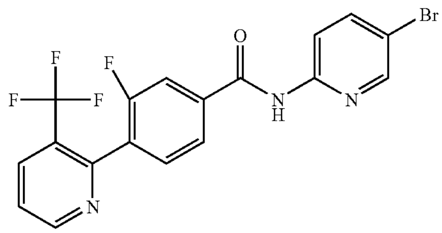 | 440.20 | 442.12 | 3.55 | 3.24 | 3.87 | |
| 1408 | 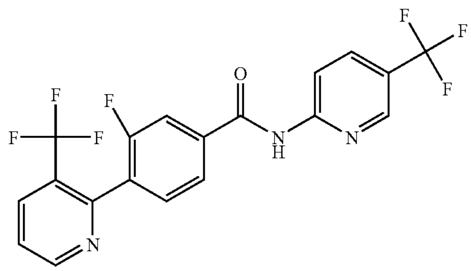 | 429.30 | 430.15 | 3.63 | 3.26 | 4.05 | |
| 1409 | 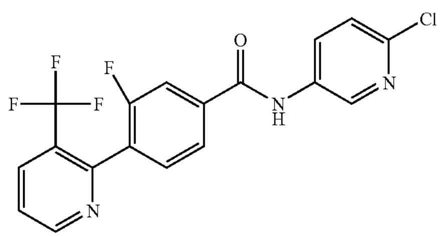 | 395.75 | 396.07 | 3.22 | 3.05 | 3.56 | |
| 1410 | 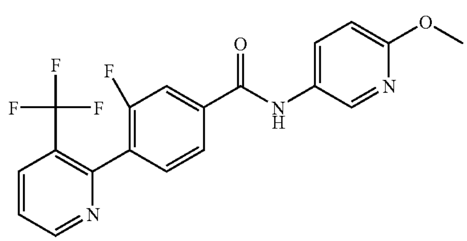 | 391.33 | 392.11 | 2.93 | 2.63 | 3.33 | |
| 1411 | 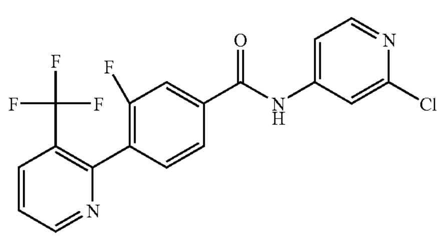 | 395.75 | 396.07 | 3.22 | 3.02 | 3.69 | |
| 1412 | 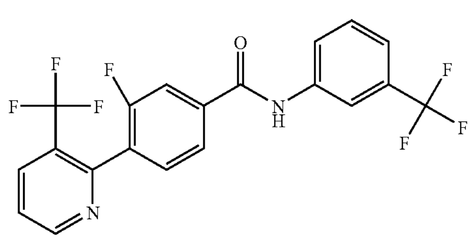 | 428.31 | 429.12 | 3.68 | 3.55 | 4.04 | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1413 | 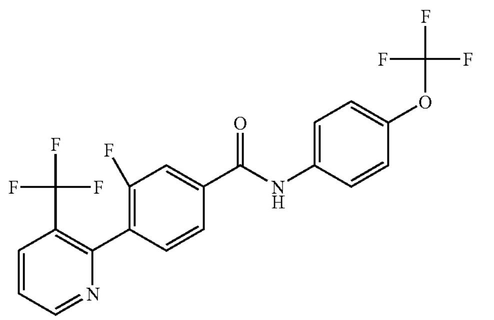 | 444.31 | 445.19 | 3.73 | 3.61 | 4.18 | |
| 1414 | 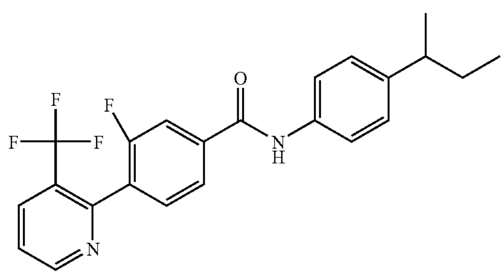 | 416.42 | 417.31 | 3.93 | 3.66 | 4.55 | |
| 1415 | 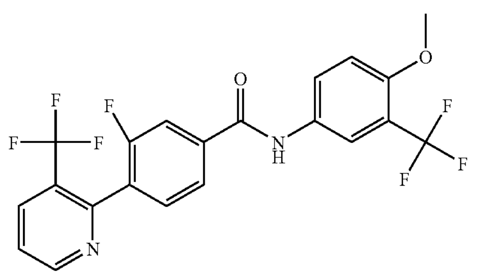 | 458.34 | 459.22 | 3.58 | 3.32 | 3.99 | |
| 1416 | 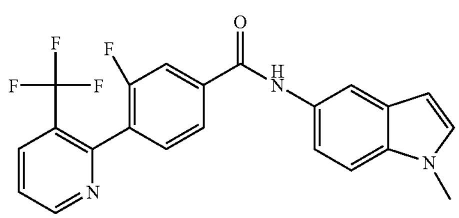 | 413.38 | 414.12 | 3.34 | 3.18 | 3.46 | |
| 1417 | 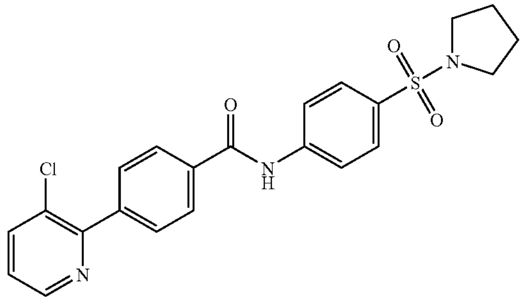 | 441.94 | | | | | |

-continued

AMIDE COMPOUNDS

| ID | STRUCTURE | MW (Calc) | MS (Obs) | HPLC RT (Min) | HPLC START TIME (Min) | HPLC END TIME (Min) | % Inhibition @ 1 uM |
|---|---|---|---|---|---|---|---|
| 1418 | 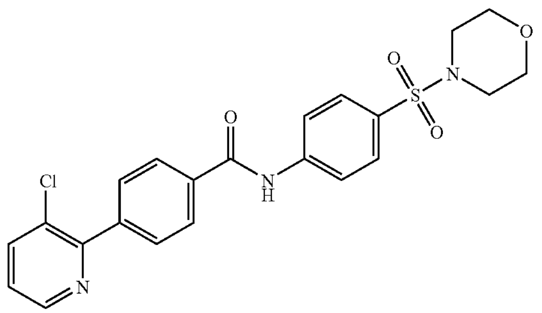 | 457.94 | | | | | |
| 1419 | 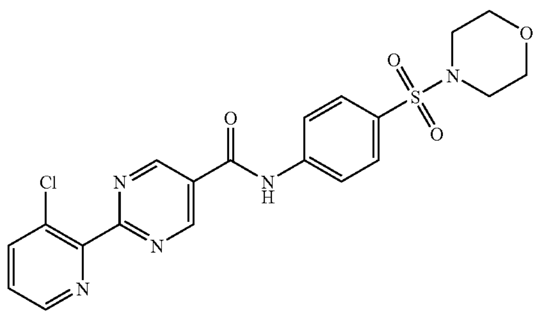 | 459.91 | | | | | |
| 1420 | 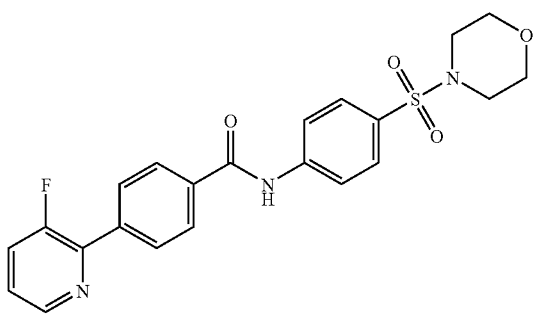 | 441.48 | | | | | |

For purposes of the Table 1, activity of each compound is expressed as follows:
"+" compound exhibited 0-25% inhibition of calcium ion influx induced by capsaicin stimulation.
"++" compound exhibited 25-50% inhibition of calcium ion influx induced by capsaicin stimulation.
"+++" compound exhibited 50-75% inhibition of calcium ion influx induced by capsaicin stimulation.
"++++" compound exhibited 75% or greater inhibition of calcium ion influx induced by capsaicin stimulation.

EXAMPLE 3

High Throughput Screening of VR1 Antagonists for Determination of in Vitro Efficacy Using a Calcium Imaging Assay VR1 protein is a heat-gated cation channel that exchanges about 10 calcium ions for every sodium ion resulting in neuronal membrane depolarization and elevated intracellular calcium ion levels. Therefore the functional activity of compounds at the VR1 receptor may be determined by measuring changes in intracellular calcium levels in 293 cells expressing capsaicin-insensitive VR1 receptor variants. A dual wavelength ratiometric dye, Fura2, was used as an indicator of relative levels of calcium ions in a 96 well format using a bench top scanning fluorometer with integrated fluidics and temperature control (Flex Station, Molecular Devices).

A dual wavelength ratiometric dye, Fura2, was used as an indicator of relative levels of [Ca2+] in a 96 well format using a bench top scanning fluorometer with integrated fluidics and temperature control (Flex Station, Molecular Devices).

293 cells were grown on PDL coated 96-well black-walled plates, in the presence of a DMEM medium containing 5% Penstrep, 5% Glutamax, 200 ug/mL Hygromycin, 5 µg/mL Blasticide and 10% heat inactivated FBS. Prior to assay, the cells were loaded with 5 µg/mL Fura2 in normal saline solution at 37° C. for 40 minutes. Cells were then washed with normal saline to remove the dye.

The assay consists of two stages; a pre-treatment phase followed by a treatment phase.

50 μl of a compound solution was added to the cells (Pre-treatment). Immediately following, 50 μl of the test compound in a saline solution at pH 5.1 was added. Fura2 was excited at 340 and 380 nM to indicate relative calcium concentration. Changes in wavelength measurements were made throughout the course of the experiment in 4 second intervals over a period of 3 minutes. Responses were measured as peak fluorescence ratio after test compound addition minus baseline fluorescence ratio prior to pre-treatment and were calculated using SoftMaxPro softwareData were expressed as percentage inhibition calculated using Excel as follows:

$$\text{Percentage Inhibition} = \frac{(\text{Compound Response}) - (\text{Control Response})}{(\text{Agonist Response} - \text{Control Response})} \times 100$$

All compounds with percentage inhibition values greater than 75% are considered hits and earmarked for further investigation at lower concentrations. The relative strengths of the percentage inhibition values are set forth in Table 1.

EXAMPLE 4

Whole-Cell Patch Clamp Electrophysiology

Dorsal root ganglion (DRG) neurons were recovered from either neonatal or adult rats and plated onto poly-D-lysine coated glass coverslips. The plated neurons were transferred into a chamber to allow drug solutions to be added to the cells using a computer-controlled solenoid-valve based perfusion system. The cells were imaged using standard DIC optics. Cells were patched using finely-pulled glass electrodes. Voltage-clamp electrophysiology experiments were carried out using an Axon Instruments Multiclamp amplified controlled by pCLAMP8 software.

Figure 3:
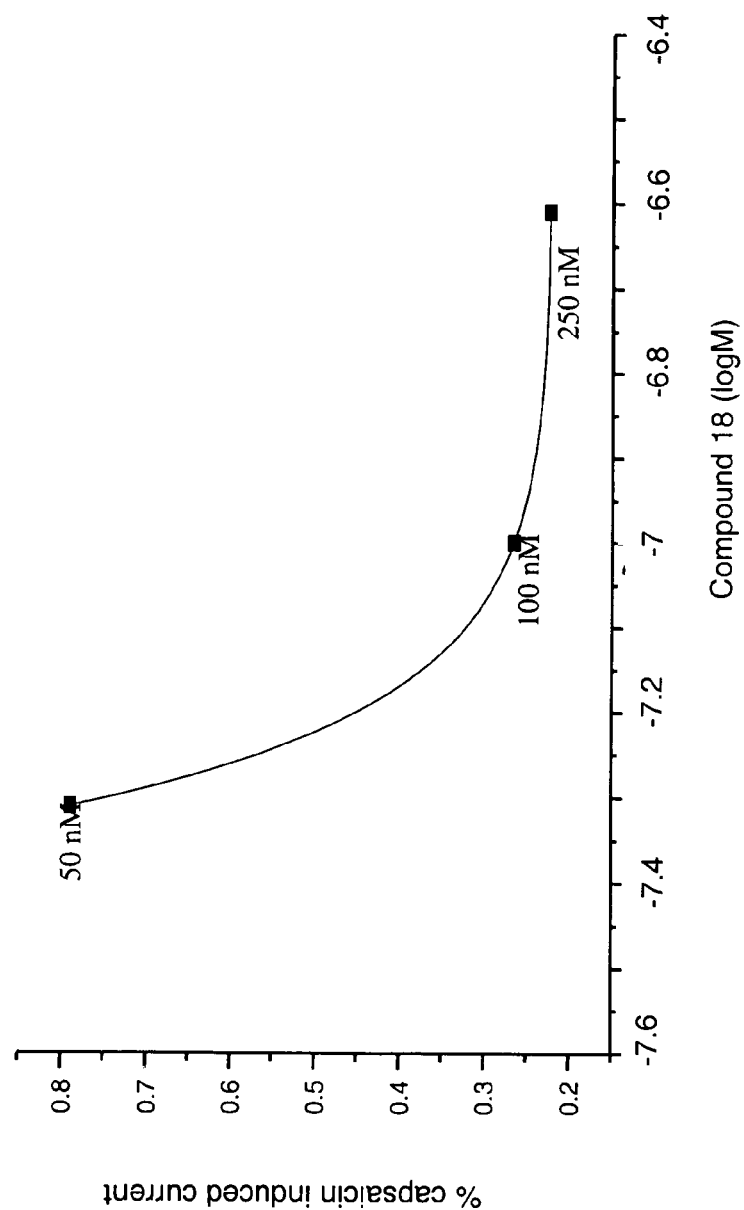
FIG. 3: A dose response curve demonstrating the increasing effectiveness of Compound 18 in inhibiting a capsaicin induced calcium ion influx at higher concentrations tested, namely 50 nM, 100 nM and 250 nM.
Figure 4:
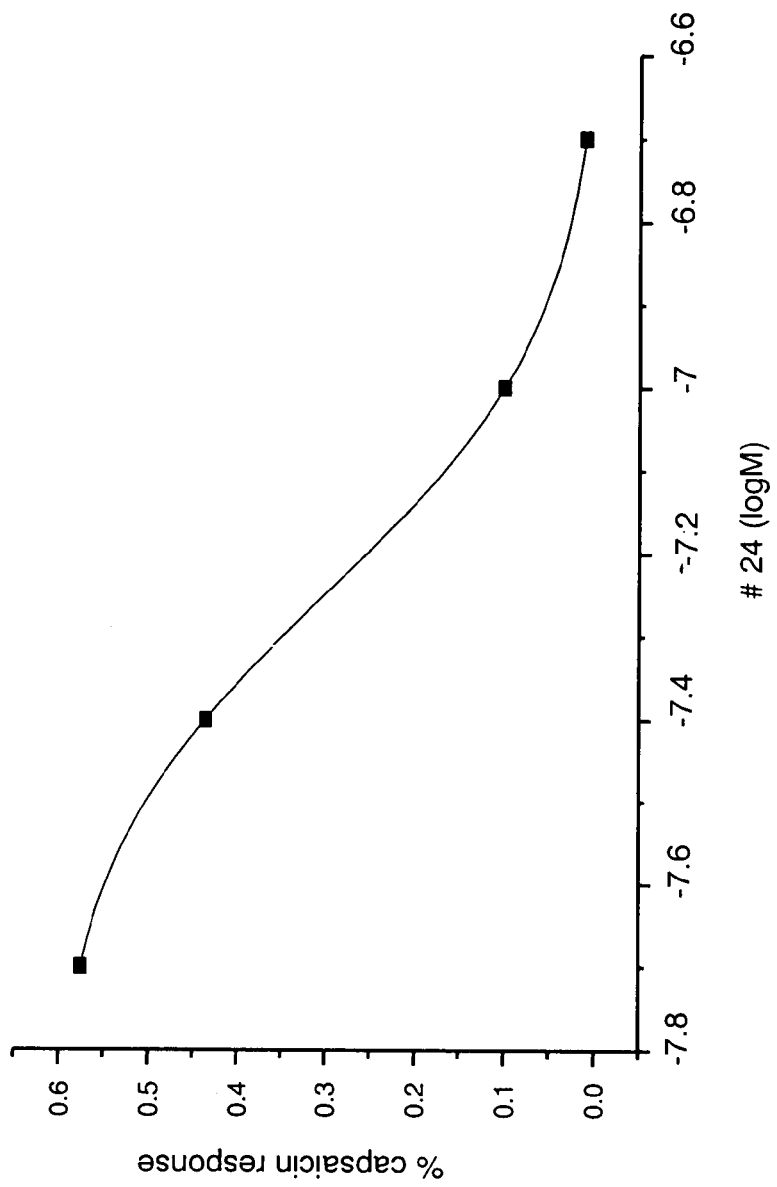
FIG. 4: A dose response curve demonstrating the increasing effectiveness of Compound 24 in inhibiting a capsaicin induced calcium ion influx at higher concentrations tested, namely 20 nM, 40 nM, 100 nM and 200 nM.

The cells were placed into a whole-cell voltage clamp and help at a voltage of −80 mV while monitoring the membrane current in gap-free recording mode. 500 nM capsaicin was added for 30 seconds as a control. Test compounds at various concentrations at ranging from (10-1000 nM) were added to the cells for 1 minute prior to a 30 second capsaicin application. Differences between control experiments and drug positive capsaicin experiments were used to determine the efficacy of each test compound. All compounds that inhibited capsaicin induced current greater than 50% were considered positives. The data obtained for compounds 24 and 18 are set forth in Table 2, below. FIG. 3 represents a dose response curve demonstrating the increasing effectiveness of compound 18 in inhibiting a capsaicin induced calcium ion influx at higher concentrations tested, namely 50 nM, 100 nM and 250 nM. Likewise, FIG. 4 represents a dose response curve demonstrating the increasing effectiveness of Compound 24 in inhibiting a capsaicin induced calcium ion influx at higher concentrations tested, namely 20 nM, 40 nM, 100 nM and 200 nM.

TABLE 2

| Compound ID | Concentration | Treatment time (seconds) | % inhibition of capsaicin induced current |
|---|---|---|---|
| 24 | 200 nM | 25 | 100 |
| 18 | 100 nM | 20 | <75 |

FIG. 1 demonstrates the activity of the compounds tested in inhibiting the capsaicin induced current.

EXAMPLE 5

Plasma Extravasation Study: A measure of Neurogenic Inflammation

The density of TRPV1 expression is enhanced during an inflammatory condition. Therefore TRPV1 antagonists have been investigated in three different models of inflammatory pain, namely plasma extravasation, paw lick assay, and thermal hyperalgesia.

Methods

Sprague-Dawley male rats obtained from Charles River, San Diego, Calif. were dosed with compound 18. Two hours later, they were injected with Evan's Blue (10 ml/kg or 150 μl). Thirty minutes after I.V. injection, 10 μl of 25 mM capsaicin in 100% ethanol was applied to the left ear of the animal, followed by 10 μl vehicle (100% EtOH) to the right ear of the mouse. Fifteen minutes later, the animal was sacrificed using $CO_2$. Each ear was removed, placed into labeled tubes and weighed. The dye was then extracted from the ears by drying the ears at 55-60° overnight. The following day, 250 μl formamide was added and left at 55-60° overnight.

An Evans blue standard curve was first generated (2.5, 5, 10, 20, 40, and 80 mg/μl). Samples (with ears) were spun for at least 1 minute before addition of 100 μl of each sample to appropriate wells. Samples were analyzed in a plate holder by SOFTmax PRO. Standards were graphed to generate a standard curve and then used to extrapolate Evans Blue concentrations of experimental samples.

Results

Figure 2:
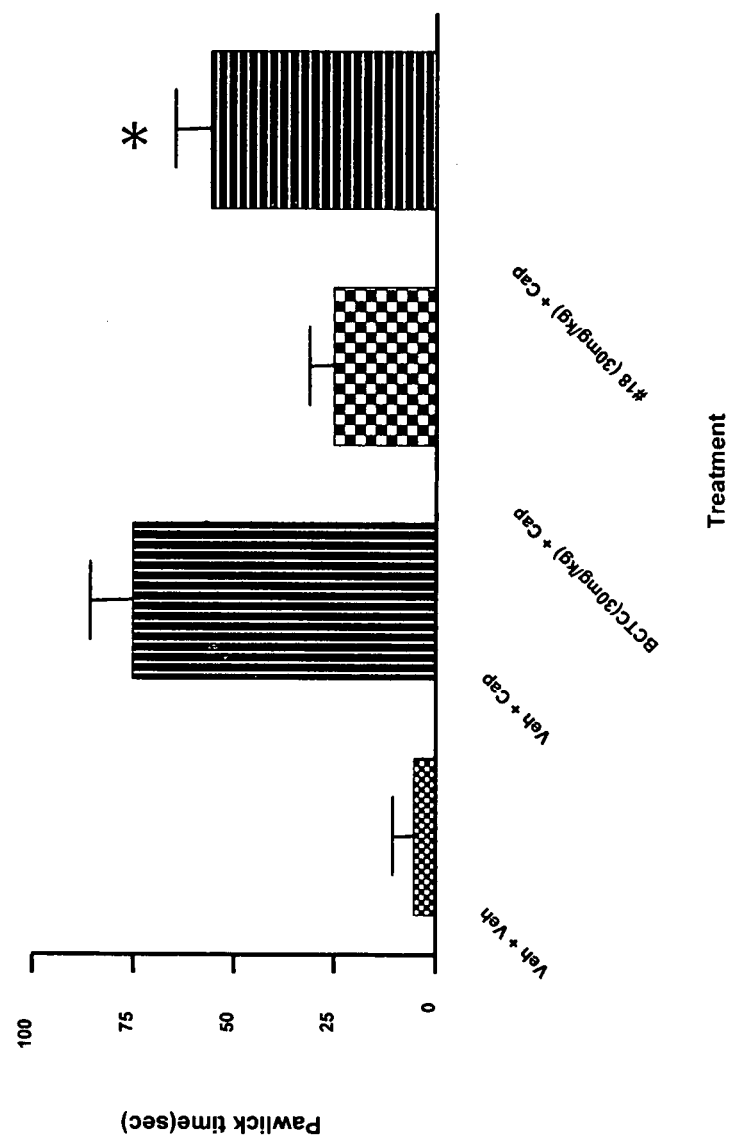
FIG. 2: A graph showing that Compound 18 at a dose of 30 mg/kg significantly blocks capsaicin induced plasma extravasation in rats. The results are expressed in µg EB/mg tissue. The results are represented for the delivery vehicle HPBCD, control compound BCTC, compound 18 at two concentrations and capsaicin alone in a delivery vehicle.

Compound 18 at a dose of 30 mg/kg significantly blocks capsaicin induced plasma extravasation in rats. FIG. 2 demonstrates the results in μg EB/mg tissue (Evans Blue). The results are represented for the delivery vehicle HPBCD, control compound BCTC, Compound 18 at two concentrations and capsaicin alone in vehicle.

EXAMPLE 6

Paw Lick Assay

This assay was performed to test the ability of Compound 18 to inhibit the response to capsaicin challenge.

Methods

Animals were acclimatized at least 2 days prior to testing by placing them in a behavioral chamber for one hour. On the day of testing, animals were trained for 30-60 minutes prior to dosing. Animals were dosed with 30 mg/kg of Compound 18 at least 30 minutes prior to testing and then placed in behavioral chambers for acclimatization. Animals were then placed into a falcon tube restrainer and injected with a 0.16 mg/ml capsaicin solution (or vehicle) into the plantar surface of their paw. Animals were then returned to the behavior chamber and monitored for paw licking behavior (including paw and leg licking behavior) over the next 5 minute interval.

Results

Figure 5:
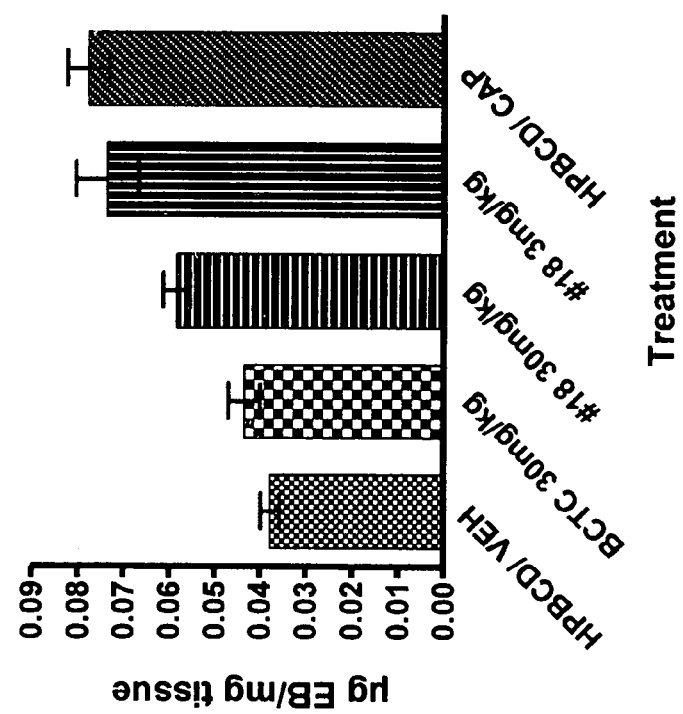
FIG. 5: A graph showing the times per second test subjects lick their paw when a delivery vehicle is administered alone, capsaicin is administered, capsaicin is administered with a control compound, and capsaicin is administered with Compound 18 to the affected area.

Compound 18 (30 mg/kg) significantly inhibited pawlick response induced by treatment with capsaicin. FIG. 5 demonstrates the pawlick times per second when a delivery vehicle is administered alone, capsaicin is administered, capsaicin is administered with a control compound, and capsaicin is administered with Compound 18.

EXAMPLE 7

Thermal Hyperalgesia

Figure 6:
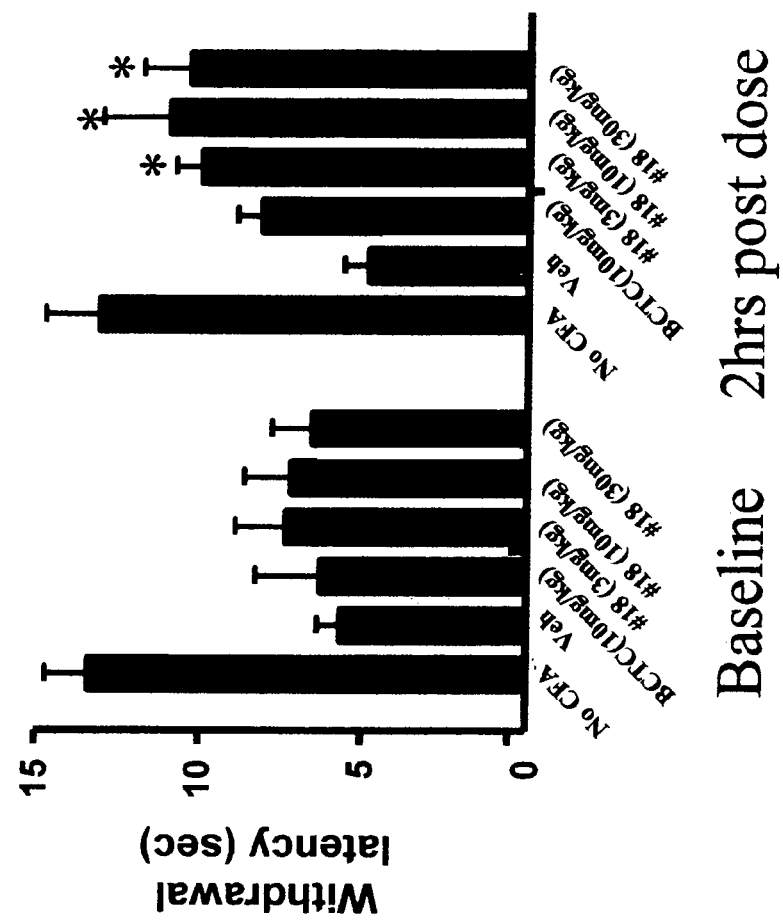
FIG. 6: A graph demonstrating that a dose of Compound 18 at 30 mg/kg significantly increases latency of paw withdrawal demonstrating reversal of thermal hyperalgesia. The figure depicts the time in seconds until animals withdraw from thermal stimulation at baseline and two hours after administration of a delivery vehicle, a control compound, and three concentrations of Compound 18.

Sprague-Dawley male rats obtained from Charles River, San Diego, Calif. were purchased at 150-175 g, and held for at least one week before testing. Pain was induced by injecting 100 µl of 2% carrageenan in 0.9% saline sub-Q into the right ventral hindpaw while the animals were under isofluorane anesthesia. Animals were then dosed one hour after with different concentrations of Compound 18 (3, 10, and 30 mg/kg). Two hours later, after acclimatizing in testing chambers for 20-30 minutes, animals were tested on both hindpaws for latency of paw withdrawal using a thermal testing apparatus. 2-3 trials were conducted with 10 minutes between trials. As demonstrated in FIG. 6, a dose of Compound 18 at 30 mg/kg significantly increased latency of paw withdrawal demonstrating reversal of thermal hyperalgesia. The figure depicts the time in seconds until animals withdraw from thermal stimulation at baseline and two hours after administration of delivery vehicle, control compound, and three concentrations of Compound 18.

EXAMPLE 8

Pharmacokinetic Profile

The pharmacokinetic profile of Compound 18 was evaluated following intravenous and oral administration in rats. Sprague-Dawley male rats obtained from Charles River, San Diego, Calif. were acclimated for 24 hours.

Compound 18 was formulated at a concentration of 0.5 mg/mL for IV administration at a 1 mg/kg dose and 1 mg/mL for oral administration at a 5 mg/kg dose. All animals were weighed before dosing. The body weight was used to calculate the actual dose for each animal. The intravenous dose was administered through the jugular vein catheter in less than 1 minute. The oral dose volume was 1.5 mL for all PO rats administered through oral lavage.

For IV dosing, blood samples were collected using a pre-heparinized syringe via the carotid artery catheter before dosing and at t=2, 5, 15, 30, 60, 120, 180, 360, and 480 minutes post dosing. For PO dosing, blood samples were collected using a pre-heparinized syringe via the carotid artery catheter before dosing and at t=5, 15, 30, 60, 120, 180, 360, and 480 minutes post dosing. 250 uL of blood was obtained at each time point from each animal. Equal volumes of 0.9% normal saline were replaced to prevent dehydration. The whole blood samples were maintained on ice until centrifugation. Blood samples were centrifuged at 14,000 rpm for 10 minutes at 4° C., and the upper plasma layer was transferred into a clean vial and store at −80° C.

The plasma was analyzed. Compound 18 demonstrates Oral Bioavailability (% F) of 30.06%, a half life (t½) of 3.71 hours, Clearance (Cl) of 0.53 L/h/Kg, a Volume of distribution (Vd) of 2.82 L/Kg, a Tmax of 180 minutes, and a Cmax of 1.75 mM.

EXAMPLE 9

Aqueous Solubility

Equilibrium solubility was measured in a pH 2.0 isotonic solution of NaCl/HCl and a pH 7.4 aqueous buffer. The pH 2.0 solution was prepared by adjusting the saline solution to a pH of 2.0 using HCl. The pH 7.4 buffer was prepared by adjusting the pH of a 0.07 M solution of $NaH_2PO_4$ to pH 7.4 with 10 N NaOH. Each buffer had an ionic strength of 0.15. At least 1 mg of powder was combined with 1 ml of buffer to make ≧1 mg/ml mixture. This sample was shaken for ≧2 hours and left to stand overnight at room temperature. The samples were then filtered through a 0.45-µm Nylon syringe filter that was first saturated with the sample. The filtrate was sampled twice, consecutively. All samples were assayed by LC/MS using electrospray ionization. The typical range of the assay is greater than 1 mg/mL to less than 0.0002 mg/mL, depending on analytical sensitivity. The results demonstrated solubility of <0.0002 mg/ml at pH 2.0 and low solubility at pH 7.4.

The partition coefficient, Log(D), between water-saturated 1-octanol and pH 7.4 buffer was determined for Compound 18. The pH 7.4 buffer was prepared by adjusting the pH of a 0.07 M solution of $NaH_2PO_4$ to pH 7.4 with 10 N NaOH. 15 µL of a 10 mM stock solution of test article were pipetted in duplicate, into test tubes containing 750 µL each of 1-octanol and pH 7.4 buffer. Then 3 µL of 50 mM testosterone was also added to each tube. Then the tubes were rotated for about one hour using a benchtop rotator. Following the rotation, the tubes sat on the bench top for about 1 hour to allow the layers to separate.

Thereafter, 400 µL of the octanol (top) layer was removed and placed into a test tube. Next 400 µL of the aqueous (bottom) layer was removed and placed into a test tube. The following serial dilutions were then made of each layer using 50% methanol as the diluent: Octanol—100×, 1000×, and 10,000× Aqueous—1×, 100×, & 100×. The 100×, 1000× and 10,000× diluted octanol samples and the undiluted, 10× and 100× diluted aqueous samples were then aliquoted into appropriate vials.

A standard curve of test article and testosterone was prepared using 50% methanol at the following concentrations: 2, 0.6, 0.2, 0.06, 0.02, 0.006, and 0.002 µM. The samples were analyzed by LC/MS monitoring both test article and testosterone. Log (D) was calculated for each duplicate sample by taking the calculated concentration of the least diluted sample for each phase that fell within the standard curve using the following equation: Log(D)=Log 10(Calc. Conc. in Organic Phase/Calc. Conc. in Aqueous Phase). The results demonstrated Log (D) values at pH 7.4 of less than 4.7 for Compound 18.

EXAMPLE 10

Analysis of Plasma Protein Binding

Membranes from Harvard/Amika with a molecular weight cutoff of 5,000 were rinsed with $dH_2O$ then placed in pH 7.4 PBS supplied by Gibco. The membranes were allowed to soak for 1 hour. A stock of the test article was pooled with Warfarin, Atropine at 2 mM in DMSO. The test article was then dosed into human plasma in sodium citrate, Rat Plasma, and Mouse Plasma to a final 10 μM concentration (0.5% DMSO v/v). The pre-soaked membranes were then placed into dialysis chambers. 500 μL of PBS was added to one side of the chamber, and 500 μL of the Matrix containing the test article was added to the other side of the chamber.

The chambers were then placed into an enclosed, heated rocker, which was pre-warmed to 37° C. and allowed to reach equilibrium for at least 22 hours. After 22 hours both sides were sampled. 100 μL of the donor side was added to 500 μL of PBS. 100 μL of the PBS side was added to 20 μL of fresh matrix. Samples then were crashed with 1:1 Acetonitrile and centrifuged at 10,000 RPM for 10 minutes. 100 μL of supernatant was placed into LC/MS vials for analysis.

Standards were prepared in a 1:5 plasma: PBS mixture at 5, 1.5, 0.5, 0.15, 0.05, 0.015 and 0.005 μM concentrations. The samples and standards were placed into HPLC vials and assayed by LC/MS. Protein binding values were calculated as follows:

% Bound=[(Concentration in Donor−Concentration in Receiver)/(Concentration in Donor)]×100.

% Recovery=[(Concentration in donor+Concentration in Receiver)]/(Concentration in Normal Initial)]×100

Compound 18 had high human plasma protein binding of more than 99.8%. Compound 18 protein binding in rat and mouse plasma could not be established due to low recovery of the test article.

EXAMPLE 11

Cytochrome p450 Inhibition Assessment

The ability of test compounds to inhibit five major human cytochrome p450 isozymes was evaluated. Cytochrome p450 inhibition assays were performed on 96-well microtiter assay plates according to the protocols described in Gentest P450 inhibition instruction manuals. The assays were performed in duplicate at 8 concentrations with the upper concentration of 100 μM followed by a 1:3 serial dilution. Reactions were initiated by the addition of 100 μL of enzyme/substrate mix to 100 μL of cofactor/serial dilution mix, and terminated by addition of 75 μL of a 4:1 acentonitrile: 0.5 M Tris base solution or by 2N NaOH for CYP3A4/DBF. Fluorescence was measured using a fluorescence plate reader (FLUOstar model 403, BMG Lab Technologies, Durham, N.C.). For reactions with inhibition greater than 50%, $IC_{50}$ values were determined by fitting the data to the Hill equation using software GraphPad Prism (Version 4.02, GraphPad Software, San Diego, Calif.).

Known CYP inhibitors inhibited respective CYP enzymes in the expected manners, indicating that CYP enzymes were active and responsive. Compound 18 did not significantly inhibit 2C9, CYP2D6 and CYP3A4 activities in the concentration range tested. It inhibited CYP2C19 activity. The $IC_{50}$ value was estimated to be 26.85 μM. It also inhibited CYP1A2 activity with an estimated $IC_{50}$ of 97.45 μM.

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

What is claimed is:

1. A compound of the formula I':

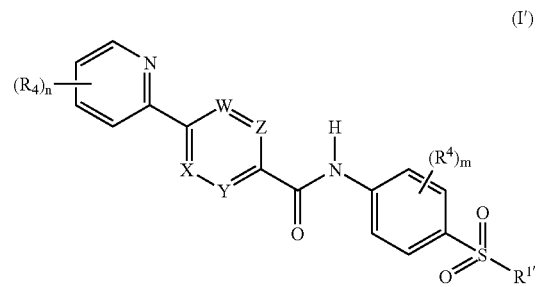

or a pharmaceutically acceptable salt, or stereoisomers, or tautomers thereof, wherein:

each of W, X, Y and Z is independently $CR^4$;

$R^{1'}$ is aryl, substituted aryl, heteroaryl, substituted heteroaryl aralkyl, heteroaralkyl, amino or substituted amino;

each $R^4$ is independently hydrogen, substituted or unsubstituted alkyl, hydroxyalkyl, haloalkyl, amino, alkylamino, dialkylamino, arylamino, alkylarylamino, alkoxy, aryloxy, heteroaryloxy, aminoalkoxy, alkoxy, cycloalkylalkoxy, alkoxycarbonyl, arylalkyloxy, aryl, heteroaryl, arylalkyl, sulfo, sulfonyl, sulfanyl, aminosulfonyl, arylsulfonyl, carboxy, carbamoyl, cyano, cycloheteroalkyl, halo, heteroalkyl, hydroxyl, or thiol; and the subscript n and the subscript m are independently 0, 1, 2, 3, or 4.

2. A compound according to claim 1, wherein the compound is of the formula II':

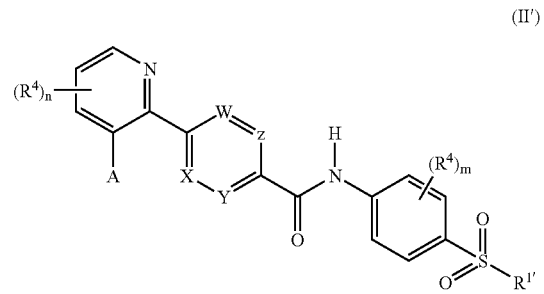

wherein W, X, Y, Z, $R^{1'}$ and $R^4$ are as in claim 1; A is halo, alkyl, substituted alkyl, alkoxy, amino, substituted amino or $SO_2R^{1''}$; $R^{1''}$ is aryl, heteroaryl, aralkyl, heteroaralkyl, amino or substituted amino; and the subscript n is 0, 1, 2, or 3.

3. A compound according to claim 2, wherein each W, X, Y and Z is CH.

4. A compound according to claim 2, wherein each $R^4$ is H.

5. A compound according to claim 1, wherein the compound is of the formula III':

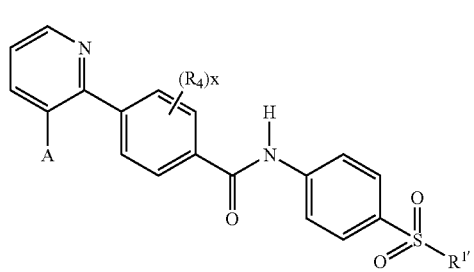

(III')

wherein A is halo, alkyl, substituted alkyl, alkoxy, amino, substituted amino or SO$_2$R$^{1''}$, R$^{1''}$ is alkyl, aryl, heteroaryl, aralkyl, heteroaralkyl, amino or substituted amino; and the subscript n is 0, 1, 2, or 3; R$^{1'}$ and R$^4$ are as in claim 1; and the subscript x is 0, 1, 2, 3, or 4.

6. A compound according to claim 5, wherein A is F, Cl, CF$_3$, OMe, NMe$_2$ or SO$_2$Me.

7. A compound according to any one of claims 2-6, wherein R$^{1'}$ is aryl, substituted aryl, heteroaryl, or substituted heteroaryl.

8. A compound according to any one of claims 2-6, wherein R$^{1'}$ is phenyl or substituted phenyl.

9. A compound according to any one of claims 2-6, wherein R$^{1'}$ is amino or substituted amino.

10. A compound according to any one of claims 2-6, wherein R$^{1'}$ is NR$^{2'}$R$^{2'}$; wherein each R$^{2'}$ is independently hydrogen, alkyl, substituted alkyl, cycloalkyl, aryl, substituted aryl, heteroaryl, or substituted heteroaryl.

11. A compound according to any one of claims 2-6, wherein R$^{1'}$ is NR$^{2'}$R$^{2'}$; and the R$^{2'}$'s are independently alkyl.

12. A compound according to any one of claims 2-6, wherein R$^{1'}$ is NR$^{2'}$R$^{2'}$; and the R$^{2'}$'s are joined together to form a cycloheteroalkyl ring of 5-7 atoms.

13. A compound according to claim 1, wherein the compound is of the formula IV':

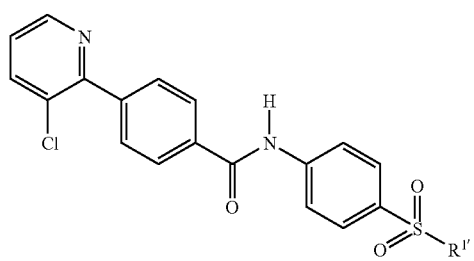

(IV')

and wherein R$^{1'}$ is aryl, substituted aryl, heteroaryl, or substituted heteroaryl.

14. A compound according to claim 13, wherein R$^{1'}$ is substituted or unsubstituted phenyl or pyridyl.

15. A compound according to claim 13, wherein R$^{1'}$ is 4-methylphenyl, 4-fluorophenyl, 4-chlorophenyl or 4-trifluoromethylphenyl.

16. A compound according to claim 13, wherein R$^{1'}$ is benzyl.

17. A compound according to claim 2, wherein the compound is of the formula V':

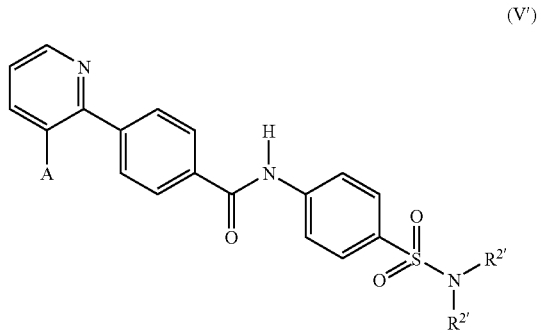

(V')

wherein each R$^{2'}$ is independently hydrogen, alkyl, substituted alkyl, cycloalkyl, aryl, substituted aryl, heteroaryl, or substituted heteroaryl.

18. A compound according to claim 1, wherein the compound is of the formula VI':

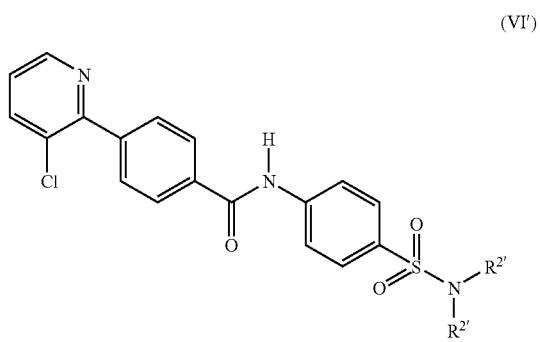

(VI')

wherein each R$^{2'}$ is independently hydrogen, alkyl, substituted alkyl, cycloalkyl, aryl, substituted aryl, heteroaryl, or substituted heteroaryl.

19. A compound according to claim 18, wherein each R$^{2'}$ is H.

20. A compound according to claim 18, wherein each R$^{2'}$ is independently alkyl.

21. A compound according to claim 18, wherein each R$^{2'}$ is independently H, Me, or Et.

22. A compound of the formula VII':

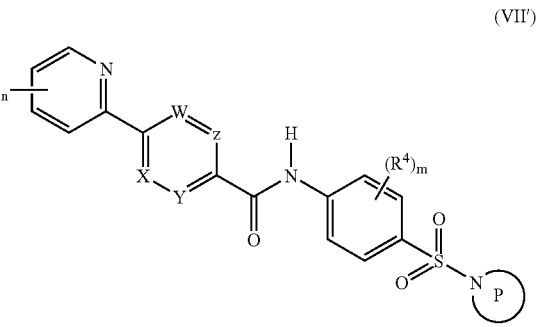

(VII')

or a pharmaceutically acceptable salt, or stereoisomers, or tautomers thereof, wherein:

each of W, X, Y and Z is independently CR⁴;

ring P is cycloheteroalkyl, substituted cycloheteroalkyl, heteroaryl, or substituted heteroaryl; each R⁴ is independently hydrogen, substituted or unsubstituted alkyl, hydroxyalkyl, haloalkyl, amino, alkylamino, dialkylamino, arylamino, alkylarylamino, alkoxy, aryloxy, heteroaryloxy, aminoalkoxy, alkoxy, cycloalkylalkoxy, alkoxycarbonyl, arylalkyloxy, aryl, heteroaryl, arylalkyl, sulfo, sulfonyl, sulfanyl, aminosulfonyl, arylsulfonyl, carboxy, carbamoyl, cyano, cycloheteroalkyl, halo, heteroalkyl, hydroxyl, or thiol; and the subscript n and the subscript m are each independently 0, 1, 2, 3, or 4.

23. A compound according to claim 22, wherein the compound is of the formula VII':

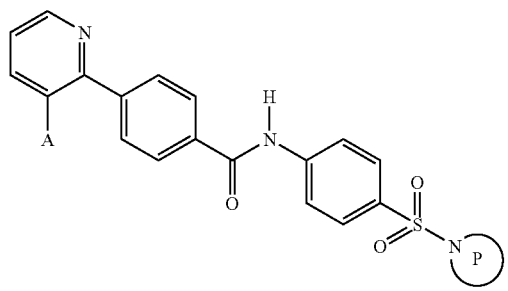

(VIIa')

wherein A is F, Cl, CF₃ or SO₂Me.

24. A compound according to either of claim 22 or 23, wherein the ring P is selected from substituted or unsubstituted

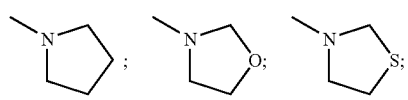

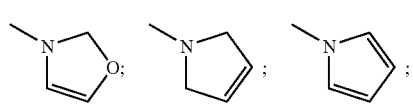

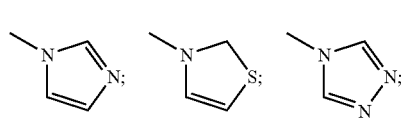

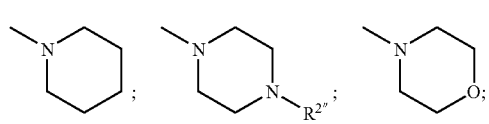

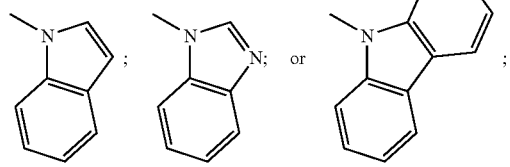

and wherein R²" is selected from H and alkyl.

25. A compound according to claim 1 selected from the group consisting of:

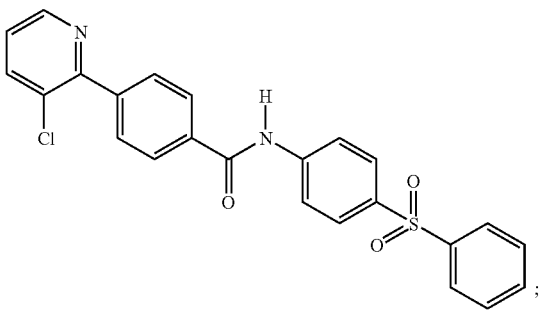

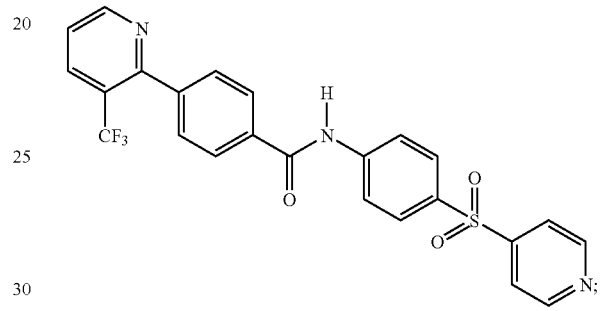

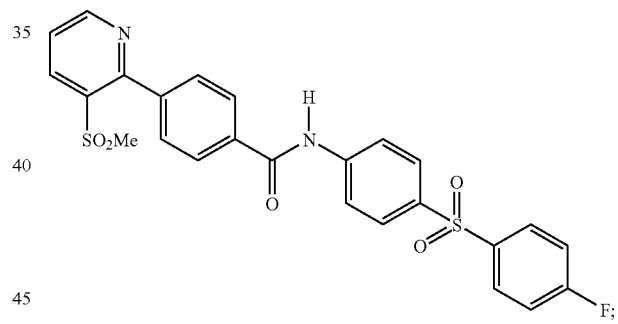

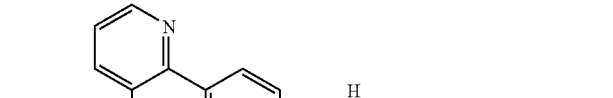

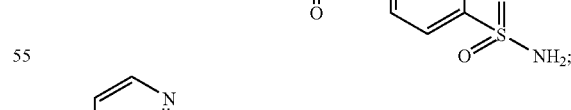

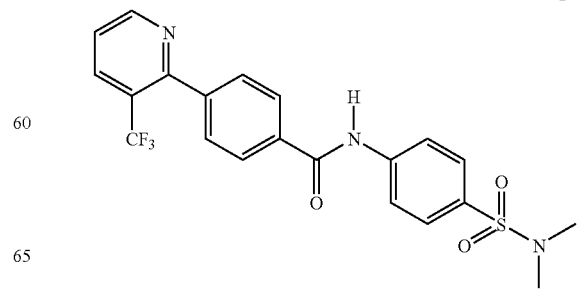

-continued
and
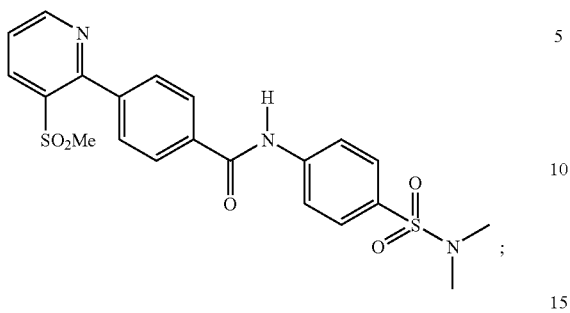
or a pharmaceutically acceptable salt, or stereoisomers, or tautomers thereof.
26. A compound selected from the group consisting of:
| STRUCTURE | NAME |
|---|---|
| 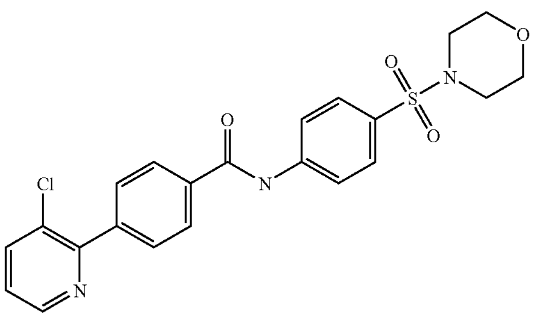 | 4-(3-Chloro-pyridin-2-yl)-N-[4-(morpholine-4-sulfonyl)-phenyl]-benzamide; |
| 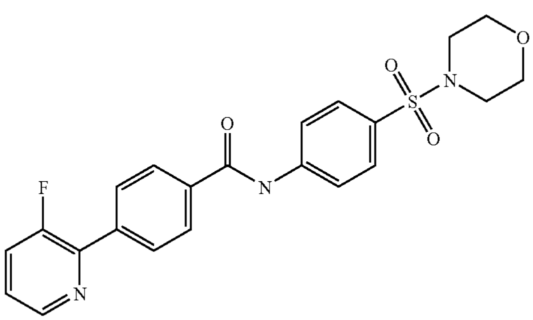 | 4-(3-Fluoro-pyridin-2-yl)-N-[4-(morpholine-4-sulfonyl)-phenyl]-benzamide; |
| 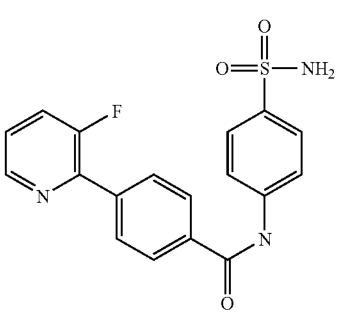 | 4-(3-Fluoro-pyridin-2-yl)-N-(4-sulfamoyl-phenyl)-benzamide; |

-continued

| STRUCTURE | NAME |
|---|---|
| 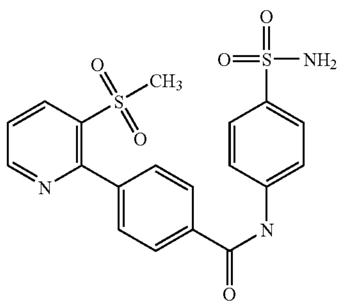 | 4-(3-Methanesulfonyl-pyridin-2-yl)-N-(4-sulfamoyl-phenyl)-benzamide; |
| 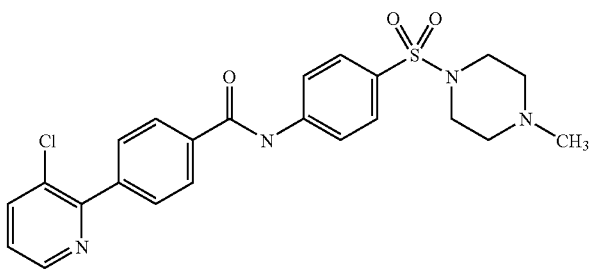 | 4-(3-Chloro-pyridin-2-yl)-N-[4-(4-methyl-piperazine-1-sulfonyl)-phenyl]-benzamide; |
| 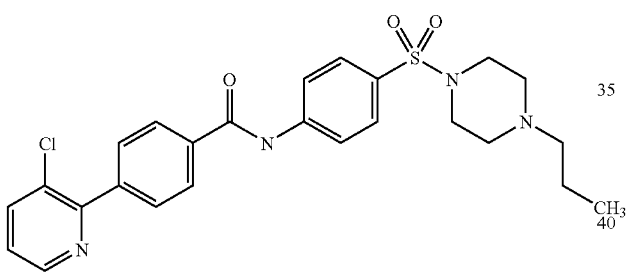 | 4-(3-Chloro-pyridin-2-yl)-N-[4-(4-propyl-piperazine-1-sulfonyl)-phenyl]-benzamide; |
| 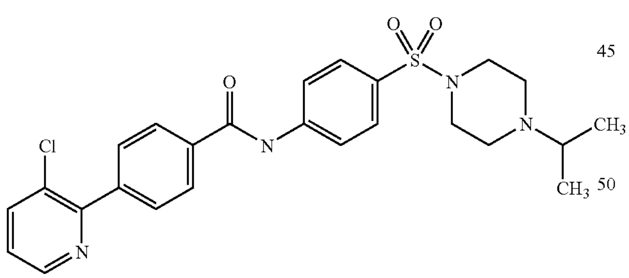 | 4-(3-Chloro-pyridin-2-yl)-N-[4-(4-isopropyl-piperazine-1-sulfonyl)-phenyl]-benzamide; and |
| 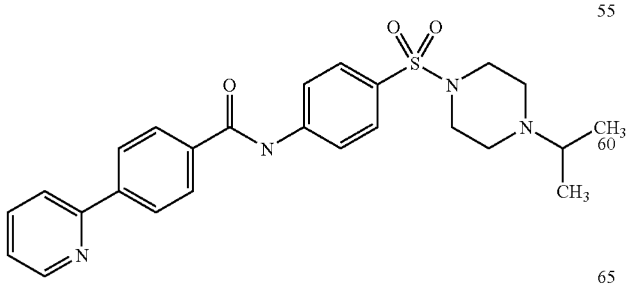 | N-[4-(4-Isopropyl-piperazine-1-sulfonyl)-phenyl]-4-pyridin-2-yl-benzamide; |

27. A pharmaceutical composition comprising a pharmaceutically acceptable carrier and a pharmaceutically effective amount of a compound of any one of claims 1, 22, and 26.

28. The pharmaceutical composition of claim 27, wherein the carrier is a parenteral carrier.

29. The pharmaceutical composition of claim 27, wherein the carrier is an oral carrier.

30. The pharmaceutical composition of claim 27, wherein the carrier is a topical carrier.

* * * * *